US008980825B2

(12) United States Patent
Hanko et al.

(10) Patent No.: US 8,980,825 B2
(45) Date of Patent: Mar. 17, 2015

(54) ROMIDEPSIN SOLID FORMS AND USES THEREOF

(71) Applicant: Celgene Corporation, Summit, NJ (US)

(72) Inventors: Jason Hanko, West Lafayette, IN (US); David Alan Engers, West Lafayette, IN (US); Eric Hagen, Lafayette, IN (US); Valeriya Smolenskaya, West Lafayette, IN (US); Jeffrey Scott Stults, Half Moon Bay, CA (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 14/281,654

(22) Filed: May 19, 2014

(65) Prior Publication Data

US 2014/0256637 A1    Sep. 11, 2014

Related U.S. Application Data

(62) Division of application No. 13/181,460, filed on Jul. 12, 2011, now abandoned.

(60) Provisional application No. 61/363,522, filed on Jul. 12, 2010.

(51) Int. Cl.

| A61K 38/15 | (2006.01) |
|---|---|
| C07K 5/12 | (2006.01) |
| C07K 11/02 | (2006.01) |
| C07K 5/103 | (2006.01) |
| A61K 38/00 | (2006.01) |

(52) U.S. Cl.
CPC .................. C07K 11/02 (2013.01); C07K 5/101 (2013.01); *A61K 38/00* (2013.01)
USPC .......................................................... 514/1.1

(58) Field of Classification Search
CPC ......... A61K 38/00; A61K 38/15; A61K 9/20; C07K 5/12; C07K 5/101; C07K 11/02; C07K 7/06; C07K 7/08
See application file for complete search history.

(56) References Cited

U.S. PATENT DOCUMENTS

| 4,977,138 A | 12/1990 | Okuhara et al. |
|---|---|---|
| 5,510,270 A | 4/1996 | Fodor et al. |
| 5,545,522 A | 8/1996 | Van Gelder et al. |
| 5,556,752 A | 9/1996 | Lockhart et al. |
| 5,578,832 A | 11/1996 | Trulson et al. |
| 5,605,793 A | 2/1997 | Stemmer |
| 5,716,785 A | 2/1998 | Van Gelder et al. |
| 5,776,905 A | 7/1998 | Gibbons et al. |
| 5,830,721 A | 11/1998 | Stemmer et al. |
| 5,837,458 A | 11/1998 | Minshull et al. |
| 5,891,636 A | 4/1999 | Van Gelder et al. |
| 6,117,679 A | 9/2000 | Stemmer |
| 6,391,640 B1 | 5/2002 | Minshull et al. |
| 6,403,555 B1 | 6/2002 | Skov |
| 6,548,479 B1 | 4/2003 | Skov |
| 6,706,686 B2 | 3/2004 | Long et al. |
| 6,777,217 B1 | 8/2004 | Schreiber et al. |
| 6,809,118 B2 | 10/2004 | Chung |
| 6,828,302 B1 | 12/2004 | Skov |
| 6,905,669 B2 | 6/2005 | DiMartino |
| 6,946,441 B2 | 9/2005 | Long et al. |
| 7,041,639 B2 | 5/2006 | Skov |
| 7,056,883 B2 | 6/2006 | Ito et al. |
| 7,056,884 B2 | 6/2006 | Nakajima et al. |
| 7,148,204 B2 | 12/2006 | Bennett et al. |
| 7,171,311 B2 | 1/2007 | Dai et al. |
| 7,314,862 B2 | 1/2008 | Naoe et al. |
| 7,354,928 B2 | 4/2008 | Wang et al. |
| 7,396,665 B2 | 7/2008 | Ueda et al. |
| 7,470,722 B2 | 12/2008 | Malecha et al. |
| 7,488,712 B2 | 2/2009 | Yoshida et al. |
| 7,857,804 B2 | 12/2010 | McCaffrey et al. |
| 2003/0162293 A1 | 8/2003 | Chu et al. |
| 2004/0018968 A1 | 1/2004 | Sgouros et al. |
| 2004/0053820 A1 | 3/2004 | Nakajima et al. |
| 2004/0072735 A1 | 4/2004 | Richon et al. |
| 2004/0077591 A1 | 4/2004 | Dangond |
| 2004/0127523 A1 | 7/2004 | Bacopoulos et al. |
| 2004/0228909 A1 | 11/2004 | Sarris et al. |
| 2005/0059682 A1 | 3/2005 | Rubinfeld |
| 2005/0070467 A1 | 3/2005 | Naoe et al. |
| 2005/0187148 A1 | 8/2005 | Naoe et al. |

(Continued)

FOREIGN PATENT DOCUMENTS

| CA | 2317003 | 8/2001 |
|---|---|---|
| EP | 0352646 | 1/1990 |

(Continued)

OTHER PUBLICATIONS

Aron et al., "Depsipeptide (FR901228) induces histone acetylation and inhibition of histone deacetylase in chronic lymphocytic leukemia cells concurrent with activation of caspase 8-mediated apoptosis and down- regulation of c-FLIP protein," Blood, 102(2):652-658 (2003).
Barbour et al., "Studies on Measurement of Plasma Magnesium: Application of the Magon Dye Method to the 'Monarch' Centrifugal Analyzer," Clin. Chem., 34:2103 (1988).
Bates et al., "Final Clinical Results of a Phase 2 NCI Multicenter Study of romidepsin in Recurrent Cutaneous T-Cell Lymphoma (Molecular Analyses Included)," ASH Annual Meeting Abstracts, 112(11): p. 1568 (2008).
Berge et al., "Pharmaceutical Salts," J Pharm Science 66:1-19, 1977.
Bhalla, "Epigenetic and chromatin modicifers as targeted therapy of hematologic malignancies," J Clin Oncol, 23(17):3971-3993 (2005).
Bishton et al., "Epigenetic target in hematological malignancies: combination therapies with HDAC's and demethylating agents," Expert Rev Anticancer Ther, 7(10):1439-1449 (2007).

(Continued)

*Primary Examiner* — Julie Ha
*Assistant Examiner* — Kristina M Hellman
(74) *Attorney, Agent, or Firm* — Jones Day

(57) ABSTRACT

The present disclosure provides solid forms of a compound of formula I. In some embodiments, the present disclosure provides crystalline forms of Compound I. In some embodiments, the present disclosure provides solvate forms of Compound I. In some embodiments, the present disclosure provides amorphous Compound I.

2 Claims, 116 Drawing Sheets

(56) References Cited

U.S. PATENT DOCUMENTS

| | | |
|---|---|---|
| 2005/0187149 A1 | 8/2005 | Naoe et al. |
| 2005/0191713 A1 | 9/2005 | Sasakawa et al. |
| 2005/0222013 A1 | 10/2005 | Jung et al. |
| 2005/0272647 A1 | 12/2005 | Yamaji et al. |
| 2006/0018921 A1 | 1/2006 | Levenson et al. |
| 2006/0019883 A1 | 1/2006 | Kronblad et al. |
| 2006/0100140 A1 | 5/2006 | Dent et al. |
| 2006/0106049 A1 | 5/2006 | Odenike |
| 2006/0128660 A1 | 6/2006 | Rajski et al. |
| 2006/0135413 A1 | 6/2006 | Naoe et al. |
| 2006/0223747 A1 | 10/2006 | Ito et al. |
| 2006/0270016 A1 | 11/2006 | Holm |
| 2007/0015787 A1 | 1/2007 | Bruncko et al. |
| 2007/0110719 A1 | 5/2007 | Holm |
| 2007/0129290 A1 | 6/2007 | Or et al. |
| 2007/0148228 A1 | 6/2007 | Cumming et al. |
| 2007/0292512 A1 | 12/2007 | Leonard et al. |
| 2008/0214446 A1 | 9/2008 | Okada et al. |
| 2008/0233562 A1 | 9/2008 | Sasakawa et al. |
| 2009/0186382 A1 | 7/2009 | Verdine et al. |
| 2009/0209616 A1 | 8/2009 | Verdine et al. |
| 2009/0221473 A1 | 9/2009 | Chan et al. |
| 2010/0093610 A1 | 4/2010 | Vrolijk et al. |

FOREIGN PATENT DOCUMENTS

| | | |
|---|---|---|
| EP | 1010705 | 6/2000 |
| EP | 1426054 | 6/2004 |
| JP | 7(1995)-64872 | 7/1995 |
| JP | 11-335375 | 12/1999 |
| JP | 2001-348340 | 12/2001 |
| WO | WO 98/39965 | 9/1998 |
| WO | WO 98/40080 | 9/1998 |
| WO | WO 01/18171 | 3/2001 |
| WO | WO 01/42282 | 6/2001 |
| WO | WO 02/06307 | 1/2002 |
| WO | WO 02/15921 | 2/2002 |
| WO | WO 02/20817 | 3/2002 |
| WO | WO 02/86498 | 4/2002 |
| WO | WO 02/97053 | 5/2002 |
| WO | WO 02/055017 | 7/2002 |
| WO | WO 02/055688 | 7/2002 |
| WO | WO 02/085400 | 10/2002 |
| WO | WO 02/090534 | 11/2002 |
| WO | WO 03/015810 | 2/2003 |
| WO | WO 03/017763 | 3/2003 |
| WO | WO 03/024442 | 3/2003 |
| WO | WO 03/035843 | 5/2003 |
| WO | WO 03/053468 | 7/2003 |
| WO | WO 03/070188 | 8/2003 |
| WO | WO 03/083067 | 10/2003 |
| WO | WO 03/084611 | 10/2003 |
| WO | WO 03/088954 | 10/2003 |
| WO | WO 03/103613 | 12/2003 |
| WO | WO 2004/009771 | 1/2004 |
| WO | WO 2004/017996 | 3/2004 |
| WO | WO 2004/024160 | 3/2004 |
| WO | WO 2004/062654 | 7/2004 |
| WO | WO 2004/064727 | 8/2004 |
| WO | WO 2004/074478 | 9/2004 |
| WO | WO 2004/096289 | 11/2004 |
| WO | WO 2004/098495 | 11/2004 |
| WO | WO 2005/000282 | 1/2005 |
| WO | WO 2005/000289 | 1/2005 |
| WO | WO 2005/000332 | 1/2005 |
| WO | WO 2005/009961 | 2/2005 |
| WO | WO 2005/018578 | 3/2005 |
| WO | WO 2005/023179 | 3/2005 |
| WO | WO 2005/027842 | 3/2005 |
| WO | WO 2005/030239 | 4/2005 |
| WO | WO 2005/051430 | 6/2005 |
| WO | WO 2005/052143 | 6/2005 |
| WO | WO 2005/053609 | 6/2005 |
| WO | WO 2005/058298 | 6/2005 |
| WO | WO 2005/079827 | 9/2005 |
| WO | WO 2005/085864 | 9/2005 |
| WO | WO 2005/087206 | 9/2005 |
| WO | WO 2005/105055 | 11/2005 |
| WO | WO 2005/105066 | 11/2005 |
| WO | WO 2005/115149 | 12/2005 |
| WO | WO 2005/117930 | 12/2005 |
| WO | WO 2006/027346 | 3/2006 |
| WO | WO 2006/055621 | 5/2006 |
| WO | WO 2006/060382 | 6/2006 |
| WO | WO 2006/060429 | 6/2006 |
| WO | WO 2006/129105 | 12/2006 |
| WO | WO 2007/009539 | 1/2007 |
| WO | WO 2007/040522 | 4/2007 |
| WO | WO 2007/058896 | 5/2007 |
| WO | WO 2007/061939 | 5/2007 |
| WO | WO 2007/145704 | 12/2007 |
| WO | WO 2007/146730 | 12/2007 |
| WO | WO 2008/013589 | 1/2008 |
| WO | WO 2008/083288 | 7/2008 |

OTHER PUBLICATIONS

Bogden et al., "Growth of Human Tumor Xenografts Implanted under the Renal Capsule of Normal Immunocompetent Mice," Exp Cell Biol 47:281-293 (1979).

Bolden et al., "Anticancer activities of histone deacetylase inhibitors," Nat Rev Drug Discovery, 5(9):769-784 (2006).

Bryn et al., "Pharmaceutical Solids: A Strategic Approach to Regulatory Considerations," Pharmaceutical Research, 12(7):945-954 (1995).

Budillon et al., "Growth arrest, apoptosis and potentiation of 5-fluorouracil and Raltitrexed cytotoxic effect induced by histone deacetylase inhibitor SAHA in colorectal cancer cells," Eur J Cancer 38:S29 (2002).

Butler et al., "Suberoylanilide Hydroxamic Acid, an Inhibitor of Histone Deacetylase, Suppresses the Growth of Prostate Cancer Cells in Vitro and in Vivo," Cancer Res 60:5165-5170 (2000).

Byrd et al., "A phase 1 and pharmacodynamic study of depsipeptide (FK228) in chronic lymphocytic leukemia and acute myeloid leukemia," Blood, 105(3):959-967 (2005).

Byrd et al., "Depsipeptide (FR901228): a novel therapeutic agent with Selective in vitro activity against human B-cell chronic lymphocytic leukemia cells ," Blood, 94(4):1401-1408 (1999).

Catley et al., "Aggresome induction by proteasome inhibitor bortezpmib and {alpha}-tubulin hyperacetylation by tubulin deacetylase (TDAC) inhibitor LBH589 are synergistic in myeloma cells," Blood 108(10):3441-3449 (2006).

Chan et al., "Depsipeptide (FR901228, NSC-630176) pharmacokinetics in the rat by LC/MS/MS ," Invest New Drugs,15(3):195-206 (1997).

Cheson et al., "New Drugs for the Treatment of Chronic Lymphocytic Leukemia," Reviews Clin Exp Hematol 4(2):145-166 (2000).

Conway et al., "Vincristine-and Cisplatin-induced Apoptosis in Human Retinoblastoma. Potentiation by Sodium Butyrate," Eur J Cancer, 34(11):1741-1748 (1998).

Dai et al., "Interactions between bortezomib and romidepsin and belinostat in chronic lymphocytic leukemia cells ," Clin Cancer Res, 14(2):549-558 ( 2008).

Database Biosis 'Online, AN-PREV200400024248, XP-002342749, "Anti-Tumor Efficacy of Four Different Histone Deacetylase Inhibitors on Hepatoma Cells in Vitro", 2003 (Abstract No. T1786).

Dokmanovic & Marks, "Prospects: histone deacetylase inhibitors ," J Cell Biochem, 96(2):293-304 (2005).

Fiebig et al., "Bcl-XL is qualitatively different from and ten times more effective than Bcl-2 when expressed in a breast cancer cell line," Cancer, 6:213 (2006).

Findley et al., "Expression and Regulation of Bcl-2, Bcl-xl, and Bax Correlate With p53 Status and Sensitivity to Apoptosis in Childhood Acute Lymphoblastic Leukemia," Blood, 89(8): 2986-2993 (1997).

Finnin et al., "Structures of a histone deacetylase homologue bound to the TSA and SAHA Inhibitors," Nature, 401(6749):188-193 (1999).

Fischer et al., 41$^{st}$ Annual Meeting of the American Society of Clinical Oncology, Abstr # 3106 (2005).

(56) References Cited

OTHER PUBLICATIONS

Fukumura et al., "A sensitive transcriptome analysis method that can detect unknown transcripts," Nucl Acids Res 31(16):e94 (2003).
Furumai et al., "FK228 (depsipeptide) as a natural prodrug that inhibits class I histone deacetylases," Cancer Res, 62(17):4916-4921 (2002).
Garcia-Manero et al., "Phase 1/2 study of the combination of 5-aza-2'-deoxycytidine with valporic acid inpatients with leukemia ," Blood, 108(10):3271-3279 (2006).
Geldof et al., "Cytotoxicity and neurocytoxicity of new marine anti-cancer agents evaluacted using in vitro assays," Cancer Chemother & Pharmacol 44(4):312-318 (1999).
Gore et al., "Combined DNA methyltransferase and histone deacetylase inhibition in the treatment of myeloid neoplasms," Cancer Res, 66(12):6361-6369 (2006).
Gore et al., "Impact of the putative differentiating agent sodium phenylbutyrate on myelodysplastic syndromes and acute myeloid leukemia ," Clin Cancer Res, 7(8):2330-2339 (2001).
Han et al., "Apicidin, a Histone Deacetylase Inhibitor Inhibits Proliferation of Tumor Cells via Induction of p21 WAF1/Cip1 and Gelsolin," Cancer Res 60(21):6068-6074 (2000).
Harrison et al., "High Response Rates with the Combination of Bortezomib, Dexamethasone and the Pan-Histone Deacetylase Inhibitor Romidepsin in Patients with Relapsed or Refractory Multiple Myeloma in Phase I/II Clinical Trial," ASH Annual Meeting Abstracts, 112(11):3698 (2008).
Inoue et al., "Subrenal capsule assay-an experimental study and clinical application to chemosensitivity tests," Gan to Kagaku Ryoho 14(5Pt2):1629-1635 (1987) (Abstract).
Jones & Baylin, "The Epigenomics of Cancer," Cell 128:683-692 (2007).
Jones & Baylin, "The fundamental role of epigenetic events in Cancer,"Nat Rev Genet, 3(6):415-428 (2002).
Jung et al., "Amide Analogues of Trichostatin A as Inhibitors of Histone Deacetylase and Inducers of Terminal Cell Differentiation," J Med Chem US 42(22):4669-4679 (1999).
Kahn et al., "Total Synthesis of the Antitumor Depsipeptide FR-901,228," J Am Chem Soc 118:7237-7238, (1996).
Kano et al., "The Joint Meeting of the $64^{th}$ Annual Meeting of the Japanese Society of Hematology and the $44^{th}$ Annual Meeting of the Japanese Society of Clinical Hematology," Japanese J Clin Hematology 43(8):116 (2002).
Kawamoto et al., "Expression Profiling by iAFLP: A PCR-Based Method for Genome-Wide Gene Expression Profiling," Genome Res 12:1305-1312 (1999).
Khan et al., "Analysis of histone deacetylase inhibitor, depsipeptide (FR901228), effect on multiple myeloma ," Br J Haematol, 125(2):156-161 (2004).
Kim et al., "Clinically significant responses Achieved with Romidepsin in Treatment-Refractory Cutaneous T-Cell Lymphoma: Final Results from a Phase 2B, International, Multicenter, Registration Study," ASH Annual Meeting Abstracts, 112(11):263 (2008).
Kimura et al., "New Enzymatic Method with Tryptophanase for Determining Potassium in Serum," Clin. Chem., 38:44 (1992).
Kisselev & Goldberg, "Proteasome inhibitors: from research tools to drug candidates," Chem Biol 8:739-758 (2001).
Kitazono et al., "Enhanced Adenovirus Transgene Expression in Malignant Cells Treated with the Histone Deacetylase Inhibitor FR901228," Cancer Res 61:6328-6330 (2001).
Kitazono et al., "Adenovirus HSV-TK Constuct with Thyroid-Specific Promoter: Enhancement of Activity and Specificity with Histone Deacetylase Inhibitors and Agents Modulating the Camp Pathway," Int J Cancer 99:453-459 (2002).
Kitazono et al., "Low Concentrations of the Histone Deacetylase Inhibitor, Depsipeptide (FR901228), Increase Expression of the Na/I Symporter and Iodine Accumulation in Poorly Differentiated Thyroid Carcinoma Cells," J Clin Endocrin 86(7):3430-3435 (2001).
Kitazono et al., Proc Amer Assoc Cancer Res Annual 43:799 (2002) (Abstract only).
Klimek et al., "Tolerability, pharmacodynamics, and pharmacokinetics studies fo depsipeptide (romidepsin) in patients with acute myelogenous leukemia or advanced myelodysplastic syndromes," Clin Cancer Res, 14(3):826-832 (2008).
Klisovic et al., "Depsipeptide (FR9801228) Inhibits Proliferation and Induces Apoptosis in Primary and metastatic Human Uveal Melanoma Cell Lines," Invest Ophthalmol Vis Sci, 44(6):2390-2398 (2003).
Koch et al., "Evaluation of a Direct Potentiometric Method for Sodium and Potassium usied in the Du Pont aca," Clin. Chem., 29:1090 (1983).
Komatsu et al., "Cyclic Cyfroxamic-acid-containing Peptide 31, a Potent Syntheic Histone Deacetylase Inhibitor with Antitumor Activity," Cancer Res 61(11):4459-4466 (2001).
Kosugi et al., "In vivo Effects of a Histone Deacetylase Inhibitor, FK228, on Human Acute Promyelocytic Leukemia in NOD/Shi-scid/scid Mice," Japanese J Cancer Res 92(5):529-536 (2001).
Kuendgen et al., "Treatment of myelodysplastic syndromes with valproic acid alone or in combination with all-trans retinoic acid," Blood, 104(5):1266-1269 (2004).
Liakopoulou et al., "Stimulation of Fetal Hemoglobin Production by Short Chain Fatty Acids," Blood, 86:3227 (1995).
Maeda et al., "Up-regulation of costimulatory/adhesion molecules by histone deacetylase ihibitors in acute myeloid leukemia cells," Blood, 96(12):3847-3856 (2000).
Magner et al., "Activation of MHC class I, II, and CD40 gene expression by histone deacetylose inhibitors ," J Immunol, 165(12):7017-7024 (2000).
Marks et al., "Histone deacetylase inhibitors: Inducers of differentiation or apoptosis of transformed cells," J Natl Cancer Inst, 92(15):1210-1216 (2000).
Marshall et al., "A phase I trial of depsipeptide (FR901228) in patients with advanced cancer ," J Exp Ther Oncol, 2(6):325-332 (2002).
Mertins et al., Proc Amer Assoc Cancer Res Annual Meetins 40:623 (1999).
Mirars, Laura, New drug bulletin: romedepsin (Istodax® —Celgene Corporation) http://healthcare.utah.edu/pharmacy/bulletins/NDB_197.pdf (2010).
Mitsiades et al., "Transcriptional signature of histone deacetylase inhibition in multiple myeloma: biological and clinical implications," Proc Natl Acad Sci USA, 101(2):540-545 (2004).
Molife et al.,"Phase II study of FK228 in patients with hormone refractory prostate cancer (HRPC)," J Clin Oncol (Meeting Abstracts), 24(18 Suppl):14554 (2006).
Murata et al., "Apoptotic Cytotoxic Effects of a Histone Deacetylase Inhibitor, FK228, on Malignant Lymphoid Cells," Japanese J Cancer Res 91:1154-1160 (2000).
Nakajima et al., ", FR901228, a potent antitumor antibiotic, is a novel histone deticetylose inhibitor," Exp Cell Res, 241(1)126-133 (1998).
Nebbioso et al., "Tumor-selective action of HDAC inhibitors involves TRAIL induction in acute myeloid leukemia cells," Nat Med, 11(1):77-84 (2005).
Nebozhyn et al., "Quantitative PCR on 5 genes reliably Identifies CTCL patients with 5% to 99% circulating tumor cells with 90% accuracy," Blood, 107(8):3189-3196 (2006).
Newbold et al., "Characterisation of the novel apoptotic and therapeutic activities of the histone deacetylase inhibitor romidepsin," Mol Cancer Ther, 7(5):1066-1079 (2008).
Niesvizky et al., "Multicenter Phase II Trial of the Histone Deacetylase Inhibitor Depsipeptide (FK228) for the Treatment of Relapsed or Refractory Multiple Myeloma (MM)," Blood ASH Annual Meeting Abstracts, 106(11):2574 (2005).
Nishimura et al., "A New Antitumor Antibiotic, FE900840," J Antibiot XLII(4):553-557 (1989).
Nuijen et al., "Development of a lyophilized parenteral pharmaceutical formulation the investicational polypeptide marine anticancer agent kahalalide F.," Medline (2001) XP-002206588.
Odenike et al., "Histone deacetylase inhibitor romidepsin has differential activity in core binding factor acute myeloid leukemia," Cancer Res, 14(21):7095-7101 (2008).

(56) References Cited

OTHER PUBLICATIONS

Paoluzzi et al., "Romidepsin and belinostat synergize the antineoplastic effect of bortezomib in mantle cell lymphoma," Clin Cancer Res, 16(2):554-565 (2010).
Peart et al., "Novel mechanisms of apoptosis induced by histone deacetylase inhibitors," Cancer Res, 63(15):4460-4471 (2003).
Peart et al., "identification and functional significance of genes regulated by structurally different histone deacetylose inhibitors," Proc Natl Acad Sci USA, 102(10):3697-3702 (2005).
Pei et al., "Synergistic induction of oxidative injury and apoptosis in human multiple myeloma cells by the proteasome inhibitor bortezpmib and histone deacetylase inhibitors," Clin Cancer Res, 10(11):3839-3852 (2004).
Piekarz et al., "Completion of the First Cohort of Patients with Cutaneous T-Cell Lymphoma Enrolled on a Phase II Trial of Depsipeptide ," ASH Annual Meeting Abstracts,106(11):231 (2005).
Piekarz et al., "Results of a Phase 2 NCI Multicenter Study of Romidepsin in Patients with Relapsed Peripheral T-Cell Lymphoma (PTCL)," ASH Annual Meeting Abstracts 112(11):1567 (2008).
Piekarz et al., "T-cell lymphoma as a model for the use of histone deacetylase inhibitors in cancer therapy: impact of depsipeptide on molecular markers, therapeutic targes, and mechanisms of resistance," Blood , 103(12):4636-4643 (2004).
Piekarz et al , "Inhibitor of histone deactylation, depsipeptide (FR901228), in the treatment of peripheral and cutaneous T-cell lymphoma: a case report," Blood , 98(9):2865-2868 (2001).
Piekarz et al., "Cardiac studies in patients treated with depsipeptide, FK228,1n a phase II trial for T-cell lymphoma," Clin Cancer Res, 12(12):3762-3773 (2006).
Pierkarz et al., "Final Results of a Phase 2 NCI Multicenter Study of Romidepsin in Patients with Relapsed Peripheral T-Cell Lymphoma (PTCL)," 51$^{st}$ Annual Meeting of the American Society of Hematology, 114(22):661-662 (2009).
Piekarz et al., "Epigenetic modifiers: basic understanding and clinical development," Clin Cancer Res, 15(12):3918-3926 (2009).
Piekarz et al., "Phase II Multi-Institutional Trial of the Histone Deacetylase Inhibitor Romidepsin As Monotherapy for Patients With Cutaneous T-Cell Lymphoma," J Clin Oncol, 27(32):5410-5417 (2009).
Piekarz et al., "A Review of Depsipeptide and Other Histone Deacetylase Inhibitors in Clinical Trials," Curr Pharm Des 10:2289-2298 (2004).
Piekarz, R., et al, "Update of the NCI multiinstutional phase II trial of romidepsin, FK228,for patients with cutaneous or peripheral T-cell lymphoma,". J Clio Oncol (Meeting Abstracts), 2007.25(18_suppl): p. 8027 (2007).
Prince et al., "Clinical studies of histone deacetylase inhibitors," Clin Cancer Res, 15(12):3958-3969 (2009).
Program of the 4th Japanese Foundation for Cancer Research, International Symposium on Cancer Therapy (ISCC), Feb. 12, 1999.
Rasheed et al., "Histone deacetylase inhibitors in cancer therapy ," Expert Opin Investig Drugs, 16(5):659-678 (2007).
Rehak et al., "Modified Magnesium Method in the aca III: Elimination of Interference by Bilirubin," Clin. Chem., 35:1031 (1989).
Richon et al., "Histone Deacetylase Inhibitors: A New Class of Potential Therapeutic Agents for Cancer Treatment," Clin Cancer Res 8(3):662-664 (2002).
Richon et al., "Histone deacetylasei inhibitor selectively induces p21WAFI expression and gene-associated histone acetylation,"Proc Natl Acad Sci USA, 97(18):10014-10019 (2000).
Robey et al., "Increased MDRI expression in normal and malignant peripheral blood mononuclear cells obtained from patients receiving depsipetide• (FR901228, FK228, NSC630176)," Clin Cancer Res, 12(5):1547-1555 (2006).
Roychowdhury et al., "Selective efficacy of depsipeptide in a xenograft model of Epstein-Barr virus-positive lymphoproliferative disorder ," J Natl Cancer Inst, 96(19):1447-1457 (2004).
Sakai et al., "MBD3 and HDACI,two components of the NuRDcomplex, are localized at Aurora-A-positive centrosomes in M phase,"J Biol Chem, 277(50):48714-48723 (2002).

Sandor et al., "P21-dependent G arrent with downregulation of cyclin D1 upregulation of cyclin E by the histone deacetylase inhibitor FR901228," Br J Cancer 83(6):817-825, (2000).
Sandor et al., "Phase I trial of the histone deacetylase Inhibitor, depsipeptide (FR901228, NSC 630176), In patients with refractory neoplasms ," Clin Cancer Res, 8(3):718-728 (2002).
Sasakawa et al., "Effects of FK228, a novel histone deacetylase inhibitor, on human lymphoma U-937 cells in vitro and in vivo," Biochem Pharmacol, 64(7):1079-1090 (2002).
Sawa et al., "Histone deacetylase Inhibitor, FK228, Induces apoptosis and suppresses cell roliferation of human glioblastoma cells In vitro and In vivo ," Acta Neuropathol (Berlin), 07(6):523-531 (2004).
Sawa et al., "Anti-tumor effects of Hitone deacetylase inhibitors against human glioma cells," Proc of Japanese Cancer Assoc 60:597 (2001) (w/English translation).
Schrump et al., "Clinical and molecular responses in lung cancer patients receiving romidepsin," Clin Cancer Res, 14(1):188-198 (2008).
Schwartsmann et al., "Marine organisms as a source of new anticancer agents," The Lancet Oncology 2(4):221-225 (2001).
Shigematsu et al., "FR901228: A novel antitumor bicyclic depsipeptide produced by chromobaterium violaceum," The Journal of Antibiotics, 47(3):311-314 (1994).
Sreedharan et al., "Relevance of circadian closing time for the tolerability of germcitabine as a single agent of combined with cisplatin in mice," Proc Amer Assoc Cancer Res 44(2 ed.):742 (2003) (XP-001154773).
Stadler et al., "A phase II study of depsipeptide in refractory metastatic renal cell cancer" Clin Genitourin Cancer, 5(1):57-60 (2006).
Su et al., "A phase II study of single agent depsipeptide (DEP) in patients (pts) with radioactive iodine (RAI)-refractory, metastatic,thyroid carcinoma: Preliminary toxicity and efficacy experience," J Clin Oncol (Meeting Abstracts), 24(18 Suppl):5554 (2006).
Sutheesophon et al., "Histone deacetylase inhibitor depsipeptide (FK228) induces apoptosis in leukemic cells by facilitating mitochondrial translocation of Bax, which is enhanced by the proteasome Inhibitor bonezpmib," Acta Haematol, 115(1-2):78-90 (2006).
Ueda et al., "Action of FR901228, a novel antitumor bicyclic depsipeptide produced by Chromobacterium violaceum No. 968, on Ha-ras transformed NIH3T3 cells ," Biosci Biotechnol Biochem, 58(9):1579-1583 (1994).
Ueda et al., "FR901228, a novel antitumor bicyclic depsipeptide produced by Chromobacterium violaceum No. 968. I. Taxonomy, fermentation, isolation, physico-chemical and biological properties, and antitumor activity," J Antibiot (Tokyo),47:301-310, (1994).
Ueda et al., "FR901228, A Novel Antitumor Bicyclic Depsipeptide Produced by Chromobacterium violaceum No. 968," J Antibiot (Tokyo) 47:315-323 (1994).
Ueda et al., "Expression of a full-length cDNA for the human "MDR1" gene confers resistance to colchicines, doxorubicin, and vinblastine," PNAS USA 84:3004 (1987).
United States Pharmacopeia, 31$^{st}$ ed. Rockville, MD: United States Pharmacopeial Convention, 372-374 (2008).
Vrana et al., "Induction of apoptosis in U937 human leukemia cells by suberoylanilide hydroxamic acid (SAHA) proceeds through pathways that are regulated by Bcl-2/Bcl-XL, c-Jun, and p21CIPI, but independent of p53," Oncogene, 18(50):7016-7025 (1999).
Wang et al., "Fungal metabolite FR901228 inhibits c-Myc Fas ligand expression," Oncogene 17:1503-1508 (1998).
Watanabe et al., "Induction of autophagy in malignant rhabdoid tumor cells by the histone deacetylase inhibitor FK228 through AIF translocation ," Int J Cancer,124(1):55-67 (2009).
Weidle et al. "Inhibition of Histone Deacetylases: a New Strategy to Target Epigentic Modifications for Anticancer Treatment," Anticancer Res 20:1471-1486 (2000).
Whitehead et al., "Phase II trial of depsipeptide (NSC-630176) in colorectal cancer patients who have received either one or two prior chemotherapy regimens for nwrARrux or locally advanced, unresectable disease: A Southwest Oncology Group study," J Clin Oncol (Meeting Abstracts), 24(18 Suppl):3598 (2006).

(56) References Cited

OTHER PUBLICATIONS

Whittaker et al., "international multicenter phaSe II study of the HDAC inhibitor (HDAC) depsipeptide (FK228) in cutaneous T-cell lymphoma (CTCL): Interim report," J Clin Oncol (Meeting Abstracts), 24(18 Suppl):3063 (2006).

Xiao et al., "Identification of thiols and glutathione conjugates of depsipeptide FK228 (FR901228), a novel hostone protein deacetylase inhibitor, in the blood," Rapid Commun Mass Spectrom 17:757-766 (2003).

Xiao et al., "Efflux of Depsipeptide FK228(FR901228, NSC-630176) Is Mediated by P-Glycoprotein and Multidrug Resistance-Associate Protein 1," J Pharm & Exp Therapeutics 313(1):268-276 (2005).

Yu et al., "The proteasome inhibitor bortezpmib interacts synergistically with histone deacetylase inhibitors to induce apoptosis in Bcr/Abl+ cells sensitive and resistant to STI571," Blood, 102(10):3765-3774 (2003).

Notice of Allowance dated Jan. 9, 2014 for U.S. Appl. No. 11/966,258.

Notice of Allowance dated Nov. 19, 2013 for U.S. Appl. No. 11/966,258.

Non-final Office Action dated Aug. 24, 2009 for U.S. Appl. No. 11/966,258.

Non-final Office Action dated Jun. 11, 2010 for U.S. Appl. No. 11/966,258.

Final Office Action dated Nov. 23, 2010 for U.S. Appl. No. 11/966,258.

Notice of Allowance dated Jan. 31, 2014 for U.S. Appl. No. 12/420,451.

Non-final Office Action dated Dec. 8, 2010 for U.S. Appl. No. 12/420,451.

Final Office Action dated Jul. 20, 2011 for U.S. Appl. No. 12/420,451.

Non-final Office Action dated Apr. 2, 2012 for U.S. Appl. No. 12/521,392.

Final Office Action dated Oct. 25, 2012 for U.S. Appl. No. 12/521,392.

Non-final Office Action dated Dec. 18, 2013 for U.S. Appl. No. 13/181,460.

(Part i)

| °2θ | d space(Å) | Intensity (%) |
|---|---|---|
| 7.07 ± 0.10 | 12.495 ± 0.179 | 10 |
| 8.28 ± 0.10 | 10.682 ± 0.130 | 97 |
| 10.07 ± 0.10 | 8.788 ± 0.088 | 21 |
| 10.73 ± 0.10 | 8.242 ± 0.077 | 6 |
| 11.45 ± 0.10 | 7.726 ± 0.068 | 100 |
| 12.19 ± 0.10 | 7.262 ± 0.060 | 38 |
| 12.92 ± 0.10 | 6.850 ± 0.053 | 19 |
| 14.14 ± 0.10 | 6.262 ± 0.044 | 27 |
| 15.18 ± 0.10 | 5.837 ± 0.038 | 10 |
| 15.73 ± 0.10 | 5.634 ± 0.036 | 5 |
| 15.91 ± 0.10 | 5.569 ± 0.035 | 11 |
| 16.60 ± 0.10 | 5.341 ± 0.032 | 34 |
| 16.93 ± 0.10 | 5.236 ± 0.031 | 16 |
| 17.30 ± 0.10 | 5.125 ± 0.030 | 7 |
| 17.74 ± 0.10 | 5.001 ± 0.028 | 5 |
| 19.16 ± 0.10 | 4.633 ± 0.024 | 25 |
| 19.66 ± 0.10 | 4.516 ± 0.023 | 9 |
| 19.91 ± 0.10 | 4.460 ± 0.022 | 22 |
| 20.21 ± 0.10 | 4.394 ± 0.022 | 13 |
| 20.71 ± 0.10 | 4.289 ± 0.021 | 5 |
| 21.13 ± 0.10 | 4.205 ± 0.020 | 47 |
| 21.60 ± 0.10 | 4.115 ± 0.019 | 15 |
| 22.33 ± 0.10 | 3.981 ± 0.018 | 5 |
| 22.55 ± 0.10 | 3.943 ± 0.017 | 8 |
| 23.03 ± 0.10 | 3.861 ± 0.017 | 22 |
| 23.52 ± 0.10 | 3.783 ± 0.016 | 24 |
| 23.79 ± 0.10 | 3.741 ± 0.016 | 18 |
| 24.04 ± 0.10 | 3.702 ± 0.015 | 8 |
| 24.22 ± 0.10 | 3.675 ± 0.015 | 10 |
| 24.49 ± 0.10 | 3.635 ± 0.015 | 14 |
| 25.16 ± 0.10 | 3.540 ± 0.014 | 7 |
| 25.47 ± 0.10 | 3.497 ± 0.014 | 10 |
| 26.04 ± 0.10 | 3.422 ± 0.013 | 8 |
| 26.24 ± 0.10 | 3.396 ± 0.013 | 7 |
| 26.51 ± 0.10 | 3.362 ± 0.013 | 9 |
| 26.96 ± 0.10 | 3.307 ± 0.012 | 8 |
| 27.75 ± 0.10 | 3.215 ± 0.011 | 4 |
| 28.11 ± 0.10 | 3.174 ± 0.011 | 5 |
| 28.48 ± 0.10 | 3.134 ± 0.011 | 4 |
| 28.93 ± 0.10 | 3.086 ± 0.010 | 7 |
| 29.48 ± 0.10 | 3.030 ± 0.010 | 6 |
| 8.28 ± 0.10 | 10.682 ± 0.130 | 97 |
| 10.07 ± 0.10 | 8.788 ± 0.088 | 21 |
| 11.45 ± 0.10 | 7.726 ± 0.068 | 100 |

FIG. 1D (Part ii)

| °2θ | d space(Å) | Intensity (%) |
|---|---|---|
| 12.19 ± 0.10 | 7.262 ± 0.060 | 38 |
| 12.92 ± 0.10 | 6.850 ± 0.053 | 19 |
| 14.14 ± 0.10 | 6.262 ± 0.044 | 27 |
| 16.60 ± 0.10 | 5.341 ± 0.032 | 34 |
| 19.16 ± 0.10 | 4.633 ± 0.024 | 25 |
| 19.91 ± 0.10 | 4.460 ± 0.022 | 22 |
| 21.13 ± 0.10 | 4.205 ± 0.010 | 47 |

FIG. 1D Cont.

| | |
|---|---|
| 749 | 1218 |
| 780 | 1253 |
| 809 | 1285 |
| 832 | 1300 |
| 844 | 1323 |
| 892 | 1370 |
| 910 | 1392 |
| 919 | 1412 |
| 928 | 1443 |
| 943 | 1465 |
| 961 | 1482 |
| 982 | 1523 |
| 1000 | 1630 |
| 1014 | 1655 |
| 1036 | 1701 |
| 1064 | 1753 |
| 1084 | 2875 |
| 1099 | 2898 |
| 1113 | 2930 |
| 1141 | 2966 |
| 1156 | 2986 |
| 1186 | 3351 |
| 1205 | |

| °2θ | d space(Å) | Intensity (%) | (Part i) |
|---|---|---|---|
| 7.12 ± 0.10 | 12.416 ± 0.177 | 6 | |
| 8.36 ± 0.10 | 10.577 ± 0.128 | 34 | |
| 10.16 ± 0.10 | 8.707 ± 0.086 | 20 | |
| 10.86 ± 0.10 | 8.147 ± 0.075 | 5 | |
| 11.56 ± 0.10 | 7.655 ± 0.067 | 100 | |
| 12.30 ± 0.10 | 7.196 ± 0.059 | 48 | |
| 13.06 ± 0.10 | 6.779 ± 0.052 | 24 | |
| 13.82 ± 0.10 | 6.408 ± 0.046 | 1 | |
| 14.28 ± 0.10 | 6.203 ± 0.044 | 26 | |
| 15.30 ± 0.10 | 5.791 ± 0.038 | 7 | |
| 15.86 ± 0.10 | 5.588 ± 0.035 | 4 | |
| 16.10 ± 0.10 | 5.505 ± 0.034 | 8 | |
| 16.78 ± 0.10 | 5.284 ± 0.031 | 18 | |
| 17.10 ± 0.10 | 5.185 ± 0.030 | 19 | |
| 17.46 ± 0.10 | 5.079 ± 0.029 | 6 | |
| 17.76 ± 0.10 | 4.994 ± 0.028 | 3 | |
| 17.84 ± 0.10 | 4.972 ± 0.028 | 3 | |
| 19.28 ± 0.10 | 4.604 ± 0.024 | 28 | |
| 19.58 ± 0.10 | 4.534 ± 0.023 | 2 | |
| 19.84 ± 0.10 | 4.475 ± 0.022 | 11 | |
| 20.08 ± 0.10 | 4.422 ± 0.022 | 17 | |
| 20.42 ± 0.10 | 4.349 ± 0.021 | 20 | |
| 20.94 ± 0.10 | 4.242 ± 0.020 | 5 | |
| 21.36 ± 0.10 | 4.160 ± 0.019 | 72 | |
| 21.78 ± 0.10 | 4.081 ± 0.019 | 14 | |
| 22.58 ± 0.10 | 3.938 ± 0.017 | 5 | |
| 22.78 ± 0.10 | 3.904 ± 0.017 | 10 | |
| 23.20 ± 0.10 | 3.834 ± 0.016 | 24 | |
| 23.78 ± 0.10 | 3.742 ± 0.016 | 27 | |
| 24.04 ± 0.10 | 3.702 ± 0.015 | 23 | |
| 24.22 ± 0.10 | 3.675 ± 0.015 | 10 | |
| 24.50 ± 0.10 | 3.633 ± 0.015 | 16 | |
| 24.76 ± 0.10 | 3.596 ± 0.014 | 22 | |
| 25.32 ± 0.10 | 3.518 ± 0.014 | 5 | |
| 25.68 ± 0.10 | 3.469 ± 0.013 | 12 | |
| 25.94 ± 0.10 | 3.435 ± 0.013 | 2 | |
| 26.28 ± 0.10 | 3.391 ± 0.013 | 12 | |
| 26.50 ± 0.10 | 3.364 ± 0.013 | 9 | |
| 26.72 ± 0.10 | 3.336 ± 0.012 | 12 | |
| 26.98 ± 0.10 | 3.305 ± 0.012 | 10 | |
| 27.26 ± 0.10 | 3.272 ± 0.012 | 12 | |
| 27.88 ± 0.10 | 3.200 ± 0.011 | 2 | |
| 28.00 ± 0.10 | 3.187 ± 0.011 | 3 | |
| 28.36 ± 0.10 | 3.147 ± 0.011 | 4 | |
| 28.80 ± 0.10 | 3.100 ± 0.011 | 3 | |

FIG. 1J (Part i)

| °2θ | d space(Å) | Intensity (%) |
|---|---|---|
| 29.22 ± 0.10 | 3.056 ± 0.010 | 8 |
| 29.60 ± 0.10 | 3.018 ± 0.010 | 1 |
| 29.84 ± 0.10 | 2.984 ± 0.010 | 6 |

(Part ii)

| °2θ | d space(Å) | Intensity (%) |
|---|---|---|
| 8.36 ± 0.10 | 10.577 ± 0.128 | 34 |
| 11.56 ± 0.10 | 7.655 ± 0.067 | 100 |
| 12.30 ± 0.10 | 7.196 ± 0.059 | 48 |
| 21.36 ± 0.10 | 4.160 ± 0.019 | 72 |

FIG. 1J Cont.

| Atom | x | y | z | U(Å²) |
|---|---|---|---|---|
| S18 | 0.67836(7) | 0.90012(4) | 0.75844(3) | 0.03773(15) |
| S19 | 0.58298(7) | 0.99670(4) | 0.81161(3) | 0.03527(15) |
| O2 | 0.45025(19) | 0.90786(12) | 0.56514(8) | 0.0447(5) |
| O5 | 0.10720(19) | 0.90977(9) | 0.44340(7) | 0.0356(4) |
| O8 | 0.0523(2) | 1.20454(10) | 0.55640(8) | 0.0401(5) |
| O9 | 0.22230(17) | 1.10715(9) | 0.59075(7) | 0.0298(4) |
| O12 | 0.03241(18) | 1.01863(11) | 0.67471(8) | 0.0381(5) |
| O15 | 0.1558(2) | 0.81383(10) | 0.73090(8) | 0.0388(5) |
| O1W | 0.2735(3) | 1.18048(14) | 0.84697(10) | 0.0589(7) |
| O2W | -0.0803(3) | 0.8244(2) | 0.65022(15) | 0.0475(9) |
| N3 | 0.2417(2) | 0.83401(12) | 0.59596(9) | 0.0310(5) |
| N6 | 0.0925(2) | 0.97569(11) | 0.53800(9) | 0.0283(5) |
| N13 | 0.1432(2) | 1.03960(12) | 0.76957(9) | 0.0297(5) |
| N16 | 0.3310(2) | 0.91899(11) | 0.71739(8) | 0.0270(4) |
| C1 | 0.4308(3) | 0.86928(13) | 0.67611(10) | 0.0289(5) |
| C2 | 0.3772(2) | 0.87319(14) | 0.60657(11) | 0.0298(6) |
| C4 | 0.1783(3) | 0.82617(13) | 0.53413(10) | 0.0303(6) |
| C5 | 0.1245(2) | 0.90715(13) | 0.50149(10) | 0.0287(6) |
| C7 | 0.0534(2) | 1.06019(13) | 0.51081(10) | 0.0264(5) |
| C8 | 0.1052(2) | 1.13273(13) | 0.55470(10) | 0.0282(5) |
| C10 | 0.2651(3) | 1.16496(14) | 0.64281(11) | 0.0329(6) |
| C11 | 0.1438(3) | 1.15980(14) | 0.69451(11) | 0.0356(6) |
| C12 | 0.1000(3) | 1.06734(15) | 0.71176(10) | 0.0324(6) |
| C14 | 0.1198(2) | 0.94883(15) | 0.78802(10) | 0.0303(6) |
| C15 | 0.2036(2) | 0.88795(13) | 0.74272(10) | 0.0291(5) |
| C17 | 0.5903(3) | 0.90529(15) | 0.68062(10) | 0.0349(6) |
| C20 | 0.6891(3) | 1.09462(15) | 0.79202(12) | 0.0404(7) |
| C21 | 0.6570(3) | 1.13128(16) | 0.72623(12) | 0.0407(7) |
| C22 | 0.4931(3) | 1.15042(15) | 0.71471(12) | 0.0368(6) |
| C23 | 0.4229(3) | 1.13726(14) | 0.66017(11) | 0.0342(6) |
| C41 | 0.1607(3) | 0.74925(15) | 0.50606(12) | 0.0362(6) |
| C42 | 0.2124(4) | 0.66309(15) | 0.53114(14) | 0.0525(8) |
| C71 | -0.2200(3) | 1.06404(18) | 0.55016(13) | 0.0427(7) |
| C72 | -0.1156(2) | 1.06593(14) | 0.49291(10) | 0.0309(6) |
| C73 | -0.1488(3) | 1.14487(15) | 0.45067(12) | 0.0387(7) |
| C141 | 0.1791(5) | 0.84163(18) | 0.87630(13) | 0.0655(11) |
| C142 | 0.1671(3) | 0.93720(16) | 0.85761(10) | 0.0354(6) |
| C143 | 0.0555(3) | 0.9866(2) | 0.90033(13) | 0.0591(8) |
| H3 | 0.194(3) | 0.8088(16) | 0.6269(12) | 0.030(6)* |
| H16 | 0.104(3) | 0.9722(15) | 0.5767(12) | 0.028(7)* |
| H13 | 0.188(3) | 1.0722(16) | 0.7950(11) | 0.027(6)* |
| H16 | 0.356(3) | 0.9745(17) | 0.7275(12) | 0.038(7)* |
| H1W1 | 0.201(5) | 1.208(3) | 0.8597(18) | 0.081(14)* |
| H1W2 | 0.306(5) | 1.154(2) | 0.8867(18) | 0.087(12)* |
| H2W1 | -0.023(6) | 0.815(3) | 0.680(3) | 0.064(16)* |
| H2W2 | -0.075(9) | 0.879(6) | 0.642(3) | 0.15(3)* |

FIG. 10

| Atom | x | y | z | U(Å²) |
|------|-------|-------|-------|-------|
| H1   | 0.431 | 0.807 | 0.690 | 0.035 |
| H7   | 0.113 | 1.066 | 0.471 | 0.032 |
| H10  | 0.269 | 1.226 | 0.627 | 0.039 |
| H14  | 0.009 | 0.936 | 0.785 | 0.036 |
| H22  | 0.435 | 1.173 | 0.749 | 0.044 |
| H23  | 0.478 | 1.107 | 0.629 | 0.041 |
| H41  | 0.111 | 0.749 | 0.466 | 0.043 |
| H72  | -0.139| 1.013 | 0.467 | 0.037 |
| H11A | 0.182 | 1.190 | 0.733 | 0.043 |
| H11B | 0.052 | 1.191 | 0.680 | 0.043 |
| H142 | 0.269 | 0.964 | 0.863 | 0.042 |
| H14A | 0.204 | 0.837 | 0.921 | 0.098 |
| H14B | 0.259 | 0.813 | 0.851 | 0.098 |
| H14C | 0.082 | 0.813 | 0.868 | 0.098 |
| H14D | -0.047| 0.964 | 0.894 | 0.089 |
| H14E | 0.058 | 1.049 | 0.890 | 0.089 |
| H14F | 0.085 | 0.979 | 0.945 | 0.089 |
| H17A | 0.588 | 0.967 | 0.667 | 0.042 |
| H17B | 0.655 | 0.873 | 0.650 | 0.042 |
| H20A | 0.666 | 1.140 | 0.824 | 0.049 |
| H20B | 0.799 | 1.081 | 0.795 | 0.049 |
| H21A | 0.716 | 1.186 | 0.721 | 0.049 |
| H21B | 0.692 | 1.089 | 0.694 | 0.049 |
| H42A | 0.280 | 0.672 | 0.567 | 0.079 |
| H42B | 0.266 | 0.631 | 0.498 | 0.079 |
| H42C | 0.124 | 0.629 | 0.545 | 0.079 |
| H71A | -0.209| 1.118 | 0.574 | 0.064 |
| H71B | -0.193| 1.015 | 0.577 | 0.064 |
| H71C | -0.325| 1.058 | 0.536 | 0.064 |
| H73A | -0.133| 1.199 | 0.475 | 0.058 |
| H73B | -0.254| 1.142 | 0.436 | 0.058 |
| H73C | -0.080| 1.144 | 0.414 | 0.058 |

Starred atoms were refined isotropically
$U_{eq} = (1/3)\Sigma_i\Sigma_j U_{ij}a^*_i a^*_j a_i.a_j$
Hydrogen atoms are included in calculation of structure factors but not refined.

FIG. 10 Cont.

| Atom 1 | Atom 2 | Distance | Atom 1 | Atom 2 | Distance |
|---|---|---|---|---|---|
| S18 | C17 | 1.821(2) | C11 | H11B | 0.990 |
| S18 | S19 | 2.0413(8) | C14 | C15 | 1.528(3) |
| S19 | C20 | 1.818(3) | C14 | C142 | 1.540(3) |
| O2 | C2 | 1.211(3) | C14 | H14 | 1.000 |
| O5 | C5 | 1.238(3) | C17 | H17A | 0.990 |
| O8 | C8 | 1.197(3) | C17 | H17B | 0.990 |
| O9 | C8 | 1.343(3) | C20 | C21 | 1.527(3) |
| O9 | C10 | 1.463(3) | C20 | H20A | 0.990 |
| O12 | C12 | 1.236(3) | C20 | H20B | 0.990 |
| O15 | C15 | 1.238(3) | C21 | C22 | 1.497(3) |
| O1W | H1W1 | 0.81(4) | C21 | H21A | 0.990 |
| O1W | H1W2 | 0.97(4) | C21 | H21B | 0.990 |
| O2W | H2W1 | 0.82(6) | C22 | C23 | 1.324(3) |
| O2W | H2W2 | 0.85(9) | C22 | H22 | 0.950 |
| N3 | C2 | 1.357(3) | C23 | H23 | 0.950 |
| N3 | C4 | 1.427(3) | C41 | C42 | 1.495(3) |
| N3 | H3 | 0.87(3) | C41 | H41 | 0.950 |
| N6 | C5 | 1.334(3) | C42 | H42A | 0.980 |
| N6 | C7 | 1.459(3) | C42 | H42B | 0.980 |
| N6 | H6 | 0.83(3) | C42 | H42C | 0.980 |
| N13 | C12 | 1.349(3) | C71 | C72 | 1.521(3) |
| N13 | C14 | 1.461(3) | C71 | H71A | 0.980 |
| N13 | H13 | 0.84(3) | C71 | H71B | 0.980 |
| N16 | C15 | 1.334(3) | C71 | H71C | 0.980 |
| N16 | C1 | 1.456(3) | C72 | C73 | 1.533(3) |
| N16 | H16 | 0.90(3) | C72 | H72 | 1.000 |
| C1 | C17 | 1.515(3) | C73 | H73A | 0.980 |
| C1 | C2 | 1.546(3) | C73 | H73B | 0.980 |
| C1 | H1 | 1.000 | C73 | H73C | 0.980 |
| C4 | C41 | 1.330(3) | C141 | C142 | 1.522(4) |
| C4 | C5 | 1.498(3) | C141 | H14A | 0.980 |
| C7 | C8 | 1.519(3) | C141 | H14B | 0.980 |
| C7 | C72 | 1.542(3) | C141 | H14C | 0.980 |
| C7 | H7 | 1.000 | C142 | C143 | 1.536(4) |
| C10 | C23 | 1.502(3) | C142 | H142 | 1.000 |
| C10 | C11 | 1.532(3) | C143 | H14D | 0.980 |
| C10 | H10 | 1.000 | C143 | H14E | 0.980 |
| C11 | C12 | 1.515(3) | C143 | H14F | 0.980 |
| C11 | H11A | 0.990 | | | |

Numbers in parentheses are estimated standard deviations in the least significant digits.

FIG. 1P

| Atom 1 | Atom 2 | Atom 3 | Angle | Atom 1 | Atom 2 | Atom 3 | Angle |
|---|---|---|---|---|---|---|---|
| C17 | S18 | S19 | 106.84(8) | C12 | C11 | H11A | 108.90 |
| C20 | S19 | S18 | 105.16(9) | C10 | C11 | H11A | 108.90 |
| C8 | O9 | C10 | 116.65(16) | C12 | C11 | H11B | 108.90 |
| H1W1 | O1W | H1W2 | 99(3) | C10 | C11 | H11B | 108.90 |
| H2W1 | O2W | H2W2 | 108(6) | H11A | C11 | H11B | 107.70 |
| C2 | N3 | C4 | 122.3(2) | O12 | C12 | N13 | 121.3(2) |
| C2 | N3 | H3 | 119.8(17) | O12 | C12 | C11 | 122.5(2) |
| C4 | N3 | H3 | 117.7(17) | N13 | C12 | C11 | 116.2(2) |
| C5 | N6 | C7 | 121.48(19) | N13 | C14 | C15 | 110.30(17) |
| C5 | N6 | H6 | 119.8(16) | N13 | C14 | C142 | 109.10(18) |
| C7 | N6 | H6 | 118.4(16) | C15 | C14 | C142 | 113.4(2) |
| C12 | N13 | C14 | 120.2(2) | N13 | C14 | H14 | 122.3(2) |
| C12 | N13 | H13 | 122.0(17) | C15 | C14 | H14 | 108.00 |
| C14 | N13 | H13 | 117.8(16) | C142 | C14 | H14 | 108.00 |
| C15 | N16 | C1 | 124.34(18) | O15 | C15 | N16 | 108.00 |
| C15 | N16 | H16 | 116.3(16) | O15 | C15 | C14 | 121.52(19) |
| C1 | N16 | H16 | 119.3(16) | N16 | C15 | C14 | 116.20(18) |
| N16 | C1 | C17 | 109.50(17) | C1 | C17 | S18 | 115.95(16) |
| N16 | C1 | C2 | 111.37(17) | C1 | C17 | H17A | 114.59(16) |
| C17 | C1 | C2 | 109.28(18) | S18 | C17 | H17A | 108.30 |
| N16 | C1 | H1 | 108.90 | C1 | C17 | H17B | 108.30 |
| C17 | C1 | H1 | 108.90 | S18 | C17 | H17B | 108.30 |
| C2 | C1 | H1 | 108.90 | H17A | C17 | H17B | 108.30 |
| O2 | C2 | N3 | 123.0(2) | C21 | C20 | S19 | 107.40 |
| O2 | C2 | C1 | 122.8(2) | C21 | C20 | H20A | 113.6(2) |
| N3 | C2 | C1 | 114.2(2) | S19 | C20 | H20A | 108.60 |
| C41 | C4 | N3 | 121.9(2) | C21 | C20 | H20B | 108.60 |
| C41 | C4 | C5 | 119.6(2) | S19 | C20 | H20B | 108.60 |
| N3 | C4 | C5 | 118.44(18) | H20A | C20 | H20B | 108.60 |
| O5 | C5 | N6 | 121.5(2) | C22 | C21 | C20 | 107.60 |
| O5 | C5 | C4 | 121.52(19) | C22 | C21 | H21A | 108.90 |
| N6 | C5 | C4 | 117.00(19) | C20 | C21 | H21A | 108.90 |
| N6 | C7 | C8 | 109.80(17) | C22 | C21 | H21B | 108.90 |
| N6 | C7 | C72 | 112.12(17) | C20 | C21 | H21B | 108.90 |
| C8 | C7 | C72 | 113.55(18) | H21A | C21 | H21B | 107.70 |

FIG. 1Q

| Atom 1 | Atom 2 | Atom 3 | Angle | Atom 1 | Atom 2 | Atom 3 | Angle |
|---|---|---|---|---|---|---|---|
| N6 | C7 | H7 | 107.00 | C23 | C22 | C21 | 124.3(3) |
| C8 | C7 | H7 | 107.00 | C23 | C22 | H22 | 117.80 |
| C72 | C7 | H7 | 107.00 | C21 | C22 | H22 | 117.80 |
| O8 | C8 | O9 | 123.5(2) | C22 | C23 | C10 | 127.1(2) |
| O8 | C8 | C7 | 125.1(2) | C22 | C23 | H23 | 116.40 |
| O9 | C8 | C7 | 111.37(17) | C10 | C23 | H23 | 116.40 |
| O9 | C10 | C23 | 104.58(18) | C4 | C41 | C42 | 126.2(2) |
| O9 | C10 | C11 | 108.95(18) | C4 | C41 | H41 | 116.90 |
| C23 | C10 | C11 | 117.5(19) | C42 | C41 | H41 | 116.90 |
| O9 | C10 | H10 | 108.50 | C41 | C42 | H42A | 109.50 |
| C23 | C10 | H10 | 108.50 | C42 | C42 | H42B | 109.50 |
| C11 | C10 | H10 | 108.50 | H42A | C42 | H42B | 109.50 |
| C12 | C11 | C10 | 113.49(18) | C41 | C42 | H42C | 109.50 |
| H42A | C42 | H42C | 109.50 | H73B | C73 | H73C | 109.50 |
| H42B | C42 | H42C | 109.50 | C142 | C141 | H14A | 109.50 |
| C72 | C71 | H71A | 109.50 | C142 | C141 | H14B | 109.50 |
| C72 | C71 | H71B | 109.50 | H14A | C141 | H14B | 109.50 |
| H71A | C71 | H71B | 109.50 | C142 | C141 | H14C | 109.50 |
| C72 | C71 | H71C | 109.50 | H14A | C141 | H14C | 109.50 |
| H71A | C71 | H71C | 109.50 | H14B | C141 | H14C | 109.50 |
| H71B | C71 | H71C | 109.50 | C141 | C142 | C143 | 111.5(2) |
| C71 | C72 | C73 | 111.27(19) | C141 | C142 | C14 | 112.2(2) |
| C71 | C72 | C7 | 112.93(19) | C143 | C142 | C14 | 109.3(2) |
| C73 | C72 | C7 | 111.90(18) | C141 | C142 | H142 | 107.90 |
| C71 | C72 | H72 | 106.80 | C143 | C142 | H142 | 107.90 |
| C73 | C72 | H72 | 106.80 | C14 | C142 | H142 | 107.90 |
| C7 | C72 | H72 | 106.80 | C142 | C143 | H14D | 109.50 |
| C72 | C73 | H73A | 109.50 | C142 | C143 | H14E | 109.50 |
| C72 | C73 | H73B | 109.50 | H14D | C143 | H14E | 109.50 |
| H73A | C73 | H73B | 109.50 | C142 | C143 | H14F | 109.50 |
| C72 | C73 | H73C | 109.50 | H14D | C143 | H14F | 109.50 |
| H73A | C73 | H73C | 109.50 | H14E | C143 | H14F | 109.50 |

Numbers in parentheses are estimated standard deviations in the least significant digits.

FIG. 1Q Cont.

(Part i)

| °2θ | d space(Å) | Intensity (%) |
|---|---|---|
| 7.54 ± 0.10 | 11.725 ± 0.157 | 100 |
| 10.39 ± 0.10 | 8.514 ± 0.083 | 17 |
| 11.86 ± 0.10 | 7.462 ± 0.063 | 34 |
| 12.28 ± 0.10 | 7.208 ± 0.059 | 10 |
| 13.51 ± 0.10 | 6.554 ± 0.049 | 10 |
| 15.34 ± 0.10 | 5.776 ± 0.038 | 15 |
| 16.00 ± 0.10 | 5.539 ± 0.035 | 5 |
| 16.66 ± 0.10 | 5.321 ± 0.032 | 30 |
| 18.73 ± 0.10 | 4.738 ± 0.025 | 8 |
| 19.63 ± 0.10 | 4.522 ± 0.023 | 11 |
| 20.50 ± 0.10 | 4.332 ± 0.021 | 20 |
| 20.95 ± 0.10 | 4.240 ± 0.020 | 24 |
| 21.52 ± 0.10 | 4.129 ± 0.019 | 13 |
| 21.94 ± 0.10 | 4.051 ± 0.018 | 6 |
| 22.75 ± 0.10 | 3.909 ± 0.017 | 17 |
| 23.71 ± 0.10 | 3.753 ± 0.016 | 7 |
| 24.67 ± 0.10 | 3.609 ± 0.014 | 6 |
| 25.39 ± 0.10 | 3.508 ± 0.014 | 10 |
| 25.87 ± 0.10 | 3.444 ± 0.013 | 3 |
| 27.16 ± 0.10 | 3.283 ± 0.012 | 13 |
| 29.44 ± 0.10 | 3.034 ± 0.010 | 3 |

(Part ii)

| °2θ | d space(Å) | Intensity (%) |
|---|---|---|
| 7.54 ± 0.10 | 11.725 ± 0.157 | 100 |
| 10.39 ± 0.10 | 8.514 ± 0.083 | 17 |
| 11.86 ± 0.10 | 7.462 ± 0.063 | 34 |
| 15.34 ± 0.10 | 5.776 ± 0.038 | 15 |
| 16.66 ± 0.10 | 5.321 ± 0.032 | 30 |
| 20.50 ± 0.10 | 4.332 ± 0.021 | 20 |
| 20.95 ± 0.10 | 4.240 ± 0.020 | 24 |

FIG. 2B

| | |
|---|---|
| 706 | 1196 |
| 731 | 1222 |
| 751 | 1242 |
| 767 | 1256 |
| 782 | 1284 |
| 802 | 1299 |
| 811 | 1328 |
| 845 | 1365 |
| 873 | 1419 |
| 893 | 1439 |
| 913 | 1471 |
| 922 | 1522 |
| 939 | 1655 |
| 961 | 1675 |
| 982 | 1698 |
| 998 | 1707 |
| 1016 | 1747 |
| 1034 | 2877 |
| 1048 | 2917 |
| 1066 | 2931 |
| 1095 | 2965 |
| 1110 | 3308 |
| 1130 | 3356 |
| 1183 | |

(Part i)

| °2θ | d space(Å) | Intensity (%) |
|---|---|---|
| 6.72 ± 0.10 | 13.147 ± 0.198 | 26 |
| 9.00 ± 0.10 | 9.830 ± 0.110 | 98 |
| 10.02 ± 0.10 | 8.832 ± 0.089 | 14 |
| 10.30 ± 0.10 | 8.589 ± 0.084 | 100 |
| 10.58 ± 0.10 | 8.359 ± 0.080 | 72 |
| 10.80 ± 0.10 | 8.191 ± 0.076 | 26 |
| 10.98 ± 0.10 | 8.054 ± 0.074 | 68 |
| 11.70 ± 0.10 | 7.562 ± 0.065 | 92 |
| 13.16 ± 0.10 | 6.729 ± 0.051 | 20 |
| 14.59 ± 0.10 | 6.070 ± 0.042 | 16 |
| 15.71 ± 0.10 | 5.639 ± 0.036 | 12 |
| 16.60 ± 0.10 | 5.341 ± 0.032 | 5 |
| 16.87 ± 0.10 | 5.256 ± 0.031 | 5 |
| 17.34 ± 0.10 | 5.116 ± 0.029 | 16 |
| 17.57 ± 0.10 | 5.048 ± 0.029 | 47 |
| 17.89 ± 0.10 | 4.959 ± 0.028 | 7 |
| 18.44 ± 0.10 | 4.812 ± 0.026 | 28 |
| 19.22 ± 0.10 | 4.617 ± 0.024 | 46 |
| 19.42 ± 0.10 | 4.570 ± 0.023 | 71 |
| 19.88 ± 0.10 | 4.467 ± 0.022 | 31 |
| 20.04 ± 0.10 | 4.430 ± 0.022 | 89 |
| 20.29 ± 0.10 | 4.376 ± 0.021 | 24 |
| 20.63 ± 0.10 | 4.306 ± 0.021 | 14 |
| 21.26 ± 0.10 | 4.179 ± 0.020 | 6 |
| 21.71 ± 0.10 | 4.093 ± 0.019 | 15 |
| 22.18 ± 0.10 | 4.008 ± 0.018 | 24 |
| 22.80 ± 0.10 | 3.900 ± 0.017 | 23 |
| 23.18 ± 0.10 | 3.837 ± 0.016 | 49 |
| 23.55 ± 0.10 | 3.778 ± 0.016 | 23 |
| 24.10 ± 0.10 | 3.692 ± 0.015 | 24 |
| 24.79 ± 0.10 | 3.592 ± 0.014 | 20 |
| 24.92 ± 0.10 | 3.573 ± 0.014 | 34 |
| 25.12 ± 0.10 | 3.545 ± 0.014 | 11 |
| 25.51 ± 0.10 | 3.492 ± 0.014 | 14 |
| 26.18 ± 0.10 | 3.405 ± 0.013 | 21 |
| 26.49 ± 0.10 | 3.364 ± 0.013 | 9 |
| 26.98 ± 0.10 | 3.305 ± 0.012 | 5 |
| 27.70 ± 0.10 | 3.221 ± 0.011 | 5 |
| 28.08 ± 0.10 | 3.178 ± 0.011 | 5 |
| 28.35 ± 0.10 | 3.148 ± 0.011 | 12 |
| 6.72 ± 0.10 | 13.147 ± 0.198 | 26 |
| 9.00 ± 0.10 | 9.830 ± 0.110 | 98 |
| 10.30 ± 0.10 | 8.589 ± 0.084 | 100 |
| 10.58 ± 0.10 | 8.359 ± 0.080 | 72 |

FIG. 3B

(Part ii)

| °2θ | d space(Å) | Intensity (%) |
|---|---|---|
| 10.80 ± 0.10 | 8.191 ± 0.076 | 26 |
| 10.98 ± 0.10 | 8.054 ± 0.074 | 68 |
| 11.70 ± 0.10 | 7.562 ± 0.065 | 92 |
| 17.57 ± 0.10 | 5.048 ± 0.029 | 47 |
| 18.44 ± 0.10 | 4.812 ± 0.026 | 28 |
| 19.22 ± 0.10 | 4.617 ± 0.024 | 46 |
| 19.42 ± 0.10 | 4.570 ± 0.023 | 71 |
| 19.88 ± 0.10 | 4.467 ± 0.022 | 31 |
| 20.04 ± 0.10 | 4.430 ± 0.022 | 89 |

FIG. 3B Cont.

| | |
|---|---|
| 752 | 1306 |
| 764 | 1337 |
| 812 | 1354 |
| 827 | 1369 |
| 838 | 1401 |
| 854 | 1439 |
| 872 | 1474 |
| 890 | 1483 |
| 909 | 1501 |
| 929 | 1531 |
| 947 | 1638 |
| 982 | 1658 |
| 995 | 1683 |
| 1013 | 1728 |
| 1040 | 2871 |
| 1091 | 2928 |
| 1115 | 2967 |
| 1157 | 3015 |
| 1177 | 3050 |
| 1203 | 3318 |
| 1229 | 3380 |
| 1253 | 3405 |

(Part i)

| °2θ | d space(Å) | Intensity (%) |
|---|---|---|
| 6.78 ± 0.10 | 13.038 ± 0.195 | 19 |
| 9.08 ± 0.10 | 9.740 ± 0.108 | 88 |
| 10.08 ± 0.10 | 8.775 ± 0.088 | 7 |
| 10.38 ± 0.10 | 8.523 ± 0.083 | 100 |
| 10.70 ± 0.10 | 8.268 ± 0.078 | 60 |
| 10.94 ± 0.10 | 8.087 ± 0.074 | 26 |
| 11.06 ± 0.10 | 8.000 ± 0.073 | 39 |
| 11.84 ± 0.10 | 7.475 ± 0.063 | 67 |
| 13.30 ± 0.10 | 6.657 ± 0.050 | 16 |
| 13.58 ± 0.10 | 6.521 ± 0.048 | 1 |
| 14.22 ± 0.10 | 6.229 ± 0.044 | 1 |
| 14.72 ± 0.10 | 6.018 ± 0.041 | 11 |
| 15.82 ± 0.10 | 5.602 ± 0.035 | 5 |
| 16.76 ± 0.10 | 5.290 ± 0.032 | 3 |
| 16.98 ± 0.10 | 5.222 ± 0.031 | 3 |
| 17.50 ± 0.10 | 5.068 ± 0.029 | 11 |
| 17.68 ± 0.10 | 5.017 ± 0.028 | 33 |
| 18.02 ± 0.10 | 4.923 ± 0.027 | 5 |
| 18.20 ± 0.10 | 4.874 ± 0.027 | 2 |
| 18.58 ± 0.10 | 4.776 ± 0.026 | 17 |
| 19.46 ± 0.10 | 4.562 ± 0.023 | 48 |
| 19.58 ± 0.10 | 4.534 ± 0.023 | 74 |
| 20.20 ± 0.10 | 4.396 ± 0.022 | 85 |
| 20.42 ± 0.10 | 4.349 ± 0.021 | 25 |
| 20.64 ± 0.10 | 4.303 ± 0.021 | 22 |
| 21.28 ± 0.10 | 4.175 ± 0.019 | 3 |
| 21.52 ± 0.10 | 4.129 ± 0.019 | 4 |
| 21.96 ± 0.10 | 4.048 ± 0.018 | 13 |
| 22.10 ± 0.10 | 4.022 ± 0.018 | 7 |
| 22.22 ± 0.10 | 4.001 ± 0.018 | 5 |
| 22.44 ± 0.10 | 3.962 ± 0.018 | 26 |
| 22.66 ± 0.10 | 3.924 ± 0.017 | 6 |
| 22.96 ± 0.10 | 3.874 ± 0.017 | 20 |
| 23.38 ± 0.10 | 3.805 ± 0.016 | 62 |
| 23.82 ± 0.10 | 3.736 ± 0.016 | 19 |
| 24.30 ± 0.10 | 3.663 ± 0.015 | 14 |
| 24.36 ± 0.10 | 3.654 ± 0.015 | 13 |
| 24.84 ± 0.10 | 3.584 ± 0.014 | 8 |
| 25.00 ± 0.10 | 3.562 ± 0.014 | 24 |
| 25.18 ± 0.10 | 3.537 ± 0.014 | 32 |
| 25.36 ± 0.10 | 3.512 ± 0.014 | 19 |
| 25.72 ± 0.10 | 3.464 ± 0.013 | 17 |
| 25.94 ± 0.10 | 3.435 ± 0.013 | 3 |
| 26.38 ± 0.10 | 3.379 ± 0.013 | 22 |
| 26.78 ± 0.10 | 3.329 ± 0.012 | 7 |

FIG. 3I

(Part i)

| °2θ | d space(Å) | Intensity (%) |
|---|---|---|
| 27.26 ± 0.10 | 3.272 ± 0.012 | 4 |
| 27.46 ± 0.10 | 3.248 ± 0.012 | 1 |
| 27.60 ± 0.10 | 3.232 ± 0.012 | 1 |
| 27.94 ± 0.10 | 3.193 ± 0.011 | 6 |
| 28.22 ± 0.10 | 3.162 ± 0.011 | 1 |
| 28.36 ± 0.10 | 3.147 ± 0.011 | 3 |
| 28.60 ± 0.10 | 3.121 ± 0.011 | 14 |
| 28.74 ± 0.10 | 3.106 ± 0.011 | 8 |
| 28.90 ± 0.10 | 3.089 ± 0.010 | 9 |
| 29.08 ± 0.10 | 3.071 ± 0.010 | 4 |
| 29.32 ± 0.10 | 3.046 ± 0.010 | 19 |
| 29.64 ± 0.10 | 3.014 ± 0.010 | 11 |
| 29.82 ± 0.10 | 2.996 ± 0.010 | 4 |

(Part ii)

| °2θ | d space(Å) | Intensity (%) |
|---|---|---|
| 6.78 ± 0.10 | 13.038 ± 0.195 | 19 |
| 9.08 ± 0.10 | 9.740 ± 0.108 | 88 |
| 10.38 ± 0.10 | 8.523 ± 0.083 | 100 |
| 10.70 ± 0.10 | 8.268 ± 0.078 | 60 |
| 11.06 ± 0.10 | 8.000 ± 0.073 | 39 |
| 11.84 ± 0.10 | 7.475 ± 0.063 | 67 |

FIG. 3I Cont.

| Atom | x | y | z | U(Å²) |
|---|---|---|---|---|
| S(18) | 0.15609(7) | 0.15485(4) | 0.42039(3) | 0.03310(17) |
| S(19) | 0.28619(6) | 0.24695(3) | 0.40147(3) | 0.02243(15) |
| O(2) | 0.3301(3) | -0.03319(16) | 0.28512(10) | 0.0715(8) |
| O(5) | 0.49807(17) | -0.12985(9) | 0.15119(9) | 0.0246(4) |
| O(8) | 0.87246(19) | 0.05419(13) | 0.17779(12) | 0.0452(6) |
| O(9) | 0.64904(17) | 0.09998(9) | 0.20231(8) | 0.0241(4) |
| O(12) | 0.50480(18) | 0.22400(11) | 0.12564(8) | 0.0308(5) |
| O(15A) | 0.0495(15) | 0.2153(6) | 0.2546(19) | 0.034(3) |
| O(15B) | 0.0510(12) | 0.2060(10) | 0.220(2) | 0.060(5) |
| O(901) | 0.3011(2) | 0.11787(10) | 0.07803(8) | 0.0271(4) |
| N(3) | 0.2139(2) | 0.00055(11) | 0.18944(9) | 0.0212(5) |
| N(6) | 0.5064(2) | -0.00274(11) | 0.13121(10) | 0.0201(5) |
| N(13) | 0.42578(19) | 0.27032(11) | 0.22721(10) | 0.0184(5) |
| N(16) | 0.2582(2) | 0.14977(11) | 0.25866(9) | 0.0197(5) |
| C(1) | 0.1914(2) | 0.08325(13) | 0.29004(11) | 0.0197(5) |
| C(2) | 0.2510(2) | 0.01127(13) | 0.25536(11) | 0.0204(5) |
| C(4) | 0.2718(2) | -0.06169(13) | 0.15135(11) | 0.0179(5) |
| C(5) | 0.4353(2) | -0.06754(13) | 0.14554(11) | 0.0181(5) |
| C(7) | 0.6651(2) | -000141(13) | 0.12209(11) | 0.0205(5) |
| C(8) | 0.7409(2) | 0.05313(14) | 0.17053(12) | 0.0230(6) |
| C(10) | 0.7092(2) | 0.15796(14) | 0.24848(11) | 0.0233(6) |
| C(11) | 0.6836(2) | 0.23605(14) | 0.21494(12) | 0.0227(6) |
| C(12) | 0.5304(2) | 0.24400(14) | 0.18486(11) | 0.0199(5) |
| C(14) | 0.2720(2) | 0.27649(13) | 0.20666(11) | 0.0196(5) |
| C(15) | 0.1817(3) | 0.21022(15) | 0.23522(14) | 0.0299(6) |
| C(17) | 0.2244(3) | 0.07775(14) | 0.36668(11) | 0.0278(6) |
| C(20) | 0.4421(3) | 0.23602(14) | 0.45868(11) | 0.0251(6) |
| C(21) | 0.5556(3) | 0.17743(15) | 0.43617(12) | 0.0288(7) |
| C(22) | 0.6167(3) | 0.19370(14) | 0.36600(12) | 0.0255(6) |
| C(23) | 0.6368(3) | 0.14343(14) | 0.3 1692(12) | 0.0251(6) |
| C(41) | 0.1890(2) | -0.11277(13) | 0.11976(11) | 0.0205(5) |
| C(42) | 0.0252(3) | -0.11698(16) | 0.12093(14) | 0.0308(7) |
| C(71) | 0.6397(3) | -0.04033(17) | -0.00220(13) | 0.0359(7) |
| C(72) | 0.7136(3) | 0.01439(13) | 0.04736(12) | 0.0244(6) |
| C(73) | 0.6914(3) | 0.09720(15) | 0.02626(13) | 0.0310(6) |
| C(141) | 0.0568(3) | 0.36864(17) | 0.19442(16) | 0.0386(8) |
| C(142) | 0.2112(2) | 0.35597(13) | 0.22270(12) | 0.0222(6) |
| C(143) | 0.3129(3) | 0.41692(15) | 0.19305(14) | 0.0332(7) |
| C(901) | 0.2070(3) | 0.12972(14) | 0.01943(11) | 0.0256(6) |
| C(902) | 0.2986(3) | 0.14338(19) | -0.04425(13) | 0.0408(8) |
| C(903) | 0.1057(4) | 0.19639(18) | 0.03344(16) | 0.0477(9) |
| C(904) | 0.1207(3) | 0.05655(17) | 0.01165(15) | 0.0384(8) |

FIG. 3N

| Atom | x | y | z | U(Å²) |
|---|---|---|---|---|
| H(3) | 0.165(5) | 0.034(3) | 0.169(2) | 0.079(14)* |
| H(6) | 0.453(4) | 0.037(2) | 0.1225(18) | 0.054(10)* |
| H(13) | 0.447(3) | 0.2919(17) | 0.2672(15) | 0.033(8)* |
| H(16) | 0.353(4) | 0.1579(19) | 02646(16) | 0.045(9)* |
| H(901) | 0.354(4) | 0.158(2) | 0.0862(18) | 0.054(10)* |
| H(1) | -0.023 | 0.261 | 0.557 | 0.022 |
| H(3) | -0.247(9) | 0.284(5) | 0.609(4) | 0.045 |
| H(6) | -0.242(11) | 0.262(5) | 0.783(4) | 0.045 |
| H(7) | -0.157 | 0.347 | 0.891 | 0.029 |
| H(10) | 0.148 | 0.149 | 0.888 | 0.037 |
| H(13) | -0.005(10) | 0.020(5) | 0.700(5) | 0.027 |
| H(14) | -0.250 | 0.043 | 0.667 | 0.025 |
| H(16) | 0.044(10) | 0.153(5) | 0.663(4) | 0.045 |
| H(22) | 0.286 | 0.065 | 0.760 | 0.034 |
| H(23) | 0.238 | 0.228 | 0.780 | 0.036 |
| H(41) | -0.430 | 0.445 | 0.706 | 0.039 |
| H(72) | -0.310 | 0.278 | 0.969 | 0.040 |
| H(11A) | -0.028 | 0.058 | 0.871 | 0.031 |
| H(11B) | 0.095 | 0.029 | 0.818 | 0.031 |
| H(142) | -0.017 | -0.018 | 0.583 | 0.034 |
| H(14A) | -0.197 | -0.055 | 0.500 | 0.055 |
| H(14B) | -0.185 | 0.041 | 0.507 | 0.055 |
| H(14C) | -0.316 | -0006 | 0.544 | 0.055 |
| H(14D) | -0.255 | -0.103 | 0.644 | 0.056 |
| H(14E) | -0.091 | -0.108 | 0.670 | 0.056 |
| H(14F) | -0.134 | -0.144 | 0.596 | 0.056 |
| H(17A) | 0.222 | 0.265 | 0.648 | 0.031 |
| H(17B) | 0.199 | 0.326 | 0.585 | 0.031 |
| H(20A) | 0.468 | 0.035 | 0.659 | 0.038 |
| H(20B) | 0.527 | 0.111 | 0.616 | 0.038 |
| H(21A) | 0.525 | 0.139 | 0.738 | 0.038 |
| H(21B) | 0.425 | 0.202 | 0.697 | 0.038 |
| H(42A) | -0.371 | 0.410 | 0.567 | 0.080 |
| H(42B) | -0.501 | 0.409 | 0.591 | 0.080 |
| H(42C) | -0.522 | 0.372 | 0.592 | 0.080 |
| H(71A) | -0.463 | 0.368 | 0.864 | 0.077 |
| H(71B) | -0.382 | 0.407 | 0.930 | 0.077 |
| H(71C) | -0.525 | 0.352 | 0.941 | 0.077 |
| H(73A) | -0.457 | 0.212 | 0.852 | 0.075 |
| H(73B) | -0.507 | 0.202 | 0.931 | 0.075 |
| H(73C) | -0.359 | 0.160 | 0.905 | 0.075 |

Starred atoms were refined isotropically
$U_{eq} = (1/3)\Sigma_i\Sigma_j U_{ij} a^*_i a^*_j a_i \cdot a_j$
Hydrogen atoms are included in calculation of structure factors but not refined.

FIG. 3N Cont.

| Atom 1 | Atom 2 | Distance | Atom 1 | Atom 2 | Distance |
| --- | --- | --- | --- | --- | --- |
| S18 | C17 | 1.831(7) | C14 | C142 | 1.539(9) |
| S18 | S19 | 2.037(2) | C14 | H14 | 1.000 |
| S19 | C20 | 1.802(7) | C17 | H17A | 0.990 |
| O2 | C2 | 1.203(8) | C17 | H17B | 0.990 |
| O5 | C5 | 1.238(8) | C20 | C21 | 1.546(10) |
| O8 | C8 | 1.184(8) | C20 | H20A | 0.990 |
| O9 | C8 | 1.357(8) | C20 | H20B | 0.990 |
| O9 | C10 | 1.458(8) | C21 | C22 | 1.506(11) |
| O12 | C12 | 1.240(8) | C21 | H21A | 0.990 |
| O15 | C15 | 1.230(8) | C21 | H21B | 0.990 |
| N3 | C2 | 1.397(9) | C22 | C23 | 1.299(10) |
| N3 | C4 | 1.417(9) | C22 | H22 | 0.950 |
| N3 | H3 | 1.07(8) | C23 | H23 | 0.950 |
| N6 | C5 | 1.329(8) | C41 | C42 | 1.496(11) |
| N6 | C7 | 1.460(8) | C41 | H41 | 0.950 |
| N6 | H6 | 0.76(8) | C42 | H42A | 0.980 |
| N13 | C12 | 1.351(9) | C42 | H42B | 0.980 |
| N13 | C14 | 1.443(9) | C42 | H42C | 0.980 |
| N13 | H13 | 0.58(9) | C71 | C72 | 1.544(11) |
| N16 | C15 | 1.350(9) | C71 | H71A | 0.980 |
| N16 | C1 | 1.467(8) | C71 | H71B | 0.980 |
| N16 | H16 | 0.86(9) | C71 | H71C | 0.980 |
| C1 | C17 | 1.509(9) | C72 | C73 | 1.495(12) |
| C1 | C2 | 1.528(9) | C72 | H72 | 1.000 |
| C1 | H1 | 1.000 | C73 | H73A | 0.980 |
| C4 | C41 | 1.356(10) | C73 | H73B | 0.980 |
| C4 | C5 | 1.497(9) | C73 | H73C | 0.980 |
| C7 | C8 | 1.532(10) | C141 | C142 | 1.520(10) |
| C7 | C72 | 1.536(10) | C141 | H14A | 0.980 |
| C7 | H7 | 1.000 | C141 | H14B | 0.980 |
| C10 | C11 | 1.497(10) | C141 | H14C | 0.980 |
| C10 | C23 | 1.510(10) | C142 | C143 | 1.520(10) |
| C10 | H10 | 1.000 | C142 | H142 | 1.000 |
| C11 | C12 | 1.512(10) | C143 | H14D | 0.980 |
| C11 | H11A | 0.990 | C143 | H14E | 0.980 |
| C11 | H11B | 0.990 | C143 | H14F | 0.980 |
| C14 | C15 | 1.530(9) | | | |

Numbers in parentheses are estimated are estimated standard deviations in the least significant digits.

FIG. 30

| Atom 1 | Atom 2 | Atom 3 | Angle | Atom 1 | Atom 2 | Atom 3 | Angle |
|---|---|---|---|---|---|---|---|
| C17 | S18 | S19 | 107.4(2) | C10 | C11 | H11B | 108.90 |
| C20 | S19 | S18 | 104.6(3) | C12 | C11 | H11B | 108.90 |
| C8 | O9 | C10 | 116.2(5) | H11A | C11 | H11B | 107.70 |
| C2 | N3 | C4 | 118.8(6) | O12 | C12 | N13 | 120.4(6) |
| C2 | N3 | H3 | 114(4) | O12 | C12 | C11 | 121.2(6) |
| C4 | N3 | H3 | 126(4) | N13 | C12 | C11 | 118.3(6) |
| C5 | N6 | C7 | 122.3(6) | N13 | C14 | C15 | 111.9(5) |
| C5 | N6 | H6 | 123(6) | N13 | C14 | C142 | 111.1(5) |
| C7 | N6 | H6 | 115(6) | C15 | C14 | C142 | 113.6(5) |
| C12 | N13 | C14 | 120.3(5) | N13 | C14 | H14 | 106.60 |
| C12 | N13 | H13 | 134(9) | C15 | C14 | H14 | 106.60 |
| C14 | N13 | H13 | 106(9) | C142 | C14 | H14 | 106.60 |
| C15 | N16 | C1 | 122.9(5) | O15 | C15 | N16 | 122.9(6) |
| C15 | N16 | H16 | 117(6) | O15 | C15 | C14 | 122.1(6) |
| C1 | N16 | H16 | 120(6) | N16 | C15 | C14 | 115.0(5) |
| N16 | C1 | C17 | 110.5(5) | C1 | C17 | S18 | 115.2(5) |
| N16 | C1 | C2 | 110.0(5) | C1 | C17 | H17A | 108.50 |
| C17 | C1 | C2 | 109.5(5) | S18 | C17 | H17A | 108.50 |
| N16 | C1 | H1 | 108.90 | C1 | C17 | H17B | 108.50 |
| C17 | C1 | H1 | 108.90 | S18 | C17 | H17B | 108.50 |
| C2 | C1 | H1 | 108.90 | H17A | C17 | H17B | 107.50 |
| O2 | C2 | N3 | 122.4(6) | C21 | C20 | S19 | 114.8(5) |
| O2 | C2 | C1 | 124.6(6) | C21 | C20 | H20A | 108.60 |
| N3 | C2 | C1 | 113.0(6) | S19 | C20 | H20A | 108.60 |
| C41 | C4 | N3 | 122.3(6) | C21 | C20 | H20B | 108.60 |
| C41 | C4 | C5 | 119.7(6) | S19 | C20 | H20B | 108.60 |
| N3 | C4 | C5 | 117.5(6) | H20A | C20 | H20B | 107.50 |
| O5 | C5 | N6 | 123.0(6) | C22 | C21 | C20 | 112.5(6) |
| O5 | C5 | C4 | 120.5(6) | C22 | C21 | H21A | 109.10 |
| N6 | C5 | C4 | 116.5(5) | C20 | C21 | H21A | 109.10 |
| N6 | C7 | C8 | 111.1(5) | C22 | C21 | H21B | 109.10 |
| N6 | C7 | C72 | 113.4(6) | C20 | C21 | H21B | 109.10 |
| C8 | C7 | C72 | 111.5(5) | H21A | C21 | H21B | 107.80 |
| N6 | C7 | H7 | 106.80 | C23 | C22 | C21 | 126.4(7) |

FIG. 3P

| Atom 1 | Atom 2 | Atom 3 | Angle | Atom 1 | Atom 2 | Atom 3 | Angle |
|---|---|---|---|---|---|---|---|
| C8 | C7 | H7 | 106.80 | C23 | C22 | H22 | 116.80 |
| C72 | C7 | H7 | 106.80 | C21 | C22 | H22 | 116.80 |
| O8 | C8 | O9 | 125.1(7) | C22 | C23 | C10 | 127.5(7) |
| O8 | C8 | C7 | 123.6(6) | C22 | C23 | H23 | 116.20 |
| O9 | C8 | C7 | 111.3(5) | C10 | C23 | H23 | 116.20 |
| O9 | C8 | C11 | 110.4(6) | C4 | C41 | C42 | 125.4(7) |
| O9 | C10 | C23 | 104.0(6) | C4 | C41 | H41 | 117.30 |
| C11 | C10 | C23 | 116.8(6) | C42 | C41 | H41 | 117.30 |
| O9 | C10 | H10 | 108.50 | C41 | C42 | H42A | 109.50 |
| C11 | C10 | H10 | 108.50 | C41 | C42 | H42B | 109.50 |
| C23 | C10 | H10 | 108.50 | H42A | C42 | H42B | 109.50 |
| C10 | C11 | C12 | 113.3(5) | C41 | C42 | H42C | 109.50 |
| C10 | C11 | H11A | 108.90 | H42A | C42 | H42C | 109.50 |
| C12 | C11 | H11A | 108.90 | H42B | C42 | H42C | 109.50 |
| C72 | C71 | H71A | 109.50 | C142 | C141 | H14A | 109.50 |
| C72 | C71 | H71B | 109.50 | C142 | C141 | H14B | 109.50 |
| H71A | C71 | H71B | 109.50 | H14A | C141 | H14B | 109.50 |
| C72 | C71 | H71C | 109.50 | C142 | C141 | H14C | 109.50 |
| H71A | C71 | H71C | 109.50 | H14A | C141 | H14C | 109.50 |
| H71B | C71 | H71C | 109.50 | H14B | C141 | H14C | 109.50 |
| C73 | C72 | C7 | 113.2(6) | C143 | C142 | C141 | 110.0(6) |
| C73 | C72 | C71 | 111.4(7) | C143 | C142 | C14 | 109.9(6) |
| C7 | C72 | C71 | 109.3(6) | C141 | C142 | C14 | 112.9(6) |
| C73 | C72 | H72 | 107.60 | C143 | C142 | H142 | 108.00 |
| C7 | C72 | H72 | 107.60 | C141 | C142 | H142 | 108.00 |
| C71 | C72 | H72 | 107.60 | C14 | C142 | H142 | 108.00 |
| C72 | C73 | H73A | 109.50 | C142 | C143 | H14D | 109.50 |
| C72 | C73 | H73B | 109.50 | C142 | C143 | H14E | 109.50 |
| H73A | C73 | H73B | 109.50 | H14D | C143 | H14E | 109.50 |
| C72 | C73 | H73C | 109.50 | C142 | C143 | H14F | 109.50 |
| H73A | C73 | H73C | 109.50 | H14D | C143 | H14F | 109.50 |
| H73B | C73 | H73C | 109.50 | H14E | C143 | H14F | 109.50 |

Numbers in prentheses are estimated standard deviations in the least significant digits.

FIG. 3P Cont.

(Part i)

| °2θ | d space(Å) | Intensity (%) |
|---|---|---|
| 8.94 ± 0.10 | 9.897 ± 0.112 | 73 |
| 9.30 ± 0.10 | 9.507 ± 0.103 | 28 |
| 9.69 ± 0.10 | 9.130 ± 0.095 | 97 |
| 10.51 ± 0.10 | 8.420 ± 0.081 | 78 |
| 10.67 ± 0.10 | 8.289 ± 0.078 | 100 |
| 11.66 ± 0.10 | 7.590 ± 0.065 | 8 |
| 11.86 ± 0.10 | 7.462 ± 0.063 | 12 |
| 13.13 ± 0.10 | 6.743 ± 0.052 | 50 |
| 13.60 ± 0.10 | 6.512 ± 0.048 | 7 |
| 14.37 ± 0.10 | 6.165 ± 0.043 | 5 |
| 16.52 ± 0.10 | 5.365 ± 0.032 | 3 |
| 17.26 ± 0.10 | 5.138 ± 0.030 | 6 |
| 18.61 ± 0.10 | 4.768 ± 0.026 | 14 |
| 18.93 ± 0.10 | 4.688 ± 0.025 | 25 |
| 19.43 ± 0.10 | 4.569 ± 0.023 | 64 |
| 20.10 ± 0.10 | 4.418 ± 0.022 | 45 |
| 20.40 ± 0.10 | 4.354 ± 0.021 | 33 |
| 21.37 ± 0.10 | 4.158 ± 0.019 | 17 |
| 21.99 ± 0.10 | 4.043 ± 0.018 | 8 |
| 22.84 ± 0.10 | 3.894 ± 0.017 | 23 |
| 23.19 ± 0.10 | 3.836 ± 0.016 | 18 |
| 24.14 ± 0.10 | 3.686 ± 0.015 | 7 |
| 24.74 ± 0.10 | 3.598 ± 0.014 | 3 |
| 25.40 ± 0.10 | 3.507 ± 0.014 | 3 |
| 26.40 ± 0.10 | 3.376 ± 0.013 | 10 |
| 27.27 ± 0.10 | 3.271 ± 0.012 | 5 |
| 27.92 ± 0.10 | 3.196 ± 0.011 | 3 |
| 28.91 ± 0.10 | 3.089 ± 0.010 | 4 |
| 29.62 ± 0.10 | 3.016 ± 0.010 | 5 |

(Part ii)

| °2θ | d space(Å) | Intensity (%) |
|---|---|---|
| 8.94 ± 0.10 | 9.897 ± 0.112 | 73 |
| 9.69 ± 0.10 | 9.130 ± 0.095 | 97 |
| 10.51 ± 0.10 | 8.420 ± 0.081 | 78 |
| 10.67 ± 0.10 | 8.289 ± 0.078 | 100 |
| 13.13 ± 0.10 | 6.743 ± 0.052 | 50 |
| 19.43 ± 0.10 | 4.569 ± 0.023 | 64 |
| 20.10 ± 0.10 | 4.418 ± 0.022 | 45 |
| 20.40 ± 0.10 | 4.354 ± 0.021 | 33 |

FIG. 4B

| | |
|---|---|
| 749 | 1355 |
| 802 | 1370 |
| 842 | 1391 |
| 848 | 1404 |
| 891 | 1439 |
| 915 | 1521 |
| 929 | 1639 |
| 981 | 1664 |
| 1001 | 1692 |
| 1015 | 1741 |
| 1044 | 2875 |
| 1092 | 2929 |
| 1110 | 2964 |
| 1157 | 3004 |
| 1178 | 3319 |
| 1221 | 3356 |
| 1257 | 3368 |
| 1302 | |
| 1337 | |

| °2θ | d space(Å) | Intensity (%) |
|---|---|---|
| 6.22 ± 0.10 | 14.221 ± 0.232 | 20 |
| 7.53 ± 0.10 | 11.741 ± 0.158 | 26 |
| 9.23 ± 0.10 | 9.587 ± 0.105 | 35 |
| 10.51 ± 0.10 | 8.421 ± 0.081 | 36 |
| 10.64 ± 0.10 | 8.312 ± 0.079 | 27 |
| 11.13 ± 0.10 | 7.951 ± 0.072 | 47 |
| 11.92 ± 0.10 | 7.422 ± 0.063 | 59 |
| 12.34 ± 0.10 | 7.173 ± 0.058 | 31 |
| 12.89 ± 0.10 | 6.867 ± 0.053 | 20 |
| 14.55 ± 0.10 | 6.086 ± 0.042 | 44 |
| 15.00 ± 0.10 | 5.905 ± 0.039 | 27 |
| 15.38 ± 0.10 | 5.760 ± 0.037 | 32 |
| 17.57 ± 0.10 | 5.049 ± 0.029 | 43 |
| 17.95 ± 0.10 | 4.943 ± 0.027 | 45 |
| 18.43 ± 0.10 | 4.814 ± 0.026 | 75 |
| 18.71 ± 0.10 | 4.743 ± 0.025 | 53 |
| 19.09 ± 0.10 | 4.650 ± 0.024 | 57 |
| 19.47 ± 0.10 | 4.559 ± 0.023 | 68 |
| 20.27 ± 0.10 | 4.382 ± 0.022 | 59 |
| 20.54 ± 0.10 | 4.324 ± 0.021 | 42 |
| 20.96 ± 0.10 | 4.239 ± 0.020 | 100 |
| 21.24 ± 0.10 | 4.184 ± 0.020 | 47 |
| 21.51 ± 0.10 | 4.131 ± 0.019 | 40 |
| 21.62 ± 0.10 | 4.111 ± 0.019 | 41 |
| 21.96 ± 0.10 | 4.047 ± 0.018 | 35 |
| 22.31 ± 0.10 | 3.985 ± 0.018 | 46 |
| 23.21 ± 0.10 | 3.832 ± 0.016 | 74 |
| 23.83 ± 0.10 | 3.734 ± 0.016 | 46 |
| 24.11 ± 0.10 | 3.691 ± 0.015 | 42 |
| 24.39 ± 0.10 | 3.650 ± 0.015 | 37 |
| 24.70 ± 0.10 | 3.605 ± 0.014 | 37 |
| 25.01 ± 0.10 | 3.560 ± 0.014 | 47 |
| 25.91 ± 0.10 | 3.439 ± 0.013 | 39 |
| 26.40 ± 0.10 | 3.377 ± 0.013 | 43 |
| 26.95 ± 0.10 | 3.308 ± 0.012 | 54 |
| 28.54 ± 0.10 | 3.127 ± 0.011 | 43 |
| 29.31 ± 0.10 | 3.047 ± 0.010 | 45 |

FIG. 5B

| | |
|---|---|
| 750 | 1257 |
| 803 | 1287 |
| 814 | 1302 |
| 826 | 1334 |
| 848 | 1353 |
| 871 | 1372 |
| 892 | 1393 |
| 912 | 1408 |
| 928 | 1437 |
| 946 | 1462 |
| 980 | 1529 |
| 1000 | 1627 |
| 1012 | 1666 |
| 1028 | 1684 |
| 1047 | 1736 |
| 1081 | 2876 |
| 1098 | 2932 |
| 1112 | 2966 |
| 1132 | 3004 |
| 1179 | 3279 |
| 1225 | 3355 |
| 1242 | |

(Part i)

| °2θ | d space(Å) | Intensity (%) |
|---|---|---|
| 6.28 ± 0.10 | 14.074 ± 0.228 | 7 |
| 7.60 ± 0.10 | 11.633 ± 0.155 | 100 |
| 9.10 ± 0.10 | 9.718 ± 0.108 | 2 |
| 9.34 ± 0.10 | 9.469 ± 0.102 | 22 |
| 10.10 ± 0.10 | 8.758 ± 0.087 | 48 |
| 10.60 ± 0.10 | 8.346 ± 0.079 | 6 |
| 10.68 ± 0.10 | 8.284 ± 0.078 | 6 |
| 11.26 ± 0.10 | 7.858 ± 0.070 | 6 |
| 12.06 ± 0.10 | 7.339 ± 0.061 | 1 |
| 12.46 ± 0.10 | 7.104 ± 0.057 | 9 |
| 13.06 ± 0.10 | 6.779 ± 0.052 | 2 |
| 14.22 ± 0.10 | 6.229 ± 0.044 | 0 |
| 14.76 ± 0.10 | 6.002 ± 0.041 | 1 |
| 15.18 ± 0.10 | 5.837 ± 0.038 | 10 |
| 15.50 ± 0.10 | 5.717 ± 0.037 | 10 |
| 15.58 ± 0.10 | 5.688 ± 0.037 | 7 |
| 16.02 ± 0.10 | 5.533 ± 0.035 | 1 |
| 16.84 ± 0.10 | 5.265 ± 0.031 | 0 |
| 17.72 ± 0.10 | 5.005 ± 0.028 | 1 |
| 17.86 ± 0.10 | 4.966 ± 0.028 | 2 |
| 18.12 ± 0.10 | 4.896 ± 0.027 | 8 |
| 18.60 ± 0.10 | 4.771 ± 0.026 | 1 |
| 18.76 ± 0.10 | 4.730 ± 0.025 | 4 |
| 18.88 ± 0.10 | 4.700 ± 0.025 | 3 |
| 19.30 ± 0.10 | 4.599 ± 0.024 | 4 |
| 19.42 ± 0.10 | 4.571 ± 0.023 | 2 |
| 19.80 ± 0.10 | 4.484 ± 0.023 | 9 |
| 20.26 ± 0.10 | 4.383 ± 0.022 | 2 |
| 20.54 ± 0.10 | 4.324 ± 0.021 | 4 |
| 20.88 ± 0.10 | 4.254 ± 0.020 | 1 |
| 21.12 ± 0.10 | 4.207 ± 0.020 | 3 |
| 21.28 ± 0.10 | 4.175 ± 0.019 | 12 |
| 21.44 ± 0.10 | 4.145 ± 0.019 | 8 |
| 21.62 ± 0.10 | 4.111 ± 0.019 | 1 |
| 21.86 ± 0.10 | 4.066 ± 0.018 | 2 |
| 22.18 ± 0.10 | 4.008 ± 0.018 | 3 |
| 22.50 ± 0.10 | 3.952 ± 0.017 | 3 |
| 22.64 ± 0.10 | 3.928 ± 0.017 | 5 |
| 22.92 ± 0.10 | 3.880 ± 0.017 | 2 |
| 23.14 ± 0.10 | 3.844 ± 0.016 | 2 |
| 23.46 ± 0.10 | 3.792 ± 0.016 | 11 |
| 24.12 ± 0.10 | 3.690 ± 0.015 | 2 |
| 24.22 ± 0.10 | 3.675 ± 0.015 | 3 |
| 24.34 ± 0.10 | 3.657 ± 0.015 | 1 |
| 24.78 ± 0.10 | 3.593 ± 0.014 | 0 |
| 25.00 ± 0.10 | 3.562 ± 0.014 | 2 |

FIG. 5H

| °2θ | d space(Å) | Intensity (%) | (Part i) |
|---|---|---|---|
| 25.32 ± 0.10 | 3.518 ± 0.014 | 4 | |
| 26.14 ± 0.10 | 3.409 ± 0.013 | 1 | |
| 26.28 ± 0.10 | 3.391 ± 0.013 | 1 | |
| 26.78 ± 0.10 | 3.329 ± 0.012 | 1 | |
| 27.00 ± 0.10 | 3.302 ± 0.012 | 2 | |
| 27.34 ± 0.10 | 3.262 ± 0.012 | 4 | |
| 27.86 ± 0.10 | 3.202 ± 0.011 | 1 | |
| 27.98 ± 0.10 | 3.189 ± 0.011 | 1 | |
| 28.30 ± 0.10 | 3.154 ± 0.011 | 1 | |
| 28.44 ± 0.10 | 3.138 ± 0.011 | 1 | |
| 28.68 ± 0.10 | 3.113 ± 0.011 | 1 | |
| 28.90 ± 0.10 | 3.089 ± 0.010 | 1 | |
| 29.00 ± 0.10 | 3.079 ± 0.010 | 1 | |
| 29.28 ± 0.10 | 3.050 ± 0.010 | 2 | |
| 29.78 ± 0.10 | 3.000 ± 0.010 | 2 | |
| 29.94 ± 0.10 | 2.985 ± 0.010 | 1 | |

| °2θ | d space(Å) | Intensity (%) | (Part ii) |
|---|---|---|---|
| 7.60 ± 0.10 | 11.633 ± 0.155 | 100 | |
| 9.34 ± 0.10 | 9.469 ± 0.102 | 22 | |
| 10.10 ± 0.10 | 8.758 ± 0.087 | 48 | |

FIG. 5H Cont.

| Atom | x | y | z | U(Å²) |
|---|---|---|---|---|
| C11A | 0.6999(5) | 0.1038(4) | 0.8772(12) | 0.109(2) |
| C11B | 0.5420(4) | 0.0501(6) | 0.900(3) | 0.161(6) |
| C12A | 0.5553(3) | 0.0691(2) | 0.9735(4) | 0.0770(12) |
| C12B | 0.6308(16) | 0.0706(5) | 0.6520(13) | 0.163(6) |
| C13A | 0.5980(2) | 0.0504(3) | 0.6850(5) | 0.0810(14) |
| C13B | 0.6962(5) | 0.0998(4) | 0.9004(13) | 0.076(2) |
| S18 | 0.34331(9) | 0.11417(5) | 0.57926(14) | 0.0579(4) |
| S19 | 0.25004(7) | 0.11931(5) | 0.70624(14) | 0.0514(3) |
| O2 | 0.5296(2) | 0.21160(15) | 0.8123(5) | 0.0696(13) |
| O5 | 0.62163(18) | 0.32738(15) | 1.0295(4) | 0.0548(10) |
| O8 | 0.4100(3) | 0.2768(2) | 1.3635(4) | 0.0760(14) |
| O9 | 0.41697(17) | 0.23981(15) | 1.1468(3) | 0.0473(9) |
| O12 | 0.32797(19) | 0.31556(15) | 1.0067(4) | 0.0511(9) |
| O15 | 0.34278(19) | 0.32578(13) | 0.65 06(3) | 0.0460(8) |
| N3 | 0.4891(2) | 0.29977(16) | 0.7501(4) | 0.0464(10) |
| N6 | 0.4933(2) | 0.32470(17) | 1.0427(4) | 0.0467(10) |
| N13 | 0.2302(2) | 0.26391(17) | 0.9194(4) | 0.0441(10) |
| N16 | 0.3431(2) | 0.23573(14) | 0.7399(4) | 0.0401(9) |
| C1 | 0.4146(3) | 0.21741(19) | 0.6723(5) | 0.0443(12) |
| C2 | 0.4831(3) | 0.24150(17) | 0.7526(5) | 0.0420(10) |
| C4 | 0.5504(3) | 0.32745(19) | 0.8131(5) | 0.0460(12) |
| C5 | 0.5588(3) | 0.3256(2) | 0.9693(6) | 0.0497(14) |
| C7 | 0.4909(3) | 0.3233(2) | 1.1926(5) | 0.0500(14) |
| C8 | 0.4361(3) | 0.2767(3) | 1.2442(5) | 0.0517(14) |
| C10 | 0.3520(3) | 0.2027(2) | 1.1734(5) | 0.0507(12) |
| C11 | 0.2801(3) | 0.2404(2) | 1.1540(5) | 0.0503(12) |
| C12 | 0.2816(2) | 0.2771(2) | 1.0230(5) | 0.0430(12) |
| C14 | 0.2359(2) | 0.29650(17) | 0.7872(5) | 0.0410(12) |
| C15 | 0.3128(3) | 0.28800(19) | 0.7184(5) | 0.0437(12) |
| C17 | 0.4183(3) | 0.15169(18) | 0.6734(5) | 0.0483(14) |
| C20 | 0.2569(3) | 0.0586(2) | 0.8272(6) | 0.0547(14) |
| C21 | 0.3148(3) | 0.0657(2) | 0.9415(6) | 0.0547(14) |
| C22 | 0.3046(3) | 0.1204(2) | 1.0278(6) | 0.0540(14) |
| C23 | 0.3593(3) | 0.1518(2) | 1.0755(5) | 0.0523(14) |
| C41 | 0.6026(3) | 0.3547(2) | 0.7335(6) | 0.0563(15) |
| C42 | 0.6034(4) | 0.3579(3) | 0.5774(7) | 0.076(2) |
| C71 | 0.398 5(4) | 0.4054(3) | 1.2189(8) | 0.078(2) |
| C72 | 0.4747(3) | 0.3826(3) | 1.2624(7) | 0.0637(17) |
| C73 | 0.5410(4) | 0.4224(3) | 1.2401(8) | 0.076(2) |
| C91 | 0.6086(3 ) | 0.0946(2) | 0.8267(8) | 0.0630(16) |
| C141 | 0.1824(4) | 0.3017(4) | 0.5363(8) | 0.091(3) |
| C142 | 0.1688(3) | 0.2796(2) | 0.6918(6) | 0.0543(14) |
| C143 | 0.0976(3) | 0.3063(3) | 0.7526(10) | 0.085(2) |
| H3 | 0.446 | 0.314 | 0.791 | 0.40(163)* |
| H6 | 0.467 | 0.293 | 1.012 | 1.2(7)* |
| H13 | 0.237 | 0.227 | 0.898 | 0.20(63)* |
| H16 | 0.320 | 0.212 | 0.798 | 0.051(153)* |

FIG. 5M

| Atom | x | y | z | U(Å²) |
|---|---|---|---|---|
| H1 | 0.416 | 0.231 | 0.572 | 0.053 |
| H7 | 0.542 | 0.311 | 1.225 | 0.060 |
| H10 | 0.354 | 0.189 | 1.273 | 0.061 |
| H14 | 0.231 | 0.338 | 0.811 | 0.049 |
| H22 | 0.254 | 0.132 | 1.048 | 0.065 |
| H23 | 0.409 | 0.142 | 1.046 | 0.063 |
| H41 | 0.642 | 0.373 | 0.782 | 0.068 |
| H72 | 0.472 | 0.375 | 1.367 | 0.077 |
| H91 | 0.588 | 0.133 | 0.800 | 0.075 |
| H11A | 0.235 | 0.215 | 1.150 | 0.061 |
| H11B | 0.274 | 0.266 | 1.238 | 0.061 |
| H142 | 0.163 | 0.237 | 0.691 | 0.066 |
| H14A | 0.142 | 0.287 | 0.475 | 0.136 |
| H14B | 0.231 | 0.288 | 0.502 | 0.136 |
| H14C | 0.182 | 0.344 | 0.535 | 0.136 |
| H14D | 0.080 | 0.283 | 0.833 | 0.128 |
| H14E | 0.058 | 0.307 | 0.680 | 0.128 |
| H14F | 0.108 | 0.345 | 0.784 | 0.128 |
| H17A | 0.418 | 0.139 | 0.773 | 0.058 |
| H17B | 0.467 | 0.140 | 0.632 | 0.058 |
| H20A | 0.207 | 0.052 | 0.872 | 0.065 |
| H20B | 0.269 | 0.024 | 0.772 | 0.065 |
| H21A | 0.366 | 0.066 | 0.898 | 0.066 |
| H21B | 0.312 | 0.032 | 1.006 | 0.066 |
| H42A | 0.652 | 0.343 | 0.542 | 0.115 |
| H42B | 0.597 | 0.398 | 0.548 | 0.115 |
| H42C | 0.562 | 0.334 | 0.539 | 0.115 |
| H71A | 0.394 | 0.445 | 1.249 | 0.117 |
| H71B | 0.359 | 0.382 | 1.263 | 0.117 |
| H71C | 0.394 | 0.403 | 1.116 | 0.117 |
| H73A | 0.549 | 0.428 | 1.139 | 0.114 |
| H73B | 0.586 | 0.405 | 1.283 | 0.114 |
| H73C | 0.530 | 0.459 | 1.285 | 0.114 |

Starred atoms were refined isotropically
$U_{eq} = (1/3)\Sigma_i\Sigma_j U_{ij} a^*_i a^*_j a_i . a_j$
Hydrogen atoms are included in calculation of structure factors but not refined.

FIG. 5M Cont.

| Atom 1 | Atom 2 | Distance | Atom 1 | Atom 2 | Distance |
|---|---|---|---|---|---|
| C11A | C91 | 1.699(10) | C11 | H11A | 0.990 |
| C11B | C91 | 1.717(10) | C11 | H11B | 0.990 |
| C12A | C91 | 1.781(8) | C14 | C15 | 1.522(7) |
| C12B | C91 | 1.789(16) | C14 | C142 | 1.543(6) |
| C13A | C91 | 1.701(7) | C14 | H14 | 1.000 |
| C13B | C91 | 1.704(8) | C17 | H17A | 0.990 |
| S18 | C17 | 1.822(6) | C17 | H17B | 0.990 |
| S18 | S19 | 2.046(2) | C20 | C21 | 1.499(8) |
| S19 | C20 | 1.823(5) | C20 | H20A | 0.990 |
| O2 | C2 | 1.217(6) | C20 | H20B | 0.990 |
| O5 | C5 | 1.250(6) | C21 | C22 | 1.523(8) |
| O8 | C8 | 1.220(6) | C21 | H21A | 0.990 |
| O9 | C8 | 1.304(6) | C21 | H21B | 0.990 |
| O9 | C10 | 1.460(6) | C22 | C23 | 1.294(8) |
| O12 | C12 | 1.224(5) | C22 | H22 | 0.950 |
| O15 | C15 | 1.211(6) | C23 | H23 | 0.950 |
| N3 | C2 | 1.361(6) | C41 | C42 | 1.479(8) |
| N3 | C4 | 1.395(7) | C41 | H41 | 0.950 |
| N3 | H3 | 0.920 | C42 | H42A | 0.980 |
| N6 | C5 | 1.352(6) | C42 | H42B | 0.980 |
| N6 | C7 | 1.419(7) | C42 | H42C | 0.980 |
| N6 | H6 | 0.920 | C71 | C72 | 1.507(8) |
| N13 | C12 | 1.372(6) | C71 | H71A | 0.980 |
| N13 | C14 | 1.467(6) | C71 | H71B | 0.980 |
| N13 | H13 | 0.897 | C71 | H71C | 0.980 |
| N16 | C15 | 1.345(5) | C72 | C73 | 1.510(9) |
| N16 | C1 | 1.481(6) | C72 | H72 | 1.000 |
| N16 | H16 | 0.880 | C73 | H73A | 0.980 |
| C1 | C17 | 1.531(6) | C73 | H73B | 0.980 |
| C1 | C2 | 1.537(7) | C73 | H73C | 0.980 |
| C1 | H1 | 1.000 | C91 | H91 | 1.000 |
| C4 | C41 | 1.351(7) | C141 | C142 | 1.578(10) |
| C4 | C5 | 1.486(7) | C141 | H14A | 0.980 |
| C7 | C8 | 1.535(7) | C141 | H14B | 0.980 |
| C7 | C72 | 1.558(8) | C141 | H14C | 0.980 |
| C7 | H7 | 1.000 | C142 | C143 | 1.518(9) |
| C10 | C23 | 1.510(8) | C142 | H142 | 1.000 |
| C10 | C11 | 1.556(8) | C143 | H14D | 0.980 |
| C10 | H10 | 1.000 | C143 | H14E | 0.980 |
| C11 | C12 | 1.507(7) | C143 | H14F | 0.980 |

Numbers in prentheses are estimated standard deviations in the least significant digits.

FIG. 5N

| Atom 1 | Atom 2 | Atom 3 | Angle | Atom 1 | Atom 2 | Atom 3 | Angle |
|---|---|---|---|---|---|---|---|
| C17 | S18 | S19 | 105.82(17) | C12 | C11 | H11B | 108.80 |
| C20 | S19 | S18 | 105.64(19) | C10 | C11 | H11B | 108.80 |
| C8 | O9 | C10 | 118.1(4) | H11A | C11 | H11B | 107.70 |
| C2 | N3 | C4 | 120.9(4) | O12 | C12 | N13 | 121.3(5) |
| C2 | N3 | H3 | 107.20 | O12 | C12 | C11 | 122.1(4) |
| C4 | N3 | H3 | 107.10 | N13 | C12 | C11 | 116.6(4) |
| C5 | N6 | C7 | 122.7(4) | N13 | C14 | C15 | 111.0(3) |
| C5 | N6 | H6 | 106.70 | N13 | C14 | C142 | 108.3(4) |
| C7 | N6 | H6 | 106.60 | C15 | C14 | C142 | 113.9(4) |
| C12 | N13 | C14 | 116.6(4) | N13 | C14 | H14 | 107.80 |
| C12 | N13 | H13 | 106.80 | C15 | C14 | H14 | 107.80 |
| C14 | N13 | H13 | 107.50 | C142 | C14 | H14 | 107.80 |
| C15 | N16 | C1 | 122.4(4) | O15 | C15 | N16 | 124.2(4) |
| C15 | N16 | H16 | 118.80 | O15 | C15 | C14 | 121.6(4) |
| C1 | N16 | H16 | 118.80 | N16 | C15 | C14 | 114.2(4) |
| N16 | C1 | C17 | 108.7(4) | C1 | C17 | S18 | 116.4(4) |
| N16 | C1 | C2 | 110.8(4) | C1 | C17 | H17A | 108.20 |
| C17 | C1 | C2 | 109.1(4) | S18 | C17 | H17A | 108.20 |
| N16 | C1 | H1 | 109.40 | C1 | C17 | H17B | 108.20 |
| C17 | C1 | H1 | 109.40 | S18 | C17 | H17B | 108.20 |
| C2 | C2 | H1 | 109.40 | H17A | C17 | H7B | 107.30 |
| O2 | C2 | N3 | 121.7(5) | C21 | C20 | S19 | 114.4(3) |
| O2 | C2 | C1 | 123.7(4) | C21 | C20 | H20A | 108.70 |
| N3 | C2 | C1 | 114.6(4) | S19 | C20 | H20A | 108.70 |
| C41 | C4 | N3 | 120.7(5) | C21 | C20 | H20B | 108.70 |
| C41 | C4 | C5 | 120.0(5) | S19 | C20 | H20B | 108.70 |
| N3 | C4 | C5 | 119.3(4) | H20A | C20 | H20B | 107.60 |
| O5 | C5 | N6 | 121.9(5) | C20 | C21 | C22 | 113.4(4) |
| O5 | C5 | C4 | 122.8(4) | C20 | C21 | H21A | 108.90 |
| N6 | C5 | C4 | 115.2(4) | C22 | C21 | H21A | 108.90 |
| N6 | C7 | C8 | 110.7(4) | C20 | C21 | H21B | 108.90 |
| N6 | C7 | C72 | 114.1(5) | C22 | C21 | H21B | 108.90 |
| C8 | C7 | C72 | 112.1(4) | H21A | C21 | H21B | 107.70 |
| N6 | C7 | H7 | 106.50 | C23 | C22 | C21 | 124.8(5) |

FIG. 50

| Atom 1 | Atom 2 | Atom 3 | Angle | Atom 1 | Atom 2 | Atom 3 | Angle |
|---|---|---|---|---|---|---|---|
| C8 | C7 | H7 | 106.50 | C23 | C22 | H22 | 117.60 |
| C72 | C7 | H7 | 106.50 | C21 | C22 | H22 | 117.60 |
| O8 | C8 | O9 | 123.9(5) | C22 | C23 | C10 | 126.4(5) |
| O8 | C8 | C7 | 122.1(5) | C22 | C23 | H23 | 116.80 |
| O9 | C8 | C7 | 113.8(4) | C10 | C23 | H23 | 116.80 |
| O9 | C10 | C23 | 106.9(4) | C4 | C41 | C42 | 126.0(6) |
| O9 | C10 | C11 | 106.9(4) | C4 | C41 | H41 | 117.00 |
| C23 | C10 | C11 | 116.1(4) | C42 | C41 | H41 | 117.00 |
| O9 | C10 | H10 | 108.90 | C41 | C42 | H42A | 109.50 |
| C23 | C10 | H10 | 108.90 | C41 | C42 | H42B | 109.50 |
| C11 | C10 | H10 | 108.90 | H42A | C42 | H42B | 109.50 |
| C12 | C11 | C10 | 113.7(4) | C41 | C42 | H42C | 109.50 |
| C12 | C11 | H11A | 108.80 | H42A | C42 | H42C | 109.50 |
| C10 | C11 | H11A | 108.80 | H42B | C42 | H42C | 109.50 |
| C72 | C71 | H71A | 109.50 | C13A | C91 | C12B | 26.6(6) |
| C72 | C71 | H71B | 109.50 | C13B | C91 | C12B | 101.6(9) |
| H71A | C71 | H71B | 109.50 | C11B | C91 | C12B | 109.7(8) |
| C72 | C71 | H71C | 109.50 | C12A | C91 | C12B | 137.2(7) |
| H71A | C71 | H71C | 109.50 | C11A | C91 | H91 | 107.60 |
| H71B | C71 | H71C | 109.50 | C13A | C91 | H91 | 107.60 |
| C71 | C72 | C73 | 116.3(6) | C13B | C91 | H91 | 111.70 |
| C71 | C72 | C7 | 111.1(4) | C11B | C91 | H91 | 113.20 |
| C73 | C72 | C7 | 109.9(5) | C12A | C91 | H91 | 107.60 |
| C71 | C72 | H72 | 106.30 | C12B | C91 | H91 | 97.30 |
| C73 | C72 | H72 | 106.30 | C142 | C141 | H14A | 109.50 |
| C7 | C72 | H72 | 106.30 | C142 | C141 | H14B | 109.50 |
| C72 | C73 | H73A | 109.50 | H14A | C141 | H14B | 109.50 |
| C72 | C73 | H73B | 109.50 | C142 | C141 | H14C | 109.50 |
| H73A | C73 | H73B | 109.50 | H14A | C141 | H14C | 109.50 |
| C72 | C73 | H73C | 109.50 | H14B | C141 | H14C | 109.50 |
| H73A | C73 | H73C | 109.50 | C143 | C142 | C14 | 108.2(5) |
| H73B | C73 | H73C | 109.50 | C143 | C142 | C141 | 110.3(5) |
| C11A | C91 | C13A | 113.8(5) | C14 | C142 | C141 | 110.2(5) |
| C11A | C91 | C13B | 8.3(8) | C143 | C142 | H142 | 109.40 |
| C13A | C91 | C13B | 117.8(4) | C14 | C142 | H142 | 109.40 |
| C11A | C91 | C11B | 128.0(8) | C141 | C142 | H142 | 109.40 |
| C13A | C91 | C11B | 83.0(10) | C142 | C143 | H14D | 109.50 |
| C13B | C91 | C11B | 120.1(8) | C142 | C143 | H14E | 109.50 |
| C11A | C91 | C12A | 109.1(5) | H14D | C143 | H14E | 109.50 |

FIG. 50 Cont.

| Atom 1 | Atom 2 | Atom 3 | Angle | Atom 1 | Atom 2 | Atom 3 | Angle |
|---|---|---|---|---|---|---|---|
| C13A | C91 | C12A | 110.8(3) | C142 | C143 | H14F | 109.50 |
| C13B | C91 | C12A | 100.7(6) | H14D | C143 | H14F | 109.50 |
| C11B | C91 | C12A | 28.3(10) | H14E | C143 | H14F | 109.50 |
| C11A | C91 | C12B | 95.2(9) | | | | |

Numbers in prentheses are estimated standard deviations in the least significant digits.

FIG. 50 Cont.

| °2θ | d space(Å) | Intensity (%) |
|---|---|---|
| 6.22 ± 0.10 | 14.214 ± 0.232 | 33 |
| 7.49 ± 0.10 | 11.806 ± 0.160 | 32 |
| 9.18 ± 0.10 | 9.638 ± 0.106 | 27 |
| 10.45 ± 0.10 | 8.469 ± 0.082 | 35 |
| 10.63 ± 0.10 | 8.323 ± 0.079 | 74 |
| 11.10 ± 0.10 | 7.973 ± 0.072 | 50 |
| 11.85 ± 0.10 | 7.468 ± 0.063 | 46 |
| 12.30 ± 0.10 | 7.195 ± 0.059 | 34 |
| 12.87 ± 0.10 | 6.879 ± 0.054 | 9 |
| 14.07 ± 0.10 | 6.293 ± 0.045 | 7 |
| 14.54 ± 0.10 | 6.092 ± 0.042 | 31 |
| 15.03 ± 0.10 | 5.897 ± 0.039 | 24 |
| 15.38 ± 0.10 | 5.763 ± 0.037 | 21 |
| 15.83 ± 0.10 | 5.599 ± 0.035 | 6 |
| 16.73 ± 0.10 | 5.299 ± 0.032 | 8 |
| 17.57 ± 0.10 | 5.049 ± 0.029 | 38 |
| 17.97 ± 0.10 | 4.937 ± 0.027 | 61 |
| 18.43 ± 0.10 | 4.813 ± 0.026 | 38 |
| 18.74 ± 0.10 | 4.736 ± 0.025 | 70 |
| 19.12 ± 0.10 | 4.642 ± 0.024 | 65 |
| 19.47 ± 0.10 | 4.559 ± 0.023 | 54 |
| 20.29 ± 0.10 | 4.377 ± 0.021 | 49 |
| 20.54 ± 0.10 | 4.324 ± 0.021 | 16 |
| 20.96 ± 0.10 | 4.239 ± 0.020 | 100 |
| 21.24 ± 0.10 | 4.183 ± 0.020 | 46 |
| 21.58 ± 0.10 | 4.119 ± 0.019 | 15 |
| 22.03 ± 0.10 | 4.035 ± 0.018 | 12 |
| 22.33 ± 0.10 | 3.982 ± 0.018 | 31 |
| 22.96 ± 0.10 | 3.873 ± 0.017 | 14 |
| 23.18 ± 0.10 | 3.837 ± 0.016 | 65 |
| 23.83 ± 0.10 | 3.734 ± 0.016 | 20 |
| 24.10 ± 0.10 | 3.693 ± 0.015 | 18 |
| 24.43 ± 0.10 | 3.643 ± 0.015 | 8 |
| 24.80 ± 0.10 | 3.590 ± 0.014 | 11 |
| 24.99 ± 0.10 | 3.564 ± 0.014 | 19 |
| 25.89 ± 0.10 | 3.442 ± 0.013 | 10 |
| 26.46 ± 0.10 | 3.369 ± 0.013 | 16 |
| 26.77 ± 0.10 | 3.330 ± 0.012 | 19 |
| 26.92 ± 0.10 | 3.312 ± 0.012 | 23 |
| 27.31 ± 0.10 | 3.266 ± 0.012 | 8 |
| 27.56 ± 0.10 | 3.237 ± 0.012 | 11 |
| 27.79 ± 0.10 | 3.210 ± 0.011 | 11 |
| 28.33 ± 0.10 | 3.151 ± 0.011 | 10 |
| 28.51 ± 0.10 | 3.131 ± 0.011 | 12 |
| 29.08 ± 0.10 | 3.071 ± 0.010 | 11 |
| 29.30 ± 0.10 | 3.049 ± 0.010 | 15 |

FIG. 5Q

| °2θ | d space(Å) | Intensity (%) |
|---|---|---|
| 6.22 ± 0.10 | 14.214 ± 0.232 | 33 |
| 7.49 ± 0.10 | 11.806 ± 0.160 | 32 |
| 9.18 ± 0.10 | 9.638 ± 0.106 | 27 |
| 10.45 ± 0.10 | 8.469 ± 0.082 | 35 |
| 10.63 ± 0.10 | 8.323 ± 0.079 | 74 |
| 11.10 ± 0.10 | 7.973 ± 0.072 | 50 |
| 11.85 ± 0.10 | 7.468 ± 0.063 | 46 |
| 12.30 ± 0.10 | 7.195 ± 0.059 | 34 |
| 14.54 ± 0.10 | 6.092 ± 0.042 | 31 |
| 15.03 ± 0.10 | 5.897 ± 0.039 | 24 |
| 15.38 ± 0.10 | 5.763 ± 0.037 | 21 |
| 17.57 ± 0.10 | 5.049 ± 0.029 | 38 |
| 17.97 ± 0.10 | 4.937 ± 0.027 | 61 |
| 18.43 ± 0.10 | 4.813 ± 0.026 | 38 |
| 18.74 ± 0.10 | 4.736 ± 0.025 | 70 |
| 19.12 ± 0.10 | 4.642 ± 0.024 | 65 |
| 19.47 ± 0.10 | 4.559 ± 0.023 | 54 |
| 20.29 ± 0.10 | 4.377 ± 0.021 | 49 |
| 20.96 ± 0.10 | 4.239 ± 0.020 | 100 |

FIG. 5R

| | |
|---|---|
| 750 | 1334 |
| 803 | 1354 |
| 828 | 1372 |
| 848 | 1393 |
| 892 | 1409 |
| 912 | 1437 |
| 928 | 1462 |
| 946 | 1529 |
| 979 | 1627 |
| 1001 | 1666 |
| 1013 | 1684 |
| 1029 | 1736 |
| 1047 | 2875 |
| 1081 | 2933 |
| 1098 | 2967 |
| 1113 | 3004 |
| 1132 | 3016 |
| 1179 | 3277 |
| 1225 | 3355 |
| 1258 | |
| 1302 | |

(Part i)

| °2θ | d space(Å) | Intensity (%) |
|---|---|---|
| 6.82 ± 0.10 | 12.961 ± 0.193 | 1 |
| 7.62 ± 0.10 | 11.602 ± 0.154 | 100 |
| 9.48 ± 0.10 | 9.330 ± 0.099 | 1 |
| 10.48 ± 0.10 | 8.441 ± 0.081 | 8 |
| 11.30 ± 0.10 | 7.831 ± 0.070 | 2 |
| 11.92 ± 0.10 | 7.425 ± 0.063 | 34 |
| 12.40 ± 0.10 | 7.138 ± 0.058 | 5 |
| 12.76 ± 0.10 | 6.938 ± 0.055 | 4 |
| 13.64 ± 0.10 | 6.492 ± 0.048 | 8 |
| 15.06 ± 0.10 | 5.883 ± 0.039 | 1 |
| 15.28 ± 0.10 | 5.799 ± 0.038 | 4 |
| 15.44 ± 0.10 | 5.739 ± 0.037 | 18 |
| 16.10 ± 0.10 | 5.505 ± 0.034 | 4 |
| 16.30 ± 0.10 | 5.438 ± 0.033 | 4 |
| 16.80 ± 0.10 | 5.277 ± 0.031 | 23 |
| 17.42 ± 0.10 | 5.091 ± 0.029 | 2 |
| 18.64 ± 0.10 | 4.760 ± 0.025 | 1 |
| 18.88 ± 0.10 | 4.700 ± 0.025 | 2 |
| 19.04 ± 0.10 | 4.661 ± 0.024 | 4 |
| 19.62 ± 0.10 | 4.525 ± 0.023 | 5 |
| 19.98 ± 0.10 | 4.444 ± 0.022 | 11 |
| 20.42 ± 0.10 | 4.349 ± 0.021 | 3 |
| 20.54 ± 0.10 | 4.324 ± 0.021 | 4 |
| 20.78 ± 0.10 | 4.275 ± 0.020 | 13 |
| 21.08 ± 0.10 | 4.215 ± 0.020 | 20 |
| 21.44 ± 0.10 | 4.145 ± 0.019 | 9 |
| 21.92 ± 0.10 | 4.073 ± 0.019 | 9 |
| 22.26 ± 0.10 | 3.994 ± 0.018 | 8 |
| 22.74 ± 0.10 | 3.911 ± 0.017 | 5 |
| 23.00 ± 0.10 | 3.867 ± 0.017 | 22 |
| 23.46 ± 0.10 | 3.792 ± 0.016 | 2 |
| 23.70 ± 0.10 | 3.754 ± 0.016 | 4 |
| 23.96 ± 0.10 | 3.714 ± 0.015 | 7 |
| 24.36 ± 0.10 | 3.654 ± 0.015 | 3 |
| 24.80 ± 0.10 | 3.590 ± 0.014 | 1 |
| 24.98 ± 0.10 | 3.565 ± 0.014 | 5 |
| 25.04 ± 0.10 | 3.556 ± 0.014 | 5 |
| 25.50 ± 0.10 | 3.493 ± 0.014 | 9 |
| 25.68 ± 0.10 | 3.469 ± 0.013 | 4 |
| 26.04 ± 0.10 | 3.422 ± 0.013 | 3 |
| 27.18 ± 0.10 | 3.281 ± 0.012 | 1 |
| 27.54 ± 0.10 | 3.239 ± 0.012 | 10 |
| 28.12 ± 0.10 | 3.173 ± 0.011 | 1 |
| 28.54 ± 0.10 | 3.128 ± 0.011 | 1 |

FIG. 6D

(Part i, cont.)

| °2θ | d space(Å) | Intensity (%) |
|---|---|---|
| 28.74 ± 0.10 | 3.106 ± 0.011 | 1 |
| 29.24 ± 0.10 | 3.054 ± 0.010 | 1 |
| 29.84 ± 0.10 | 2.994 ± 0.010 | 3 |

(Part ii)

| °2θ | d space(Å) | Intensity (%) |
|---|---|---|
| 7.62 ± 0.10 | 11.605 ± 0.154 | 100 |
| 11.92 ± 0.10 | 7.425 ± 0.063 | 34 |

FIG. 6D Cont.

| Atom | x | y | z | U(Å²) |
|---|---|---|---|---|
| S(18) | 0.72619(8) | 0.79926(4) | 0.87055(3) | 0.04457(17) |
| S(19) | 0.73741(6) | 0.92412(4) | 0.84650(3) | 0.03317(15) |
| O(2) | 0.39616(18) | 0.64887(10) | 0.76186(8) | 0.0316(4) |
| O(5) | 0.0571(2) | 0.62101(11) | 0.66529(8) | 0.0396(5) |
| O(8) | 0.2957(2) | 0.87917(12) | 0.55988(7) | 0.0402(5) |
| O(9) | 0.39738(16) | 0.83625(9) | 0.64311(7) | 0.0254(4) |
| O(12) | 0.21318(16) | 0.93294(10) | 0.71561(7) | 0.0276(4) |
| O(15) | 0.20258(18) | 0.87081(9) | 0.86375(7) | 0.0289(4) |
| O(992) | 0.3942(5) | 0.6203(2) | 0.92113(13) | 0.1061(13) |
| N(3) | 0.1983(2) | 0.72504(11) | 0.79174(8) | 0.0244(4) |
| N(6) | 0.1562(2) | 0.75285(12) | 0.67265(8) | 0.0254(4) |
| N(13) | 0.3770(2) | 1.01303(11) | 0.76464(8) | 0.0225(4) |
| N(16) | 0.4148(2) | 0.85655(11) | 0.81354(8) | 0.0244(4) |
| C(1) | 0.4394(2) | 0.76649(13) | 0.82829(10) | 0.0260(5) |
| C(2) | 0.3452(2) | 0.70730(12) | 0.79036(9) | 0.0239(5) |
| C(4) | 0.0942(2) | 0.67541(13) | 0.76015(10) | 0.0261(5) |
| C(S) | 0.1014(2) | 0.68069(13) | 0.69542(10) | 0.0284(5) |
| C(7) | 0.1870(3) | 0.75932(14) | 0.61150(9) | 0.0277(5) |
| C(8) | 0.2956(2) | 0.83207(14) | 0.60104(9) | 0.0267(5) |
| C(10) | 0.4987(2) | 0.90872(13) | 0.64219(10) | 0.0257(5) |
| C(11) | 0.4173(2) | 0.99065(13) | 0.66184(10) | 0.0262(5) |
| C(12) | 0.3269(2) | 0.97681(12) | 0.71596(9) | 0.0217(5) |
| C(14) | 0.3019(2) | 0.99764(13) | 0.81940(9) | 0.0237(5) |
| C(15) | 0.3019(2) | 0.90227(13) | 0.83411(9) | 0.0241(4) |
| C(17) | 0.6039(3) | 0.74551(14) | 0.82038(12) | 0.0345(6) |
| C(20) | 0.8888(2) | 0.92924(16) | 0.79557(12) | 0.0353(6) |
| C(21) | 0.8554(2) | 0.89294(15) | 0.73661(12) | 0.0349(6) |
| C(22) | 0.7200(2) | 0.92846(14) | 0.70797(10) | 0.0305(5) |
| C(23) | 0.6273(2) | 0.88080(14) | 0.67815(10) | 0.0278(5) |
| C(41) | -0.0031(3) | 0.62508(14) | 0.78584(11) | 0.0307(6) |
| C(42) | -0.0133(3) | 0.60926(17) | 0.84949(11) | 0.0387(6) |
| C(71) | -0.0326(3) | 0.8500(2) | 0.57879(14) | 0.0561(8) |
| C(72) | 0.0486(3) | 0.76556(19) | 0.57366(12) | 0.0410(7) |
| C(73) | 0.0804(4) | 0.7427(2) | 0.51117(13) | 0.0546(9) |
| C(141) | 0.3102(7) | 1.0316(2) | 0.92611(14) | 0.0858(16) |
| C(142) | 0.3747(3) | 1.05278(14) | 0.86738(11) | 0.0366(6) |
| C(143) | 0.3533(4) | 1.14704(15) | 0.85388(12) | 0.0425(7) |
| C(991) | 0.2516(10) | 0.5310(5) | 0.9888(3) | 0.148(3) |
| C(992) | 0.3885(10) | 0.5929(3) | 0.9682(2) | 0.136(3) |
| C(993) | 0.4703(13) | 0.5908(12) | 1.0100(3) | 0.317(9) |
| C(994) | 0.6139(11) | 0.6577(8) | 0.9894(3) | 0.213(5) |
| H(3) | 0.168(3) | 0.7622(18) | 0.8161(12) | 0.028(7)* |
| H(6) | 0.194(3) | 0.791(2) | 0.6909(13) | 0.036(7)* |
| H(13) | 0.451(3) | 1.0506(16) | 0.7618(11) | 0.022(6)* |
| H(16) | 0.483(4) | 0.8801(19) | 0.7926(13) | 0.038(8)* |

FIG. 6H

| Atom | x | y | z | U(Å²) |
|---|---|---|---|---|
| H(1) | 0.412 | 0.757 | 0.870 | 0.031 |
| H(7) | 0.239 | 0.705 | 0.600 | 0.033 |
| H(10) | 0.534 | 0.917 | 0.602 | 0.031 |
| H(14) | 0.197 | 1.016 | 0.815 | 0.028 |
| H(22) | 0.700 | 0.988 | 0.711 | 0.037 |
| H(23) | 0.644 | 0.821 | 0.680 | 0.033 |
| H(41) | -0.072 | 0.596 | 0.762 | 0.037 |
| H(72) | -0.021 | 0.721 | 0.588 | 0.049 |
| H(11A) | 0.491 | 1.036 | 0.669 | 0.031 |
| H(11B) | 0.351 | 1.010 | 0.630 | 0.031 |
| H(142) | 0.483 | 1.040 | 0.868 | 0.044 |
| H(14A) | 0.355 | 1.068 | 0.955 | 0.129 |
| H(14B) | 0.330 | 0.972 | 0.935 | 0.129 |
| H(14C) | 0.203 | 1.041 | 0.925 | 0.129 |
| H(14D) | 0.248 | 1.160 | 0.852 | 0.064 |
| H(14E) | 0.399 | 1.160 | 0.817 | 0.064 |
| H(14F) | 0.399 | 1.182 | 0.884 | 0.064 |
| H(17A) | 0.633 | 0.761 | 0.781 | 0.041 |
| H(17B) | 0.617 | 0.683 | 0.825 | 0.041 |
| H(20A) | 0.919 | 0.990 | 0.791 | 0.042 |
| H(20B) | 0.974 | 0.898 | 0.812 | 0.042 |
| H(21A) | 0.941 | 0.904 | 0.711 | 0.042 |
| H(21B) | 0.844 | 0.830 | 0.740 | 0.042 |
| H(42A) | 0.069 | 0.638 | 0.869 | 0.058 |
| H(42B) | -0.008 | 0.548 | 0.857 | 0.058 |
| H(42C) | -0.107 | 0.632 | 0.864 | 0.058 |
| H(71A) | -0.051 | 0.862 | 0.619 | 0.084 |
| H(71B) | -0.127 | 0.846 | 0.558 | 0.084 |
| H(71C) | 0.028 | 0.896 | 0.562 | 0.084 |
| H(73A) | 0.151 | 0.784 | 0.495 | 0.082 |
| H(73B) | -0.012 | 0.745 | 0.489 | 0.082 |
| H(73C) | 0.122 | 0.685 | 0.509 | 0.082 |
| H(99A) | 0.170 | 0.566 | 1.003 | 0.222 |
| H(99B) | 0.286 | 0.493 | 1.020 | 0.222 |
| H(99C) | 0.218 | 0.497 | 0.956 | 0.222 |
| H(99D) | 0.506 | 0.532 | 1.017 | 0.380 |
| H(99E) | 0.420 | 0.613 | 1.045 | 0.380 |
| H(99F) | 0.609 | 0.668 | 0.948 | 0.320 |
| H(99G) | 0.708 | 0.631 | 0.999 | 0.320 |
| H(99H) | 0.605 | 0.712 | 1.010 | 0.320 |

Starred atoms were refined isotropically. Hydrogen atoms included in calculation of structure factors but not refined. $U_{eq} = (1/3)\Sigma_i\Sigma_j U_{ij}a^*_i a^*_j a_i . a_j$

FIG. 6H Cont.

| Atom 1 | Atom 2 | Distance | Atom 1 | Atom 2 | Distance |
|---|---|---|---|---|---|
| S18 | C17 | 1.814(3) | C20 | H20A | 0.990 |
| S18 | S19 | 2.0354(9) | C20 | H20B | 0.990 |
| S19 | C20 | 1.812(3) | C21 | C22 | 1.502(3) |
| O2 | C2 | 1.219(3) | C21 | H21A | 0.990 |
| O5 | C5 | 1.234(3) | C21 | H21B | 0.990 |
| O8 | C8 | 1.206(3) | C22 | C23 | 1.319(3) |
| O9 | C8 | 1.344(3) | C22 | H22 | 0.950 |
| O9 | C10 | 1.460(2) | C23 | H23 | 0.950 |
| O12 | C12 | 1.238(3) | C41 | C42 | 1.500(4) |
| O15 | C15 | 1.235(3) | C41 | H41 | 0.950 |
| O992 | C992 | 1.174(5) | C42 | H42A | 0.980 |
| N3 | C2 | 1.360(3) | C42 | H42B | 0.980 |
| N3 | C4 | 1.425(3) | C42 | H42C | 0.980 |
| N3 | H3 | 0.86(3) | C71 | C72 | 1.518(5) |
| N6 | C5 | 1.342(3) | C71 | H71A | 0.980 |
| N6 | C7 | 1.449(3) | C71 | H71B | 0.980 |
| N6 | H6 | 0.80(3) | C71 | H71C | 0.980 |
| N13 | C12 | 1.343(3) | C72 | C73 | 1.521(4) |
| N13 | C14 | 1.461(3) | C72 | H72 | 1.000 |
| N13 | H13 | 0.89(3) | C73 | H73A | 0.980 |
| N16 | C15 | 1.337(3) | C73 | H73B | 0.980 |
| N16 | C1 | 1.468(3) | C73 | H73C | 0.980 |
| N16 | H16 | 0.87(3) | C141 | C142 | 1.519(4) |
| C1 | C17 | 1.537(3) | C141 | H14A | 0.980 |
| C1 | C2 | 1.537(3) | C141 | H14B | 0.980 |
| C1 | H1 | 1.000 | C141 | H14C | 0.980 |
| C4 | C41 | 1.324(3) | C142 | C143 | 1.521(3) |
| C4 | C5 | 1.505(3) | C142 | H142 | 1.000 |
| C7 | C8 | 1.524(3) | C143 | H14D | 0.980 |
| C7 | C72 | 1.534(3) | C143 | H14E | 0.980 |
| C7 | H7 | 1.000 | C143 | H14F | 0.980 |
| C10 | C23 | 1.498(3) | C991 | C992 | 1.645(10) |
| C10 | C11 | 1.548(3) | C991 | H99A | 0.980 |
| C10 | H10 | 1.000 | C991 | H99B | 0.980 |
| C11 | C12 | 1.514(3) | C991 | H99C | 0.980 |
| C11 | H11A | 0.990 | C992 | C993 | 1.221(11) |
| C11 | H11B | 0.990 | C993 | C994 | 1.737(18) |
| C14 | C15 | 1.532(3) | C993 | H99D | 0.990 |
| C14 | C142 | 1.556(3) | C993 | H99E | 0.990 |
| C14 | H14 | 1.000 | C994 | H99F | 0.980 |
| C17 | H17A | 0.990 | C994 | H99G | 0.980 |
| C17 | H17B | 0.990 | C994 | H99H | 0.980 |
| C20 | C21 | 1.512(4) | | | |

Numbers in prentheses are estimated standard deviations in the least significant digits.

FIG. 6I

| Atom 1 | Atom 2 | Atom 3 | Angle | Atom 1 | Atom 2 | Atom 3 | Angle |
|---|---|---|---|---|---|---|---|
| C17 | S18 | S19 | 107.47(8) | C12 | C11 | H11B | 109.10 |
| C20 | S19 | S18 | 105.01(9) | C10 | C11 | H11B | 109.10 |
| C8 | O9 | C10 | 117.31(17) | H11A | C11 | H11B | 107.80 |
| C2 | N3 | C4 | 121.61(19) | O12 | C12 | N13 | 121.38(19) |
| C2 | N3 | H3 | 118.0(19) | O12 | C12 | C11 | 121.60(19) |
| C4 | N3 | H3 | 119.8(19) | N13 | C12 | C11 | 117.02(18) |
| C5 | N6 | C7 | 121.01(19) | N13 | C14 | C15 | 110.75(16) |
| C5 | N6 | H6 | 125(2) | N13 | C14 | C142 | 109.46(18) |
| C7 | N6 | H6 | 113(2) | C15 | C14 | C142 | 112.42(17) |
| C12 | N13 | C14 | 120.29(17) | N13 | C14 | H14 | 108.00 |
| C12 | N13 | H13 | 118.0(16) | C15 | C14 | H14 | 108.00 |
| C14 | N13 | H13 | 121.4(16) | C142 | C14 | H14 | 108.00 |
| C15 | N16 | C1 | 123.18(19) | O15 | C15 | N16 | 122.88(19) |
| C15 | N16 | H16 | 121(2) | O15 | C15 | C14 | 120.84(18) |
| C1 | N16 | H16 | 115(2) | N16 | C15 | C14 | 116.27(18) |
| N16 | C1 | C17 | 108.95(18) | C1 | C17 | S18 | 114.61(18) |
| N16 | C1 | C2 | 111.18(17) | C1 | C17 | H17A | 108.60 |
| C17 | C1 | C2 | 109.94(18) | S18 | C17 | H17A | 108.60 |
| N16 | C1 | H1 | 108.90 | C1 | C17 | H17B | 108.60 |
| C17 | C1 | H1 | 108.90 | S18 | C17 | H17B | 108.60 |
| C2 | C1 | H1 | 108.90 | H17A | C17 | H17B | 107.60 |
| O2 | C2 | N3 | 122.4(2) | C21 | C20 | S19 | 114.94(16) |
| O2 | C2 | C1 | 123.57(19) | C21 | C20 | H20A | 108.50 |
| N3 | C2 | C1 | 114.00(18) | S19 | C20 | H20A | 108.50 |
| C41 | C4 | N3 | 122.2(2) | C21 | C20 | H20B | 108.50 |
| C41 | C4 | C5 | 120.7(2) | S19 | C20 | H20B | 108.50 |
| N3 | C4 | C5 | 117.05(18) | H20A | C20 | H20B | 107.50 |
| O5 | C5 | N6 | 122.3(2) | C22 | C21 | C20 | 115.1(2) |
| O5 | C5 | C4 | 120.6(2) | C22 | C21 | H21A | 108.50 |
| N6 | C5 | C4 | 117.04(19) | C20 | C21 | H21A | 108.50 |
| N6 | C7 | C8 | 109.42(18) | C22 | C21 | H21B | 108.50 |
| N6 | C7 | C72 | 114.0(2) | C20 | C21 | H21B | 108.50 |
| C8 | C7 | C72 | 112.88(19) | H21A | C21 | H21B | 107.50 |
| N6 | C7 | H7 | 106.70 | C23 | C22 | C21 | 122.8(2) |

FIG. 6J

| Atom 1 | Atom 2 | Atom 3 | Angle | Atom 1 | Atom 2 | Atom 3 | Angle |
|---|---|---|---|---|---|---|---|
| C8 | C7 | H7 | 106.70 | C23 | C22 | H22 | 118.60 |
| C72 | C7 | H7 | 106.70 | C21 | C22 | H22 | 118.60 |
| O8 | C8 | O9 | 123.0(2) | C22 | C23 | C10 | 128.5(2) |
| O8 | C8 | C7 | 125.7(2) | C22 | C23 | H23 | 115.80 |
| O9 | C8 | C7 | 111.31(18) | C10 | C23 | H23 | 115.80 |
| O9 | C10 | C23 | 104.73(16) | C4 | C41 | C42 | 125.6(2) |
| O9 | C10 | C11 | 109.88(16) | C4 | C41 | H41 | 117.20 |
| C23 | C10 | C11 | 116.62(18) | C42 | C41 | H41 | 117.20 |
| O9 | C10 | H10 | 108.40 | C41 | C42 | H42A | 109.50 |
| C23 | C10 | H10 | 108.40 | C41 | C42 | H42B | 109.50 |
| C11 | C10 | H10 | 108.40 | H42A | C42 | H42B | 109.50 |
| C12 | C11 | C10 | 112.53(17) | C41 | C42 | H42C | 109.50 |
| C12 | C11 | H11A | 109.10 | H42A | C42 | H42C | 109.50 |
| C10 | C11 | H11A | 109.10 | H42B | C42 | H42C | 109.50 |
| C72 | C71 | H71A | 109.50 | C14 | C142 | H142 | 108.60 |
| C72 | C71 | H71B | 109.50 | C142 | C143 | H14D | 109.50 |
| H71A | C71 | H71B | 109.50 | C142 | C143 | H14E | 109.50 |
| C72 | C71 | H71C | 109.50 | H14D | C143 | H14E | 109.50 |
| H71A | C71 | H71C | 109.50 | C142 | C143 | H14F | 109.50 |
| H71B | C71 | H71C | 109.50 | H14D | C143 | H14F | 109.50 |
| C71 | C72 | C73 | 111.8(3) | H14E | C143 | H14F | 109.50 |
| C71 | C72 | C7 | 114.0(2) | C992 | C991 | H99A | 109.50 |
| C73 | C72 | C7 | 112.1(2) | C992 | C991 | H99B | 109.50 |
| C71 | C72 | H72 | 106.10 | H99A | C991 | H99B | 109.50 |
| C73 | C72 | H72 | 106.10 | C992 | C991 | H99C | 109.50 |
| C7 | C72 | H72 | 106.10 | H99A | C991 | H99C | 109.50 |
| C72 | C73 | H73A | 109.50 | H99B | C991 | H99C | 109.50 |
| C72 | C73 | H73B | 109.50 | O992 | C992 | C993 | 136.2(12) |
| H73A | C73 | H73B | 109.50 | O992 | C992 | C991 | 121.3(8) |
| C72 | C73 | H73C | 109.50 | C993 | C992 | C991 | 102.1(8) |
| H73A | C73 | H73C | 109.50 | C992 | C993 | C994 | 102.7(9) |
| H73B | C73 | H73C | 109.50 | C992 | C993 | H99D | 111.20 |
| C142 | C141 | H14A | 109.50 | C994 | C993 | H99D | 111.20 |
| C142 | C141 | H14B | 109.50 | C992 | C993 | H99E | 111.20 |
| H14A | C141 | H14B | 109.50 | C994 | C993 | H99E | 111.20 |
| C142 | C141 | H14C | 109.50 | H99D | C993 | H99E | 109.10 |
| H14A | C141 | H14C | 109.50 | C993 | C994 | H99F | 109.50 |
| H14B | C141 | H14C | 109.50 | C993 | C994 | H99G | 109.50 |
| C141 | C142 | C143 | 110.3(2) | H99F | C994 | H99G | 109.50 |
| C141 | C142 | C14 | 110.9(2) | C993 | C994 | H99H | 109.50 |

FIG. 6J Cont.

| Atom 1 | Atom 2 | Atom 3 | Angle | Atom 1 | Atom 2 | Atom 3 | Angle |
|---|---|---|---|---|---|---|---|
| C143 | C142 | C14 | 109.7(2) | H99F | C994 | H99H | 109.50 |
| C141 | C142 | H142 | 108.60 | H99G | C944 | H99H | 109.50 |
| C143 | C142 | H142 | 108.60 | | | | |

Numbers in parentheses are estimated standard deviations in the least significant digits.

FIG. 6J Cont.

| °2θ | d space(Å) | Intensity (%) |
|---|---|---|
| 7.44 ± 0.10 | 11.885 ± 0.162 | 41 |
| 9.33 ± 0.10 | 9.483 ± 0.103 | 6 |
| 10.33 ± 0.10 | 8.564 ± 0.083 | 18 |
| 11.21 ± 0.10 | 7.890 ± 0.071 | 19 |
| 11.80 ± 0.10 | 7.500 ± 0.064 | 69 |
| 12.17 ± 0.10 | 7.274 ± 0.060 | 9 |
| 13.40 ± 0.10 | 6.606 ± 0.049 | 13 |
| 14.79 ± 0.10 | 5.989 ± 0.041 | 11 |
| 14.89 ± 0.10 | 5.949 ± 0.040 | 15 |
| 15.24 ± 0.10 | 5.813 ± 0.038 | 100 |
| 15.88 ± 0.10 | 5.582 ± 0.035 | 11 |
| 16.60 ± 0.10 | 5.342 ± 0.032 | 46 |
| 17.26 ± 0.10 | 5.136 ± 0.030 | 13 |
| 18.57 ± 0.10 | 4.779 ± 0.026 | 14 |
| 19.45 ± 0.10 | 4.563 ± 0.023 | 35 |
| 19.57 ± 0.10 | 4.536 ± 0.023 | 25 |
| 19.77 ± 0.10 | 4.491 ± 0.023 | 21 |
| 19.87 ± 0.10 | 4.468 ± 0.022 | 25 |
| 20.07 ± 0.10 | 4.424 ± 0.022 | 18 |
| 20.22 ± 0.10 | 4.391 ± 0.022 | 16 |
| 20.42 ± 0.10 | 4.349 ± 0.021 | 23 |
| 20.57 ± 0.10 | 4.317 ± 0.021 | 18 |
| 20.82 ± 0.10 | 4.266 ± 0.020 | 27 |
| 21.51 ± 0.10 | 4.131 ± 0.019 | 25 |
| 21.84 ± 0.10 | 4.069 ± 0.018 | 11 |
| 22.66 ± 0.10 | 3.924 ± 0.017 | 32 |
| 22.85 ± 0.10 | 3.893 ± 0.017 | 30 |
| 23.20 ± 0.10 | 3.835 ± 0.016 | 9 |
| 23.70 ± 0.10 | 3.755 ± 0.016 | 13 |
| 24.53 ± 0.10 | 3.629 ± 0.015 | 11 |
| 24.80 ± 0.10 | 3.590 ± 0.014 | 12 |
| 24.99 ± 0.10 | 3.564 ± 0.014 | 10 |
| 25.27 ± 0.10 | 3.525 ± 0.014 | 12 |
| 25.72 ± 0.10 | 3.464 ± 0.013 | 10 |
| 25.89 ± 0.10 | 3.442 ± 0.013 | 17 |
| 26.97 ± 0.10 | 3.306 ± 0.012 | 12 |

FIG. 6L

| °2θ | d space(Å) | Intensity (%) |
|---|---|---|
| 7.44 ± 0.10 | 11.885 ± 0.162 | 41 |
| 10.33 ± 0.10 | 8.564 ± 0.083 | 18 |
| 11.21 ± 0.10 | 7.890 ± 0.071 | 19 |
| 11.80 ± 0.10 | 7.500 ± 0.064 | 69 |
| 15.24 ± 0.10 | 5.813 ± 0.038 | 100 |
| 16.60 ± 0.10 | 5.342 ± 0.032 | 46 |

FIG. 6M

| | |
|---|---|
| 751 | 1254 |
| 781 | 1284 |
| 811 | 1300 |
| 845 | 1328 |
| 851 | 1348 |
| 860 | 1366 |
| 893 | 1404 |
| 913 | 1438 |
| 923 | 1470 |
| 939 | 1519 |
| 982 | 1654 |
| 998 | 1674 |
| 1034 | 1707 |
| 1102 | 1747 |
| 1111 | 2877 |
| 1174 | 2914 |
| 1183 | 2935 |
| 1197 | 2973 |
| 1224 | 3361 |
| 1244 | |

```
873
891
978
1121
1186
1252
1301
1351
1372
1392
1406
1438
1468
1519
1665
1743
2934
2964
```

(Part i)

| °2θ | d space(Å) | Intensity (%) |
|---|---|---|
| 7.11 ± 0.10 | 12.425 ± 0.177 | 13 |
| 8.12 ± 0.10 | 10.892 ± 0.136 | 58 |
| 8.64 ± 0.10 | 10.238 ± 0.120 | 46 |
| 8.95 ± 0.10 | 9.883 ± 0.111 | 74 |
| 10.06 ± 0.10 | 8.797 ± 0.088 | 25 |
| 10.78 ± 0.10 | 8.206 ± 0.077 | 48 |
| 11.30 ± 0.10 | 7.830 ± 0.070 | 37 |
| 11.47 ± 0.10 | 7.712 ± 0.068 | 32 |
| 11.96 ± 0.10 | 7.401 ± 0.062 | 28 |
| 12.75 ± 0.10 | 6.941 ± 0.055 | 25 |
| 14.80 ± 0.10 | 5.987 ± 0.041 | 31 |
| 15.45 ± 0.10 | 5.734 ± 0.037 | 28 |
| 16.04 ± 0.10 | 5.525 ± 0.034 | 27 |
| 16.84 ± 0.10 | 5.265 ± 0.031 | 44 |
| 17.36 ± 0.10 | 5.109 ± 0.029 | 38 |
| 17.88 ± 0.10 | 4.962 ± 0.028 | 45 |
| 18.15 ± 0.10 | 4.887 ± 0.027 | 47 |
| 18.71 ± 0.10 | 4.743 ± 0.025 | 85 |
| 19.37 ± 0.10 | 4.584 ± 0.024 | 51 |
| 20.06 ± 0.10 | 4.427 ± 0.022 | 53 |
| 20.44 ± 0.10 | 4.345 ± 0.021 | 74 |
| 20.96 ± 0.10 | 4.239 ± 0.020 | 60 |
| 21.27 ± 0.10 | 4.177 ± 0.020 | 100 |
| 21.75 ± 0.10 | 4.085 ± 0.019 | 47 |
| 23.07 ± 0.10 | 3.855 ± 0.017 | 53 |
| 23.90 ± 0.10 | 3.723 ± 0.015 | 52 |
| 24.49 ± 0.10 | 3.635 ± 0.015 | 46 |
| 24.73 ± 0.10 | 3.600 ± 0.014 | 42 |
| 26.02 ± 0.10 | 3.425 ± 0.013 | 47 |
| 26.99 ± 0.10 | 3.304 ± 0.012 | 50 |

(Part ii)

| °2θ | d space(Å) | Intensity (%) |
|---|---|---|
| 8.12 ± 0.10 | 10.892 ± 0.136 | 58 |
| 8.95 ± 0.10 | 9.883 ± 0.111 | 74 |
| 10.78 ± 0.10 | 8.206 ± 0.077 | 48 |
| 18.71 ± 0.10 | 4.743 ± 0.025 | 85 |

FIG. 8B

| °2θ | d space(Å) | Intensity (%) |
|---|---|---|
| 3.95 ± 0.10 | 22.395 ± 0.582 | 3 |
| 5.85 ± 0.10 | 15.106 ± 0.262 | 3 |
| 7.89 ± 0.10 | 11.207 ± 0.144 | 100 |
| 9.66 ± 0.10 | 9.155 ± 0.096 | 5 |
| 9.98 ± 0.10 | 8.865 ± 0.090 | 16 |
| 10.55 ± 0.10 | 8.388 ± 0.080 | 8 |
| 11.10 ± 0.10 | 7.973 ± 0.072 | 38 |
| 11.25 ± 0.10 | 7.866 ± 0.070 | 49 |
| 11.42 ± 0.10 | 7.752 ± 0.068 | 23 |
| 11.78 ± 0.10 | 7.511 ± 0.064 | 5 |
| 11.90 ± 0.10 | 7.437 ± 0.063 | 5 |
| 12.60 ± 0.10 | 7.024 ± 0.056 | 14 |
| 12.72 ± 0.10 | 6.960 ± 0.055 | 25 |
| 13.64 ± 0.10 | 6.493 ± 0.048 | 5 |
| 13.76 ± 0.10 | 6.438 ± 0.047 | 6 |
| 14.81 ± 0.10 | 5.983 ± 0.040 | 9 |
| 14.92 ± 0.10 | 5.936 ± 0.040 | 9 |
| 15.34 ± 0.10 | 5.775 ± 0.038 | 8 |
| 15.96 ± 0.10 | 5.553 ± 0.035 | 18 |
| 16.81 ± 0.10 | 5.273 ± 0.031 | 45 |
| 17.83 ± 0.10 | 4.974 ± 0.028 | 26 |
| 18.68 ± 0.10 | 4.749 ± 0.025 | 16 |
| 19.02 ± 0.10 | 4.666 ± 0.024 | 12 |
| 19.40 ± 0.10 | 4.575 ± 0.023 | 48 |
| 19.75 ± 0.10 | 4.494 ± 0.023 | 17 |
| 20.06 ± 0.10 | 4.428 ± 0.022 | 25 |
| 20.31 ± 0.10 | 4.373 ± 0.021 | 21 |
| 20.52 ± 0.10 | 4.328 ± 0.021 | 42 |
| 20.96 ± 0.10 | 4.239 ± 0.020 | 47 |
| 21.28 ± 0.10 | 4.176 ± 0.019 | 28 |
| 21.79 ± 0.10 | 4.078 ± 0.019 | 38 |
| 22.75 ± 0.10 | 3.910 ± 0.017 | 21 |
| 23.03 ± 0.10 | 3.862 ± 0.017 | 17 |
| 23.38 ± 0.10 | 3.805 ± 0.016 | 17 |
| 23.71 ± 0.10 | 3.752 ± 0.016 | 13 |
| 23.87 ± 0.10 | 3.729 ± 0.015 | 18 |
| 24.45 ± 0.10 | 3.641 ± 0.015 | 26 |
| 24.75 ± 0.10 | 3.597 ± 0.014 | 18 |
| 25.14 ± 0.10 | 3.543 ± 0.014 | 6 |
| 25.35 ± 0.10 | 3.513 ± 0.014 | 6 |
| 25.62 ± 0.10 | 3.477 ± 0.013 | 6 |
| 26.19 ± 0.10 | 3.403 ± 0.013 | 10 |
| 26.41 ± 0.10 | 3.375 ± 0.013 | 14 |
| 27.22 ± 0.10 | 3.276 ± 0.012 | 5 |
| 27.48 ± 0.10 | 3.246 ± 0.012 | 5 |
| 27.76 ± 0.10 | 3.214 ± 0.011 | 5 |

FIG. 8D

| °2θ | d space(Å) | Intensity (%) |
|---|---|---|
| 7.89 ± 0.10 | 11.207 ± 0.144 | 100 |
| 9.98 ± 0.10 | 8.865 ± 0.090 | 16 |
| 11.10 ± 0.10 | 7.973 ± 0.072 | 38 |
| 11.25 ± 0.10 | 7.866 ± 0.070 | 49 |
| 11.42 ± 0.10 | 7.752 ± 0.068 | 23 |
| 12.72 ± 0.10 | 6.960 ± 0.055 | 25 |
| 15.96 ± 0.10 | 5.553 ± 0.035 | 18 |
| 16.81 ± 0.10 | 5.273 ± 0.031 | 45 |
| 17.83 ± 0.10 | 4.974 ± 0.028 | 26 |
| 19.40 ± 0.10 | 4.575 ± 0.023 | 48 |

FIG. 8E

| | |
|---|---|
| 753 | 1343 |
| 765 | 1353 |
| 800 | 1375 |
| 816 | 1402 |
| 851 | 1419 |
| 868 | 1442 |
| 911 | 1478 |
| 981 | 1489 |
| 1000 | 1516 |
| 1029 | 1551 |
| 1047 | 1643 |
| 1100 | 1657 |
| 1123 | 1669 |
| 1176 | 1732 |
| 1205 | 2924 |
| 1227 | 2964 |
| 1254 | 3295 |
| 1291 | 3359 |
| 1304 | 3376 |
| 1320 | 3391 |
| 1330 | |

| °2θ | d space(Å) | Intensity (%) |
|---|---|---|
| 6.80 ± 0.10 | 12.999 ± 0.194 | 9 |
| 8.87 ± 0.10 | 9.970 ± 0.113 | 92 |
| 9.44 ± 0.10 | 9.369 ± 0.100 | 47 |
| 10.28 ± 0.10 | 8.605 ± 0.084 | 100 |
| 10.64 ± 0.10 | 8.315 ± 0.079 | 95 |
| 11.00 ± 0.10 | 8.044 ± 0.074 | 56 |
| 11.27 ± 0.10 | 7.851 ± 0.070 | 56 |
| 11.81 ± 0.10 | 7.494 ± 0.064 | 49 |
| 13.10 ± 0.10 | 6.758 ± 0.052 | 48 |
| 14.15 ± 0.10 | 6.259 ± 0.044 | 7 |
| 14.84 ± 0.10 | 5.970 ± 0.040 | 9 |
| 16.13 ± 0.10 | 5.495 ± 0.034 | 10 |
| 17.18 ± 0.10 | 5.162 ± 0.030 | 10 |
| 17.84 ± 0.10 | 4.972 ± 0.028 | 37 |
| 18.80 ± 0.10 | 4.720 ± 0.025 | 25 |
| 19.37 ± 0.10 | 4.583 ± 0.024 | 94 |
| 20.30 ± 0.10 | 4.375 ± 0.021 | 97 |
| 21.23 ± 0.10 | 4.185 ± 0.020 | 23 |
| 21.95 ± 0.10 | 4.049 ± 0.018 | 17 |
| 22.67 ± 0.10 | 3.922 ± 0.017 | 86 |
| 23.30 ± 0.10 | 3.818 ± 0.016 | 34 |
| 23.72 ± 0.10 | 3.751 ± 0.016 | 17 |
| 24.08 ± 0.10 | 3.696 ± 0.015 | 16 |
| 24.71 ± 0.10 | 3.603 ± 0.014 | 15 |
| 25.40 ± 0.10 | 3.507 ± 0.014 | 27 |
| 26.24 ± 0.10 | 3.396 ± 0.013 | 13 |
| 26.51 ± 0.10 | 3.362 ± 0.013 | 18 |
| 27.17 ± 0.10 | 3.282 ± 0.012 | 12 |

FIG. 9B

| °2θ | d space(Å) | Intensity (%) |
|---|---|---|
| 8.87 ± 0.10 | 9.970 ± 0.113 | 92 |
| 9.44 ± 0.10 | 9.369 ± 0.100 | 47 |
| 10.28 ± 0.10 | 8.605 ± 0.084 | 100 |
| 10.64 ± 0.10 | 8.315 ± 0.079 | 95 |
| 11.00 ± 0.10 | 8.044 ± 0.074 | 56 |
| 11.27 ± 0.10 | 7.851 ± 0.070 | 56 |
| 11.81 ± 0.10 | 7.494 ± 0.064 | 49 |
| 13.10 ± 0.10 | 6.758 ± 0.052 | 48 |

FIG. 9C

| °2θ | d space(Å) | Intensity (%) |
|---|---|---|
| 6.74 ± 0.10 | 13.114 ± 0.197 | 16 |
| 8.76 ± 0.10 | 10.092 ± 0.116 | 46 |
| 10.17 ± 0.10 | 8.701 ± 0.086 | 69 |
| 10.28 ± 0.10 | 8.603 ± 0.084 | 44 |
| 10.57 ± 0.10 | 8.372 ± 0.080 | 64 |
| 10.92 ± 0.10 | 8.104 ± 0.075 | 34 |
| 11.19 ± 0.10 | 7.911 ± 0.071 | 42 |
| 11.77 ± 0.10 | 7.519 ± 0.064 | 42 |
| 13.04 ± 0.10 | 6.789 ± 0.052 | 38 |
| 14.11 ± 0.10 | 6.277 ± 0.045 | 15 |
| 14.80 ± 0.10 | 5.988 ± 0.041 | 9 |
| 16.08 ± 0.10 | 5.511 ± 0.034 | 35 |
| 16.63 ± 0.10 | 5.330 ± 0.032 | 13 |
| 17.13 ± 0.10 | 5.175 ± 0.030 | 13 |
| 17.80 ± 0.10 | 4.982 ± 0.028 | 63 |
| 18.25 ± 0.10 | 4.860 ± 0.027 | 11 |
| 18.79 ± 0.10 | 4.723 ± 0.025 | 28 |
| 19.34 ± 0.10 | 4.589 ± 0.024 | 91 |
| 20.04 ± 0.10 | 4.430 ± 0.022 | 55 |
| 20.28 ± 0.10 | 4.380 ± 0.021 | 100 |
| 21.16 ± 0.10 | 4.198 ± 0.020 | 16 |
| 21.91 ± 0.10 | 4.056 ± 0.018 | 9 |
| 22.40 ± 0.10 | 3.969 ± 0.018 | 30 |
| 22.63 ± 0.10 | 3.929 ± 0.017 | 82 |
| 23.28 ± 0.10 | 3.820 ± 0.016 | 54 |
| 23.69 ± 0.10 | 3.757 ± 0.016 | 13 |
| 24.04 ± 0.10 | 3.702 ± 0.015 | 16 |
| 24.60 ± 0.10 | 3.618 ± 0.015 | 20 |
| 24.87 ± 0.10 | 3.580 ± 0.014 | 9 |
| 25.26 ± 0.10 | 3.526 ± 0.014 | 33 |
| 25.44 ± 0.10 | 3.501 ± 0.014 | 26 |
| 26.46 ± 0.10 | 3.369 ± 0.013 | 23 |
| 27.03 ± 0.10 | 3.299 ± 0.012 | 14 |
| 27.75 ± 0.10 | 3.215 ± 0.011 | 7 |
| 28.23 ± 0.10 | 3.161 ± 0.011 | 14 |
| 28.52 ± 0.10 | 3.130 ± 0.011 | 17 |
| 28.80 ± 0.10 | 3.100 ± 0.011 | 15 |
| 29.17 ± 0.10 | 3.062 ± 0.010 | 19 |

FIG. 9E

| °2θ | d space(Å) | Intensity (%) |
|---|---|---|
| 6.74 ± 0.10 | 13.114 ± 0.197 | 16 |
| 8.76 ± 0.10 | 10.092 ± 0.116 | 46 |
| 10.17 ± 0.10 | 8.701 ± 0.086 | 69 |
| 10.28 ± 0.10 | 8.603 ± 0.084 | 44 |
| 10.57 ± 0.10 | 8.372 ± 0.080 | 64 |
| 10.92 ± 0.10 | 8.104 ± 0.075 | 34 |
| 11.19 ± 0.10 | 7.911 ± 0.071 | 42 |
| 11.77 ± 0.10 | 7.519 ± 0.064 | 42 |
| 13.04 ± 0.10 | 6.789 ± 0.052 | 38 |
| 14.11 ± 0.10 | 6.277 ± 0.045 | 15 |
| 16.08 ± 0.10 | 5.511 ± 0.034 | 35 |
| 17.80 ± 0.10 | 4.982 ± 0.028 | 63 |
| 18.79 ± 0.10 | 4.723 ± 0.025 | 28 |
| 19.34 ± 0.10 | 4.589 ± 0.024 | 91 |
| 20.04 ± 0.10 | 4.430 ± 0.022 | 55 |
| 20.28 ± 0.10 | 4.380 ± 0.021 | 100 |

FIG. 9F

| | |
|---|---|
| 748 | 1403 |
| 828 | 1439 |
| 848 | 1479 |
| 892 | 1513 |
| 929 | 1641 |
| 982 | 1667 |
| 999 | 1734 |
| 1043 | 2876 |
| 1080 | 2929 |
| 1091 | 2964 |
| 1116 | 3005 |
| 1155 | 3340 |
| 1177 | 3365 |
| 1258 | 3394 |
| 1292 | 3424 |
| 1304 | |
| 1338 | |
| 1360 | |
| 1370 | |
| 1383 | |

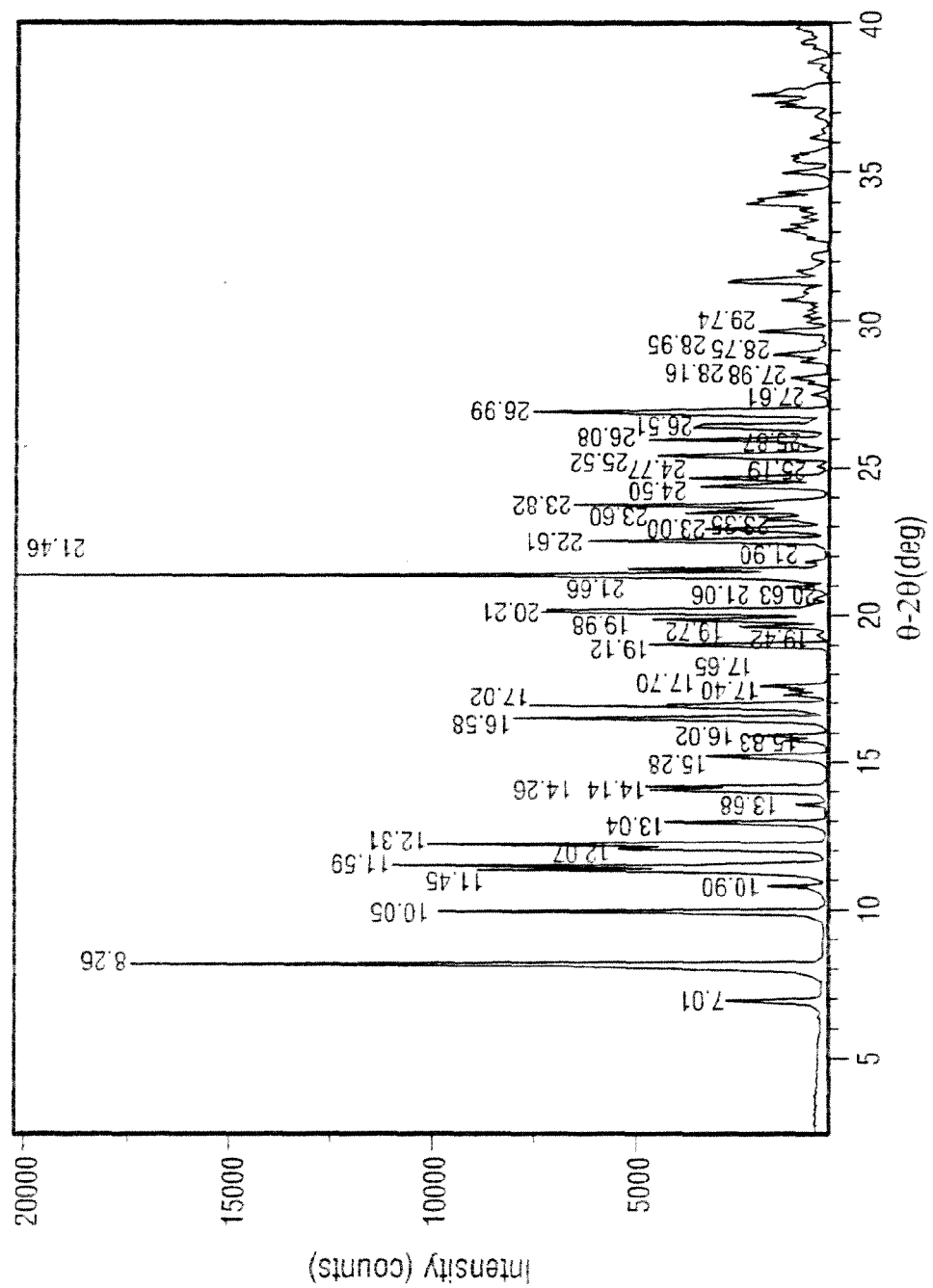

| °2θ | d space(Å) | Intensity (%) |
|---|---|---|
| 7.04 ± 0.10 | 12.555 ± 0.181 | 14 |
| 8.26 ± 0.10 | 10.703 ± 0.131 | 86 |
| 10.05 ± 0.10 | 8.802 ± 0.088 | 49 |
| 10.90 ± 0.10 | 8.116 ± 0.075 | 9 |
| 11.45 ± 0.10 | 7.726 ± 0.068 | 44 |
| 11.59 ± 0.10 | 7.638 ± 0.066 | 54 |
| 12.17 ± 0.10 | 7.272 ± 0.060 | 27 |
| 12.31 ± 0.10 | 7.193 ± 0.059 | 50 |
| 13.04 ± 0.10 | 6.789 ± 0.052 | 21 |
| 13.68 ± 0.10 | 6.475 ± 0.047 | 5 |
| 14.14 ± 0.10 | 6.262 ± 0.044 | 23 |
| 14.26 ± 0.10 | 6.211 ± 0.044 | 24 |
| 15.28 ± 0.10 | 5.799 ± 0.038 | 16 |
| 15.83 ± 0.10 | 5.598 ± 0.035 | 7 |
| 16.02 ± 0.10 | 5.534 ± 0.035 | 12 |
| 16.58 ± 0.10 | 5.346 ± 0.032 | 40 |
| 17.02 ± 0.10 | 5.210 ± 0.031 | 38 |
| 17.40 ± 0.10 | 5.096 ± 0.029 | 7 |
| 17.55 ± 0.10 | 5.053 ± 0.029 | 6 |
| 17.70 ± 0.10 | 5.010 ± 0.028 | 10 |
| 19.12 ± 0.10 | 4.641 ± 0.024 | 23 |
| 19.42 ± 0.10 | 4.570 ± 0.023 | 3 |
| 19.72 ± 0.10 | 4.501 ± 0.023 | 12 |
| 19.98 ± 0.10 | 4.445 ± 0.022 | 23 |
| 20.21 ± 0.10 | 4.394 ± 0.022 | 36 |
| 20.68 ± 0.10 | 4.296 ± 0.021 | 3 |
| 21.06 ± 0.10 | 4.218 ± 0.020 | 7 |
| 21.46 ± 0.10 | 4.140 ± 0.019 | 100 |
| 21.66 ± 0.10 | 4.102 ± 0.019 | 26 |
| 21.90 ± 0.10 | 4.059 ± 0.018 | 4 |
| 22.62 ± 0.10 | 3.932 ± 0.017 | 30 |
| 23.00 ± 0.10 | 3.867 ± 0.017 | 17 |
| 23.35 ± 0.10 | 3.810 ± 0.016 | 9 |
| 23.60 ± 0.10 | 3.770 ± 0.016 | 19 |
| 23.82 ± 0.10 | 3.736 ± 0.016 | 32 |
| 24.50 ± 0.10 | 3.633 ± 0.015 | 17 |
| 24.77 ± 0.10 | 3.594 ± 0.014 | 19 |
| 25.19 ± 0.10 | 3.536 ± 0.014 | 3 |
| 25.52 ± 0.10 | 3.490 ± 0.013 | 24 |
| 25.87 ± 0.10 | 3.443 ± 0.013 | 5 |
| 26.08 ± 0.10 | 3.417 ± 0.013 | 23 |

FIG. 10B

| °2θ | d space(Å) | Intensity (%) |
|---|---|---|
| 26.51 ± 0.10 | 3.362 ± 0.013 | 18 |
| 26.99 ± 0.10 | 3.303 ± 0.012 | 37 |
| 27.61 ± 0.10 | 3.231 ± 0.012 | 4 |
| 27.98 ± 0.10 | 3.189 ± 0.011 | 4 |
| 28.16 ± 0.10 | 3.169 ± 0.011 | 7 |
| 28.75 ± 0.10 | 3.105 ± 0.011 | 5 |
| 28.97 ± 0.10 | 3.083 ± 0.010 | 9 |
| 29.74 ± 0.10 | 3.005 ± 0.010 | 10 |

FIG. 10B Cont.

| °2θ | d space(Å) | Intensity (%) |
|---|---|---|
| 7.04 ± 0.10 | 12.555 ± 0.181 | 14 |
| 8.26 ± 0.10 | 10.703 ± 0.131 | 86 |
| 10.05 ± 0.10 | 8.802 ± 0.088 | 49 |
| 11.45 ± 0.10 | 7.726 ± 0.068 | 44 |
| 11.59 ± 0.10 | 7.638 ± 0.066 | 54 |
| 12.17 ± 0.10 | 7.272 ± 0.060 | 27 |
| 12.31 ± 0.10 | 7.193 ± 0.059 | 50 |
| 13.04 ± 0.10 | 6.789 ± 0.052 | 21 |
| 15.28 ± 0.10 | 5.799 ± 0.038 | 16 |
| 16.58 ± 0.10 | 5.346 ± 0.032 | 40 |
| 17.02 ± 0.10 | 5.210 ± 0.031 | 38 |
| 19.12 ± 0.10 | 4.641 ± 0.024 | 23 |

FIG. 10C

| | | |
|---|---|---|
| 748 | 1205 | 2965 |
| 781 | 1244 | 3222 |
| 809 | 1255 | 3257 |
| 830 | 1282 | 3344 |
| 845 | 1290 | 3366 |
| 892 | 1301 | |
| 910 | 1392 | |
| 919 | 1405 | |
| 929 | 1443 | |
| 942 | 1464 | |
| 961 | 1495 | |
| 980 | 1533 | |
| 998 | 1623 | |
| 1022 | 1654 | |
| 1035 | 1665 | |
| 1065 | 1701 | |
| 1099 | 1752 | |
| 1112 | 2832 | |
| 1141 | 2875 | |
| 1156 | 2895 | |
| 1182 | 2934 | |

| Form | Family and Space Group | Z'/Z[a] | Volume (Å³/cell) | Volume (Å³/molecule) | Data Type | Temperature | Material Type[b] |
|---|---|---|---|---|---|---|---|
| A | Monoclinic P2₁ (No.4) | 1/2 | 1415.45(4) | 708 | single crystal | 173K | anhydrous |
| B | Orthorhombic P2₁2₁2₁ (No.19) | 1/4 | 2914.1(4) | 729 | single crystal | 150K | anhydrous |
| C | Orthorhombic P2₁2₁2₁ (No.19) | 1/4 | 2862.26(16) | 716 | single crystal | 150K | hydrate (1-2 moles water) |
| E | Orthorhombic P2₁2₁2₁ (No.19) | 1/4 | 3120.66(19) | 780 | single crystal | 150K | solvate (1 mole tert-butanol) |
| I | Orthorhombic P2₁2₁2₁ (No.18) | 1/4 | 3900.1(2) | 975 | single crystal | 150K | solvate (1 mole chloroform)[c] |
| J | Orthorhombic P2₁2₁2₁ (No.19) | 1/4 | 3290.08(9) | 823 | single crystal | 150K | solvate (1 mole MEK)[d] |
| K | Orthorhombic P2₁2₁2₁ (No.19) | 2/8 | 6438.0 | 805 | XRPD | ambient temperature (283-303K) | unknown (¹H-NMR suggested 1 mole nitromethane) |
| L | Orthorhombic P2₁2₁2₁ (No.19) | 1/4 | 2894.604 | 724 | single crystal | ambient temperature (283-303K) | solvate (1 mole methanol) |
| N | Orthorhombic P2₁2₁2₁ (No.18) | 1/4 | 2860.5 | 715 | XRPD | ambient temperature (283-303K) | unknown (¹H-NMR suggests 1/3 mole nitromethane) |

[a] Z'=molecules of Compound I in asymmetric unit, Z=molecules of compound I in unit cell.
[b] Moles of solvent based on molecules of solvent in asymmetric unit from single crystal solution unless specified.
[c] Solution suggests additional chloroform outside of unit cell.
[d] MEK=methyl ethyl ketone (2-butanone).

FIG. 12

ROMIDEPSIN SOLID FORMS AND USES THEREOF

This application claims priority to U.S. Provisional Application No. 61/363,522, filed Jul. 12, 2010, which is incorporated herewith by reference in its entirety.

FIELD

Provided herein are solid forms of romidepsin and compositions comprising these forms. In some embodiments, provided are polymorphic forms of romidepsin. In some embodiments, provided are solvate forms of romidepsin. In some embodiments, provided is amorphous romidepsin. Also provided are methods for producing such forms and compositions.

BACKGROUND

Romidepsin is a natural product which was isolated from *Chromobacterium violaceum* by Fujisawa Pharmaceuticals. See Published Japanese Patent Application Hei 7 (1995)-64872; and U.S. Pat. No. 4,977,138, issued Dec. 11, 1990, each of which is incorporated herein by reference. Various preparations and purifications of romidepsin are described in PCT Publication WO 02/20817, which is incorporated herein by reference.

It is a bicyclic peptide consisting of four amino acid residues (D-valine, D-cysteine, dehydrobutyrine, and L-valine) and a novel acid (3-hydroxy-7-mercapto-4-heptenoic acid). Romidepsin is a depsipeptide which contains both amide and ester bonds. In addition to the production of *C. violaceum* using fermentation, romidepsin can also be prepared by synthetic or semi-synthetic means. The total synthesis of romidepsin reported by Kahn et al. (*J. Am. Chem. Soc.* 118: 7237-7238, 1996) involves 14 steps and yields romidepsin in 18% overall yield. The structure of romidepsin is shown below and referred to hereinafter as "Compound I":

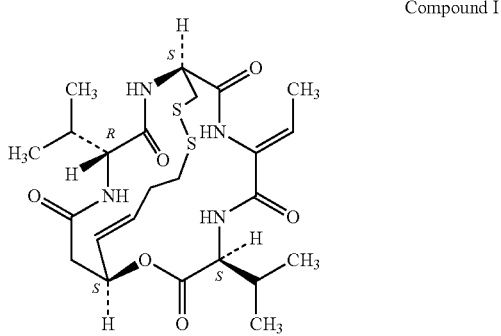

Compound I

Compound I has been shown to have anti-microbial, immunosuppressive, and anti-tumor activities. Compound I is approved in the U.S. for treatment of cutaneous T-cell lymphoma (CTCL) and peripheral T-cell lymphoma (PTCL), and is currently being tested, for example, for use in treating patients with other hematological malignancies (e.g., myeloma, etc.) and solid tumors (e.g., prostate cancer, pancreatic cancer, etc.). It is thought to act by selectively inhibiting deacetylases (e.g., histone deacetylase, tubulin deacetylase), promising new targets for the development of a new class of anti-cancer therapies (Nakajima et al., *Experimental Cell Res.* 241:126-133, 1998). One mode of action involves the inhibition of one or more classes of histone deacetylases (HDAC).

SUMMARY

In one aspect, provided herein are solid forms of Compound I.

In some embodiments, provided herein is a method of preparation of crystalline form C of Compound I and its characterization.

In some embodiments, provided herein is a method of preparation of crystalline form D of Compound I and its characterization.

In some embodiments, provided herein is a method of preparation of crystalline form E of Compound I and its characterization.

In some embodiments, provided herein is a method of preparation of crystalline form I of Compound I and its characterization.

In some embodiments, provided herein is a method of preparation of crystalline form J of Compound I and its characterization.

In some embodiments, provided herein is a method of preparation of crystalline form K of Compound I and its characterization.

In some embodiments, provided herein is a method of preparation of crystalline form L of Compound I and its characterization.

In some embodiments, provided herein is a method of preparation of crystalline form N of Compound I and its characterization.

In some embodiments, provided herein is a method of preparation of amorphous Compound I and its characterization.

In some embodiments, Compound I, and solid forms thereof, are used for the preparation of pharmaceutical compositions. In some embodiments, provided are compositions and formulations (e.g., pharmaceutical compositions and formulations) comprising solid forms of Compound I.

In another aspect, provided herein are methods to treat proliferative diseases, immune-mediated diseases, infectious diseases, certain circulatory diseases, and certain neurodegenerative diseases using Compound I, its solid forms and compositions comprising same. In some embodiments, provided herein are methods to treat cancer. In some embodiments, cancers include, but are not limited to, carcinomas, sarcomas, leukemias, lymphomas and the like. In certain embodiments, cancer is a hematological malignancy. In certain embodiments, cancer is a solid tumor.

In another aspect, provided herein are methods of electrolyte supplementation for patients receiving Compound I therapy.

DESCRIPTION OF THE DRAWINGS

FIG. 1(*b*) depicts a molecular structure for Compound I.

FIG. 1(*c*) depicts an XRPD for Compound I Form C collected at room temperature.

FIG. 1(*d*) tabulates observed peaks (part i); and prominent peaks (part ii) present in the XRPD of FIG. 1(*c*).

FIG. 1(*e*) depicts a DSC thermogram obtained for Compound I Form C.

FIG. 1(*f*) depicts a TGA thermogram obtained for Compound I Form C.

FIG. 2(b) tabulates observed peaks (part i); and prominent peaks (part ii) present in the XRPD of FIG. 2(a).

FIG. 3(b) tabulates observed peaks (part i); and prominent peaks (part ii) present in the XRPD of FIG. 3(a).

FIG. 3(i) depicts theoretical observed peaks (part i); and representative peaks (part ii) present in the XRPD of FIG. 3(h).

FIG. 3(n) tabulates positional parameters and estimated standard deviations for Compound I, Form E.

FIG. 3(o) tabulates bond distances (Angstroms) for Compound I, Form E.

FIG. 3(p) tabulates bond angles (degrees) for Compound I, Form E.

FIG. 4(b) tabulates observed peaks (part i); and prominent peaks (part ii) present in the XRPD of FIG. 4(a).

FIG. 5(b) tabulates observed peaks present in the XRPD of FIG. 5(a).

FIG. 5(h) depicts theoretical observed peaks (part i); and representative peaks (part ii) present in the XRPD of FIG. 5(g).

FIG. 5(m) tabulates positional parameters and estimated standard deviations for Compound I, Form I.

FIG. 5(n) tabulates bond distances (Angstroms) for Compound I, Form I.

FIG. 5(o) tabulates bond angles (degrees) for Compound I, Form I.

FIG. 5(q) tabulates observed peaks present in the XRPD of FIG. 5(p).

FIG. 5(r) tabulates prominent peaks present in the XRPD of FIG. 5(p).

FIG. 6(d) depicts theoretical observed peaks (part i); and prominent peaks (part ii) present in the XRPD of FIG. 6(c).

FIG. 6(h) tabulates positional parameters and estimated standard deviations for Compound I, Form J.

FIG. 6(i) tabulates bond distances (Angstroms) for Compound I, Form J.

FIG. 6(j) tabulates bond angles (degrees) for Compound I, Form J.

FIG. 6(l) tabulates observed peaks present in the XRPD of FIG. 6(k).

FIG. 6(m) tabulates prominent peaks present in the XRPD of FIG. 6(k).

FIG. 8(b) tabulates observed peaks (part i); and prominent peaks (part ii); present in the XRPD of FIG. 8(a).

FIG. 8(d) tabulates observed peaks present in the XRPD of FIG. 8(c).

FIG. 8(e) tabulates prominent peaks present in the XRPD of FIG. 8(c).

FIG. 9(b) tabulates observed peaks present in the XRPD of FIG. 9(a).

FIG. 9(c) tabulates prominent peaks present in the XRPD of FIG. 9(a).

FIG. 9(e) tabulates observed peaks present in the XRPD of FIG. 9(d).

FIG. 9(f) tabulates prominent peaks present in the XRPD of FIG. 9(d).

FIG. 10(a) depicts an XRPD for Compound I Form L.

FIG. 10(b) tabulates observed peaks present in the XRPD of FIG. 10(a).

FIG. 10(c) tabulates prominent peaks present in the XRPD of FIG. 10(a).

Figure 10D:
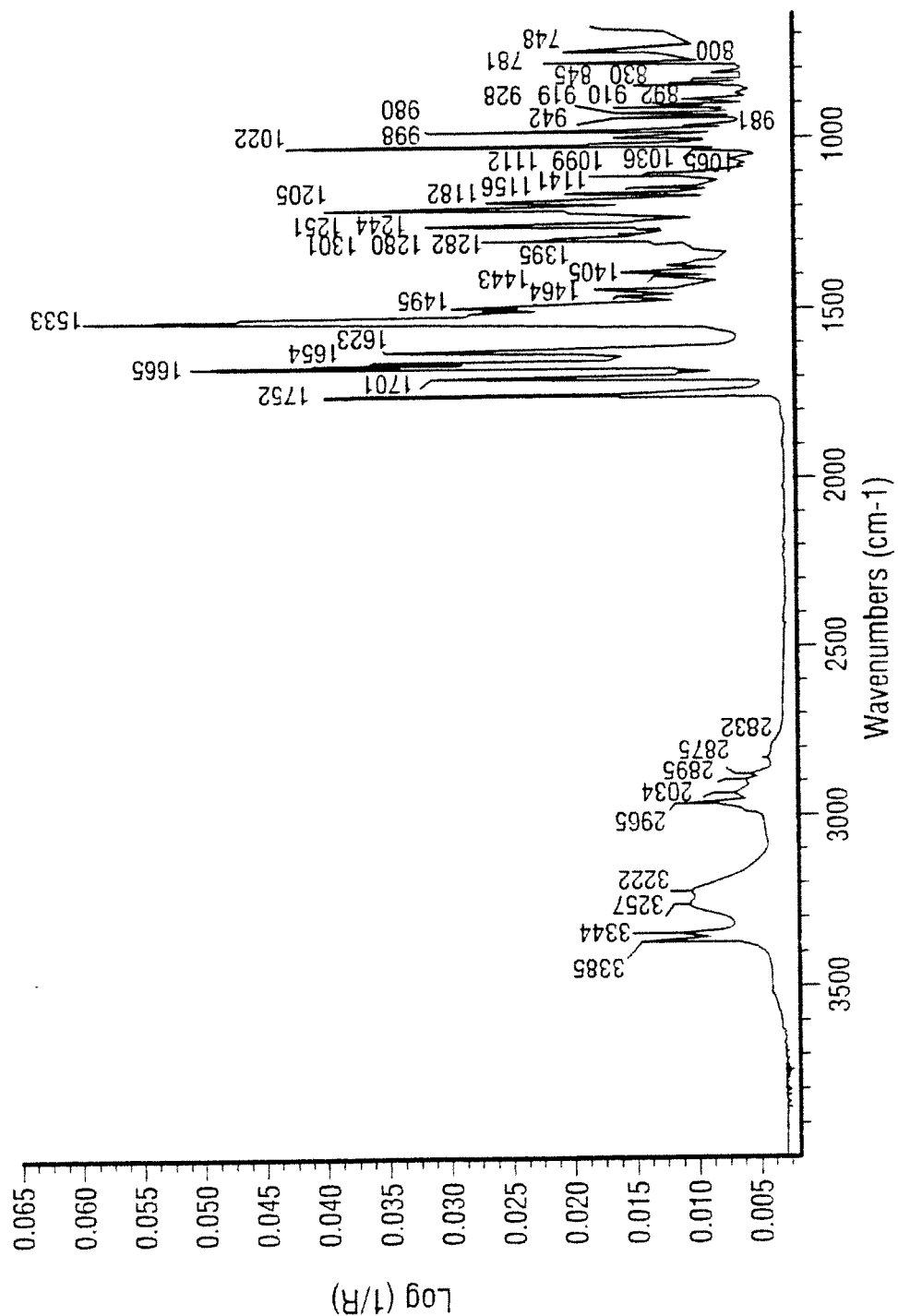

FIG. 10(d) depicts an FT-IR spectrum obtained for Compound I Form L.

Figures 10E, 10F:
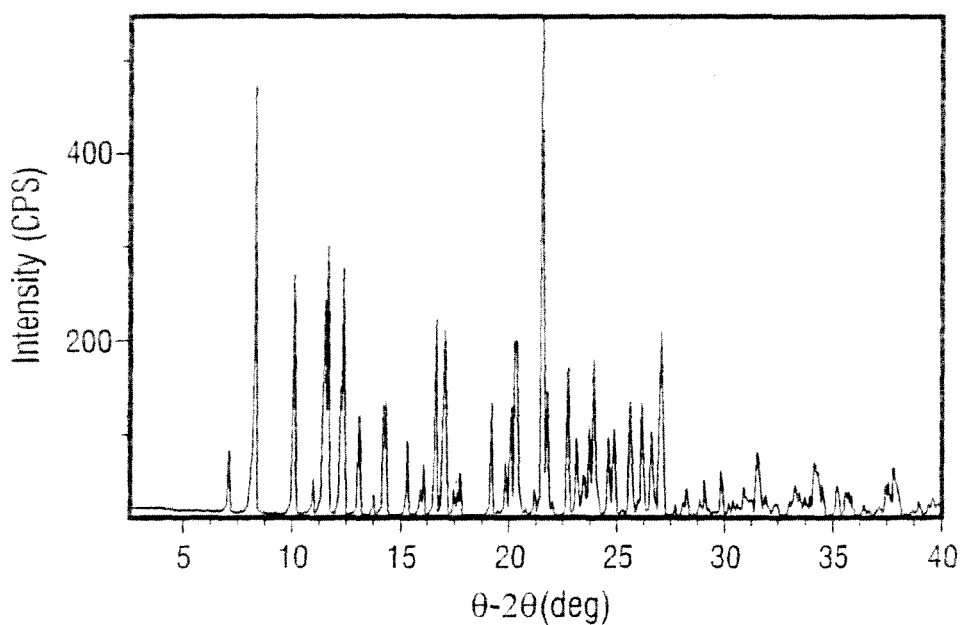

FIG. 10(e)) tabulates peak positions of bands present in the FT-IR spectrum of FIG. 10(d).

FIG. 10 (f) depicts Panalytical X-Pert Pro MPD PW3040 data for Compound I Form L.

Figure 10G:
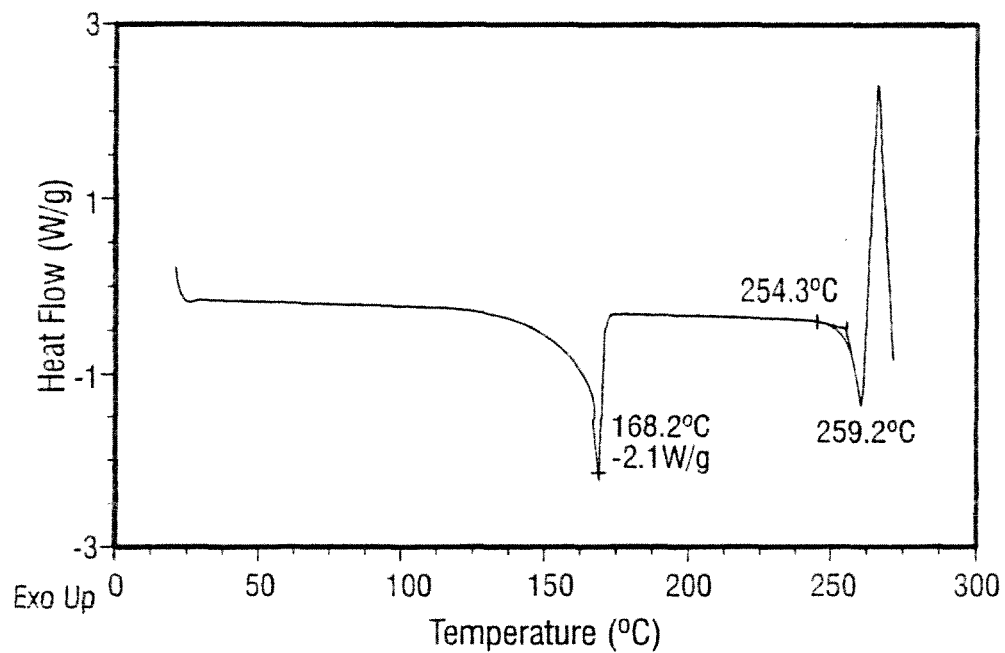

FIG. 10(g) depicts a DSC thermogram obtained for Compound I Form L.

Figure 10H:
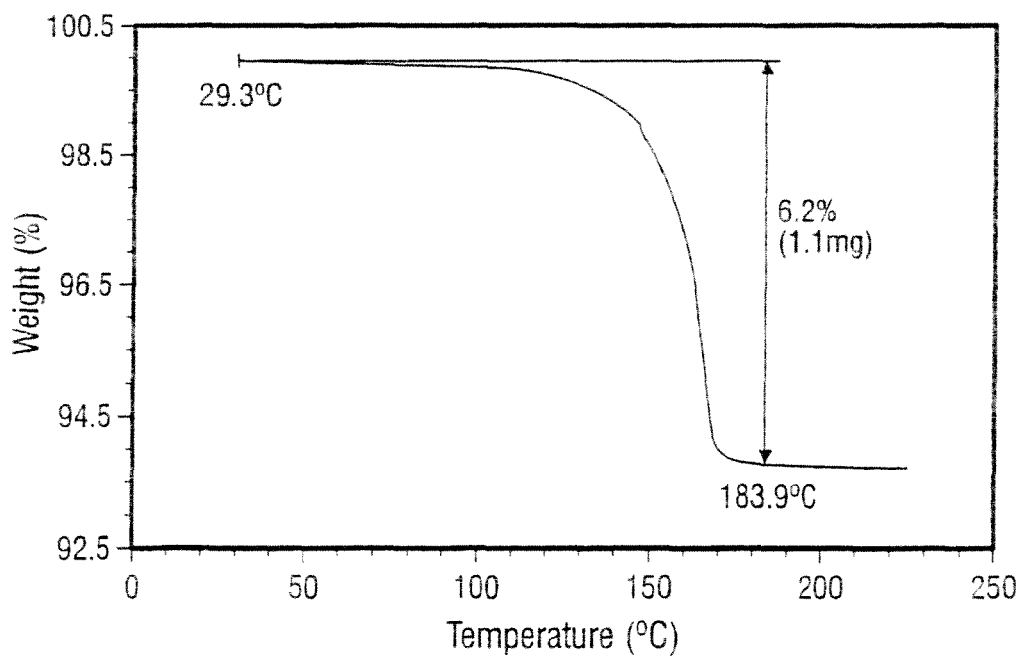

FIG. 10(h) depicts a TGA thermogram obtained for Compound I Form L.

Figure 10I:
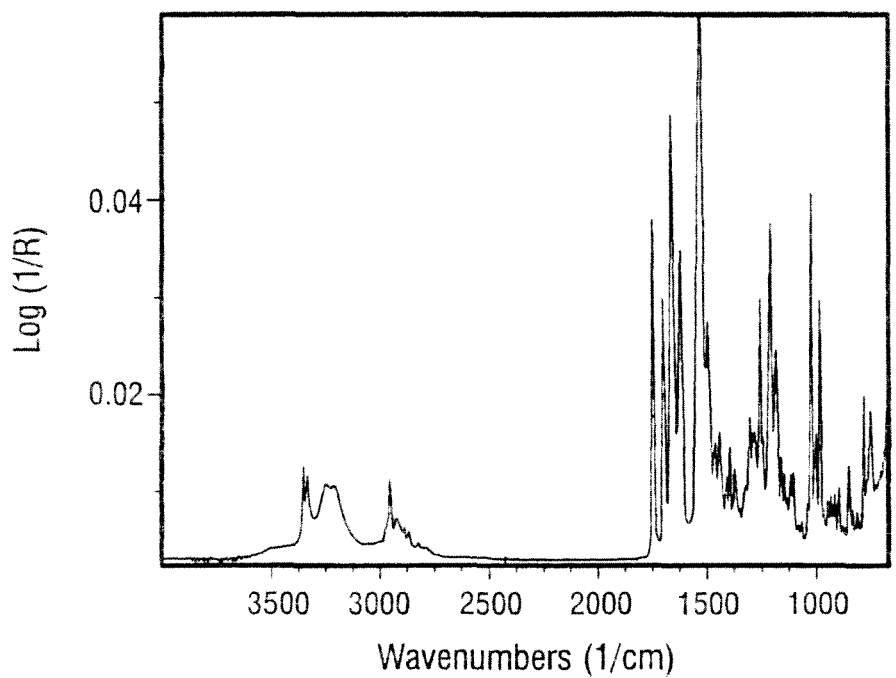

FIG. 10(i) depicts data for Compound I Form L.

FIG. 11 (a) depicts an XRPD for Compound I Form N.

Figure 11A:
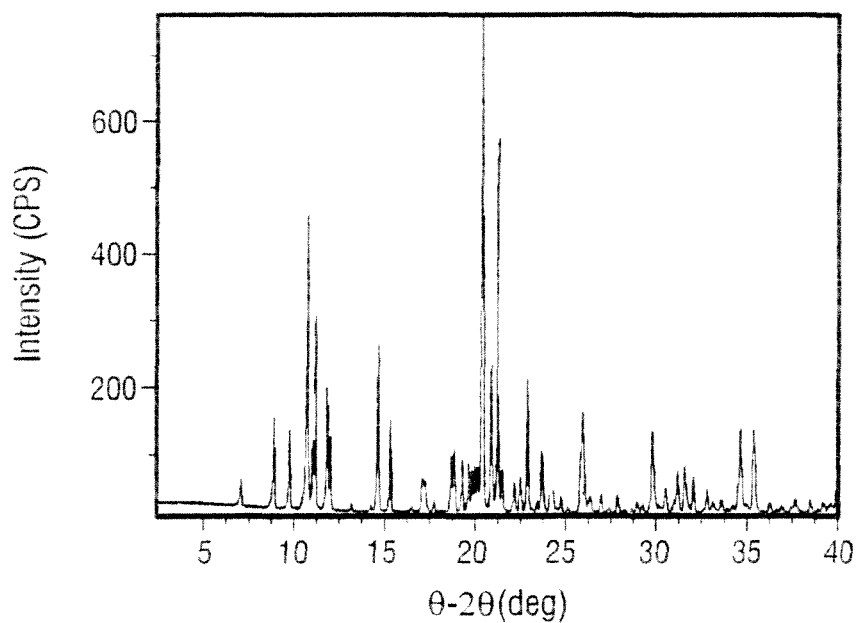
Figure 11B:
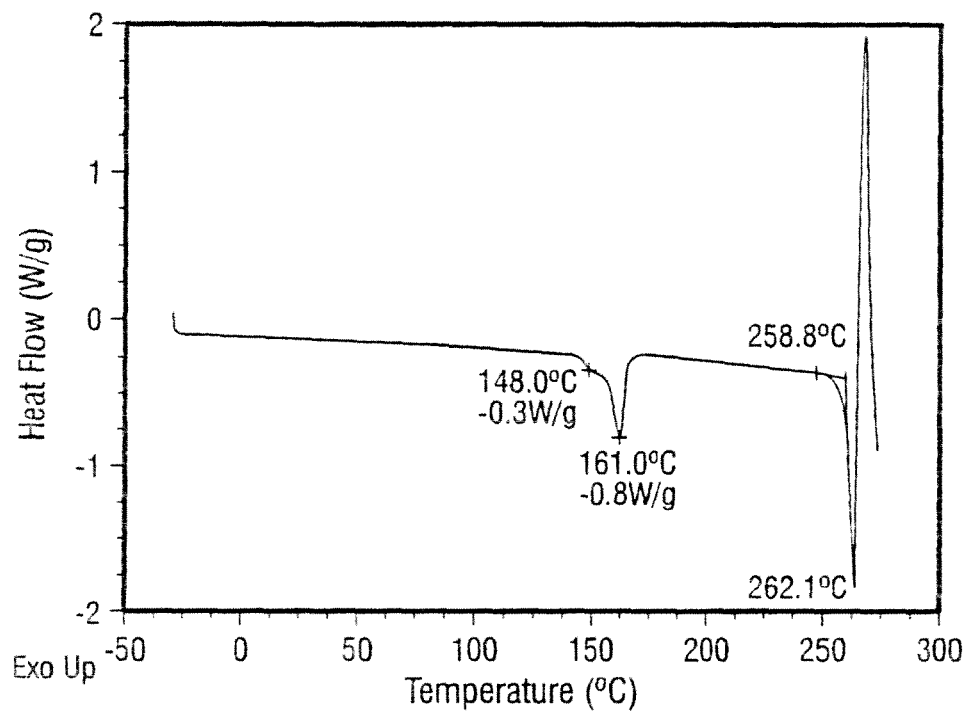

FIG. 11(b) depicts a DSC thermogram obtained for Compound I Form N.

Figure 11C:
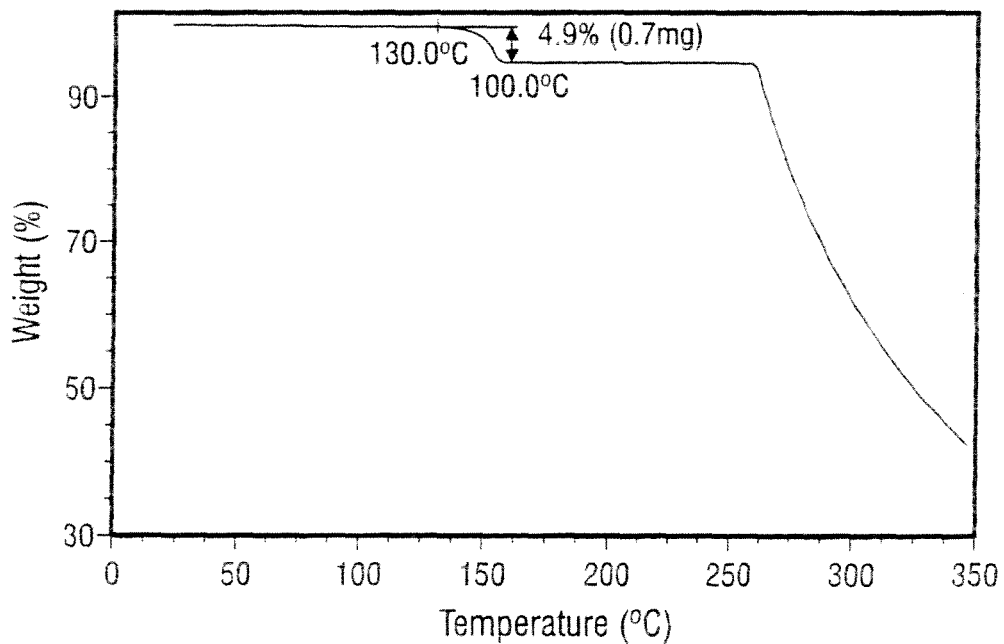

FIG. 11(c) depicts a TGA thermogram obtained for Compound I Form N.

FIG. 12 tabulates a single crystal structure summary for solid forms of Compound I.

DEFINITIONS

The terms "treat", "treating" or "treatment", as used herein, refer to a method of alleviating or abrogating a disease and/or its attendant symptoms. The terms "prevent", "preventing" or "prevention", as used herein, refer to a method of barring a subject from acquiring a disease.

The term "therapeutically effective amount" refers to that amount of the compound being administered sufficient to prevent development of or alleviate to some extent one or more of the symptoms of the condition or disorder being treated.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

The term "pharmaceutically acceptable salts" is meant to include salts of active compounds which are prepared with relatively nontoxic acids. Acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, et al. (1977) *J. Pharm. Sci.* 66:1-19).

A pharmaceutically acceptable salt form of a compound can be prepared in situ during the final isolation and purification of the compound, or separately by reacting the free base functionality with a suitable organic or inorganic acid. Examples of typical pharmaceutically acceptable, nontoxic acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods used in the art such as ion exchange. Other pharmaceutically acceptable salts can include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts can include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The terms, "polymorphs" and "polymorphic forms" and related terms refer to one of a variety of different crystal structures that can be adopted by a particular compound. In some embodiments, polymorphs occur when a particular chemical compound can crystallize in more than one structural arrangement. Different polymorphs may have different physical properties such as, for example, melting temperatures, heats of fusion, solubilities, dissolution rates and/or vibrational spectra as a result of the arrangement or conformation of the molecules in the crystal lattice. The differences in physical properties exhibited by polymorphs affect pharmaceutical parameters such as storage stability, compressibility and density (important in formulation and product manufacturing), and dissolution rates (an important factor in determining bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing, for example, one polymorph might be more likely to form solvates or might be difficult to filter and wash free of impurities (i.e., particle shape and size distribution might be different between one polymorph relative to the other).

Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion and sublimation. Polymorphism can be detected using thermal analysis, e.g., differential scanning calorimetry (DSC) and thermogravimetry (TGA).

Techniques for characterizing polymorphs include, but are not limited to, differential scanning calorimetry (DSC), X-ray powder diffractometry (XRPD), single crystal X-ray diffractometry, vibrational spectroscopy, e.g, IR and Raman spectroscopy, solution calorimetry, solid state NMR, hot stage optical microscopy, scanning electron microscopy (SEM), electron crystallography and quantitative analysis, particle size analysis (PSA), surface area analysis, solubility studies and dissolution studies.

The term, "solvate", as used herein, refers to a crystal form of a substance which contains solvent. The term "hydrate" refers to a solvate wherein the solvent is water.

The term, "desolvated solvate", as used herein, refers to a crystal form of a substance which can only be made by removing the solvent from a solvate.

The term "prodrug", as used herein, refers to structurally modified forms of the compound that readily undergo chemical changes under physiological conditions to provide the compound. Additionally, prodrugs can be converted to the compound by chemical or biochemical methods in an ex vivo environment. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity.

As used herein, the term "about", when used in reference to any degree 2-theta value recited herein, refers to the stated value±0.1 degree 2-theta.

The term "anhydrous", as used herein, refers to a form of a compound that is substantially free of water. One of skill in the art will appreciate that an anhydrous solid can contain various amounts of residual water wherein that water is not incorporated in the crystalline lattice. Such incorporation of residual water can depend upon a compound's hygroscopicity and storage conditions.

The term "hydrate", as used herein, refers to a crystal form adopted by a particular compound in which either a stoichiometric or non-stoichiometric amount of water is incorporated into the crystal lattice.

The term "carrier", as used herein, refers to any chemical (e.g., solvents, diluents, or other liquid vehicles, dispersion or suspension aids, surface active agents, isotonic agents, thickening or emulsifying agents, preservatives, solid binders, lubricants, and the like, as suited to the particular dosage form desired, Remington's *Pharmaceutical Sciences*, Fifteenth Edition, E. W. Martin (Mack Publishing Co., Easton, Pa., 1975)) consistent with the stability of Compound I. In certain embodiments, the term "carrier" refers to a pharmaceutically acceptable carrier. An exemplary carrier herein is water.

The term "characterized by", as used herein, means that a crystalline form is associated with a particular data set (e.g., one or more XRPD peaks, melting point, DSC, TGA, DSC-TGA, and/or other characterization methods known to one of skill in the art, or combinations thereof). In some embodiments, a solid form is "characterized by" a set of data when that set of data distinguishes the form from other known forms of the relevant compound and/or detects the presence of a particular form in a composition containing other entities (e.g., other forms of the compound and/or components that are not the compound). The present disclosure contains representative data obtained from a variety of different solid forms; comparison of provided data allows one of skill in the art to determine data sets that "characterize" any of the solid forms described herein.

The term "electrolyte supplementation", as used herein, refers to administration to a subject of a composition comprising one or more electrolytes in order to increase serum electrolyte levels in the subject. For purposes of the present disclosure, when electrolyte supplementation is administered "prior to, during, or after" therapy, it may be administered prior to initiation of combination inhibitor therapy (i.e., prior to administration of any dose) or prior to, concurrently with, or after any particular dose or doses.

The term "formulation", as used herein, refers to a composition that includes at least one active compound (e.g., at least a provided form of Compound I) in combination with one or more excipients or other pharmaceutical additives for administration to a patient. In general, particular excipients and/or other pharmaceutical additives are selected in accordance with knowledge in the art to achieve a desired stability, release, distribution and/or activity of active compound(s).

The phrase "in combination", as used herein, refers to administration of two or more agents to a subject. It will be appreciated that two or more agents are considered to be administered "in combination" whenever a subject is simultaneously exposed to both (or more) of the agents. Each of the two or more agents may be administered according to a different schedule; it is not required that individual doses of different agents be administered at the same time, or in the same composition. Rather, so long as both (or more) agents remain in the subject's body, they are considered to be administered "in combination".

The term "isostructural" or "isostructure", as used herein, refers to two or more solid forms of a compound containing essentially the same three-dimensional arrangement of geometrically similar structural units. In some embodiments, "isostructural" forms show with similar or identical unit cell dimensions, the same space group, and similar or identical atomic coordinates for common atoms. In some embodiments, "isostructural" forms have the same structure, but not the same cell dimensions nor the same chemical composition, and have comparable variability in their atomic coordinates to that of the cell dimensions and chemical composition. In some embodiments, the present disclosure describes a set of isostructural forms of Compound I including, for example, taken from forms of Compound I described infra. In some embodiments, the present disclosure describes a set of isostructural forms including, for example, Form J and/or Form D. In some embodiments, the present disclosure describes a set of isostructural forms including, for example, Form E and/or Form H. In some embodiments, the present disclosure describes a set of isostructural forms including, for example, Form C and/or the methanol solvate reported in Shigematsu et al., The Journal of Antibiotics, Vol. 47, No. 3, "FR901228, A Novel Antitumor Bicyclic Depsipeptide Produced by *Chromobacterium violaceum* No. 968, pp. 311-314 (March 1994).

The term "lyophilize", as used herein, refers to the process of isolating a solid substance from solution and/or removal of solvent. In some embodiments, this may be achieved by various techniques known to one of skill in the art, including, for example, evaporation (e.g., under vacuum, for example by rotary evaporation), freeze drying, and/or freezing the solution and vaporizing frozen solvent away under vacuum conditions, etc.

The term "parenteral" as used herein includes subcutaneous, intravenous, intramuscular, intra-articular, intra-synovial, intrasternal, intrathecal, intrahepatic, intralesional and intracranial injection or infusion techniques.

The term "substantially all", as used herein, when used to describe X-ray powder diffraction ("XRPD") peaks of a compound typically means that the XRPD of that compound includes at least about 80% of the peaks when compared to a reference. For example, when an XRPD is said to include "substantially all" of the peaks in a reference list, or all of the peaks in a reference XRPD, it means that the XRPD includes at least 80% of the peaks in the specified reference. In other embodiments, the phrase "substantially all" means that the XRPD of that compound includes at least about 85, 90, 95, 97, 98, or 99% of the peaks when compared to a reference.

The term "substantially free of", as used herein, means containing no more than an insignificant amount. In some embodiments, a composition or preparation is "substantially free of" a recited element if it contains less than 5%, 4%, 3%, 2%, or 1%, by weight of the element. In some embodiments, the composition or preparation contains less than 0.9%, 0.8%, 0.7%, 0.6%, 0.5%, 0.4%, 0.3%, 0.2%, 0.1% or less of the recited element. In some embodiments, the composition or preparation contains an undetectable amount of the recited element.

The term "substantially similar," as used herein, refers to data sets (e.g., spectra/thermograms) that share similarities with each other and/or that differentiate them from one or more reference data sets. In certain embodiments, data sets are considered to be "substantially similar" to one another when their similarities to each other and differences from one or more reference data sets are sufficient to permit a conclusion that the two compared data sets are taken of the same form of a compound, whereas the reference data set is/are taken of a different form of the compound. In some embodiments, two "substantially similar" data sets are the same (i.e., are identical within experimental error). In some embodiments, presence in a data set of one or more data points characteristic of a particular form of a compound, but absence of some or all data points that are characteristic of a different form (e.g., data points that are usually present in reference data set) defines data sets as substantially similar to each other.

The expression "unit dose", as used herein, refers to a physically discrete unit of a formulation appropriate for a subject to be treated (e.g., for a single dose); each unit containing a predetermined quantity of an active agent selected to produce a desired therapeutic effect (it being understood that multiple doses may be required to achieve a desired or optimum effect), optionally together with a pharmaceutically acceptable carrier, which may be provided in a predetermined amount. The unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may contain a variety of components in addition to the therapeutic agent(s). For example, acceptable carriers (e.g., pharmaceutically acceptable carriers), diluents, stabilizers, buffers, preservatives, etc., may be included as described infra. It will be understood, however, that the total daily usage of a formulation of the present disclosure will be decided by the attending physician within the scope of sound medical judgment. The specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

DETAILED DESCRIPTION

It has been found that Compound I can exist in a variety of solid forms. Such solid forms include neat crystal forms. Such solid forms also include solvated forms and amorphous forms. The present disclosure provides certain such solid forms of Compound I. In certain embodiments, the present disclosure provides compositions comprising Compound I in a form described herein. In some embodiments of provided compositions, Compound I is present as a mixture of one or more solid forms; in some embodiments of provided compositions, Compound I is present in only a single form.

In certain embodiments of the present disclosure, Compound I is provided as a crystalline solid. In certain embodiments, Compound I is provided as a crystalline solid substantially free of amorphous Compound I. In certain embodiments, Compound I is provided as an amorphous form. In certain embodiments, Compound I is provided as a solvated form.

In some embodiments, all of Compound I that is present in a particular composition is present in a particular form; in some such embodiments, the composition is substantially free of any other form of Compound I. In some embodiments, a composition comprises a Compound I, present in a combination of different forms.

In some embodiments, the present disclosure provides a lyophilate of Compound I containing one or more solid forms described herein. In some embodiments, a lyophilate comprises amorphous Compound I. In some embodiments, a lyophilate comprises one or more crystalline forms. In some embodiments, a lyophilate is substantially free of one or more crystalline forms. In some embodiments, a lyophilate is substantially free of any crystalline form.

In some embodiments, the present disclosure provides one or more solid forms as described herein, in combination with one or more other components. In some such embodiments, other components are selected from the group consisting of, for example, buffers, carriers, crystallization inhibitors, diluents, excipients, pH adjustors, solvents, or other pharmaceutical additives for administration to a patient.

In certain embodiments, where Compound I is in amorphous form (e.g., in certain lyophilates), such compositions comprise one or more crystallization inhibitors.

To characterize individual crystal forms of a particular compound, and/or to detect the presence of a particular form in a complex composition techniques known to those of skill in the art, such as that X-ray diffraction patterns, differential scanning calorimeter thermograms, thermal gravimetic analyzer thermograms, melting point information, polarized light microscopy, hotstage microscopy photomicrographs, dynamic vapor sorption/desorption information, water content, IR spectra, NMR spectra, and hygroscopicity profiles, to name a few, are used. Those of skill in the art will further appreciate that precise identity of all peaks, for example, in an X-ray diffraction pattern, is not required to reveal a match of crystal form. Rather, presence or absence of particular characteristic peaks, and/or patterns of peaks and intensities, are typically both necessary and sufficient to characterize and/or identify a particular form.

Solid Forms

The present disclosure provides solid forms of Compound I. In certain embodiments, the present disclosure provides Compound I in a crystalline form. In some embodiments, crystalline forms are substantially free of solvent. In some embodiments, crystalline forms are a solvate. In some embodiments, the present disclosure provides Compound I in an amorphous form. A summary table of the romidepsin solid forms (Table 1 is provided below.

In one embodiment, solid forms of Compound I provided herein possess improved properties. These properties include, but are not limited to, bioavailability, (including, without limitation, light and heat stability), solubility, compressability, flowability, electrostatic properties, bulk density, and rate of dissolution.

TABLE 1

| Romidepsin Solid Forms | | | | | | |
|---|---|---|---|---|---|---|
| Solid Form | | | | | | |
| | Form A (Desired Form) | Form B | Form C | Form D | Form E | Form H |
| Crystallization solvent system | Acetone/water (85/15)[1] | Acetone/hexanes (85/15) or acetone | Acetone/water (1/3) | Acetone/hexanes (1/4) or acetone | Tert-butyl alcohol/water (60/40) | Chloroform |

TABLE 1-continued

Romidepsin Solid Forms

| | | | | | | |
|---|---|---|---|---|---|---|
| Crystallization temperature | Room temperature | Room temperature | Cold (−5° C.) | Cold (−20° C.) | Room temperature | rotary evaporation at 60° C. |
| Thermal analysis (DSC)[3] | 254.4° C. (endo)[4] | 258.3° C. (endo)[4] | 83.6° C. (endo) 126.8° C. (endo) 171.9° C. (exo) 257.8° C. (endo) | 91.4° C. (exo) 260.6° C. (endo) | 158.1° C. (endo) 255.2° C. (endo) | 96.3° C. (endo) 256.6° C. (endo) |
| Slurry interconversion | Remains A | A + B → A (2 hrs) | A + C → A (2 hrs) | A + D → A, trace C (2.5 hrs) | A + E → A, trace E (2.5 hrs) | — |

[1]Crystallization occurs with addition of water to a final 15/85 acetone/water ratio.
[2]Crystallization occurs with seeding after addition of water to a final 1/3 acetone/water ratio.
[3] Samples analyzed in a crimped aluminum pan at 10° C./min, unless noted otherwise
[4] Sample analyzed in a crimped aluminum pan at 10° C./min with manual pinhole.

| | Solid Form | | | | | |
|---|---|---|---|---|---|---|
| | Form F | Form I | Form J | Form K | Form L | Form N |
| Crystallization solvent system | Chloroform | Chloroform slurry or vapor stress | Methyl ethyl ketone | Nitromethane | Dissolved solids in acetone and diffused with methanol | Nitromethane |
| Crystallization temperature | Room temperature | Room temperature | Room temperature or cold (−20° C.) | Room temperature | Room temperature | Room temperature |
| Thermal analysis (DSC)[1] | 83.6° C. (minor endo) 97.3° C. (endo) 256.4° C. (endo) | 73.8° C. (endo) 100.2° C. (endo) 257.8° C. (endo) | 130.3° C. (endo) 260.0° C. (endo)[2] | 68.8° C. (endo) 81.3° C. (endo) 145.9° C. (endo) 257.2° C. (endo) | 168.2° C. (endo) 259.2° C. (endo) | 150.0° C. (event) 259.1° C. (endo) |
| Slurry interconversion | — | — | — | — | — | — |

[1]Samples analyzed in a crimped aluminum pan at 10° C./min, unless noted otherwise.
[2]Sample analyzed in a hermetically-sealed aluminum pan at 10° C./min.

Crystalline Form A and Crystalline Form B

Compound I is known to exist in different crystalline forms, known as Form A and Form B. These forms are described in PCT Publication No. WO02/020817, filed Aug. 22, 2001, which is incorporated herein by reference.

Crystalline Form C

In some embodiments, the present disclosure provides Form C of Compound I, and compositions comprising Form C. In some embodiments, a composition comprising Compound I, contains at least some of Compound I in a crystalline form, which crystalline form comprises Form C.

In one embodiment, Compound I Form C is obtained from an acetone/water mixture.

In one embodiment, Compound I Form C is analyzed by one or more of optical microscopy, X-ray powder diffraction, differential scanning calorimetry, modulated differential scanning calorimetry, thermogravimetric analysis, infrared spectroscopy, nuclear magnetic resonance spectroscopy, and raman spectroscopy.

In some embodiments, crystalline Form C of Compound I is characterized by the presence of one or more, two or more, three or more, four or more, five or more, or six or more peaks from its XRPD pattern, which peaks, when taken alone or together with other characteristic data, distinguish Form C from other forms, as described infra. In one embodiment, Compound I Form C shows an X-ray diffraction having peaks substantially similar to those in FIG. 1(c). For example, Form C is characterized by a peak in the XRPD at about 11.45 2θ. Other characteristic peaks include 8.28, 12.19, and 21.13 2θ.

Figure 1A:
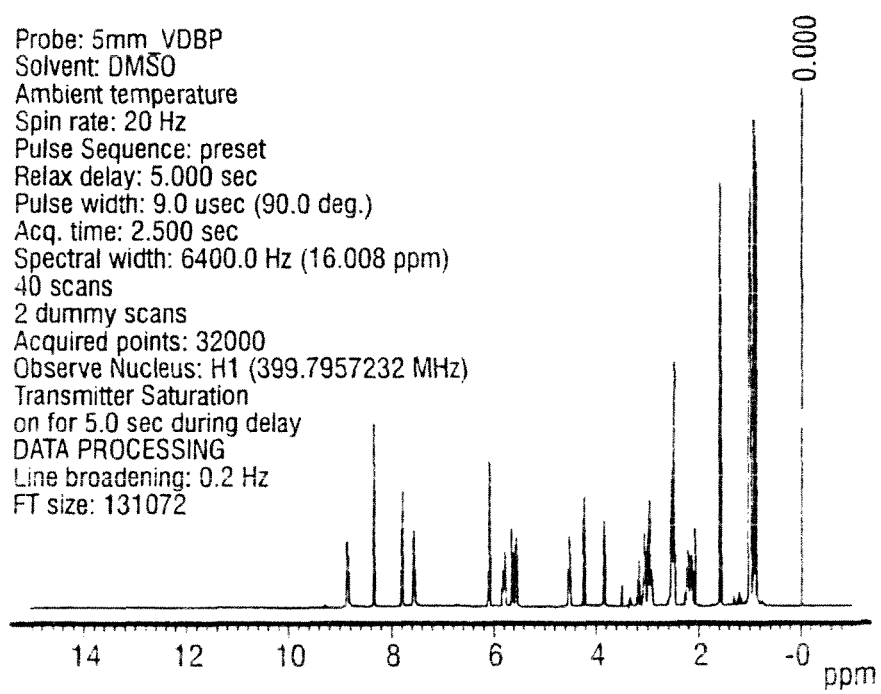
FIG. 1(*a*) depicts a representative solution $^1$HNMR spectrum obtained for Compound I.
FIG. 1(g) depicts an FT-IR spectrum obtained for Compound I Form C.
FIG. 1(h) tabulates peak positions of bands present in the FT-IR spectrum of FIG. 1(g).
FIG. 1(i) depicts a calculated XRPD for Compound I Form C collected at subambient temperature.
FIG. 1(j) depicts theoretical observed peaks (part i); and representative peaks (part ii) present in the XRPD of FIG. 1(i).
FIG. 1(k) depicts an ORTEP drawing of Compound I, Form C, water molecules not shown.
FIG. 1(l) depicts a packing diagram of Compound I, Form C viewed down the crystallographic a axis.
FIG. 1(m) depicts a packing diagram of Compound I, Form C viewed down the crystallographic b axis.
FIG. 1(n) depicts a packing diagram of Compound I, Form C viewed down the crystallographic c axis.
FIG. 1(o) tabulates positional parameters and estimated standard deviations for Compound I, Form C.
FIG. 1(p) tabulates bond distances (Angstroms) for Compound I, Form C.
FIG. 1(q) tabulates bond angles (degrees) for Compound I, Form C.
Figure 1B:
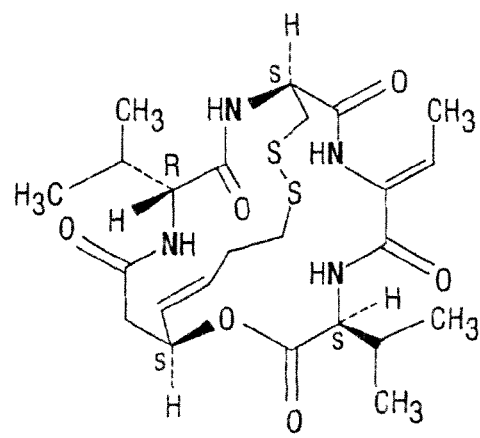
Figure 1C:
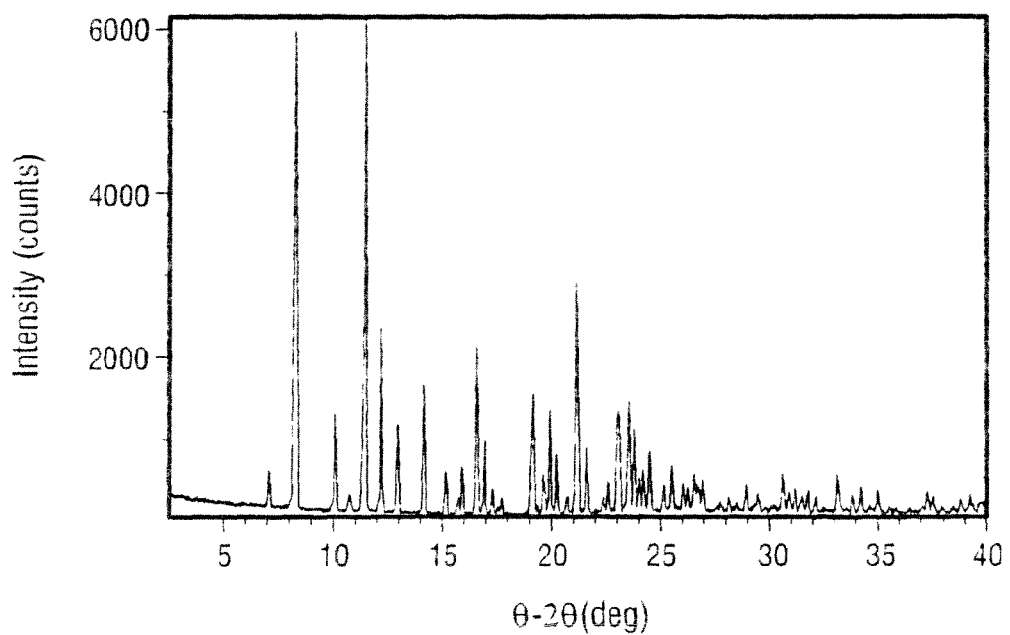

As described herein, crystalline Form C of Compound I is characterized, for example, by some or all, of the exemplary data provided in FIGS. 1(c) through 1(q), infra (and discussed in Example 2). In one embodiment, a DSC thermogram obtained for Compound I Form C exhibits broad endothermic events at ~140° C. (min); an endotherm at ~257° C. (min); and a minor exothermic event at approximately 177° C. (max). In one embodiment, a TGA thermogram obtained for Compound I Form C exhibits a weight loss of ~5.3%.

In some embodiments, Form C is isostructural with the methanol solvate reported in Shigematsu et al., *The Journal of Antibiotics*, Vol. 47(3) "FR901228, A Novel Antitumor Bicyclic Depsipeptide Produced by *Chromobacterium violaceum* No. 968, pp. 311-314 (March 1994).

Crystalline Form D

In some embodiments, the present disclosure provides a crystalline form obtained from acetone. In some embodiments, the acetone is cold. In some embodiments, the acetone has a temperature of −15° C. or lower (e.g., −25° C., −35° C., −50° C., −70° C. or lower). In some embodiments, such a crystalline form is a solvate. In some embodiments, an acetone solvate is referred to as Form D of Compound I. In some embodiments, Form D may be isostructural with Form J described infra.

In one embodiment, Compound I Form D is analyzed by one or more of optical microscopy, X-ray powder diffraction, differential scanning calorimetry, modulated differential scanning calorimetry, thermogravimetric analysis, infrared spectroscopy, nuclear magnetic resonance spectroscopy, and raman spectroscopy.

In some embodiments, the present disclosure provides Form D of Compound I, and compositions comprising Form D. In some embodiments, a composition comprising Compound I contains at least some of Compound I in a crystalline form, which crystalline form comprises Form D. In some embodiments, a composition comprising Compound I contains at least some of Compound I in a solvated crystalline form, which crystalline form comprises Form D. In certain embodiments, the solvated form is an acetone solvate.

In some embodiments, crystalline Form D of Compound I is characterized by the presence of one or more, two or more, three or more, four or more, five or more, or six or more peaks from its XRPD pattern, which peaks, when taken alone or together with other characteristic data, distinguish Form D from other forms, as described infra. In one embodiment, Compound I Form D shows an X-ray diffraction having peaks substantially similar to those in FIG. 2(a). For example, Form D is characterized by a peak in the XRPD at about 7.54 2θ. Other characteristic peaks include 11.86 and 16.66 2θ.

As described herein, Compound I Form D is characterized by some or all of the exemplary data provided in 2(a) through 2(f), infra (and discussed in Example 3). In one embodiment, a DSC thermogram obtained for Compound I Form D exhibits a small endothermic event at ~91° C. (min); and an endotherm at ~261° C. (min); followed by apparent decomposition. In one embodiment, a TGA thermogram obtained for Compound I Form D exhibits a weight loss of ~10.9%.

Crystalline Form E

In some embodiments, the present disclosure provides a crystalline form obtained from t-butanol. In some embodiments, the present disclosure provides a crystalline form obtained from a mixture of t-butanol and water. In some embodiments, such a crystalline form is a solvate. In some embodiments, a t-butanol solvate is referred to as Form E of Compound I. In some embodiments, Form E may be isostructural with Form H described infra.

In some embodiments, the present disclosure provides Form E of Compound I, and compositions comprising Form E. In some embodiments, a composition comprising Compound I, contains at least some of Compound I in a crystalline form, which crystalline form comprises Form E. In some embodiments, a composition comprising Compound I, contains at least some of Compound I in a solvated crystalline form, which crystalline form comprises Form E. In certain embodiments, the solvated form is a t-butanol solvate.

In one embodiment, Compound I Form E is analyzed by one or more of optical microscopy, X-ray powder diffraction, differential scanning calorimetry, modulated differential scanning calorimetry, thermogravimetric analysis, infrared spectroscopy, nuclear magnetic resonance spectroscopy, and raman spectroscopy.

In some embodiments, crystalline Form E of Compound I is characterized by the presence of one or more, two or more, three or more, four or more, five or more, or six or more peaks from its XRPD pattern, which peaks, when taken alone or together with other characteristic data, distinguish Form E from other forms, as described infra. In one embodiment, Compound I Form E shows an X-ray diffraction having peaks substantially similar to those in FIG. 3(a). For example, Form E is characterized by a peak in the XRPD at about 10.3 2θ. Other characteristic peaks include 9.0, 11.7, and 20.04 2θ.

Figure 2A:
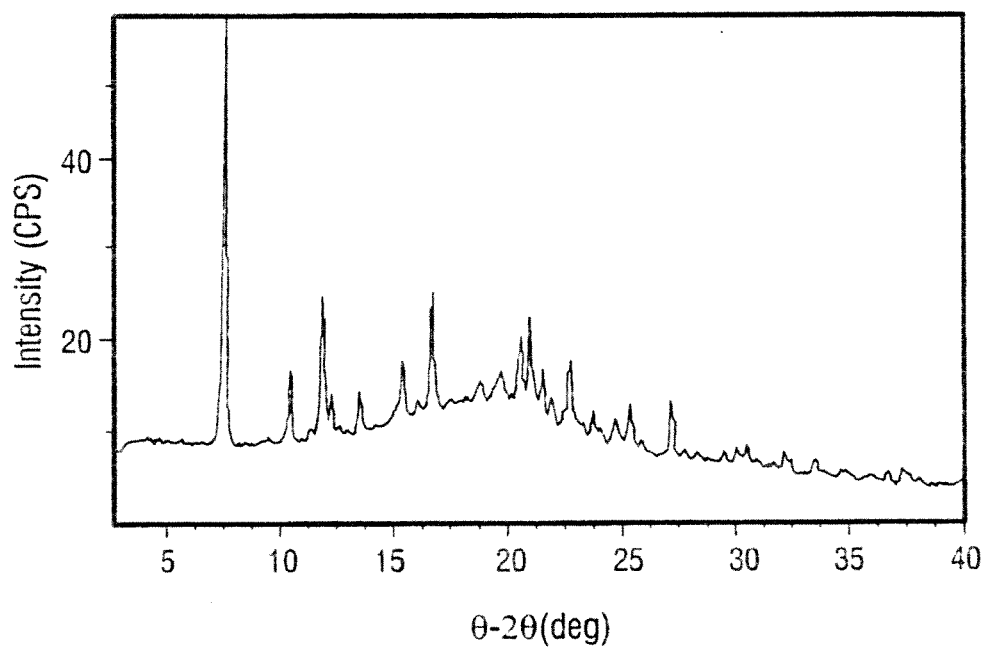
FIG. 2(a) depicts an XRPD for Compound I Form D collected at room temperature.
Figure 2C:
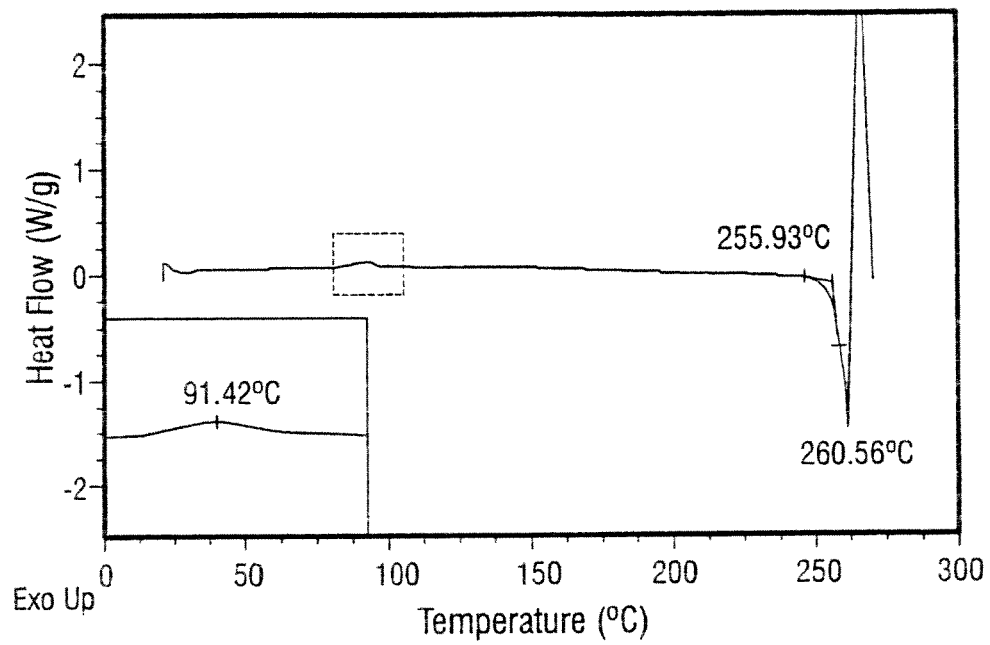
FIG. 2(c) depicts a DSC thermogram obtained for Compound I Form D.
Figure 2D:
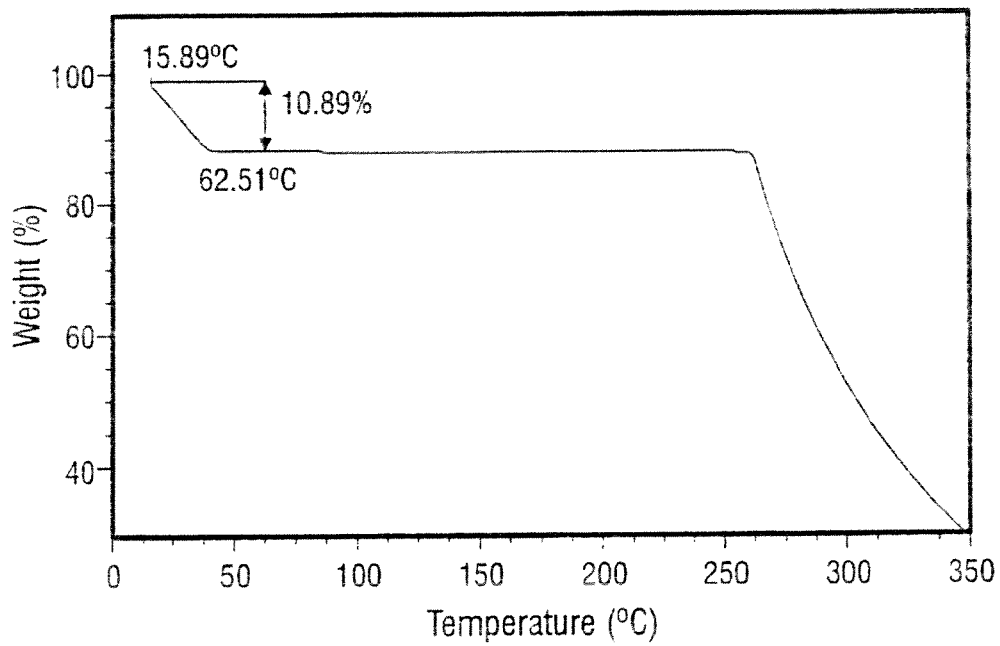
FIG. 2(d) depicts a TGA thermogram obtained for Compound I Form D.
Figure 2E:
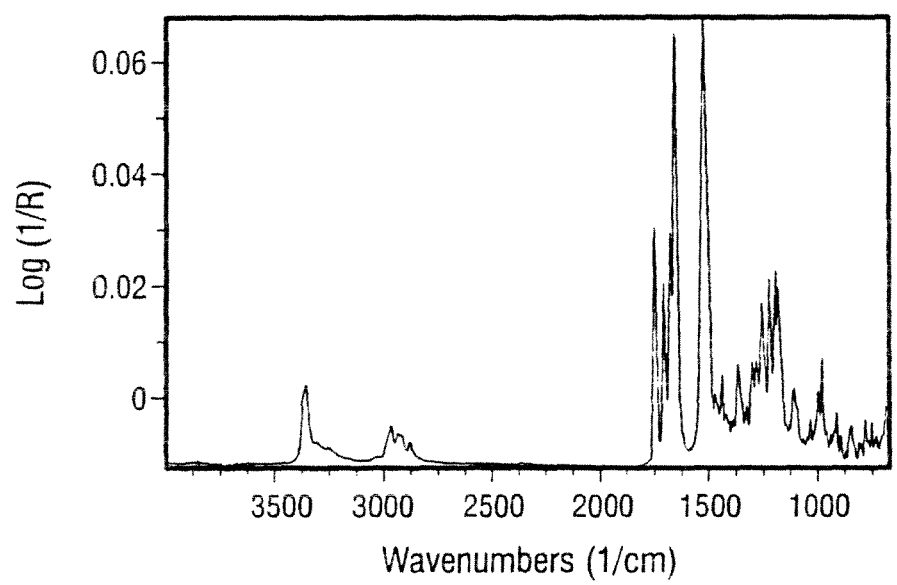
FIG. 2(e) depicts an FT-IR spectrum obtained for Compound I Form D.
Figures 2F, 3A:
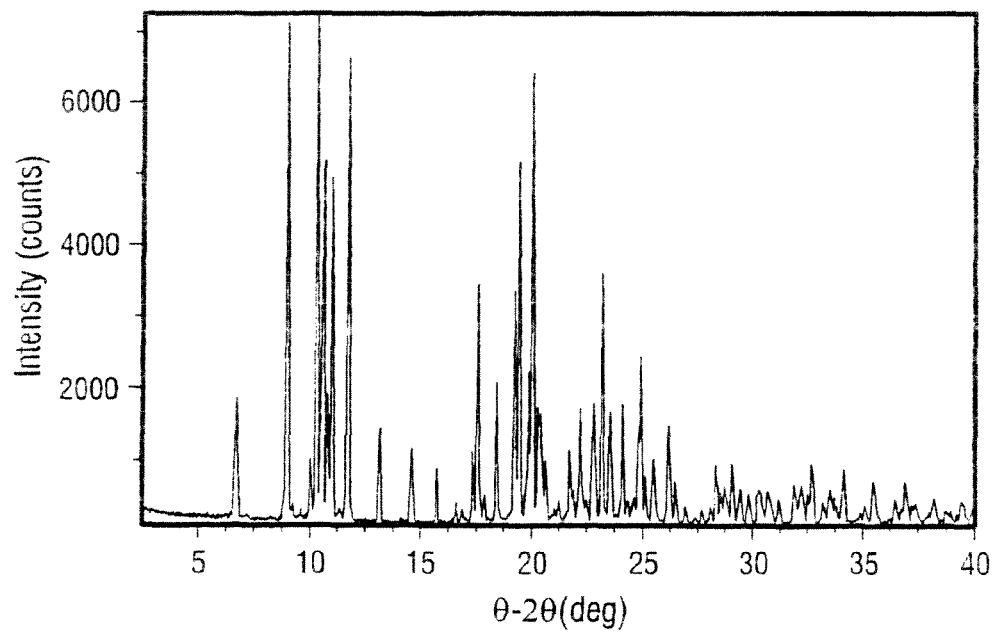
FIG. 2(f) tabulates peak positions of bands present in the FT-IR spectrum of FIG. 2(e).
FIG. 3(a) depicts an XRPD for Compound I Form E collected at room temperature.

As described herein, Compound I Form E is characterized by some or all of the exemplary data provided in FIGS. 3(a) through 3(p), infra (and discussed in Example 4). In one embodiment, a DSC thermogram obtained for Compound I Form E exhibits an endothermic event at ~158° C. (min); an endotherm at ~255° C. (min); followed by apparent decomposition. In one embodiment, a TGA thermogram obtained for Compound I Form E exhibits a weight loss of ~10.9%.

Crystalline Form F

In some embodiments, the present disclosure provides a crystalline form obtained from chloroform.

In some embodiments, the present disclosure provides Form F of Compound I, and compositions comprising Form F. In some embodiments, a composition comprising Compound I, contains at least some of Compound I in a crystalline form, which crystalline form comprises Form F. In some embodiments, such a crystalline form is a solvate.

In some embodiments, Compound I Form F is analyzed by one or more of optical microscopy, X-ray powder diffraction, differential scanning calorimetry, modulated differential scanning calorimetry, thermogravimetric analysis, infrared spectroscopy, nuclear magnetic resonance spectroscopy, and raman spectroscopy.

Figure 9A:
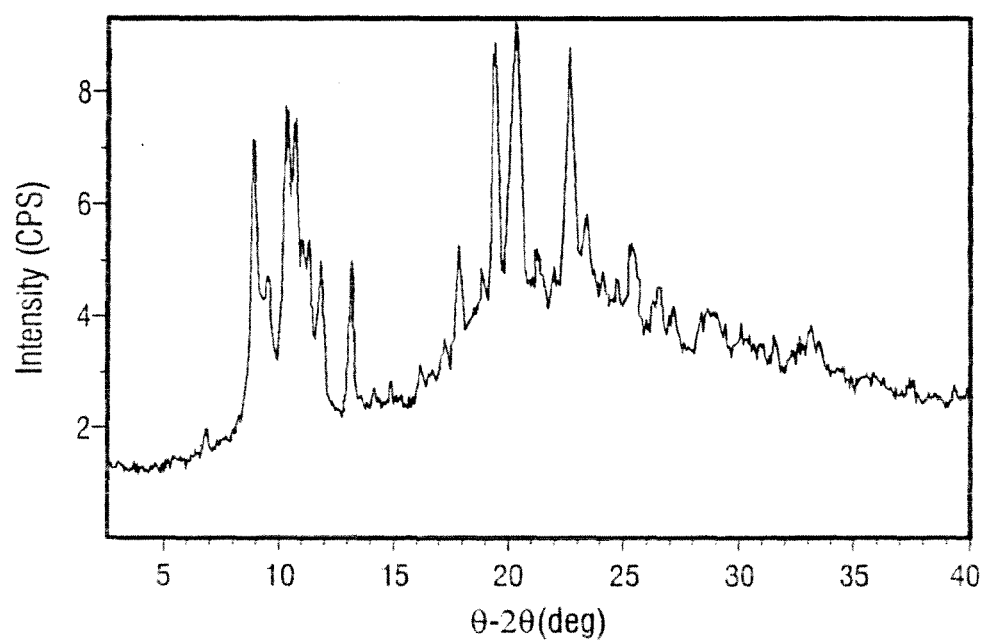
FIG. 9(a) depicts an XRPD for Compound I Form F.
Figure 9D:
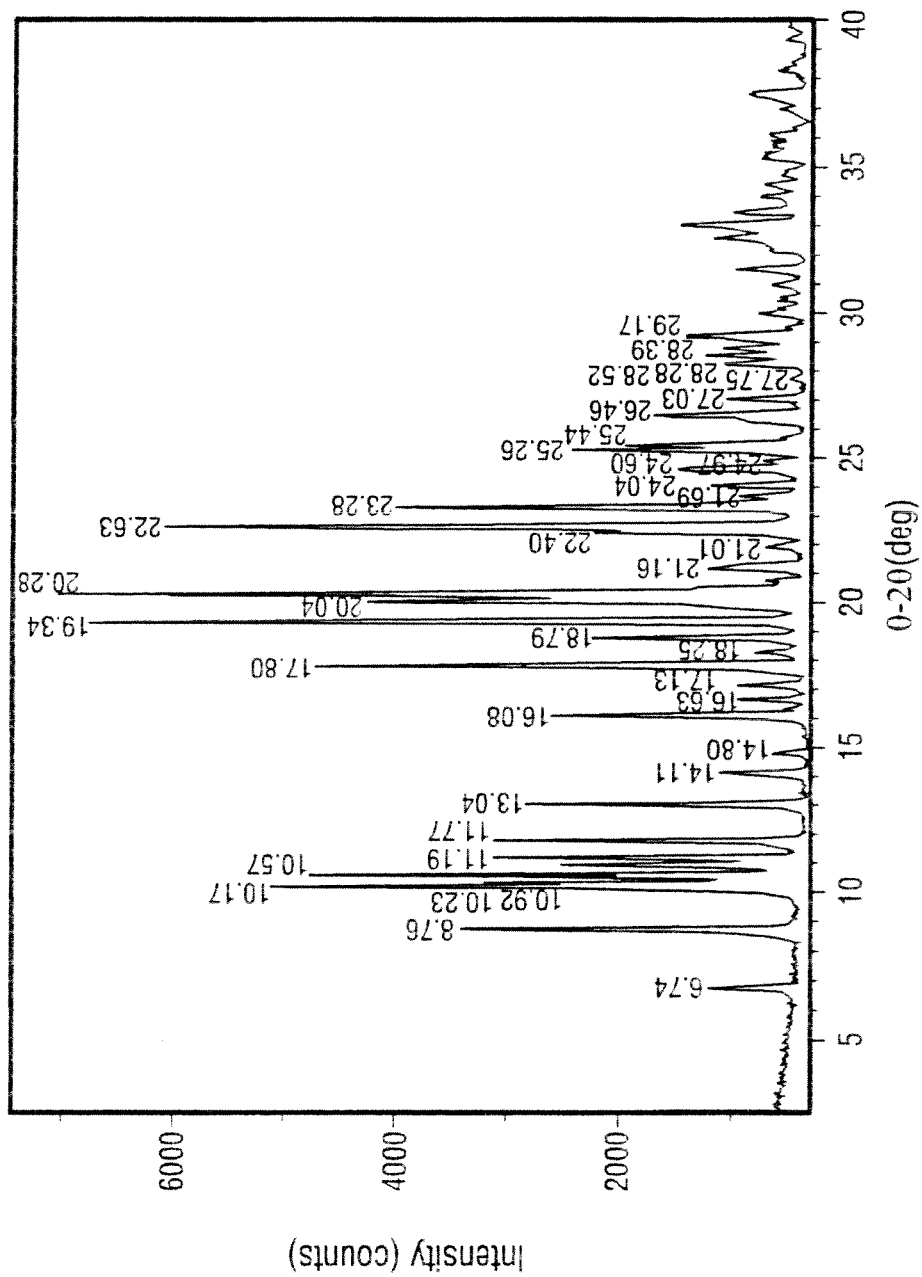
FIG. 9(d) depicts an XRPD for Compound I Form F.
Figure 9G:
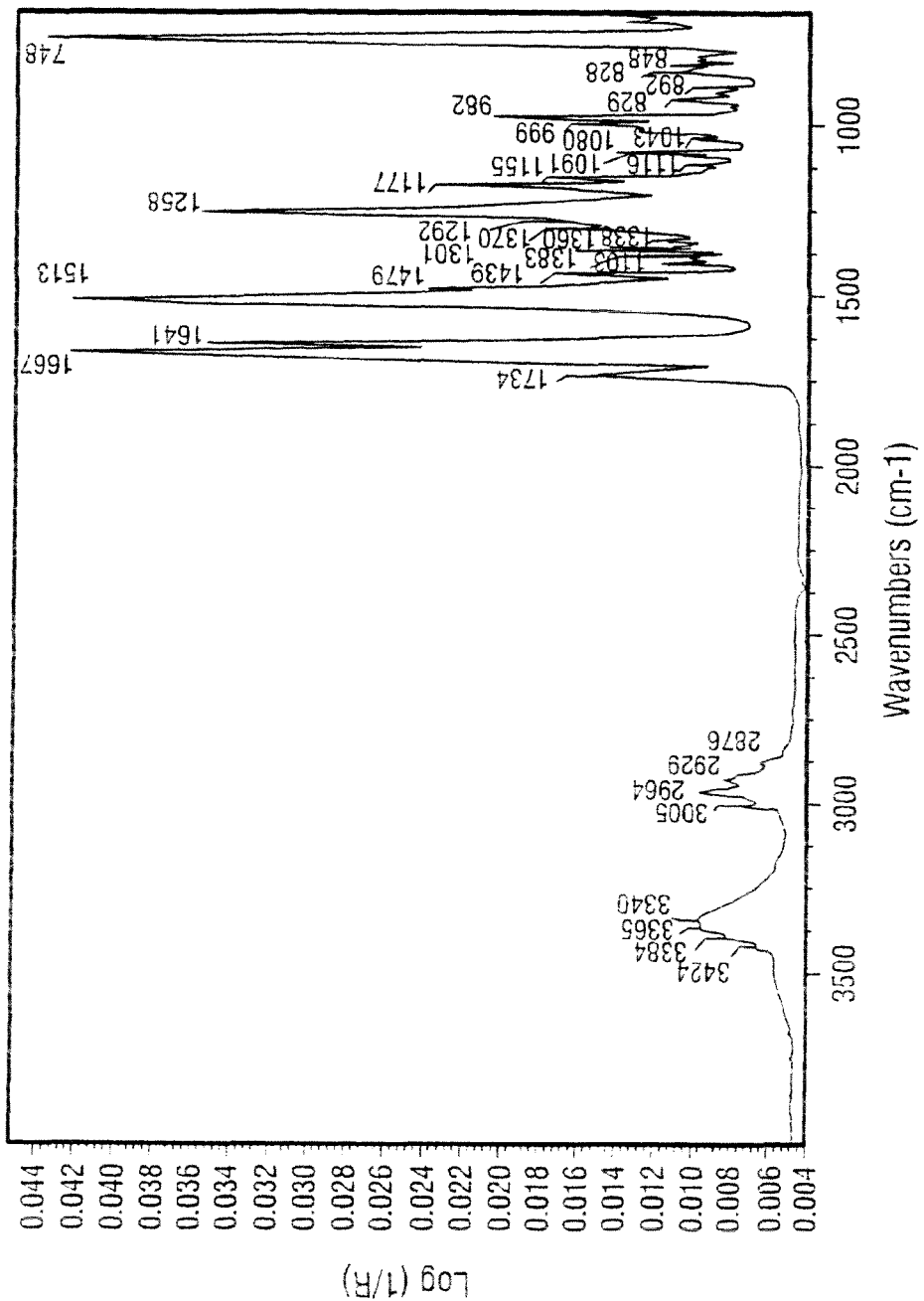
FIG. 9(g) depicts an FT-IR spectrum obtained for Compound I Form F.
Figures 9H, 9I:
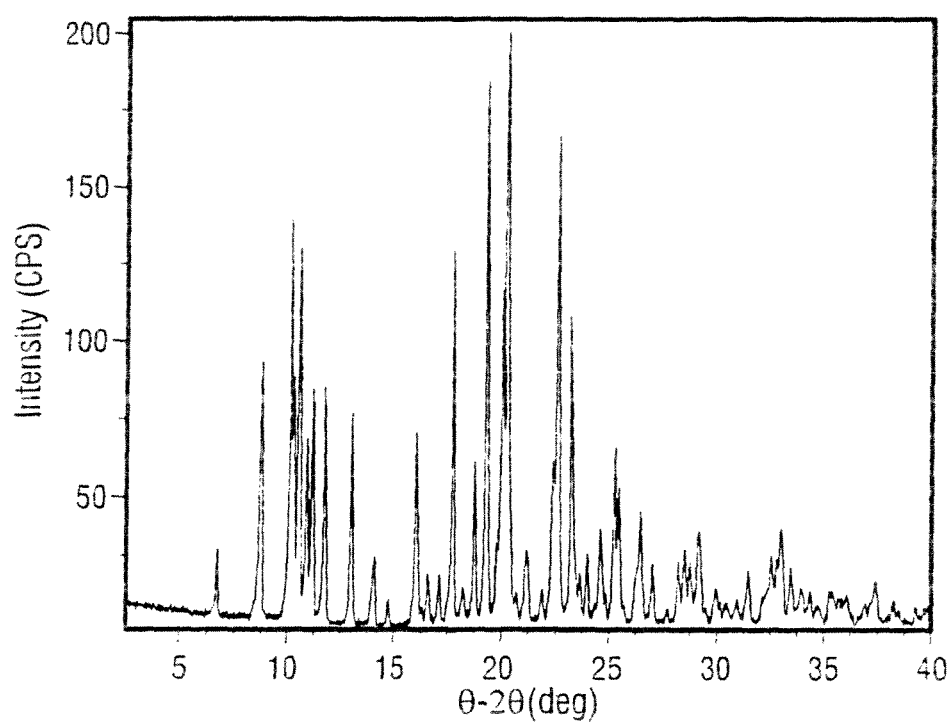
FIG. 9(h)) tabulates peak positions of bands present in the FT-IR spectrum of FIG. 9(g).
FIG. 9(i) depicts Panalytical X-Pert Pro MPD PW3040 data for Compound I Form F.
Figure 9J:
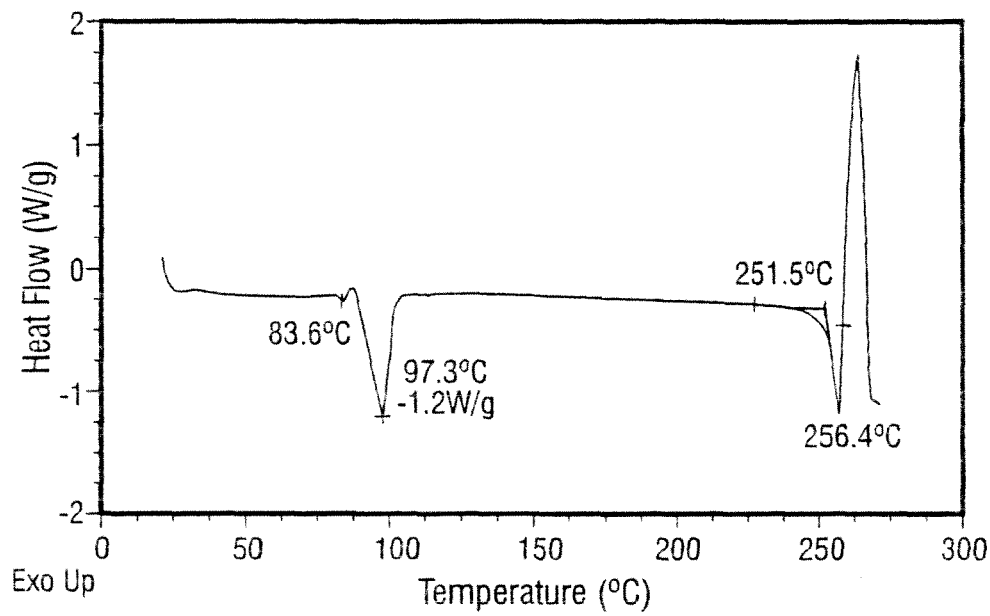
FIG. 9(j) depicts a DSC thermogram obtained for Compound I Form F.
Figure 9K:
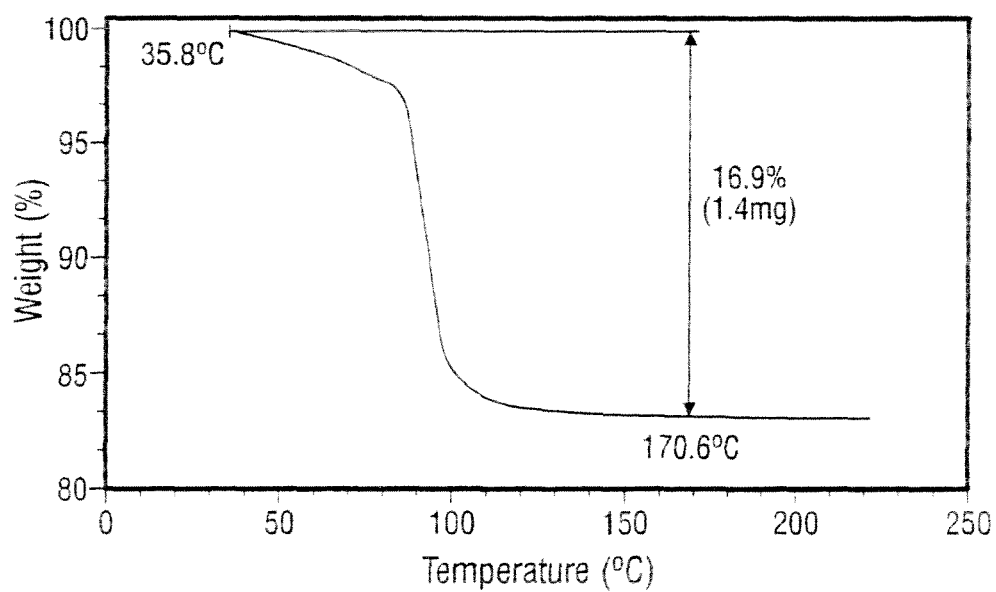
FIG. 9(k) depicts a TGA thermogram obtained for Compound I Form F.
Figure 9L:
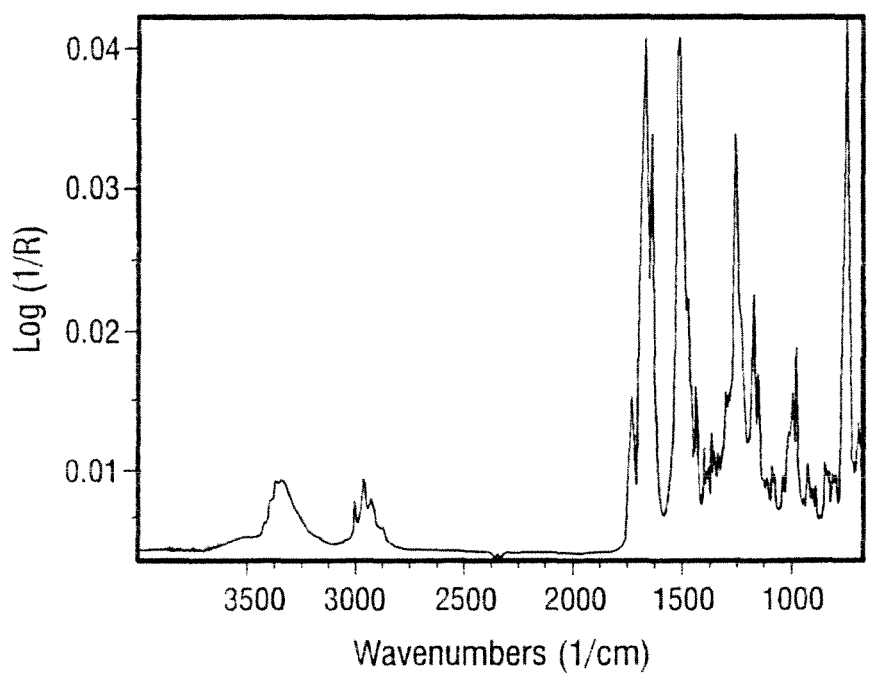
FIG. 9(l) depicts an FT-IR spectrum obtained for Compound I Form F.

In some embodiments, crystalline Form F of Compound I is characterized by the presence of one or more, two or more, three or more, four or more, five or more, or six or more peaks from its XRPD pattern, which peaks, when taken alone or together with other characteristic data, distinguish Form F from other forms, as described infra. In one embodiment, Compound I Form F shows an X-ray diffraction having peaks substantially similar to those in FIG. 9(a) or 9(d). For example, Form F is characterized by a peak in the XRPD at about 20.28 2θ. Other characteristic peaks include 10.17, 17.8, 19.34, 20.04, and 22.63 2θ.

As described herein, Compound I Form F is characterized by some or all of the exemplary data provided in 9(a) through (9l), infra (and discussed in Example 5). In one embodiment, a DSC thermogram obtained for Compound I Form F exhibits a broad endothermic event at ~97° C. (min); and an endotherm at ~256° C. (min). In one embodiment, a TGA thermogram obtained for Compound I Form F exhibits a weight loss of ~17%. In one embodiment, provided is the Panalytical X-Pert Pro MPD PW3040 data for Compound I Form F obtained under the following conditions: X-ray Tube: Cu (1.54059 A°), Voltage: 45 kV; Amperage 40 mA; Scan range: 1.00-39.98 °2θ; step size: 0.017 °2θ; collection time: 721 sec.; scan speed: 3.2°/min; slit: DS:1/2°; SS: null; revolution time: 1.0 sec., mode: transmission. In one embodiment, provided is the data for Compound I Form F obtained under the following conditions: detector: DTGS KBr; number of scans: 512; resolution: 2 cm$^{-1}$.

Crystalline Form H

In some embodiments, the present disclosure provides a crystalline form obtained from chloroform. In some embodiments, such a crystalline form is a solvate. In some embodiments, a chloroform solvate is referred to as Form H of Compound I. In some embodiments, Form H may be isostructural with Form E described infra.

In some embodiments, the present disclosure provides Form H of Compound I, and compositions comprising Form H. In some embodiments, a composition comprising Compound I, contains at least some of Compound I in a crystalline form, which crystalline form comprises Form H. In some embodiments, a composition comprising Compound I, contains at least some of Compound I in a solvated crystalline form, which crystalline form comprises Form H. In some embodiments, the solvated form is a chloroform solvate.

In some embodiment, Compound I Form H is analyzed by one or more of optical microscopy, X-ray powder diffraction, differential scanning calorimetry, modulated differential scanning calorimetry, thermogravimetric analysis, infrared spectroscopy, nuclear magnetic resonance spectroscopy, and raman spectroscopy.

In some embodiments, crystalline Form H of Compound I is characterized by the presence of one or more, two or more, three or more, four or more, five or more, or six or more peaks from its XRPD pattern, which peaks, when taken alone or together with other characteristic data, distinguish Form H from other forms, as described infra. In one embodiment, Compound I Form H shows an X-ray diffraction having peaks substantially similar to those in FIG. 4(a). For example, Form H is characterized by a peak in the XRPD at about 10.67 2θ. Other characteristic peaks include 8.94, 9.69, 10.51, 13.13, and 19.43 2θ.

As described herein, Compound I Form H is characterized by some or all of the exemplary data provided in 4(a) through 4(f), infra (and discussed in Example 6). In one embodiment, a DSC thermogram obtained for Compound I Form H exhibits an endothermic event at ~96° C. (min); and an endotherm at ~257° C. (min). In one embodiment, a TGA thermogram obtained for Compound I Form H exhibits a weight loss of ~10.1%.

Crystalline Form I

In some embodiments, the present disclosure provides a crystalline form obtained from chloroform. In some embodiments, such a crystalline form is a solvate. In some embodiments, a chloroform solvate is referred to as Form I of Compound I.

In some embodiments, the present disclosure provides Form I of Compound I, and compositions comprising Form I. In some embodiments, a composition comprising Compound I, contains at least some of Compound I in a crystalline form, which crystalline form comprises Form I. In some embodiments, a composition comprising Compound I, contains at least some of Compound I in a solvated crystalline form, which crystalline form comprises Form I. In some embodiments, the solvated form is a chloroform solvate.

In some embodiments, Compound I Form I is analyzed by one or more of optical microscopy, X-ray powder diffraction, differential scanning calorimetry, modulated differential scanning calorimetry, thermogravimetric analysis, infrared spectroscopy, nuclear magnetic resonance spectroscopy, and raman spectroscopy.

In some embodiments, crystalline Form I of Compound I is characterized by the presence of one or more, two or more, three or more, four or more, five or more, or six or more peaks from its XRPD pattern, which peaks, when taken alone or together with other characteristic data, distinguish Form I from other forms, as described infra. In one embodiment, Compound I Form I shows an X-ray diffraction having peaks substantially similar to those in FIG. 5(a) or 5(p). For example, Form I is characterized by a peak in the XRPD at about 20.96 2θ. Other characteristic peaks include 10.63, 17.97, 18.74, 19.12, and 23.18 2θ.

As described herein, crystalline Form I of Compound I is characterized by some or all of the exemplary data provided in 5(a) through 5(y), infra (and discussed in Example 7). In one embodiment, a DSC thermogram obtained for Compound I Form I exhibits a broad endothermic event at ~74° C. (min); an endothermic event at ~100° C. (min); and an endotherm at 256.4° C. (min) (10° C./min, C). In another embodiment, a DSC thermogram obtained for Compound I Form I exhibits a broad endothermic event at ~88° C. (min); an endothermic event at ~113° C. (min); and an endotherm at ~256° C. (min) (10° C./min, C). In one embodiment, a TGA thermogram obtained for Compound I Form I exhibits a weight loss of ~33%. In another embodiment, a TGA thermogram obtained for Compound I Form I exhibits a weight loss of ~27%. In one embodiment, provided is the Panalytical X-Pert Pro MPD PW3040 data for Compound I Form I obtained under the following conditions: X-ray Tube: Cu (1.54059 A°), Voltage: 45 kV; Amperage 40 mA; Scan range: 1.00-39.99 °2θ; step size: 0.017 °2θ; collection time: 718 sec.; scan speed: 3.3°/min; slit: DS:1/2°; SS: null; revolution time: 1.0 sec., mode: transmission. In one embodiment, provided is the data for Compound I Form I obtained under the following conditions: detector: DTGS KBr; number of scans: 512; resolution: 2 cm$^{-1}$.

Crystalline Form J

In some embodiments, the present disclosure provides a crystalline form obtained from methylethylketone. In some embodiments, such a crystalline form is a solvate. In some embodiments, a methylethylketone solvate is referred to as Form J of Compound I. In some embodiments, Form J may be isostructural with Form D described infra.

In some embodiments, the present disclosure provides Form J of Compound I, and compositions comprising Form J of Compound I. In some embodiments, a composition comprising Compound I, contains at least some of Compound I in a crystalline form, which crystalline form comprises Form J. In some embodiments, a composition comprising Compound I, contains at least some of Compound I in a solvated crystalline form, which crystalline form comprises Form J. In certain embodiments, the solvated form is a methylethylketone solvate.

In some embodiments, Compound I Form J is analyzed by one or more of optical microscopy, X-ray powder diffraction, differential scanning calorimetry, modulated differential scanning calorimetry, thermogravimetric analysis, infrared spectroscopy, nuclear magnetic resonance spectroscopy, and raman spectroscopy.

Figure 6A:
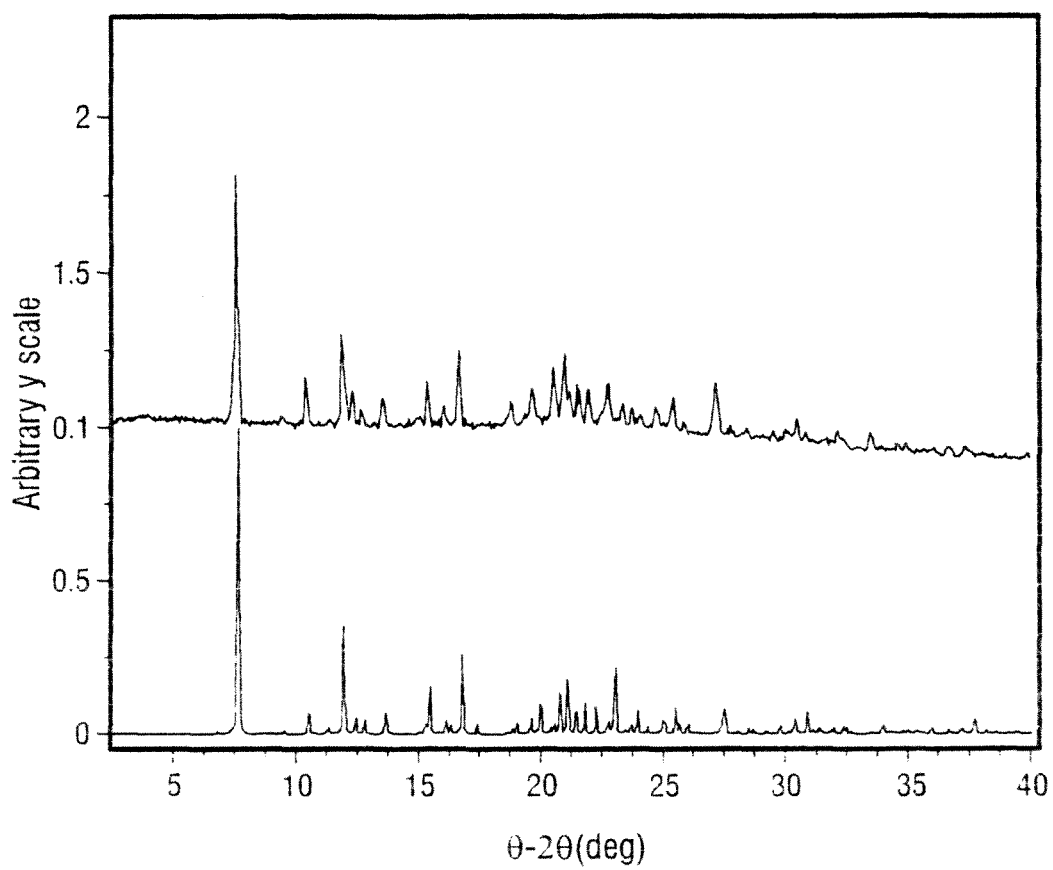
FIG. 6(a) depicts an X-ray diffraction pattern overlay of Compound I Form D and the calculated X-ray diffraction pattern of Compound I Form J.
Figure 6B:
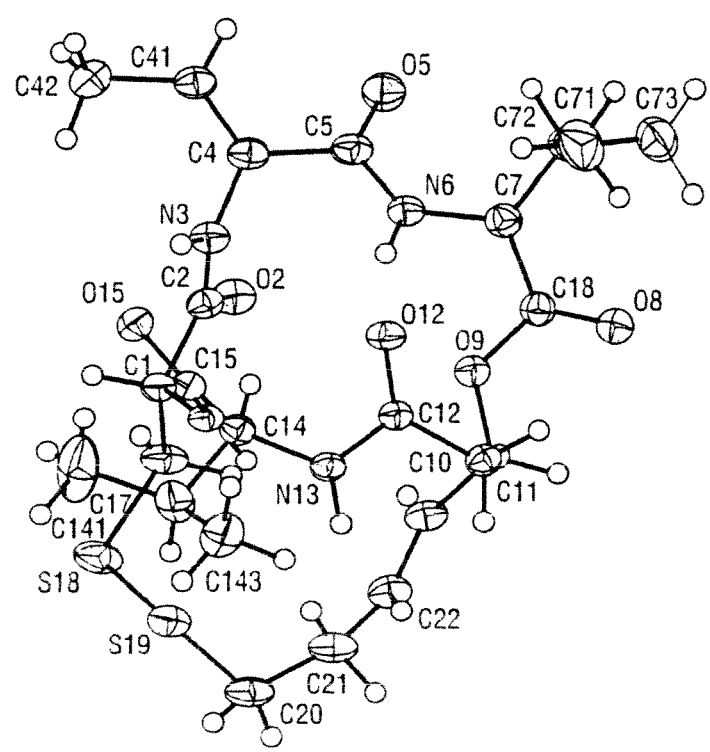
FIG. 6(b) depicts an ORTEP drawing of the single crystal structure of Compound I Form J.
Figure 6C:
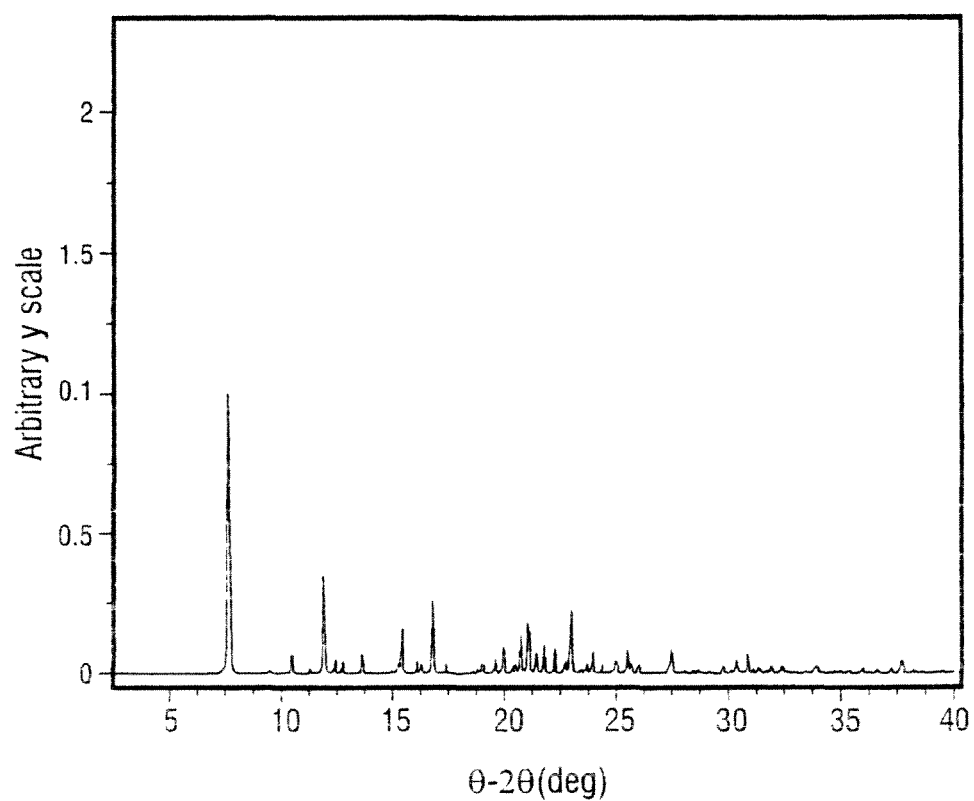
FIG. 6(c) depicts a calculated XRPD for Compound I Form J collected at subambient temperature.
Figure 6E:
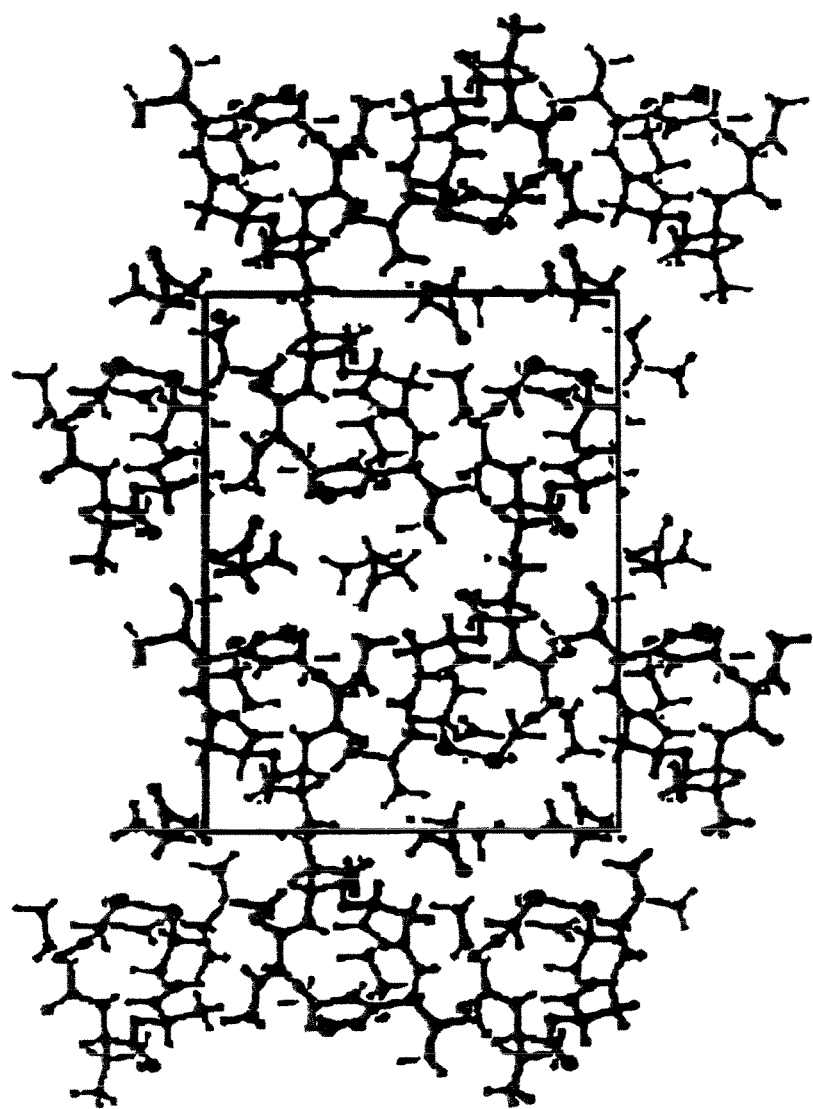
FIG. 6(e) depicts a packing diagram of Compound I, Form J viewed down the crystallographic a axis.
Figure 6F:
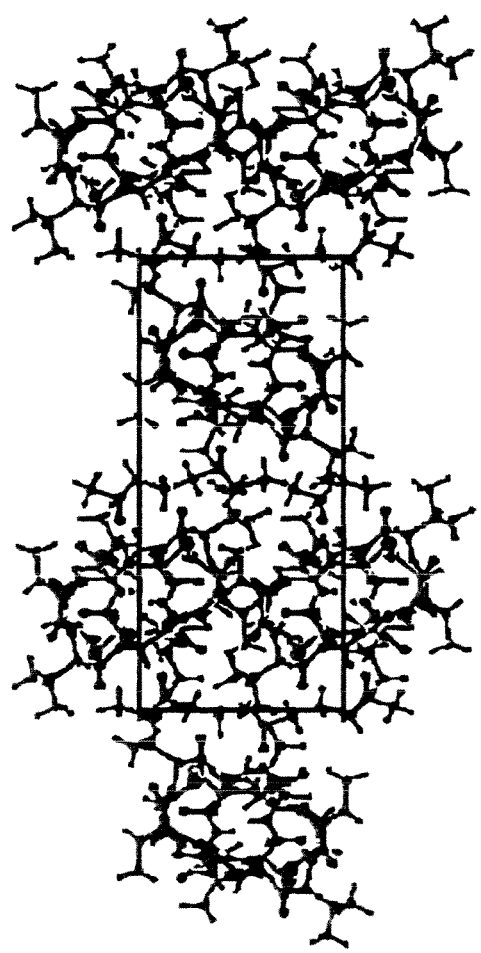
FIG. 6(f) depicts a packing diagram of Compound I, Form J viewed down the crystallographic b axis.
Figure 6G:
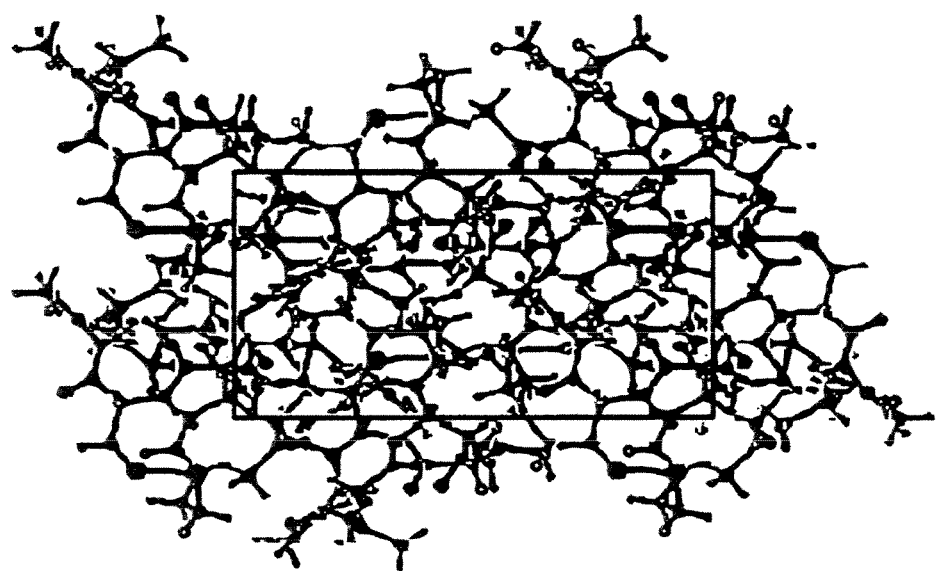
FIG. 6(g) depicts a packing diagram of Compound I, Form J viewed down the crystallographic c axis.
Figure 6K:
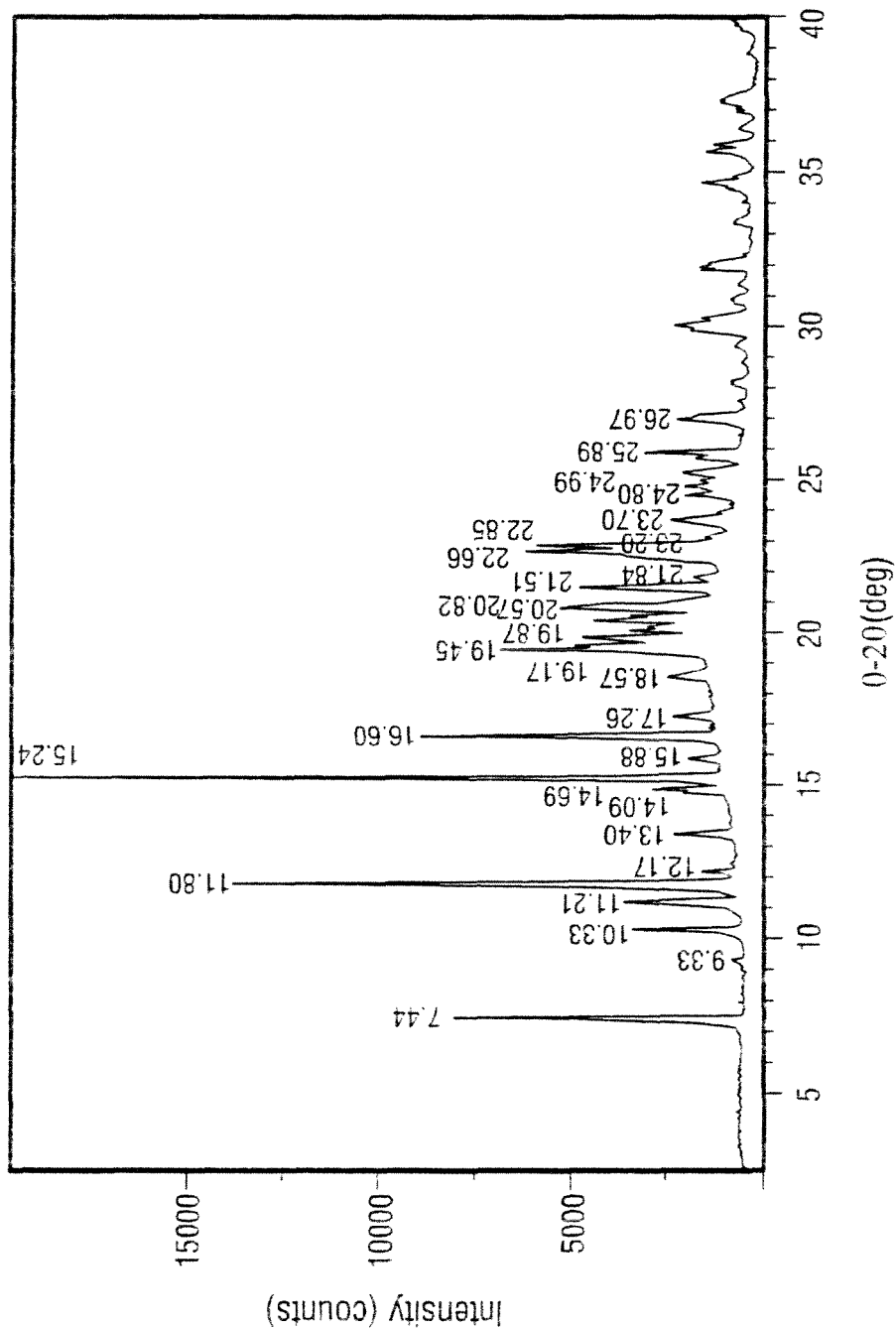
FIG. 6(k) depicts an XRPD for Compound I Form J.
Figure 6N:
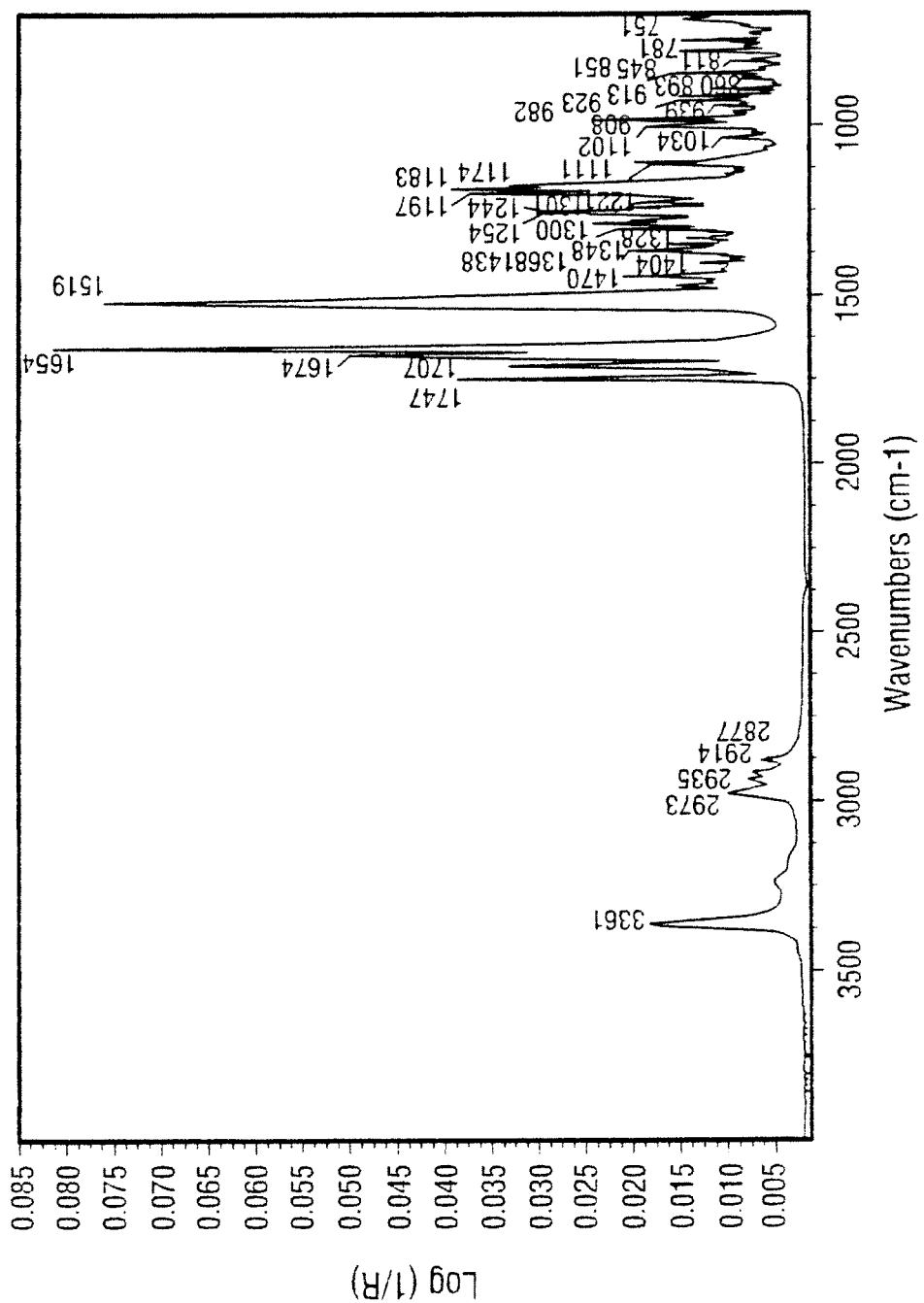
FIG. 6(n) depicts an FT-IR spectrum obtained for Compound I Form J.
Figures 6O, 6P:
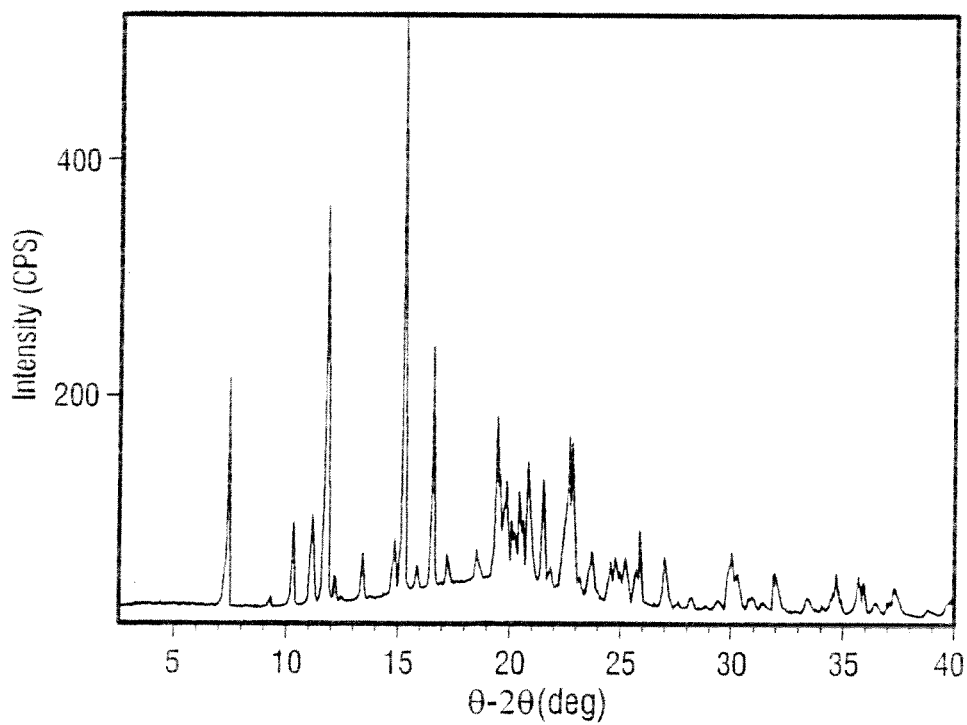
FIG. 6(o) tabulates peak positions of bands present in the FT-IR spectrum of FIG. 6(n).
FIG. 6(p) depicts Panalytical X-Pert Pro MPD PW3040 data for Compound I Form J.
Figure 6Q:
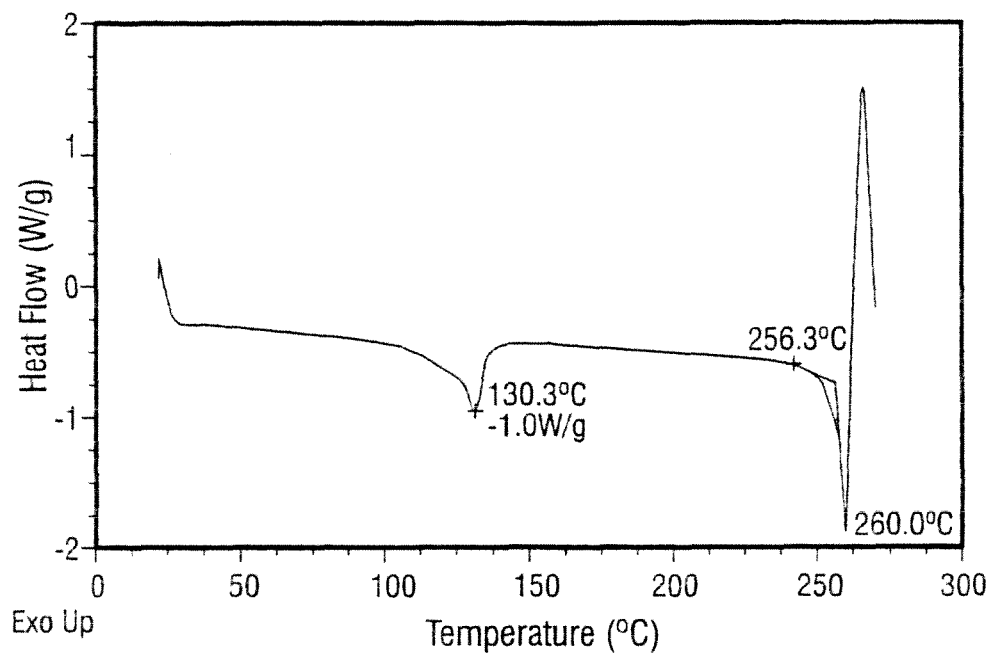
FIG. 6(q) depicts a DSC thermogram obtained for Compound I Form J.
Figure 6R:
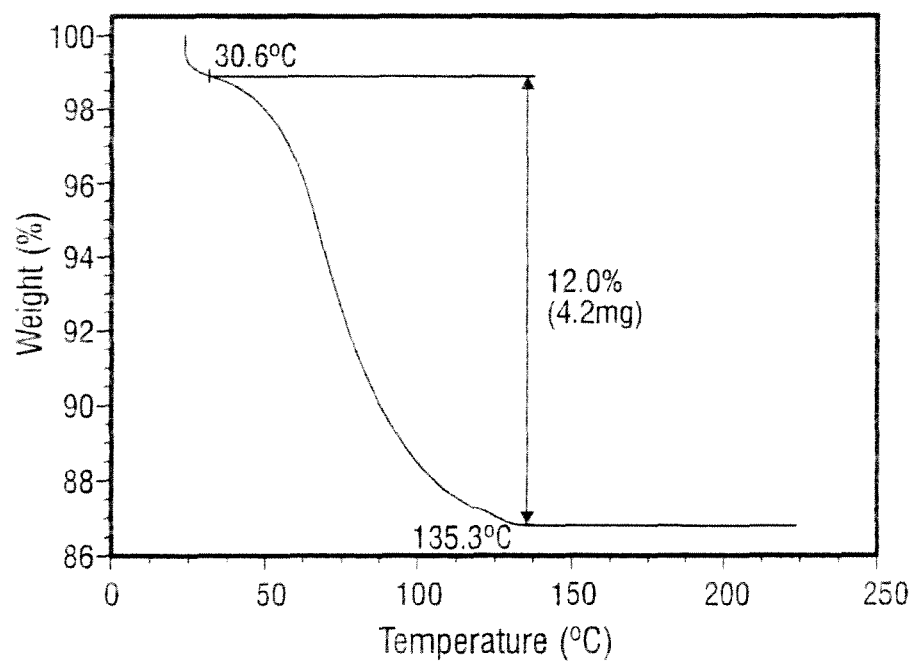
FIG. 6(r) depicts a TGA thermogram obtained for Compound I Form J.

In some embodiments, crystalline Form J of Compound I is characterized by the presence of one or more, two or more, three or more, four or more, five or more, or six or more peaks from its XRPD pattern, which peaks, when taken alone or together with other characteristic data, distinguish Form J from other forms, as described infra. In one embodiment, Compound I Form J shows an X-ray diffraction having peaks substantially similar to those in FIG. 6(k). For example, Form J is characterized by a peak in the XRPD at about 15.24 2θ. Other characteristic peaks include 7.44, 11.80, and 16.60 2θ.

As described herein, crystalline Compound I Form J is characterized by some or all of the exemplary data provided in 6(a) through 6(u), infra (and discussed in Example 8). In one embodiment, a DSC thermogram obtained for Compound I Form J exhibits a broad endothermic event at ~130° C. (min); and an endotherm at ~260° C. (min). In one embodiment, a TGA thermogram obtained for Compound I Form J exhibits a weight loss of ~12%. In one embodiment, provided is the Panalytical X-Pert Pro MPD PW3040 data for Compound I Form J obtained under the following conditions: X-ray Tube: Cu (1.54059 A°), Voltage: 45 kV; Amperage 40 mA; Scan range: 1.00-39.99 °2θ; step size: 0.017 °2θ; collection time: 718 sec.; scan speed: 3.3°/min; slit: DS:1/2°; SS: null; revolution time: 1.0 sec., mode: transmission. In one embodiment, provided is the data for Compound I Form J obtained under the following conditions: detector: DTGS KBr; number of scans: 512; resolution: 2 cm$^{-1}$.

Crystalline Form K

In some embodiments, the present disclosure provides Form K of Compound I, and compositions comprising Form K. In some embodiments, a composition comprising Compound I contains at least some of Compound I in a crystalline form, which crystalline form comprises Form K. In some embodiments, a composition comprising Compound I contains at least some of Compound I in a solvated crystalline form, which crystalline form comprises Form K. In one embodiment, Compound I Form K is obtained from nitromethane. In one embodiment, Compound I Form K is a nitromethane solvate.

In some embodiments, Compound I Form K is analyzed by one or more of optical microscopy, X-ray powder diffraction, differential scanning calorimetry, modulated differential scanning calorimetry, thermogravimetric analysis, infrared spectroscopy, nuclear magnetic resonance spectroscopy, and raman spectroscopy.

Figure 8A:
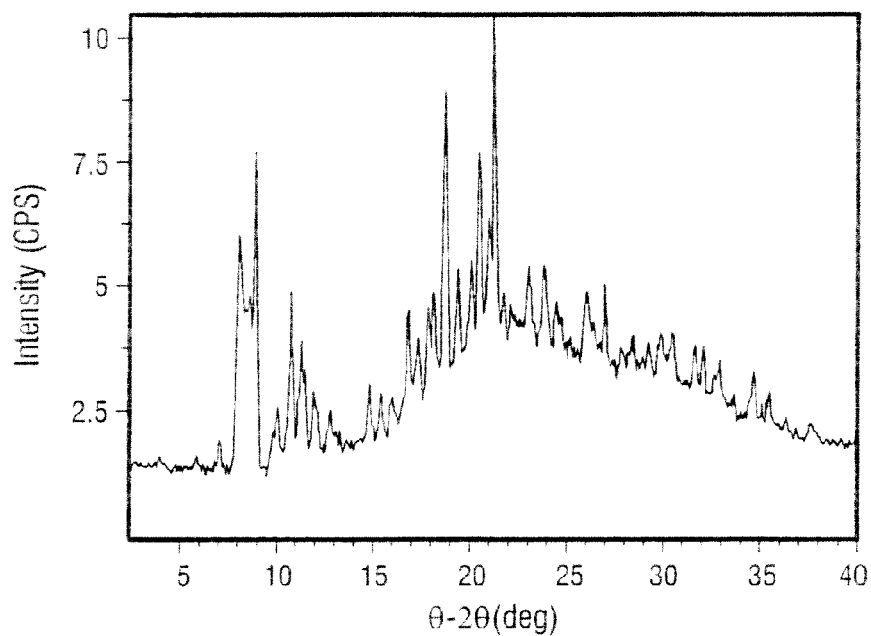
FIG. 8(a) depicts an XRPD for Compound I, Form K collected at room temperature.
Figure 8C:
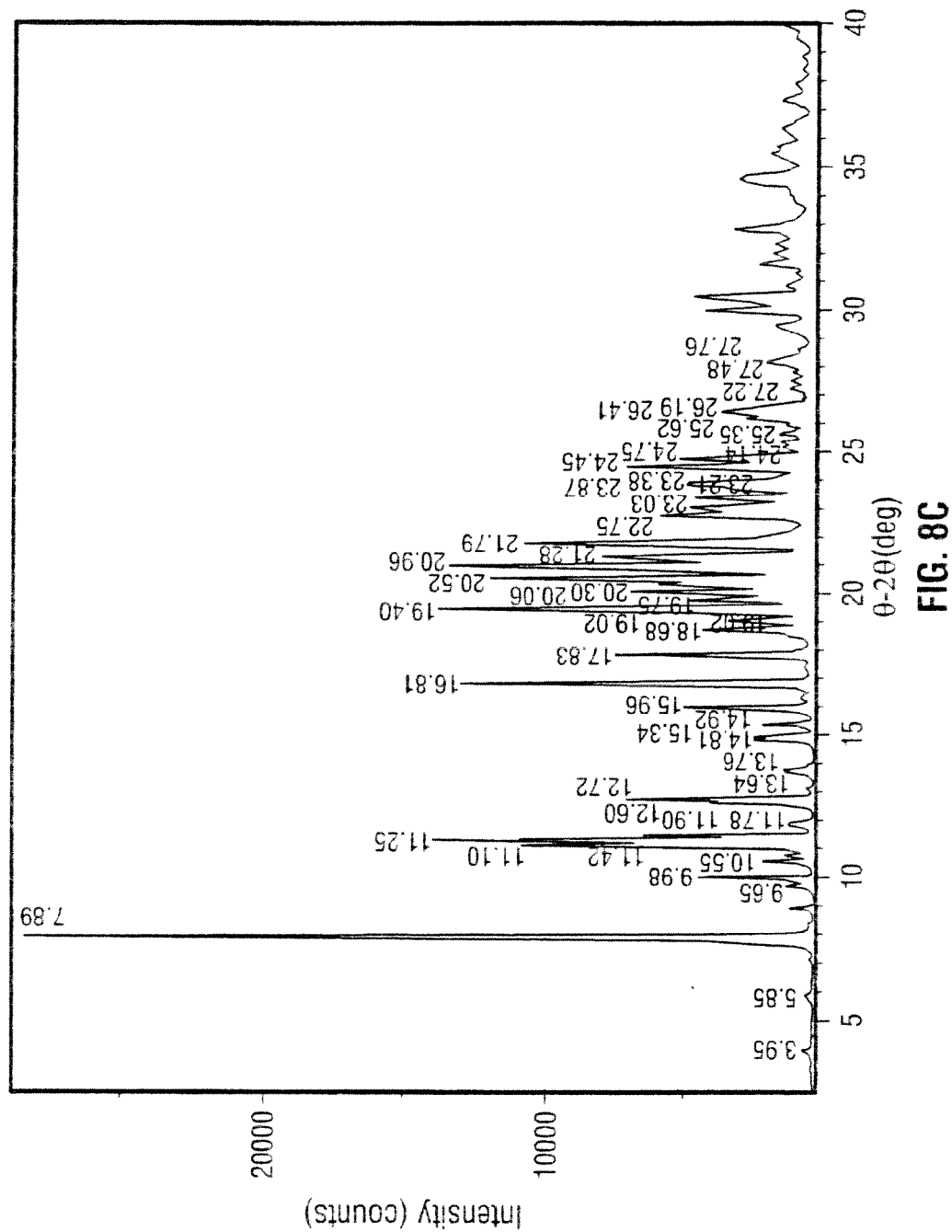
FIG. 8(c) depicts an XRPD for Compound I, Form K.
Figure 8F:
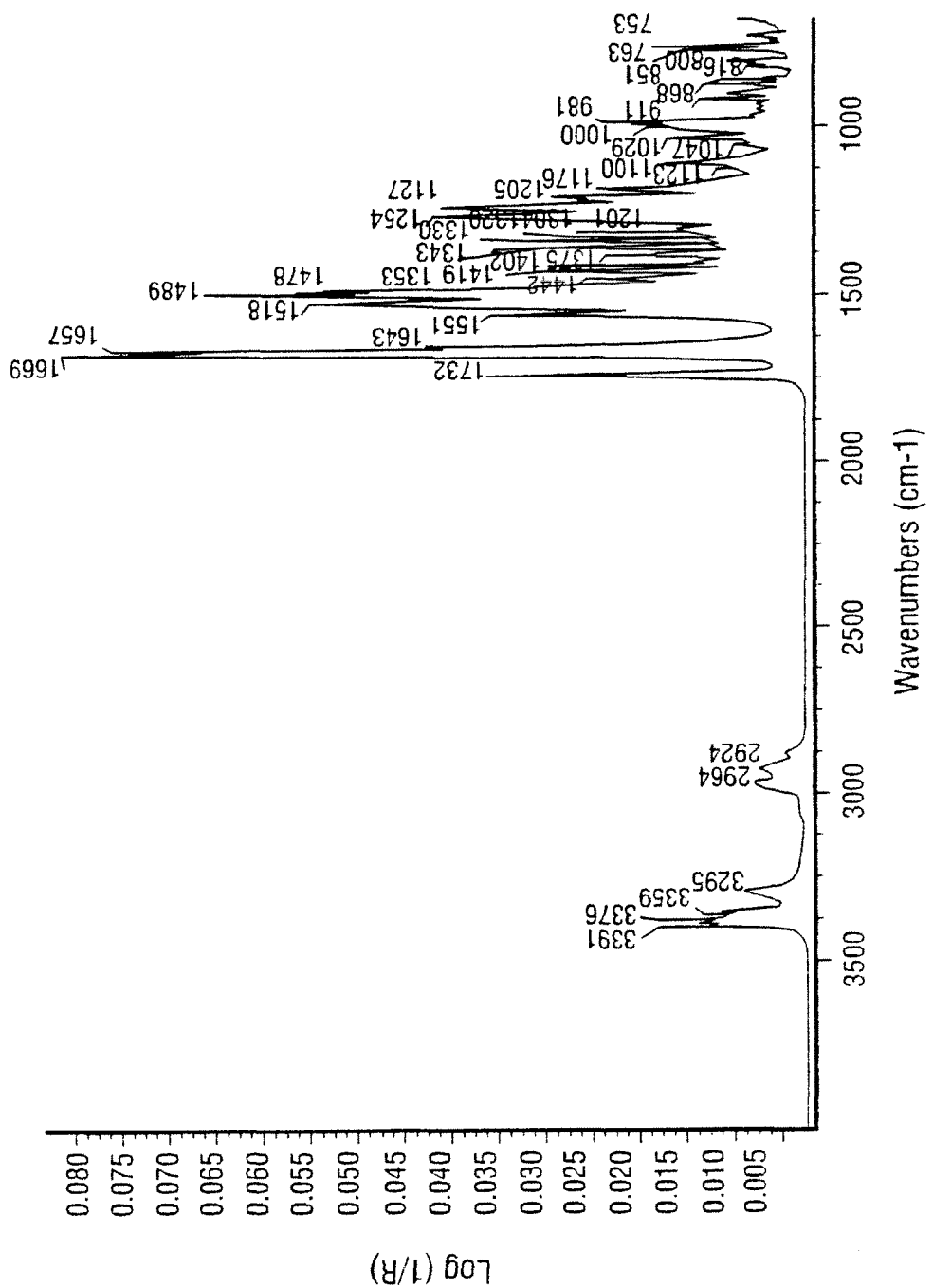
FIG. 8(f) depicts an FT-IR spectrum obtained for Compound I Form K.
Figures 8G, 8H:
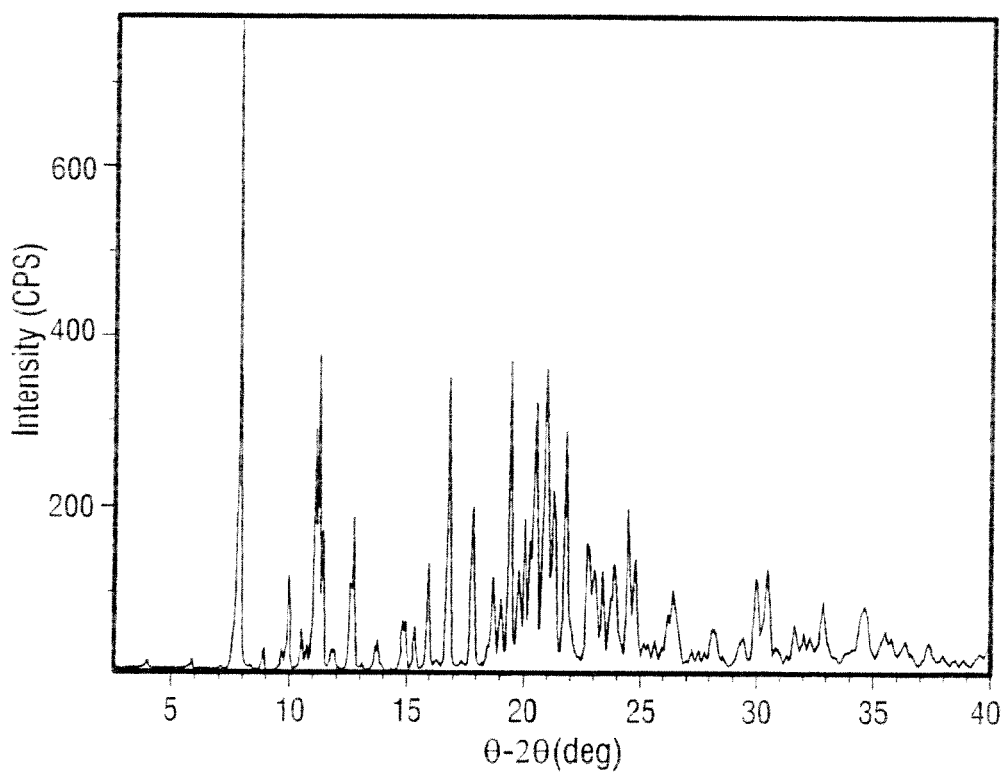
FIG. 8(g) tabulates peak positions of bands present in the FT-IR spectrum of FIG. 8(f).
FIG. 8(h) depicts Panalytical X-Pert Pro MPD PW3040 data for Compound I Form K.
Figure 8I:
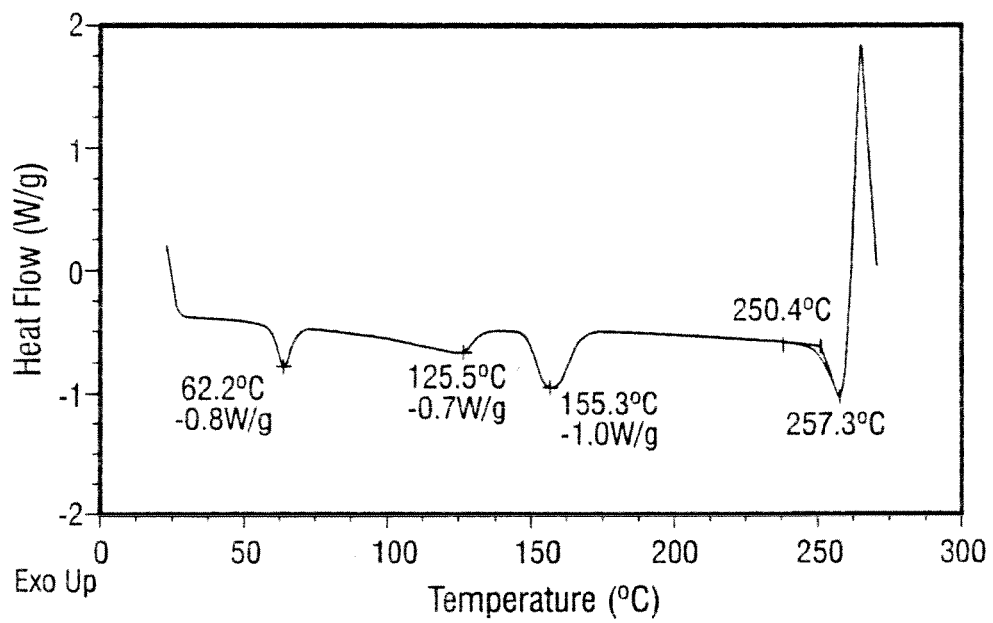
FIG. 8(i) depicts a DSC thermogram obtained for Compound I Form K.
Figure 8J:
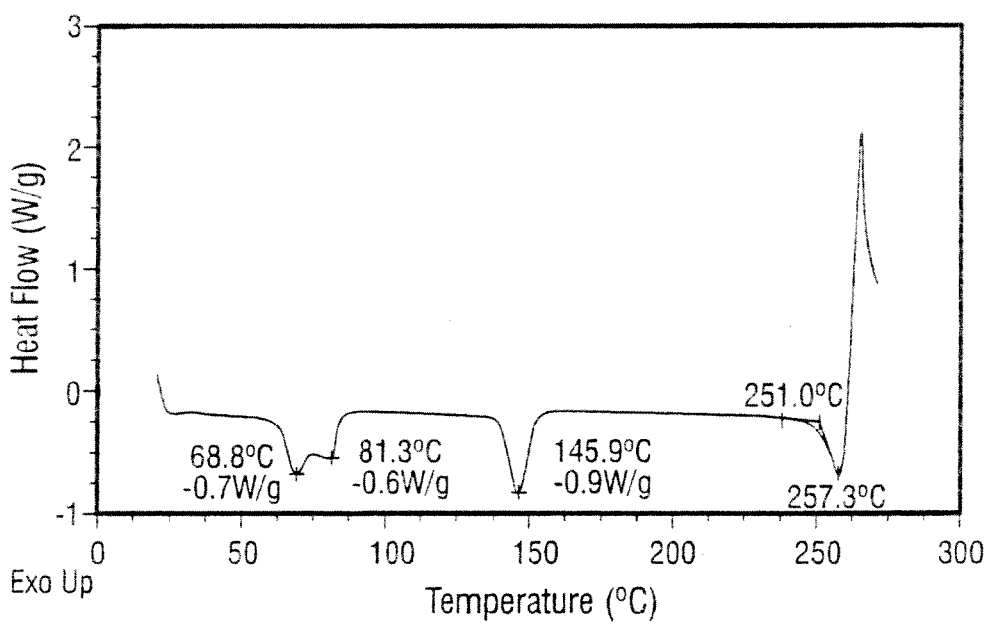
FIG. 8(j) depicts a DSC thermogram obtained for Compound I Form K.
Figure 8K:
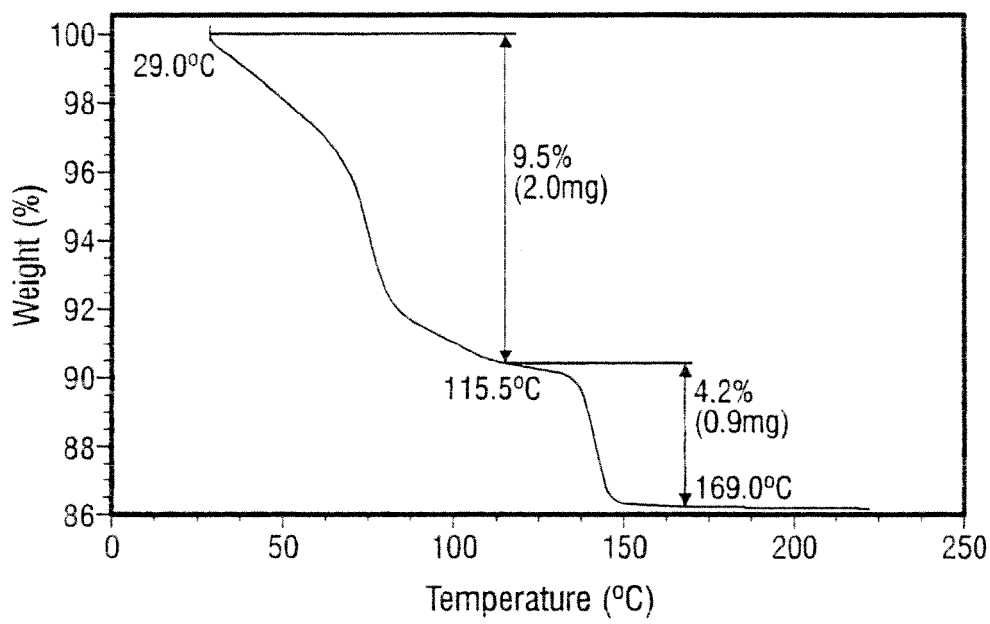
FIG. 8(k) depicts a TGA thermogram obtained for Compound I Form K.
Figure 8L:
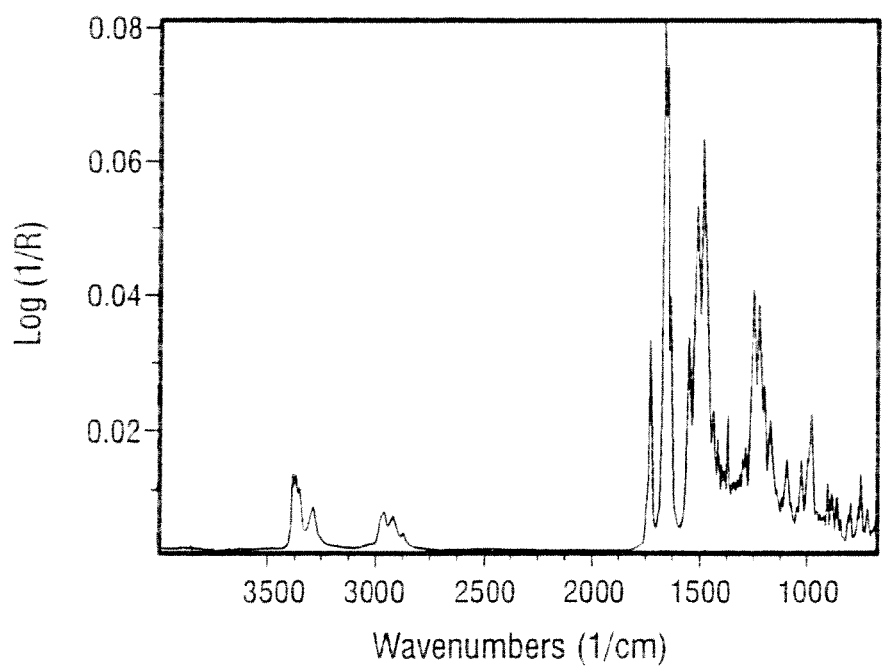
FIG. 8(l) depicts data for Compound I Form K.

In some embodiments, crystalline Form K of Compound I is characterized by the presence of one or more, two or more, three or more, four or more, five or more, or six or more peaks from its XRPD pattern, which peaks, when taken alone or together with other characteristic data, distinguish Form K from other forms, as described infra. In one embodiment, Compound I Form K shows an X-ray diffraction having peaks substantially similar to those in FIG. 8(c). For example, Form K is characterized by a peak in the XRPD at about 7.89 2θ. Other characteristic peaks include 11.25, 16.81, 19.40, and 20.96 2θ.

As described herein, Compound I Form K is characterized by some or all of the exemplary data provided in 8(a) through 8(l), infra (and discussed in Example 10). In one embodiment, a DSC thermogram obtained for Compound I Form K exhibits a broad endothermic event at ~62° C. (min); another broad endothermic event at ~155° C. (min); and an endotherm at ~257° C. (min). In another embodiment, a DSC thermogram obtained for Compound I Form K exhibits a broad endothermic event at ~69° C. and 81° C.; another broad endothermic event at ~146° C. (min); and an endotherm at ~257° C. (min). In one embodiment, a TGA thermogram obtained for Compound I Form K exhibits a weight loss of ~9.5%. In one embodiment, provided is the Panalytical X-Pert Pro MPD PW3040 data for Compound I Form K obtained under the following conditions: X-ray Tube: Cu (1.54059 A°), Voltage: 45 kV; Amperage 40 mA; Scan range: 1.00-39.99 °2θ; step size: 0.017 °2θ; collection time: 717 sec.; scan speed: 3.3°/min; slit: DS:1/2°; SS: null; revolution time: 1.0 sec., mode: transmission. In one embodiment, provided is the data for Compound I Form K obtained under the following conditions: detector: DTGS KBr; number of scans: 512; resolution: 2 cm$^{-1}$.

Crystalline Form L

In some embodiments, the present disclosure provides a crystalline form obtained from acetone and diffused with methanol.

In some embodiments, the present disclosure provides Form L of Compound I, and compositions comprising Form L. In some embodiments, a composition comprising Compound I, contains at least some of Compound I in a crystalline form, which crystalline form comprises Form L. In one embodiment, Compound I Form L is a methanol solvate.

In some embodiments, Compound I Form L is analyzed by one or more of optical microscopy, X-ray powder diffraction, differential scanning calorimetry, modulated differential scanning calorimetry, thermogravimetric analysis, infrared spectroscopy, nuclear magnetic resonance spectroscopy, and raman spectroscopy.

In some embodiments, crystalline Form L of Compound I is characterized by the presence of one or more, two or more, three or more, four or more, five or more, or six or more peaks from its XRPD pattern, which peaks, when taken alone or together with other characteristic data, distinguish Form L from other forms, as described infra. In one embodiment, Compound I Form L shows an X-ray diffraction having peaks substantially similar to those in FIG. 10(a). For example, Form L is characterized by a peak in the XRPD at about 21.46 2θ. Other characteristic peaks include 8.26, 10.05, 11.59, and 12.31 2θ.

As described herein, Compound I Form L is characterized by some or all of the exemplary data provided in 10(a) through 10(i), infra (and discussed in Example 11). In one embodiment, a DSC thermogram obtained for Compound I Form L exhibits an endothermic event at ~168° C. (min); and an endotherm at ~259° C. (min). In one embodiment, a TGA thermogram obtained for Compound I Form L exhibits a weight loss of ~6%. In one embodiment, provided is the Panalytical X-Pert Pro MPD PW3040 data for Compound I Form L obtained under the following conditions: X-ray Tube: Cu (1.54059 A°), Voltage: 45 kV; Amperage 40 mA; Scan range: 1.00-39.98 °2θ; step size: 0.017 °2θ; collection time: 716 sec.; scan speed: 3.2°/min; slit: DS:1/2°; SS: null; revolution time: 1.0 sec., mode: transmission. In one embodiment, provided is the data for Compound I Form L obtained under the following conditions: detector: DTGS KBr; number of scans: 512; resolution: 2 cm$^{-1}$.

Crystalline Form N

In some embodiments, the present disclosure provides a crystalline form obtained from nitromethane.

In some embodiments, the present disclosure provides Form N of Compound I, and compositions comprising Form N. In some embodiments, a composition comprising Compound I, contains at least some of Compound I in a crystalline form, which crystalline form comprises Form N. In one embodiment, Form N of Compound I is a nitromethane solvate.

In some embodiments, Compound I Form N is analyzed by one or more of optical microscopy, X-ray powder diffraction, differential scanning calorimetry, modulated differential scanning calorimetry, thermogravimetric analysis, infrared spectroscopy, nuclear magnetic resonance spectroscopy, and raman spectroscopy.

In some embodiments, crystalline Form N of Compound I is characterized by the presence of one or more, two or more, three or more, four or more, five or more, or six or more peaks from its XRPD pattern, which peaks, when taken alone or together with other characteristic data, distinguish Form N from other forms, as described infra. In one embodiment, Compound I Form N shows an X-ray diffraction having peaks substantially similar to those in FIG. 11(a). For example, Form N is characterized by a peak in the XRPD at about 8.92 2θ. Other characteristic peaks include 7.07, 9.76, 10.75, 11.22, 15.46, 20.37, and 21.31 2θ.

As described herein, Compound I Form N is characterized by some or all of the exemplary data provided in 11(a) through 11(c), infra (and discussed in Example 12). In one embodiment, a DSC thermogram obtained for Compound I Form N exhibits an endotherm at ~150° C. (min). In one embodiment, a TGA thermogram obtained for Compound I Form N exhibits a weight loss of ~5%. In one embodiment, provided is the Panalytical X-Pert Pro MPD PW3040 data for Compound I Form N obtained under the following conditions: X-ray Tube: Cu (1.54059 A°), Voltage: 45 kV; Amperage 40 mA; Scan range: 1.00-39.99 °2θ; step size: 0.017 °2θ; collection time: 717 sec.; scan speed: 3.3°/min; slit: DS:1/2°; SS: null; revolution time: 1.0 sec., mode: transmission.

Amorphous Form

In some embodiments, the present disclosure provides amorphous Compound I, and compositions comprising amorphous Compound I. In some embodiments, the present disclosure provides compositions comprising Compound I in which substantially all of Compound I is an amorphous form (i.e., the composition is substantially free of crystalline compound I). In some embodiments, the present disclosure provides compositions containing Compound I in which at least some of the Compound I is in a form other than amorphous (e.g., is in a crystalline form such as, for example, Form A, Form B, Form C, Form D, Form E, Form F, Form H, Form I, Form J, Form K, Form L, Form N, and combinations thereof).

In some embodiments, amorphous Compound I is characterized by the absence of defined peaks above background in an XRPD pattern. In some embodiments, amorphous Compound I is characterized by the absence of characteristic peaks that may be present in Compound I Form A, Form B, Form C, Form D, Form E, Form F, Form H, Form I, Form J, Form K, Form L, Form N, and combinations thereof. In some embodiments, amorphous Compound I is characterized by having a powder X-ray diffraction pattern substantially similar to FIG. 7(a). In some embodiments, amorphous Compound I is obtained from a water/dichloromethane mixture, or an isopropanol-trifluoroethanol/methanol mixture As described herein, amorphous Compound I is characterized by the exemplary data provided in 7(a) through 7(f), infra (see Example 9). In one embodiment, a DSC thermogram obtained for amorphous Compound I exhibits a glass transition temperature of ~91° C. In one embodiment, a TGA thermogram obtained for amorphous Compound I exhibits a weight loss of ~3.5%.

Compositions Comprising Provided Forms of Compound I

The present disclosure provides compositions that comprise and/or are prepared from solid forms of Compound I as described herein. Any of the forms provided herein of Compound I may be incorporated into a composition. In some embodiments, the present disclosure provides pharmaceutical compositions that comprise and/or are prepared from solid forms of Compound I as described herein. In some embodiments, a pharmaceutical composition comprises a therapeutically effective amount of Compound I and at least one pharmaceutically acceptable carrier or excipient.

In some embodiments, compositions comprising Compound I are provided as lyophilates. In some embodiments, the present disclosure provides a lyophilate of Compound I comprising one or more solid forms described herein. In some embodiments, a lyophilate comprises amorphous Compound I. In some embodiments, a lyophilate comprises one or more crystalline forms. In some embodiments, a lyophilate is substantially free of one or more crystalline forms. In some embodiments, a lyophilate is substantially free of any crystalline form.

In some embodiments, the present disclosure provides compositions comprising or prepared from Compound I solid forms described herein, which compositions further comprise one or more additional components.

In some embodiments, provided compositions comprise, in addition to Compound I, at least one other component, such as a carrier (e.g., pharmaceutically acceptable carrier). Except insofar as any conventional carrier medium is incompatible with compounds or forms described herein, such as by producing any undesirable biological effect or otherwise interacting in a deleterious manner with any other component(s) of compositions and/or the use thereof is contemplated to be within the scope of this disclosure.

In some embodiments, materials which can serve as acceptable carriers (e.g., pharmaceutically acceptable carriers) include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; Cremophor; Solutol; excipients such as cocoa butter and suppository waxes; oils such as peanut oil, cottonseed oil; sunflower oil; sesame oil; olive oil; corn oil and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions; as well as other non-toxic compatible lubricants such as sodium lauryl sulfate and magnesium stearate; as well as coloring agents, releasing agents, coating agents, sweetening, flavoring and perfuming agents, preservatives and antioxidants can also be present in the composition, according to the judgment of the formulator.

Compositions comprising Compound I as described herein may be formulated orally, parenterally, by inhalation spray, topically, rectally, nasally, buccally, vaginally or via an implanted reservoir. In some embodiments, compositions are administered orally or parenterally.

In some embodiments, compositions are administered parenterally. In some embodiments, compositions are administered intraperitoneally or intravenously.

As is known in the art, injectable formulations are often provided as solutions or suspensions, e.g., aqueous or oleaginous suspension. Such solutions or suspensions may be formulated according to techniques known in the art, for example, using suitable dispersing or wetting agents and suspending agents. Injectable formulations are typically sterile. In some embodiments, an injectable solution or suspension comprises a non-toxic parenterally acceptable diluent or solvent. Exemplary vehicles and solvents typically employed include water, Ringer's solution, isotonic sodium chloride solution, acetone, chloroform, dichloromethane, isopropanol, methanol, methylethylketone, tert-butyl alcohol, trifluoroethanol and 1,3-butanediol, and combinations thereof.

In some embodiments, sterile, fixed oils are conventionally employed as a solvent or suspending medium. Any bland fixed oil may be employed including synthetic mono- or di-glycerides. Fatty acids, such as oleic acid and its glyceride derivatives are often useful in the preparation of injectables, as are natural pharmaceutically-acceptable oils, such as olive oil or castor oil, including their polyoxyethylated versions. In some embodiments, such oil solutions or suspensions contain a long-chain alcohol diluent or dispersant, such as carboxymethyl cellulose or similar dispersing agents that are commonly used in the formulation of pharmaceutically acceptable dosage forms including emulsions and suspensions. In some embodiments, commonly used surfactants, such as Tweens, Spans and other emulsifying agents or bioavailability enhancers which are commonly used in the manufacture of acceptable (e.g., pharmaceutically acceptable) solid, liquid, or other dosage forms may also be used for the purposes of formulation.

Orally acceptable dosage forms include, but are not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents commonly include lactose and dried cornstarch. When aqueous suspensions are prepared for oral delivery, the active ingredient is typically combined with emulsifying and suspending agents, optionally much as discussed above with respect to parenteral formulations. If desired, certain sweetening, flavoring or coloring agents may also be added.

Administration of oral compositions can be desirably linked to periods of food intake. For example, in some embodiments, oral compositions are administered with food; in some embodiments, oral compositions are administered without food, or within a particular time frame relative to consumption of food. In some embodiments, oral compositions are administered with little or no regard to the timing of food intake.

Compositions for oral administration can be formulated as solid or liquid preparation. In some embodiments, a liquid formulation such as syrup, injection, eye drops or the like, is prepared with a pH adjustor (e.g., hydrochloric acid), solubilizer, isotonizing agent or the like, as well as a solubilizing aid, stabilizer, buffering agent, suspending agent, antioxidant, etc., if necessary. In some embodiments, a liquid formulation is lyophilized, and an injection is administered intravenously, subcutaneously or intramuscularly. Suspending agents that can be used include, but not limited to, methyl cellulose, polysorbate 80, hydroxyethyl cellulose, gum arabic, tragacanth powder, sodium carboxymethylcellulose, polyoxyethylene sorbitan monolaurate and the like. Solubilizing aids that can be used include, but not limited to, polyoxyethylene hydrogenated castor oil, polysorbate 80, nicotinamide, polyoxyethylene sorbitan monolaurate and the like. Stabilizing agents that can be used include, but not limited to, t sodium sulfite, sodium metasulfite, ether and the like. Preservatives that can be used include, but not limited to, methyl paraoxybenzoate, ethyl paraoxybenzoate, sorbic acid, phenol, cresol, chlorocresol, and the like.

In some embodiments, provided compositions may be formulated for rectal administration, e.g., as suppositories. Such rectally-appropriate forms can be prepared, for example, by mixing the agent with a suitable non-irritating excipient that is solid at room temperature but liquid at rectal temperature and therefore will melt in the rectum to release the drug. Such materials include cocoa butter, beeswax and/or polyethylene glycols.

In some embodiments, provided compositions are formulated for topical administration, for example, the treatment site includes areas or organs readily accessible by topical application, for example, the eye, the skin, or the lower intestinal tract.

Topical application to the lower intestinal tract can often be effected with a rectal suppository formulation (see above) or in a suitable enema formulation. In some embodiments, topical or transdermal patches may be used.

In some embodiments, topical formulations are prepared in a suitable ointment containing an active component suspended or dissolved in one or more carriers. Carriers for topical administration typically include, but are not limited to, mineral oil, liquid petrolatum, white petrolatum, propylene glycol, polyoxyethylene, polyoxypropylene compound, emulsifying wax and water. Topical compositions can be formulated in a suitable lotion or cream, for example, containing one or more active components suspended or dissolved in one or more pharmaceutically acceptable carriers. Suitable carriers may include, but are not limited to, mineral oil, sorbitan monostearate, polysorbate 60, cetyl esters wax, cetearyl alcohol, 2-octyldodecanol, benzyl alcohol and water, and combinations thereof.

Formulations for ophthalmic delivery are often prepared as solutions or suspensions (e.g., isotonic, pH adjusted sterile saline). In some embodiments, one or more preservatives (e.g., benzylalkonium chloride) is/are also included. Ophthalmic compositions may be formulated in an ointment such as petrolatum.

Compositions for nasal delivery are commonly formulated as aerosols. Such aerosol formulations may, for example, be or include solutions or suspensions (e.g., in saline), optionally containing one or more preservatives (e.g., benzyl alcohol), absorption promoters (e.g., to enhance bioavailability), and/or solubilizing or dispersing agents (e.g., fluorocarbons).

In some embodiments, compositions (e.g., pharmaceutical compositions) as described herein may include one or more processing agents and/or crystallization inhibitors, or combinations thereof.

In some embodiments, provided compositions contain one or more processing agents. In some embodiments, the processing agent is water. In some embodiments, the processing agent is tert-butyl alcohol. In some embodiments, the processing agent is talc. In some embodiments, the processing agent is lactose. In some embodiments, the processing agent is precipitated calcium carbonate. In some embodiments, the processing agent is titanium dioxide. In some embodiments, the processing agent is silica. In some embodiments, the processing agent is microcrystalline cellulose.

In some embodiments, provided compositions comprise one or more crystallization inhibitors. In some embodiments, the crystallization inhibitor is water soluble. In certain embodiments, the crystallization inhibitor is water insoluble.

Exemplary crystallization inhibitors include, but are not limited to, polyvinylpyrrolidone (PVP or povidone), including homo- and copolymers of polyvinylpyrrolidone and homopolymers or copolymers of N-vinylpyrrolidone; crospovidone; gums; cellulose derivatives (e.g., HPMC polymers, hydroxypropyl cellulose, ethyl cellulose, hydroxyethylcellulose, sodium carboxymethyl cellulose, calcium carboxymethyl cellulose, sodium carboxymethyl cellulose); dextran; acacia; homo- and copolymers of vinyllactam, and mixtures thereof; cyclodextrins; gelatins; hypromellose phthalate; sugars; sugar alcohols including mannitol; polyhydric alcohols; polyethylene glycol (PEG); polyethylene oxides; polyoxyethylene derivatives; polyvinyl alcohol; propylene glycol derivatives and the like, SLS, Tweens, Eudragits (methacrylic acid copolymers); and combinations thereof; amino acids such as prolin.

In some embodiments, the Compound I in the composition is amorphous. In some embodiments, the crystallization inhibitor is polyvinylpyrrolidone (PVP or povidone). In some embodiments, the crystallization inhibitor is povidone USP/NF, Ph. Eur, or JPE. In some embodiments, the amount of Compound I and the amount of povidone is present in a composition in a ratio of about 1:2 (by weight). In some embodiments, the amount of Compound I and the amount of povidone is present in a composition in a ratio of about 1:1 (by weight). In some embodiments, the amount of Compound I and the amount of povidone is present in a composition in a ratio of about 2:1 (by weight). In some embodiments, the amount of Compound I and the amount of povidone is present in a composition in a ratio of about 3:1 (by weight). In some embodiments, the amount of Compound I and the amount of povidone is present in a composition in a ratio of about 4:1 (by weight)). In some embodiments, the amount of Compound I and the amount of povidone is present in a composition in a ratio of about 5:1 (by weight).

In certain embodiments, a crystallization inhibitor employed by the present disclosure is a PVP polymer.

In certain embodiments, PVP polymers employed in the present disclosure have a molecular weight of about 2,000 to about 50,000 Daltons, about 2,000 to about 30,000 Daltons, about 2,000 to about 20,000 Daltons, about 2,500 to about 15,000 Daltons, about 2,500 to about 10,000 Daltons, or about 3,000 to about 10,000 Daltons.

In certain embodiments, PVP polymers employed in the present disclosure have a dynamic viscosity (10% in water at 20° C.) of about 1.3 to about 700, about 1.5 to about 500, about 1.8 to about 300, about 2.0 to about 200, about 2.2 to about 150, about 2.5 to about 100, about 2.8 to about 70, about 3.0 to about 40, about 3.2 to about 25, or about 3.5 to about 8.5 mPas.

Any type of povidone can be used in the compositions provides herein. In some embodiments, povidone is selected from Plasdone® PVP polymers, which are synthetic, water-soluble homopolymers of N-vinyl-2-pyrrolidone. Plasdone polymers useful in the compositions provided herein include, but are not limited to, Plasdone C-12 and Plasdone C-17.

In some embodiments, povidone possesses K values between 12 and 17. In some embodiments, povidone possesses K values between 12 and 15.

In certain embodiments, PVP polymers employed in the present disclosure are selected from Kollidon® PVP polymers (e.g., Kollidon® 12PF, Kollidon® 17PF).

In certain embodiments, a crystallization inhibitor employed by the present disclosure is a PEG polymer.

In certain embodiments, PEG polymers employed in the present disclosure have has an average molecular about 5,000-20,000 Dalton, about 5,000-15,000 Dalton, or about 5,000-10,000 Dalton.

In certain embodiments, a crystallization inhibitor employed by the present disclosure is a surfactant. In certain embodiments, the crystallization inhibitor is a Tween® surfactant. Exemplary Tweens® include Tween®20, Tween®40, Tween®60, Tween®65 and Tween®80.

In certain embodiments, a crystallization inhibitor employed by the present disclosure is an HPMC (hydroxypropylmethyl cellulose) polymer.

HPMC polymers vary in the chain length of their cellulosic backbone and consequently in their viscosity as measured for example at a 2% (w/w) in water. In certain embodiments, the HPMC polymer has a viscosity in water (at a concentration of 2% (w/w)), of about 100 to about 100,000 cP, about 1000 to about 15,000 cP, for example about 4000 cP. In certain embodiments, the molecular weight of the HPMC polymer has greater than about 10,000, but not greater than about 1,500,000, not greater than about 1,000,000, not greater than about 500,000, or not greater than about 150,000.

HPMC polymers also vary in the relative degree of substitution of available hydroxyl groups on the cellulosic backbone by methoxy and hydroxypropoxy groups. With increasing hydroxypropoxy substitution, the resulting HPMC polymer becomes more hydrophilic in nature. In certain embodiments, the HPMC polymer has about 15% to about 35%, about 19% to about 32%, or about 22% to about 30%, methoxy substitution, and having about 3% to about 15%, about 4% to about 12%, or about 7% to about 12%, hydroxypropoxy substitution.

Exemplary HPMC polymers include, but are not limited to, hydroxypropylmethylcellulose (HPMC), hydroxypropylmethylcellulose acetate phthalate (HPMC-AP), hydroxypropylmethylcellulose acetate succinate (HPMC-AS), hydroxypropylmethylcellulose acetate trimellitate (HPMC-AT) and hydroxypropylmethylcellulose phthalate (HPMC-P).

Grades of hydroxypropylmethylcellulose (HPMC) include, but are not limited to, 3FG, 4FG, 5FG, 6FG, 15FG, 50FG and K100M. Grades of hydroxypropylmethylcellulose acetate succinate (HPMC-AS) include HPMC-AS-LF, HPMC-AS-MF, HPMC-AS-HF, HPMC-AS-LG, HPMC-AS-MG and HPMC-AS-HG. Grades of hydroxypropyl-methylcellulose phthalate (HPMC-P) include 50, 55, 55S.

Other exemplary HPMC polymers are available under the brand names Methocel™ of Dow Chemical Co. and Metolose™ of Shin-Etsu Chemical Co. Examples of suitable HPMC polymers having medium viscosity include Methocel™ E4M, and Methocel™ K4M, both of which have a viscosity of about 4000 cP at 2% (w/w) water. Examples of HPMC polymers having higher viscosity include Methocel™ E10M, Methocel™ K15M, and Methocel™ K100M, which have viscosities of about 10,000 cP, 15,000 cP, and 100,000 cP respectively viscosities at 2% (w/w) in water.

In some embodiments, provided formulation may include one or more crystallization inhibitors. In certain embodiments, the second crystallization inhibitor is a PVP polymer. In certain embodiments, the second crystallization inhibitor is a PEG polymer. In certain embodiments, the second crystallization inhibitor is a Tween® surfactant. In certain embodiments, the formulation or composition comprises an amount of one or more crystallization inhibitors of at least about 1%, 5%, 10%, 12%, 15%, 18%, 20%, 25%, 30%, 35%, 40%, 45%, 50%, 55%, 60%, 65%, 70%, 75%, 80%, 85%, 90%, 95% or 99% (w/w), based on the total weight of the formulation or composition.

In some embodiments, the composition is prepared by lyophilization from a solution. In particular embodiments, the composition is prepared by lyophilization from a solution of (60:40) (v/v) t-butanol/water. In some embodiments, the solvent is tert-butanol. In some embodiments, the solvent is a mixture of tert-butanol and water. In some embodiments, the pH adjustor is hydrochloric acid.

ISTODAX® Label

ISTODAX® is supplied as a kit which includes a sterile, lyophilized powder in a single-use vial containing 10 mg of Compound I and 20 mg of the bulking agent, povidone, USP. Additionally, each kit includes 1 sterile vial containing 2 mL of the Diluent composed of 80% propylene glycol, USP, and 20% dehydrated alcohol, USP.

The K value of Povidone USP is 17. The molecular weight of povidone USP is about 10.000 Dalton.

ISTODAX® is administered at a dose of 14 mg/m$^2$ intravenously over a 4-hour period on days 1, 8 and 15 of a 28-day cycle. Cycles are repeated every 28 days.

Uses

Conditions to be Treated

Provided are methods and compositions relating to treatment of cell proliferative disorders, diseases or conditions. Cell proliferative disorders, diseases or conditions include a variety of conditions characterized by aberrant cell growth, preferably abnormally increased cellular proliferation. Cell proliferative disorders, diseases, or conditions that can be treated using the provided compositions and methods include, but are not limited to, cancer, immune-mediated responses and diseases (e.g., transplant rejection, graft vs. host disease, immune reaction to gene therapy, autoimmune diseases, pathogen-induced immune dysregulation, etc.), certain circulatory diseases, and certain neurodegenerative diseases.

In certain embodiments, provided are methods of treating cancer. Cancer is a group of diseases which are characterized by uncontrolled growth and spread of abnormal cells. Cancers include, but are not limited to, carcinomas, sarcomas, leukemias, lymphomas and the like. In certain embodiments, cancer is a hematological malignancy. In certain embodiments, cancer is a solid tumor.

In certain embodiments the present disclosure relates to treatment of hematological malignancies. Manifestations of hematological malignancies include circulating malignant cells and malignant masses. Hematological malignancies are types of cancers that affect the blood, bone marrow, and/or lymph nodes. Hematological malignancies that may be treated using romidepsin include, but are not limited to: acute lymphoblastic leukemia (ALL), acute myelogenous leukemia (AML), chronic myelogenous leukemia (CML), chronic lymphocytic leukemia (CLL), hairy cell leukemia, Hodgkin's lymphoma, non-Hodgkin's lymphoma, cutaneous T-cell lymphoma (CTCL), peripheral T-cell lymphoma (PTCL), multiple myeloma, and myelodysplastic syndromes. In certain embodiments, romidepsin is used to treat multiple myeloma. In certain particular embodiments, the cancer is relapsed and/or refractory multiple myeloma. In other embodiments, romidepsin is used to treat chromic lymphocytic leukemia (CLL). In certain particular embodiments, the cancer is relapsed and/or refractory CLL. In other embodiments, romidepsin is used to treat chromic myelogenous leukemia (CML). In certain embodiments, romidepsin is used to treat acute lymphoblastic leukemia (ALL). In certain embodiments, romidepsin is used to treat acute myelogenous leukemia (AML). In certain embodiments, the cancer is cutaneous T-cell lymphoma (CTCL). In other embodiments, the cancer is peripheral T-cell lymphoma (PTCL). In certain embodiments, the cancer is a myelodysplastic syndrome.

In some embodiments of the present disclosure, cancers treated include, but are not limited to, leukemias and lymphomas such as cutaneous T-cell lymphoma (CTCL), peripheral T-cell lymphoma, lymphomas associated with human T-cell lymphotropic virus (HTLV) such as adult T-cell leukemia/lymphoma (ATLL), B-cell lymphomas, acute lymphocytic leukemia, acute nonlymphocytic leukemias, chronic lymphocytic leukemia, chronic myelogenous leukemia, acute myelogenous leukemia, Hodgkin's disease, non-Hodgkin's lymphomas, multiple myeloma, myelodysplastic syndromes.

In some such embodiments the disclosure relates to treatment of solid tumors such as lung, breast, colon, liver, pancreas, renal, prostate, ovarian, and/or brain. In some embodiments, the disclosure relates to treatment of pancreatic cancer. In some embodiments, the disclosure relates to treatment of renal cancer. In some embodiments, the disclosure relates to treatment of prostate cancer. In some embodiments, the disclosure relates to treatment of sarcomas. In some embodiments, the disclosure relates to treatment of soft tissue sarcomas.

In some embodiments, cancers that can be treated are solid cancers that include, but are not limited to, mesothelioma, common solid tumors of adults such as head and neck cancers (e.g., oral, laryngeal and esophageal), genitourinary cancers (e.g., prostate, bladder, renal, uterine, ovarian, testicular, rectal and colon), melanoma and other skin cancers, stomach cancer, brain tumors, liver cancer and thyroid cancer, and/or childhood solid tumors such as brain tumors, neuroblastoma, retinoblastoma, Wilms' tumor, bone tumors, and soft-tissue sarcomas. In some embodiments, the disclosure relates to treatment of solid tumors.

Cancers that may be treated using the methods provided herein, including combination therapy, include but not limited to, colon cancer, lung cancer, bone cancer, pancreatic cancer, stomach cancer, esophageal cancer, skin cancer, brain cancer, liver cancer, ovarian cancer, cervical cancer, uterine cancer, testicular cancer, prostate cancer, bladder cancer, kidney cancer, and neuroendocrine cancer.

In certain embodiments, cancer is pancreatic cancer. In certain embodiments, cancer is prostate cancer. In certain specific embodiments, the prostate cancer is hormone refractory prostate cancer.

In some particular embodiments, provided are methods to treat leukemias. In some embodiments, leukemia is chronic lymphocytic leukemia, chronic myelogenous leukemia, acute lymphocytic leukemia, acute myelogenous leukemia, or adult T cell leukemia/lymphoma.

In some embodiments, provided are methods of treating lymphomas. In some embodiments, lymphoma is Hodgkin's or non-Hodgkin's (e.g., T-cell lymphomas such as peripheral T-cell lymphoma, cutaneous T-cell lymphoma, etc.) lymphoma.

In some embodiments, the disclosure relates to the treatment of multiple myeloma and/or myelodysplastic syndromes.

In some embodiments, provided are methods of treating one or more immune-mediated responses and diseases including, but not being limited to, rejection following transplantation of synthetic or organic grafting materials, cells, organs, or tissue to replace all or part of the function of tissues, such as heart, kidney, liver, bone marrow, skin, cornea, vessels, lung, pancreas, intestine, limb, muscle, nerve tissue, duodenum, small-bowel, pancreatic-islet-cell, including xeno-transplants, etc.; graft vs host disease; autoimmune diseases, such as rheumatoid arthritis, systemic lupus erythematosus, thyroiditis, Hashimoto's thyroiditis, multiple sclerosis, myasthenia gravis, type I diabetes, juvenile-onset or recent-onset diabetes mellitus, uveitis, Graves' disease, psoriasis, atopic dermatitis, Crohn's disease, ulcerative colitis, vasculitis, auto-antibody mediated diseases, aplastic anemia, Evan's syndrome, autoimmune hemolytic anemia, and the like.

In some embodiments, provided are methods of treating of one or more infectious diseases causing aberrant immune response and/or activation, such as traumatic or pathogen induced immune dysregulation, including for example, that which are caused by hepatitis B and C infections, HIV, *Staphylococcus aureus* infection, viral encephalitis, sepsis, parasitic diseases wherein damage is induced by an inflammatory response (e.g., leprosy).

In some embodiments, provided are methods of treatment of graft vs host disease, rheumatoid arthritis, systemic lupus erythematosus, psoriasis, atopic dermatitis, Crohn's disease, ulcerative colitis, or multiple sclerosis.

In some embodiments, provided are methods of treatment of an immune response associated with a gene therapy treatment, such as the introduction of foreign genes into autologous cells and expression of the encoded product. In some embodiments, provided are methods of treating of circulatory diseases, such as arteriosclerosis, atherosclerosis, vasculitis, polyarteritis nodosa or myocarditis.

In some embodiments, provided are methods of treatment of any of a variety of neurodegenerative diseases, a non-exhaustive list of which includes:

I. Disorders characterized by progressive dementia in the absence of other prominent neurologic signs, such as Alzheimer's disease; Senile dementia of the Alzheimer type; and Pick's disease (lobar atrophy);

II. Syndromes combining progressive dementia with other prominent neurologic abnormalities such as: A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration); and B) syndromes appearing mainly in children or young adults (e.g., Hallervorden-Spatz disease and progressive familial myoclonic epilepsy);

III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome;

IV. Syndromes of progressive ataxia such as cerebellar degenerations (e.g., cerebellar cortical degeneration and olivopontocerebellar atrophy (OPCA)); and spinocerebellar degeneration (Friedreich's ataxia and related disorders);

V. Syndromes of central autonomic nervous system failure (Shy-Drager syndrome);

VI. Syndromes of muscular weakness and wasting without sensory changes (motoneuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg-Welander) and other forms of familial spinal muscular atrophy), primary lateral sclerosis, and hereditary spastic paraplegia;

VII. Syndromes combining muscular weakness and wasting with sensory changes (progressive neural muscular atrophy; chronic familial polyneuropathies) such as peroneal muscular atrophy (Charcot-Marie-Tooth), hypertrophic interstitial polyneuropathy (Dejerine-Sottas), and miscellaneous forms of chronic progressive neuropathy;

VIII. Syndromes of progressive visual loss such as pigmentary degeneration of the retina (retinitis pigmentosa), and hereditary optic atrophy (Leber's disease).

In some embodiments, the neurodegenerative disease is Alzheimer's disease, Parkinson's disease, and/or Huntington's disease.

In some embodiments, the diseases or conditions are associated with chromatin remodeling.

Dosing

In some embodiments, Compound I and/or compositions containing Compound I is/are administered according to a standard dosing regimen. In some embodiments, Compound I and/or compositions containing Compound I is/are administered according to an accelerated dosing regimen.

Standard Dosing for Compound I

In some embodiments, unit doses of Compound I are within the range of about 0.5 mg/m$^2$ to about 28 mg/m$^2$ body surface area. In some embodiments, the range of about 6 to about 18 mg/m$^2$ is used. In some embodiments, the range is about 10 mg/m$^2$ to about 17 mg/m$^2$. In some embodiments, particular unit doses are 10 mg/m$^2$, 12 mg/m$^2$, 13 mg/m$^2$, 14 mg/m$^2$, and 15 mg/m$^2$.

In some embodiments, Compound I is administered intravenously. In some embodiments, intravenous dosing regimens include daily dosing for 2 weeks, twice weekly dosing for 4 weeks, thrice weekly dosing for 4 weeks, and various other intermittent schedules (e.g., on days 1, 3, and 5; on days 4 and 10; on days 1, 8 and 15; on days 1 and 15; on days 5 and 12; or on days 5, 12, and 19 of 21 or 28 day cycles).

In some embodiments, Compound I is administered in individual unit doses over 4 hours on days 1, 8, and 15, with courses repeating every 28 days. Often, several courses (e.g., at least 4, at least 6, or more) are administered. Indeed, instances have been reported of as many as 72 courses being administered. In some embodiments, individual unit doses are administered by 4 hour infusion.

Accelerated Dosing for Compound I

Accelerated dosing regimens for Compound I may be utilized, in which one or more individual unit doses is administered intravenously over a period of time that is less than or equal to about one hour. In some embodiments, one or more individual doses are administered intravenously over a period of time that is less than about 50 minutes, 40 minutes, 30 minutes, 20 minutes, or less. Any regimen that includes at least one unit dose administered over a period of time that is less than about one hour (60 minutes) may be considered an accelerated dosing regimen in accordance with the present disclosure.

In some embodiments, all unit doses within a regimen are administered intravenously over a time period that is less than or equal to about one hour. In some embodiments, only some of the unit doses within a regimen are administered over a time period that is less than or equal to about one hour. In some embodiments, one or more unit doses within a regimen are administered by a route other than intravenous administration (e.g., oral, subcutaneous, nasal, topical, etc).

Accelerated dosing regimens of Compound I can be administered without a significant increase in toxicity or adverse events, particularly in serious adverse events, as compared with a comparable regimen (e.g., an otherwise identical regimen) in which individual unit doses are administered intravenously over a 4-hour period. Accelerated dosing regimens can be administered without a significant increase in toxicity or adverse events, particularly in serious adverse events, as compared with a standard regimen of Compound I administered by 4-hour intravenous infusion of a dose of about 6-14 mg/m$^2$ on days 1, 8, and 15 of a 28 day cycle.

In some embodiments, Compound I is administered in an accelerated dosing regimen that is identical to a standard dosing regimen (see above) except that one or more unit doses is administered over a time period that is less than about 1 hour (e.g., rather than over a time period of about 4 hours).

In some embodiments, unit doses of Compound I are within the range of about 0.5 mg/m$^2$ to about 28 mg/m$^2$. In certain embodiments, unit doses are in the range of about 1 mg/m$^2$ to about 25 mg/m$^2$. In certain embodiments, unit doses are in the range of about 0.5 mg/m$^2$ to about 15 mg/m$^2$. In certain embodiments, unit doses are the range of about 1 mg/m$^2$ to about 15 mg/m$^2$. In certain embodiments, unit doses are in the range of about 1 mg/m$^2$ to about 8 mg/m$^2$. In certain embodiments, unit doses are in the range of about 0.5 mg/m$^2$ to about 5 mg/m$^2$. In certain embodiments, the unit doses are in the range of about 2 mg/m$^2$ to about 10 mg/m$^2$. In some embodiments, unit doses are in the range of about 10 mg/m$^2$ to about 20 mg/m$^2$. In certain embodiments, unit doses are in the range of about 5 mg/m$^2$ to about 10 mg/m$^2$. In some embodiments, unit doses are in the range of about 10 mg/m$^2$ to about 15 mg/m$^2$. In some embodiments, unit doses are in the range of about 6 to about 19 mg/m$^2$. In some embodiments, unit doses are approximately 8 mg/m$^2$. In still other embodiments, the unit doses are approximately 9 mg/m$^2$. In still other embodiments, unit doses are approximately 10 mg/m$^2$. In still other embodiments, unit doses are approximately 11 mg/m$^2$. In still other embodiments, unit doses are approximately 12 mg/m$^2$. In still other embodiments, unit doses are approximately 13 mg/m$^2$. In still other embodiments, unit doses are approximately 14 mg/m$^2$. In still other embodiments, unit doses are approximately 15 mg/m$^2$. In still other embodiments, unit doses are approximately 30 mg/m$^2$.

In certain embodiments, different individual unit doses within a Compound I therapy regimen are different. In some embodiments, increasing doses of Compound I are administered over the course of a cycle. In certain embodiments, a dose of approximately 8 mg/m$^2$ is administered, followed by a dose of approximately 10 mg/m$^2$, followed by a dose of approximately 12 mg/m$^2$ may be administered over a cycle.

An amount of Compound I administered in individual unit doses varies depending on the form of Compound I being administered. The dosages given herein are dose equivalents with respect to the active ingredient, Compound I.

In certain embodiments, individual unit doses of Compound I are administered on one day followed by several days on which Compound I is not administered. In certain embodiments, Compound I is administered twice a week. In certain embodiments, Compound I is administered once a week. In other embodiments, Compound I is administered every other week.

In some embodiments, Compound I is administered daily (for example for 2 weeks), twice weekly (for example for 4 weeks), thrice weekly (for example for 4 weeks), or on any of a variety of other intermittent schedules (e.g., on days 1, 3, and 5; on days 4 and 10; on days 1 and 15; on days 5 and 12; or on days 5, 12, and 19 of 21 or 28 day cycles).

In certain embodiments, Compound I is administered on days 1, 8, and 15 of a 28 day cycle. In certain particular embodiments, an 8 mg/m$^2$ dose of Compound I is administered on day 1, a 10 mg/m$^2$ dose of Compound I is administered on day 8, and a 12 mg/m$^2$ dose of Compound I is administered on day 15. In certain embodiments, Compound I is administered on days 1 and 15 of a 28 day cycle with day 8 being skipped. A 28 day dosing cycle may be repeated. In certain embodiments, a 28 day cycle is repeated 2-10, 2-7, 2-5, or 3-10 times. In certain embodiments, the treatment includes 5 cycles. In certain embodiments, the treatment includes 6 cycles. In certain embodiments, the treatment includes 7 cycles. In certain embodiments, the treatment includes 8 cycles. In certain embodiments, 10 cycles are administered. In certain embodiments, greater than 10 cycles are administered.

In certain embodiments, one or more unit doses within a Compound I dosing regimen may be administered via a route other than intravenous administration. In some embodiments, one or more doses may be administered orally. In certain embodiments, Compound I is dosed orally in the range of 10 mg/m$^2$ to 300 mg/m$^2$. In certain embodiments, Compound I is dosed orally in the range of 25 mg/m$^2$ to 100 mg/m$^2$. In certain embodiments, Compound I is dosed orally in the range of 100 mg/m$^2$ to 200 mg/m$^2$. In certain embodiments, Compound I is dosed orally in the range of 200 mg/m$^2$ to 300 mg/m$^2$. In certain embodiments, Compound I is dosed orally at greater than 300 mg/m$^2$. In certain embodiments, Compound I is dosed orally in the range of 50 m g/m$^2$ to 150 mg/m$^2$. In other embodiments, the oral dosage ranges from 25 mg/m$^2$ to 75 mg/m$^2$.

In certain embodiments, Compound I is administered orally on a daily basis. In some embodiments, Compound I is administered orally every other day. In still other embodiments, Compound I is administered orally every third, fourth, fifth, or sixth day. In certain embodiments, Compound I is administered orally every week. In certain embodiments, Compound I is administered orally every other week.

In some embodiments, one or more unit doses of Compound I is administered topically.

As will be appreciated by one of skill in the art, the dosage, timing and/or routes of administration of particular unit doses of Compound I may vary depending on the patient and condition being treated. In certain embodiments, the cycles are continued as long as the patient is responding. Therapy may be terminated once there is disease progression, a cure or remission is achieved, or side effects become intolerable. Adverse side effects may also call for lowering the dosage of Compound I administered, or for adjusting the schedule by which doses are administered.

Toxicity and Adverse Events with Compound I

Compound I has been administered to patients in a variety of different clinical contexts and studies. Observed toxicities include fatigue, nausea, vomiting, and myelosuppression (thrombocytopenia and/or neutropenia, e.g., Grade 3). Nonspecific S-T segment changes on ECG and prolongation of QTc intervals occur in many patients. Observed toxicities were mild to moderate. Observed changes in ECGs did not correlate with elevated serial serum troponin levels and multiple gated acquisition (MUGA) scans, both of which were consistently normal.

In early development, 6 deaths occurred (out of more than 450 patients) during clinical investigations of Compound I. In all but one of the deaths, significant cardiovascular risk factors were either present at the time of entry into the Compound I study or appeared during the course of the study. The sixth patient had a history of sarcoidosis and was simultaneously administered another drug that also is known to cause QTc prolongation.

Hematologic Events

Administration of Compound I may cause neutropenia and/or thrombocytopenia It is generally recommended that further treatment be withheld from patients with Grade 3 or Grade 4 neutropenia or thrombocytopenia, until their specific cytopenia returns to Grade 1 (i.e., ANC recovered to >1.9× 10$^9$/L and platelet count recovered to ≥75×10$^9$/L) or below, at which point therapy can be continued at full dose. If Grade 4 neutropenia or thrombocytopenia lasting more than 5 days or associated with bleeding, then it is generally recommended that treatment be withheld until specific cytopenia returns to Grade 1 or below, at which point therapy can continue, preferably at a reduced dose (e.g., 10 mg/m$^2$). If Grade 4 febrile (≥38.5° C.) neutropenia or thrombocytopenia that requires platelet transfusion is observed, it is generally recommended that treatment be withheld until the specific cytopenia returns to Grade 1 or below, at which point therapy can continue, preferably at a reduced dose (e.g., 10 mg/m$^2$).

Hematologic events are typically observed at a rate of about 21-52% with standard Compound I dosing regimens (National Cancer Institute IND 57,810 Annual Report, 2007). For example, the NCI-2007 Annual Report provides the following rates for the following blood and bone marrow abnormalities: platelets (52%), hemoglobin/anemia (41%), abnormal white blood cell count (39%), abnormal ANC/AGC (37%), and lymphopenia (21%) (National Cancer Institute IND 57,810 Annual Report, 2007).

Cardiac Events

Cardiac events observed with Compound I administration can include any or all of the following:

Prolongation of QTc to ≥500 msec or an increase of ≥60 msec from pretreatment baseline for the current treatment cycle;

Ventricular arrhythmia (i.e., ventricular tachycardia or ventricular fibrillation [≥3 beats in a row)'

Sinus tachycardia (pulse >140/min after recumbency);

New occurrence of atrial dysrhythmias (SVT, atrial fibrillation, or atrial flutter), ST and T-wave changes indicative of repolarization abnormalities or ischemia (e.g., ST depression of ≥2 mm [measured from isoelectric line to ST segment] and/or T-wave inversion of ≥4 mm [measured from isoelectric line to peak of T-wave] as long as the main QRS vector is positive).

The literature reports that the median change in QTc from baseline is 16.5 milliseconds (see, Piekarz et al., *Clin Cancer Res* 12:3762, 2006). Table 2 presents common recommendations for dose modification when cardiac events are observed.

TABLE 2

Recommendation for dose modification during cardiac events

| Parameters/Symptoms | Change | Action | Dosing/Continuation |
|---|---|---|---|
| Sinus tachycardia | Pulse > 140/min after recumbancy | Hold further dosing, consult local cardiologist, and treat appropriately | If resolved, restart treatment, preferably at a reduced dose (e.g., 10 mg/m$^2$) If not resolved, discontinue therapy |
| Atrial dysrhythmia (SVT, atrial fibrillation, or atrial flutter) | New occurrence | | |
| Prolongation of QTcf | To ≥500 msec | | |

TABLE 2-continued

Recommendation for dose modification during cardiac events

| Parameters/Symptoms | Change | Action | Dosing/Continuation |
|---|---|---|---|
| compared to pre-treatment baseline in a treatment cycle | OR Increase by ≥60 msec | | |
| Ventricular tachycardia | ≥3 beats in a row | | |
| Ventricular fibrillation | New occurrence | Hold further dosing and treat appropriately. The medical monitor should be notified and local cardiologist should be consulted | Hold further dosing until medical monitor and cardiologist evaluation is complete |
| A subsequent episode of any of the above, despite dose reduction | | | Discontinue Compound I administration |
| T-wave morphology | Inversion of ≥4 mm[a] | Hold further dosing, consult local cardiologist, and treat appropriately | If resolved, restart treatment, preferably at a reduced dose (e.g., 10 mg/m$^2$) In some patients, ST segment and T-wave morphology changes may recur despite a dose reduction. In such cases, further treatment should be withheld until the ECG changes resolve. If the patient experiences no concomitant clinical events, treatment may be resumed, preferably at the reduced dose level. If not resolved, discontinue therapy. |
| ST-segment | Depression of ≥2 mm[b] | | |

[a] Measured from isoelectric line to peak of T-wave
[b] Measured from isoelectric line to ST segment Cardiac events are typically observed at a rate of about 24% with standard Compound I dosing regimens (National Cancer Institute IND 57,810 Annual Report, 2007).

Gastrointestinal Events

Gastrointestinal events are typically observed at a rate of about 15-64% with standard Compound I dosing regimens (National Cancer Institute IND 57,810 Annual Report, 2007). For example, the NCI-2007 Annual Report provides the following rates for the following gastrointestinal events: nausea (64%), anorexia (39%), vomiting (39%), constipation (19%), dysguesia (18%), and diarrhea (15%) (National Cancer Institute IND 57,810 Annual Report, 2007).

Compound I can be administered via accelerated dosing regimens without a clinically significant increase in relevant toxicities (e.g., in the rate and/or severity of one or more of dose limiting toxicities, serious adverse events, and/or adverse events). In some embodiments, provided are accelerated dosing regimens for Compound I in which the rate of observed toxicities (e.g., fatigue, hematological toxicities, cardiac toxicities, gastrointestinal toxicities, constitutional toxicities, or a combination thereof) is not materially worse than that observed for administration of a comparable dosing regimen that differs only in that unit doses of Compound I are administered intravenously over a time period of about 4 hours. In some embodiments, provided are accelerated dosing regimens for Compound I in which the rate of observed toxicities is not materially worse than that observed for administration of a standard Compound I therapy regimen.

In some embodiments, provided are accelerated dosing regimens for Compound I in which the subject receiving Compound I does not suffer one or more particular adverse events, or serious adverse events, within a designated time period. In some embodiments, the designated time period is during administration of the accelerated dose. In some embodiments, the designated time period is within about 2 to about 6 hours after the end of infusion of the accelerated dose. In some embodiments, the designated time period is within about 2, 4, 6, 8, 10, 12, 14, 16, 18, 20, 22, 24, 26, 28, 30, 32, 34, 36, 38, 40 42, 44, 46, 48 or more hours after the end of infusion of the accelerated dose.

Any side effect, toxicity, or adverse event may be absent from the designated time period. In some embodiments, the subject's QTc remains below about 500 msec during the designated time period; in some embodiments, the subject does not suffer a ventricular arrhythmia during the designated time period; in some embodiments, the subject does not suffer sinus tachycardia during the designated time period; in some embodiments, the subject does not suffer an atrial dysrhythmia during the designated time period; in some embodiments the subject does not suffer ST or T-wave changes indicative of repolarization during the designated time period.

Combination Therapy

In some embodiments, Compound I is administered in combination with one or more other pharmaceutical agents. In some embodiments, Compound I is administered in combination with one or more other chemotherapeutic agents and/or in combination with one or more other pharmaceutical agents (e.g., pain relievers, anti-inflammatories, antibiotics, steroidal agents, anti-folates, kinase inhibitors, methyl transferase inhibitors, antibodies, etc.).

In certain embodiments, Compound I is administered in combination with one or more cytotoxic agents. Exemplary cytotoxic agents include, but are not limited to, gemcitabine, decitabine, and flavopiridol. In certain embodiments, Compound I is administered in combination with one or more taxanes and/or one or more proteasome inhibitors. Exemplary proteasome inhibitors include, but are not limited to, bortezomib (VELCADE®), peptide boronates, salinosporamide A (NPI-0052), lactacystin, epoxomicin (Ac(Me)-Ile-Ile-Thr-Leu-EX), MG-132 (Z-Leu-Leu-Leu-al), PR-171, PS-519, eponemycin, aclacinomycin A, CEP-1612, CVT-63417, PS-341 (pyrazylcarbonyl-Phe-Leu-boronate), PSI (Z-Ile-Glu (OtBu)-Ala-Leu-al), MG-262 (Z-Leu-Leu-Leu-bor), PS-273 (MNLB), omuralide (clasto-lactacystin-β-lactone), NLVS (Nip-Leu-Leu-Leu-vinyl sulfone), YLVS (Tyr-Leu-Leu-Leu-vs), dihydroeponemycin, DFLB (dansyl-Phe-Leu-boronate), ALLN (Ac-Leu-Leu-Nle-al), 3,4-dichloroisocoumarin, 4-(2-aminoethyl)-benzenesulfonyl fluoride, TMC-95A, gliotoxin, EGCG ((−)-epigallocatechin-3-gallate), YU101 (Ac-hFLFL-ex), and combinations thereof.

In certain embodiments, Compound I is administered in combination with one or more anti-folates. In some such embodiments, Compound I is administered in combination with one or more of: folinic acid (leucovorin), methotrexate, pralatrexate, premextred, triazinate, or combinations thereof.

In certain embodiments, Compound I is administered in combination with one or more kinase inhibitors (e.g., tyrosine kinase inhibitors). In some embodiments, Compound I is administered in combination with one or more antibodies that act as a kinase inhibitor. In some embodiments, Compound I is administered in combination with one or more of ABT-869, AC220, AZD7762, BIBW 2992, BMS-690154, CDKIAT7519, CYC116, ISIS3521, GSK690693, GSK-461364, MK-0457, MLN8054, MLN8237, MP470, ON 01910.Na, OSI-930, PHA-739358, R935788, SNS-314, TLN-232, XL147, XL228, XL281, XL418, or XL765.

In certain embodiments, Compound I is administered in combination with one or more methyl transferase inhibitors.

In certain embodiments, Compound I is administered in combination with one or more therapeutic antibodies. In some embodiments, Compound I is administered in combination with one or more of: bevacizumab, cetuximab, dasatinib, erlotinib, geftinib, imatinib, lapatinib, nilotinib, panitumumab, pegaptanib, ranibizumab, sorafenib, sunitinib, trastuzumab, or any antibody that binds to an antigen bound by one of these moieties.

In some embodiments, Compound I is administered in combination with an anti-inflammatory agent, pain reliever, anti-nausea medication, or anti-pyretic. Anti-inflammatory agents useful in the methods provided herein include, but are not limited to, aspirin, ibuprofen, and acetaminophen, etc.

In certain embodiments, Compound I is administered in combination with a steroidal agent. In certain embodiments, Compound I is administered in combination with a steroidal agent selected from the group consisting of alclometasone diprorionate, amcinonide, beclomethasone diprorionate, betamethasone, betamethasone benzoate, betamethasone diprorionate, betamethasone sodium phosphate, betamethasone sodium phosphate and acetate, betamethasone valerate, clobetasol proprionate, clocortolone pivalate, cortisol (hydrocortisone), cortisol (hydrocortisone) acetate, cortisol (hydrocortisone) butyrate, cortisol (hydrocortisone) cypionate, cortisol (hydrocortisone) sodium phosphate, cortisol (hydrocortisone) sodium succinate, cortisol (hydrocortisone) valerate, cortisone acetate, desonide, desoximetasone, dexamethasone, dexamethasone acetate, dexamethasone sodium phosphate, diflorasone diacetate, fludrocortisone acetate, flunisolide, fluocinolone acetonide, fluocinonide, fluorometholone, flurandrenolide, halcinonide, medrysone, methylprednisolone, methylprednisolone acetate, methylprednisolone sodium succinate, mometasone furoate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, or combinations thereof. In some embodiments, Compound I is administered in combination with dexamethasone.

In certain embodiments, Compound I is administered in combination with an agent to treat gastrointestinal disturbances such as nausea, vomiting, and diarrhea. Such agents may include anti-emetics, anti-diarrheals, fluid replacement, electrolyte replacement, etc.

In certain embodiments, Compound I is administered in combination with electrolyte replacement or supplementation such as potassium, magnesium, and calcium. In certain embodiments, Compound I is administered in combination with electrolyte replacement or supplementation such as potassium, magnesium.

In certain embodiments, Compound I is administered in combination with an anti-arrhythmic agent.

In certain embodiments, Compound I is administered in combination with an agent that increases the production of platelets.

In certain embodiments, Compound I is administered in combination with an agent to boost the production of blood cells. In certain embodiments, the agent is erythropoietin.

In some embodiments, Compound I is administered in combination with an agent to prevent hyperglycemia.

In certain embodiments, Compound I is administered with another HDAC or DAC inhibitor.

Electrolyte Supplementation

In some embodiments, electrolyte supplementation is administered to subjects receiving Compound I therapy. Individuals with low electrolyte levels (e.g., low potassium and/or magnesium levels) are susceptible to development of unwanted side effects if administered Compound I therapy (see, for example, published application No. US 2008/0124403, which is incorporated herein by reference).

Such patients may be particularly susceptible to development of cardiac repolarization effects, including QTc prolongation (though potentially with no significant cardiac function changes), and/or cardiac dysrhythmias. Particular abnormalities that may be observed include an increase in QTc interval and/or abnormalities of the ST segment (e.g., ST segment depression) and/or the T-wave (e.g., T-wave flattening) on ECG.

An individual with a potassium serum concentration below about 3.5 mmol/L (3.5 mEq/L) and/or a serum magnesium concentration below about 0.8 mml/L (1.95 mEq/L) suffers an increased risk of developing cardiac repolarization effects and/or dysrhythmias.

Serum concentrations of potassium are generally considered to be "normal" when they are within the range of about 3.5-5.5 mEq/L or about 3.5-5.0 mEq/L. It is often desirable to ensure that an individuals' serum potassium concentration is within these ranges prior to (and/or during) administration of Compound I therapy.

Serum concentrations of magnesium are generally considered to be "normal" when they are within the range of about 1.5-2.5 mEq/L or about 1.5-2.2 mEq/L or about 1.25-2.5 mEq/L or about 1.25-2.2 mEq/L. It is often desirable to ensure that an individual's serum magnesium concentration is within these ranges prior to (and/or during) administration of Compound I therapy.

In some embodiments, an individual's serum potassium and/or magnesium concentration(s) is/are at the high end of the normal range prior to (and/or during) administration of Compound I therapy. In some embodiments, an individual's serum potassium concentration is at least about 3.8 mEq/L, 3.9 mEq/L, 4.0 mEq/L, or more prior to and/or during administration of Compound I therapy. In some embodiments, care is taken not to increase serum potassium concentration above about 5.0 mEq/L, 5.2 mEq/L, or 5.5 mEq/L. In some embodiments, an individual's serum magnesium concentration is at least about 1.9 mEq/L or more prior to and/or during administration of Compound I therapy. In some embodiments, care is taken not to increase magnesium concentration above about 2.5 mEq/L.

In some embodiments of the present disclosure, an individual's serum potassium concentration is at least about 3.5 mEq/L (in some embodiments at least about 3.8 mEq/L, 3.9 mEq/L, 4.0 mEq/L, or above) and the individual's serum magnesium concentration is at least about 1.85 mEq/L (in some embodiments at least about 1.25 mEq/L, 1.35 mEq/L, 1.45 mEq/L, 1.55 mEq/L, 1.65 mEq/L, 1.75 mEq/L, 1.85 mEq/L, 1.95 mEq/L, or above) prior to and/or during administration of Compound I therapy.

In some embodiments, electrolyte levels (e.g., potassium and/or magnesium levels, optionally calcium levels) are assessed more than once during the course of Compound I therapy; in some embodiments, different assessments are separated by a regular interval (e.g., 0.5 days or less, 1 day, 2 days, 3 days, 4 days, 5 days, 6 days, 7 days, 8 days, 9 days, 10 days, 11 days, 12 days, 13 days, 14 days, 1 month, 2 months, 3 months, 4 months, 5 months, 6 months, etc.). In some embodiments, electrolyte levels are assessed prior to each administration of Compound I.

An individual's serum potassium and/or magnesium and/or other electrolyte concentration(s) may be assessed by any available means. For example, samples may be collected from venous or arterial blood and processed for plasma or serum analysis. In some embodiments, venous sampling is utilized. Any available assay may be utilized for assessment. In some embodiments, potassium is measured by flame photometry, direct potentiometry (see, for example, Koch et al., *Clin. Chem.* 29:1090, 1983), enzymatic methods (e.g., by using tryptophanase; see, for example, Kimura et al., *Clin. Chem.* 38:44, 1992), colorimetric methods (e.g., using tetraphenyl borate), etc. In some embodiments, magnesium is measured by complexometric titration, flame emission photometry, atomic absorption spectophotometry, other spectrophotometric techniques including enzymatic techniques and dye binding methods (e.g., Magnon dye binding and bichromatic absorbance; see, for example, Barbour et al., *Clin. Chem.* 34:2103, 1988; elimination of interference by bilirubin; see, for example, Rehak et al., *Clin. Chem* 35:1031, 1989; etc.). In many embodiments, assays are performed in an automated clinical chemistry analyzer (e.g., the Abbott ARCHITECT®, etc.).

Where both potassium and magnesium levels are assessed, they may be assessed separately or together. Assessment of potassium and/or magnesium levels may be performed prior to, at the same time as, and/or after initiation of Compound I therapy.

In some embodiments, if an individual is determined to have serum potassium and/or magnesium concentration(s) that is/are below normal, or below the high end of normal as described herein, potassium and/or magnesium supplementation is administered prior to, at the same time as, or after initiation of Compound I therapy. In some embodiments, Compound I therapy is suspended or delayed until serum potassium and/or magnesium levels are increased. In some embodiments, Compound I therapy is suspended or delayed until serum potassium and/or magnesium levels are increased to within the normal range, or to within the upper end of the normal range. In some embodiments, Compound I therapy is suspended or delayed until serum potassium concentration is above about 3.5 mEq/L; or is above about 3.8 mEq/L. In some embodiments, Compound I therapy is suspended or delayed until serum magnesium concentration is above about 1.25 mEq/L; or is above about 1.8 mEq/L; or is above about 1.9 mEq/L. In some embodiments, Compound I therapy is suspended or delayed until both serum potassium and serum magnesium concentrations are increased as described.

In some embodiments, electrolyte supplementation may be administered prior to, concurrently with, and/or subsequent to initiation of Compound I therapy, and may include potassium and/or magnesium supplementation. In some embodiments, electrolyte supplementation may include supplementation of one or more electrolytes selected from the group consisting of sodium, potassium, chloride, calcium, magnesium, bicarbonate, phosphate, sulfate, and combinations thereof.

A variety of different potassium supplemental forms is available (see, for example, the web page at the following world-wide-web address: pdrhealth.com). For example, potassium supplements in the form of potassium chloride, potassium citrate, potassium gluconate, potassium bicarbonate, potassium aspartate and/or potassium orotate can readily be obtained.

One of potassium supplemental forms is high-potassium (up to 800 milligrams per serving), low-sodium vegetable juices. Some soft drinks are rich in potassium. Some soft drinks contain potassium gluconate which has a less bitter taste than some other potassium supplements. Salt substitutes are high in potassium.

Certain foods high in potassium such as raisins, figs, apricots, sardines, veal, bananas, avocado, and broccoli may be used as potassium supplements. Foods high in potassium may provide potassium that is easily bioavailable and/or may reduce gastrointestinal side effects associated with the administration of potassium salts. The potassium supplement may also be provided as part of a multivitamin.

Potassium is typically supplemented orally or intravenously, though other modes of delivery are within the scope of the present disclosure.

Certain commercially available forms of potassium supplements include, for example, potassium acetate (e.g., 2 mEq/mL or 4 mEq/mL for injection); potassium acetate (e.g., 75 mg, 95 mg, 99 mg, and 180 mg tablets and/or 2 mEq/mL, 10 mEq/50 mL, 20 mEq/50 mL, 10 mEq/100 mL, 20 mEq/100 mL, 30 mEq/100 mL, 40 mEq/100 mL for injection and/or 20 mEq/15 mL, 40 mEq/15 mL liquid and/or 20 mEq or 25 mEq powder for reconstitution, and/or 9 mEq, 10 mEq, or 20 mEq extended release tablets), and potassium gluconate (e.g., 486 mg, 500 mg, 550 mg, 595 mg, 610 mg, and 620 mg tablets).

A variety of different magnesium supplemental forms are also available. For example, supplements in the form of magnesium chloride, magnesium gluconate, magnesium lactate, magnesium oxide and/or magnesium sulfate can readily be obtained.

Certain foods high in magnesium such as artichoke, banana, figs, almonds, cashews, pine nuts, brazil nuts, beans, spinach, and tomatoes may be used as magnesium supplements. The magnesium supplement may also be provided as part of a multivitamin.

Certain commercially available forms of magnesium supplements include magnesium chloride (e.g., 200 mg/ml for injection, 535 mg extended release tablets), magnesium gluconate (3.25 mg/mL, 1000 mg/5 mL liquid; 500 mg tablet); magnesium lactate (84 mg extended release tablet); magnesium oxide (e.g., 140 mg, 600 mg capsules, powder, and/or 200 mg, 250 mg, 400 mg, 420 mg, and 500 mg tablets), magnesium sulfate (e.g., 40 mg/mL, 80 mg/mL, 125 mg/mL, 500 mg/mL, for injection).

In some embodiments, electrolyte supplementation is administered in an amount sufficient to reduce or delay onset of one or more cardiac toxicities associated with Compound I therapy. In some embodiments, the electrolyte administration may also reduce one or more of nausea, vomiting, fatigue (lethargy, malaise, asthenia), increased creatine phospho kinase (CPK), hyperuricemia, hypocalcemia, hyperglycemia, fever, gastritis, diarrhea, abdominal pain, dehydration, weight loss, hypophosphatemia, hyponatremia, hypokalemia, hypomagnesemia, syncope, hypoxia, pleural effusion, hypotension, myocardial ischemia, increased cardiac troponin I, confusion, and/or myelosuppression, and combinations thereof. In some embodiments, cardiac toxicities are selected from the group consisting of heart-rate corrected QT (QTc) interval prolongation, supraventricular arrhythmias (supraventricular tachycardia (SVT)/atrial fibrillation/flutter), and combinations thereof. In some embodiments, QTc prolongation and/or other electrophysiological changes are reduced to normal values or ranges after electrolyte supplementation.

Unless otherwise defined, all technical and scientific terms used herein are accorded the meaning commonly known to one of skill in the art. All publications, patents, published patent applications, and other references mentioned herein are hereby incorporated by reference in their entirety. The embodiments of the disclosure should not be deemed to be mutually exclusive and can be combined.

EXAMPLES

General Procedures for Characterization of Solid Forms

Provided herein is an assortment of characterizing information to describe provided forms of Compound I. It should be understood, however, that not all such information is required for one skilled in the art to determine that such particular form is present in a given composition, but that the determination of a particular form can be achieved using any portion of the characterizing information that one skilled in the art would recognize as sufficient for establishing the presence of a particular form, e.g., even a single distinguishing peak can be sufficient for one skilled in the art to appreciate that such particular form is present. *United States Pharmacopeia* provides additional guidance with respect to characterization of crystalline forms (see, X-Ray Diffraction, <941>. *United States Pharmacopeia*, 31st ed. Rockville, Md.: United States Pharmacopeial Convention; 2008:372-374), which is incorporated herein by reference.

Materials

Solvents were either HPLC grade or ACS grade, unless stated otherwise. Samples were prepared from Compound I Form A solids or from samples generated from these solids. Form designation for the materials was based on X-ray powder diffraction (XRPD). Care was taken to protect samples from light, unless stated otherwise. Prior to characterization, solids were stored as follows: Form A and Form B (may have contained Form A solids as well) under ambient conditions, Form E and Form H over desiccant in a freezer, Form C in contact with mother liquor in a refrigerator, Form D in contact with mother liquor in a freezer, and Form I in contact with mother liquor under ambient conditions or in a freezer. Due to apparent instability of Form D, all characterization data except solution proton nuclear magnetic resonance spectroscopy ($^1$H-NMR) were collected for Form D on the same day. Although the $^1$H-NMR analysis was not run until a few days later, the solution for the analysis was prepared on the same day as the rest of the characterization.

Instrumental Techniques

Optical Microscopy

Optical microscopy was performed using a Leica MZ12.5 stereomicroscope. Samples were viewed in situ or on a glass slide (sometimes covered in Paratone-N oil) with crossed polarizers and a first order red compensator. Various objectives were used, ranging from 0.8-10×.

X-Ray Powder Diffraction (XRPD) (Inel)

XRPD patterns were collected using an Inel XRG-3000 diffractometer equipped with a curved position sensitive detector with a 2θ range of 120°. An incident beam of Cu Kα radiation (40 kV, 30 mA) was used to collect data in real time at a resolution of 0.03° 2θ. Prior to the analysis, a silicon standard (NIST SRM 640c) was analyzed to verify the Si 111 peak position. Samples were prepared for analysis by packing them into thin-walled glass capillaries. Each capillary was mounted onto a goniometer head and rotated during data acquisition. The monochromator slit was set at 5 mm by 160 μm.

PANalytical Transmission

XRPD patterns were collected using a PANalytical X'Pert Pro diffractometer. An incident beam of Cu Kα radiation was produced using an Optix long, fine-focus source. An elliptically graded multilayer mirror was used to focus the Cu Kα X-rays of the source through the specimen and onto the detector. Data were collected and analyzed using X'Pert Pro Data Collector software (v.2.2b). Prior to the analysis, a silicon specimen (NIST SRM 640c) was analyzed to verify the Si 111 peak position. The specimen was sandwiched between 3 μm thick films, analyzed in transmission geometry, and rotated to optimize orientation statistics. A beam-stop was used (sometimes with helium gas) to minimize the background generated by air scattering. Soller slits were used for the incident and diffracted beams to minimize axial divergence. Diffraction patterns were collected using a scanning position-sensitive detector (X'Celerator) located 240 mm from the specimen.

PANalytical Reflection

XRPD patterns were collected using a PANalytical X'Pert Pro diffractometer. An incident beam of Cu Kα radiation was produced using a ceramic tube with a long, fine-focus source and a nickel filter. The diffractometer was configured using the symmetric Bragg-Brentano geometry with a reflection stage and a manually operated spinner. Data were collected and analyzed using X'Pert Pro Data Collector software (v. 2.2b). Prior to the analysis, a silicon specimen (NIST SRM 640c) was analyzed to verify the Si 111 peak position. The specimen was prepared as a thin, circular layer centered on a silicon zero-background substrate. Anti-scatter slits were used to minimize the background generated by air scattering. Soller slits were used for the incident and diffracted beams to minimize axial divergence. Diffraction patterns were collected using a scanning position-sensitive detector (X'Celerator) located 240 mm from the specimen.

Peak Identification Process (XRPD)

Peaks within the range of up to about 30° 2θ were selected. Different rounding algorithms were used to round each peak to the nearest 0.01° 2θ, depending upon the instrument used to collect the data and/or the inherent peak resolution. The location of the peaks along the x-axis (° 2θ) in both the figures and the tables were automatically determined using proprietary software[1] and rounded to two significant figures after the decimal point based upon the above criteria. Peak position variabilities are given to within ±0.1° 2θ based upon recommendations outlined in the USP discussion of variability in x-ray powder diffraction[2]. For d-space listings, the wavelength used to calculate d-spacings was 1.541874 Å, a weighted average of the Cu—$K_{\alpha 1}$ and Cu—$K_{\alpha 2}$ wavelengths. Variability associated with d-spacing estimates was calculated from the USP recommendation, at each d-spacing, and provided in the respective data tables.

[1] PatternMatch™ 3.0.4.
[2] United States Pharmacopeia, USP 32, NF 27, Vol. 1, pg. 392, May 1, 2009 <941> X-Ray Diffraction.

For samples with only one XRPD pattern and no other means to evaluate whether the sample provides a good approximation of the powder average, peak tables contain data identified only as "Prominent Peaks". These peaks are a subset of the entire observed peak list. Prominent peaks are selected from observed peaks by identifying preferably non-overlapping, low-angle peaks, with strong intensity.

If multiple diffraction patterns are available, then assessments of particle statistics (PS) and/or preferred orientation (PO) are possible. Reproducibility among XRPD patterns from multiple samples analyzed on a single diffractometer indicates that the particle statistics are adequate. Consistency of relative intensity among XRPD patterns from multiple diffractometers indicates good orientation statistics. Alternatively, the observed XRPD pattern may be compared with a calculated XRPD pattern based upon a single crystal structure, if available. Two-dimensional scattering patterns using area detectors can also be used to evaluate PS/PO. If the effects of both PS and PO are determined to be negligible, then the XRPD pattern is representative of the powder average intensity for the sample and prominent peaks may be identified as "Representative Peaks".

"Characteristic peaks" are a subset of Representative Peaks and are used to differentiate one crystalline polymorph from another crystalline polymorph. Characteristic peaks are determined by evaluating which representative peaks, if any, are present in one crystalline polymorph of a compound against all other known crystalline polymorphs of that compound to within ±0.1 °2θ. Not all crystalline polymorphs of a compound necessarily have at least one characteristic peak.

Differential Scanning Calorimetry (DSC)

DSC was performed using a TA Instruments Q2000 differential scanning calorimeter. Temperature calibration was performed using NIST traceable indium metal. The sample was placed into an aluminum DSC pan, and the weight was accurately recorded. The pan was covered with a lid, and the lid was crimped. A weighed, crimped aluminum pan was placed on the reference side of the cell. The sample cell was equilibrated at the initial temperature and heated under a nitrogen purge. Reported temperatures are at the transition maxima, unless stated otherwise.

Modulated Differential Scanning Calorimetry (MDSC)

MDSC data were obtained on a TA Instruments Q2000 differential scanning calorimeter equipped with a refrigerated cooling system (RCS). Temperature calibration was performed using NIST traceable indium metal. The sample was placed into an aluminum DSC pan, and the weight was accurately recorded. The pan was covered with a lid perforated with a laser pinhole, and the lid was crimped or crimped then hermetically-sealed pan. A weighed, crimped aluminum pan was placed on the reference side of the cell. Data were obtained using a modulation amplitude of ±0.50° C. and a 60 second period with an underlying heating rate of 2.00° C./minute from −50.00 to 200.00° C. The reported glass transition temperatures are obtained from the inflection point of the step change in the reversing heat flow versus temperature curve.

Thermogravimetric Analysis (TGA)

TG analysis was performed using a TA Instruments 2050 thermogravimetric analyzer. Temperature calibration was performed using nickel and Alumel™. The sample was placed in an aluminum pan and inserted into the TG furnace. In one embodiment, the pan was left open. The sample cell was equilibrated at the initial temperature and the furnace was heated under nitrogen. In another embodiment, the instrument was operated under a flow of helium at 10 and 90 cc/min for the purge and balance, respectively, and the furnace was heated under helium at a rate of 20° C./minute to a final temperature of 250° C.

Infrared Spectroscopy (FT-IR)

In one embodiment, FT-IR spectra for solid forms described herein were acquired on Magna-IR 860® Fourier transform infrared (FT-IR) spectrophotometer (Thermo Nicolet) equipped with an Ever-Glo mid/far IR source, an extended range potassium bromide (KBr) beamsplitter, and a deuterated triglycine sulfate (DTGS) detector. Some amorphous solid form FT-IR spectra were acquired using Nexus 670®, equipped in the same way as described for Magna-IR 860® above. Wavelength verification for Magna-IR 860® and Nexus 670® were performed using NIST SRM 1921b (polystyrene). An attenuated total reflectance (ATR) accessory (Thunderdome™, Thermo Spectra-Tech), with a germanium (Ge) crystal was used for data acquisition. A background data set was acquired with a clean Ge crystal. A Log 1/R (R=reflectance) spectrum was obtained by taking a ratio of these two data sets against each other.

In another embodiment, FT-IR spectra were acquired on a Nexus 670® Fourier transform infrared spectrophotometer (Thermo Nicolet) equipped with an Ever-Glo mid/far IR source, a potassium bromide (KBr) beamsplitter, and a deuterated triglycine sulfate (DTGS) detector. Wavelength verification was performed using NIST SRM 1921b (polystyrene). An attenuated total reflectance (ATR) accessory (Thunderdome™, Thermo Spectra-Tech), with a germanium (Ge) crystal was used for data acquisition. Each spectrum represents 512 co-added scans collected at a spectral resolution of 2 $cm^{-1}$. A background data set was acquired with a clean Ge crystal. A Log 1/R (R=reflectance) spectrum was obtained by taking a ratio of these two data sets against each other.

Peak positions were determined using standard spectral software. Peak position variabilities are given to within ±2 $cm^{-1}$, based on the observed sharpness of the peaks picked and acquisition of data using a 1 $cm^{-1}$ data point spacing (2 $cm^{-1}$ resolution). The accuracy and precision associated with any particular measurement reported herein has not been determined.

Nuclear Magnetic Resonance (NMR)

Solution proton nuclear magnetic resonance spectra ($_1$H-NMR) were acquired with a
Varian UNITYINOVA-400 spectrometer. Samples were prepared as solutions in deuterated dimethylsulfoxide (DMSO-$d_6$).

Raman Spectroscopy

Raman spectra were acquired on a FT-Raman 960 spectrometer (Thermo Nicolet) equipped with a germanium (Ge) detector. Wavelength verification was performed using sulfur and cyclohexane. Each sample was prepared for analysis by placing the sample into a 13 mm diameter gold-coated cup and leveling the material. Each spectrum represents 512 co-added scans collected at a spectral resolution of 2 $cm_{-1}$.

Example 1

General Preparation of Compound I

Various preparations and purifications of Compound I were described in U.S. Pat. No. 4,977,138, issued Dec. 11, 1990 and International PCT Application WO02/20817, filed Aug. 22, 2001, each of which is incorporated herein by reference in their entireties.

In some embodiments, producing, purifying and/or storing Compound I at an apparent pH less than approximately 6.5 and/or at an apparent pH of about less than approximately 6.0 has been found to prevent the formation of dimerized, oligomerized or polymerized Compound I, as described in US Patent Application Publication No. US 20090186382, filed Dec. 28, 2007, which is incorporated herein by reference. In one embodiment, one or more of the purification steps are performed at an apparent pH less than 6.5. In another embodiment, one or more of the purification steps are performed at an apparent pH less than 6.0. In certain embodiments, one or more purification steps are performed at an apparent pH ranging from 4.0 to 6.0. In certain embodiments, all of the purification steps are carried out at an apparent pH ranging from approximately 4.0 to approximately 6.0. In order to prevent the formation of undesired contaminants, the apparent pH of a solution containing Compound I is not allowed to reach an apparent pH above approximately 7.0, or more preferably above approximately 6.0. The apparent pH of all purification processes is preferably monitored and subsequently adjusted, if need be, to an apparent pH below approximately 6.0. In certain embodiments, it is maintained within the apparent pH range of approximately 4.0 to approximately 6.0. The control of apparent pH in purification steps towards the end of the process or steps using aqueous solutions have been found to be particularly useful in diminishing or eliminating the formation of undesired contaminants. Any acid or buffer may be used to control pH. In certain embodiments, an organic acid such as acetic acid or formic acid is used to control pH in one of more of the purification steps. In certain embodiments, an inorganic acid such as phosphoric acid or hydrochloric acid is used.

Any procedure for purifying Compound I, whether from fermentation, semi-synthesis, or total synthesis, can be modified based on the present disclosure to prevent the formation of undesired side products by monitoring apparent pH and reducing the apparent pH, if necessary.

Exemplary data for Compound I in the form of $^1$H-NMR in depicted in FIG. 1(a) and a molecular structure of Compound I is depicted in FIG. 1(b). The $^1$H-NMR depicted in FIG. 1(a) displays chemical shifts and integration consistent with Compound I, has residual acetone present (at approximately 2.08 ppm) and the water peak (occurring at 3.33 ppm) has been truncated.

Example 2

Preparation and Characterization of Form C and/or Compositions Containing Form C Compound I Form C was prepared via serial seeding of saturated solutions of romidepsin Form A with solids containing Compound I Form C, with the resulting X-ray powder diffraction (XRPD) pattern of each generated material exhibiting more reflections present in the Compound I Form C pattern than the last. The series included three experiments: (a) First Seeding Procedure; (b) Second Seeding Procedure; and (c) Final Preparation of Compound I Form C. An XRPD pattern collected for final product Compound I Form C does not appear to exhibit reflections from Compound I Form A. The experiments were conducted as follows:

(a) First Seeding Procedure-Preparation of Portion 1 and Portion 2 Samples

Compound I Form A (103 mg, 0.2 mmol) and acetone (5 mL) were charged to a glass vial and vortexed for approximately 1 minute, generating a clear solution. The vial was immersed in a −5° C. bath, as measured by a NIST-traceable thermometer. The sample was left in the bath unstirred for approximately 26 hours, producing a slight precipitate. The precipitate was removed via filtration through a 0.2 μm nylon filter disc to a clean glass vial, resulting in a clear solution.

While the solution was still cold, cold water (15 mL) was added, without agitation. The solution remained clear and cold, with no visible precipitate, and the sample was returned to the −5° C. bath. The sample was left in the bath unstirred for approximately 5 days. After the first night, the vial was gently shaken before returning to the bath, resulting in no apparent change in the sample. After the 5 days, solids were observed on the bottom of the vial.

The supernatant was decanted off and the solids were gently crushed, producing slurry. A portion of the slurry ("portion 1") was centrifuged in small aliquots at ambient temperature in a 1.0 mm glass capillary, for analysis by X-ray powder diffraction. Centrifugation was done in increments of several seconds to approximately 10 minutes, with total centrifugation more than 20 minutes. X-ray powder diffraction analysis showed evidence of reflections present in Compound I Form A and Compound I Form C, suggesting the recovered solids were a mixture of phases.

A second portion ("portion 2") was left open in a vial at ambient temperature to partially dry the solids while a capillary was being prepared. Both capillary and bulk samples were stored in a refrigerator before and after the analysis. The capillary sample was analyzed shortly after preparation and the bulk sample was used as seed on the day of its isolation.

(b) Second Seeding Procedure

Compound I Form A (1.03 g, 1.9 mmol) and acetone (37 mL) were charged to a glass vial and vortexed briefly, generating a clear solution. The vial was immersed in a −5° C. bath, as measured by a NIST-traceable thermometer. The sample was left in the bath unstirred for approximately 1.5 hours, producing a relatively small amount of precipitate. The precipitate was removed via cold filtration through a 0.2 μm nylon filter disc to a clean glass round bottom flask.

The flask contained solids from "portion 2" (the amount approximately that of a spatula tip) as seed, to encourage formation of Compound I Form C. No precipitate was apparent but the seed solids remained. Additional solids from "portion 2" (the amount approximately that of a spatula tip) were added. No precipitate was apparent but the seed solids remained.

Cold water (111 mL) was poured in all at once. After a few minutes, there appeared to be a slight precipitate. The flask was immersed in the −5° C. bath overnight. Only a slight precipitate was observed. The sample was briefly shaken and returned to the bath for approximately 2 hours, resulting in substantial precipitate. Solids were gently scraped down from the flask walls.

Targeting solids on the flask bottom, "portion 3" was centrifuged in small aliquots at ambient temperature in a 1.0 mm glass capillary, for analysis by X-ray powder diffraction. Centrifugation was done in increments of several seconds. X-ray powder diffraction analysis showed the recovered solids to consist mainly of Compound I Form C, and indications of presence of Compound I Form A.

The sample was stored in a refrigerator before and after the analysis but was not analyzed until the next day. Analysis occurred shortly after removal from the refrigerator ("portion 4"). "Portion 4" was left sealed at ambient temperature while the capillary was being prepared, returned to the −5° C. bath for approximately 3 days and then stored in a refrigerator briefly before being used as seed.

(c) Final Preparation of Form C

Compound I, Form A (1.09 g, 2.0 mmol) and acetone (39 mL) were charged to a glass vial, vortexed and briefly bath sonicated, generating a clear solution. The vial was immersed in a −5° C. bath, as measured by a NIST-traceable thermometer. The sample was left in the bath unstirred for approximately 2.5 hours, producing a relatively small amount of precipitate. The solid precipitate was removed via cold filtration through a 0.2 μm nylon filter disc to a clean glass round bottom flask, resulting in a clear solution.

The flask was seeded with slurry from "portion 4" (approximately 1 mL), to encourage formation of Compound I Form C. No precipitate was apparent but the seed solids remained.

Cold water (400 mL) was poured in all at once. There appeared to be a very slight precipitate and the seed solids persisted. Additional slurry from "portion 4" (approximately 1 mL) was added, with the same result, even after briefly swirling the flask. The flask was immersed in the −5° C. bath for approximately 3 days, freezing the solvent.

After leaving the flask in the refrigerator overnight, the solvent melted but solids remained. The flask was swirled and the sample was centrifuged in 50 mL aliquots at ambient temperature in two plastic centrifuge tubes simultaneously. Centrifugation was done in increments of approximately 5 to 10 minutes, minimizing warming of the sample and ensuring clear supernatant was generated. The resulting supernatants were decanted off to a clean HDPE bottle. The final flask aliquot included rinsing once with liquid from the bottle (several mL) to recover additional solids from the flask walls. These solids did not appear to be new precipitate but collected on the walls when pouring sample from the flask into the tubes. Little residual sample was present in the flask and this residual was not recovered. After the flask sample was exhausted, the centrifuged samples were recovered to one tube, rinsing the other tube twice with liquid from the bottle (approximately 15 mL per rinse). The final supernatant was left with the solids. The tubes, flask and bottle were stored in a refrigerator when not being manipulated. This included overnight storage since the centrifugation was completed over two days and solids were not isolated until the day after centrifugation.

Targeting the solids on the tube bottom, a portion of final product Compound I Form C was centrifuged in small aliquots at ambient temperature in a 1.0 mm glass capillary, for immediate analysis by X-ray powder diffraction. Centrifugation was done in increments of several seconds.

Exemplary data for Compound I Form C in the form of X-ray diffraction patterns (XRPD), differential scanning calorimeter thermograms (DSC), thermogravimetric analysis thermograms (TGA), infrared spectrums (FT-IR), and single crystal structure data (e.g., ORTEP drawings, packing diagrams, positional parameters, bond distances and bond angles) are depicted in FIGS. 1(c) through 1(q), supra. A summary of exemplary data presented in FIGS. 1(c) through 1(q) is as follows.

Form C is a crystalline non-stoichiometric hydrate of Compound I, as determined from single crystal data (see FIGS. 1(i) through 1(q)). The crystal structure contains one fully occupied water molecule and a second water site with a refined occupancy of approximately 73%. The characterization of Compound I, Form C is summarized in Table 3.

TABLE 3

Characterization of Compound I Form C

| Analysis | Result | Figure References |
|---|---|---|
| XRPD | Form C | 1(c), 1(d), 1(i), 1(j) |
| DSC | 96.6° C. (broad endo, min) 139.6° C. (broad endo, min) 177.2° C. (broad exo, max) 257.1° C. (endo, min) followed by decomp. | 1(e) |
| TGA | 5.3 wt % loss to 103° C. | 1(f) |
| FT-IR | reference spectrum | 1(g), 1(h) |
| Single Crystal X-ray (non-GMP) | Form C (non-stoichiometric hydrate, ~1.7 waters) | 1(i)-1(q) |

Figure 1E:
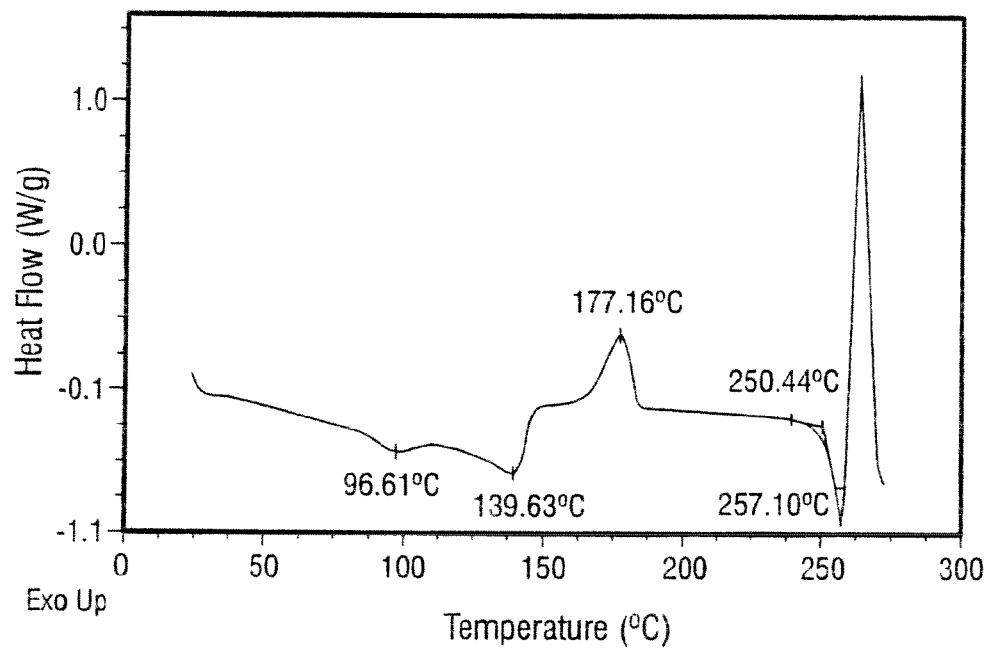
Figure 1F:
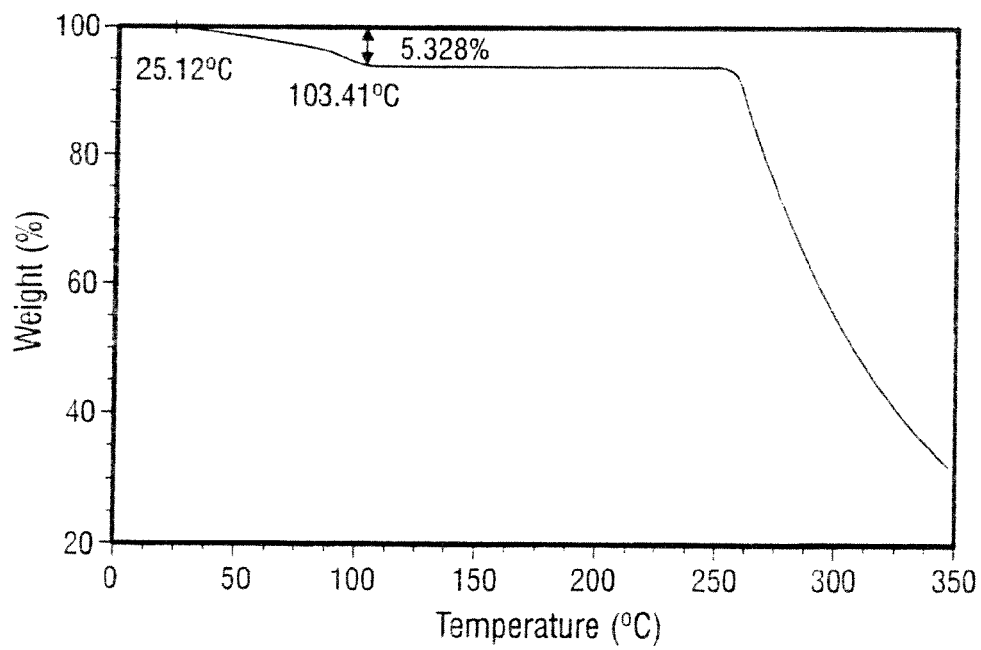
Figures 1G, 1H:
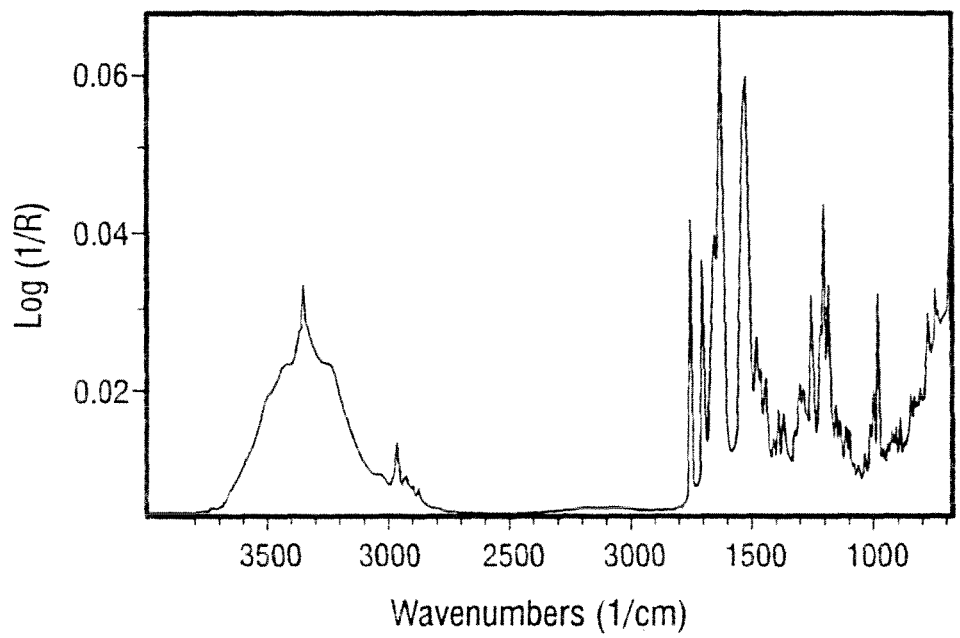
Figure 1I:
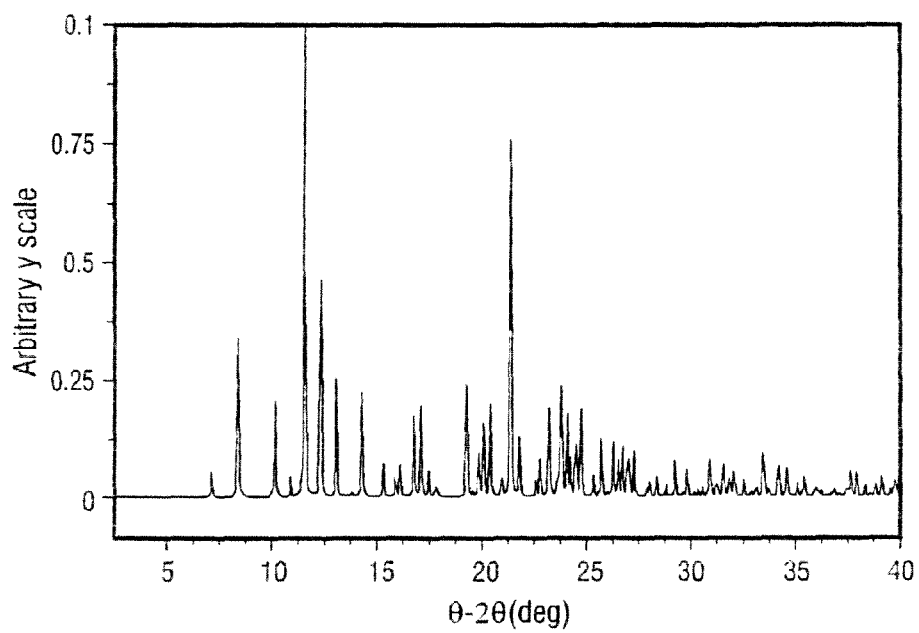
Figure 1K:
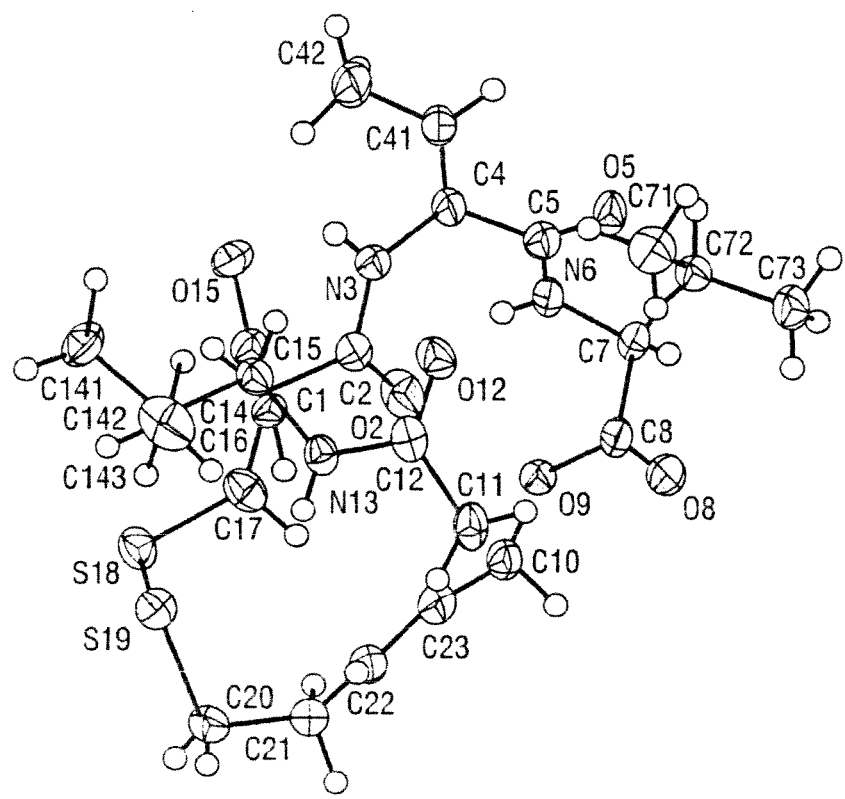
Figure 1L:
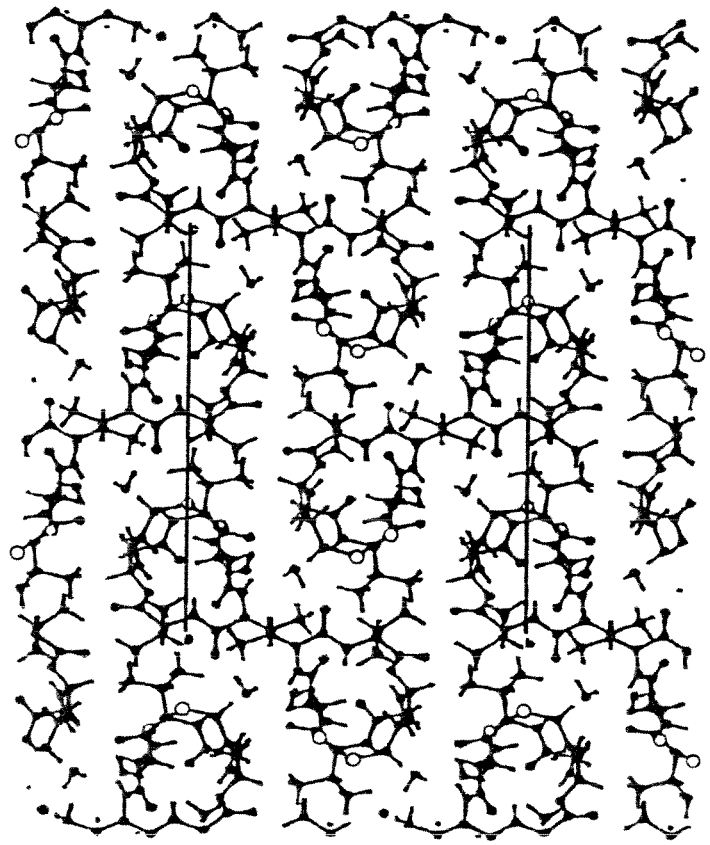
Figure 1M:
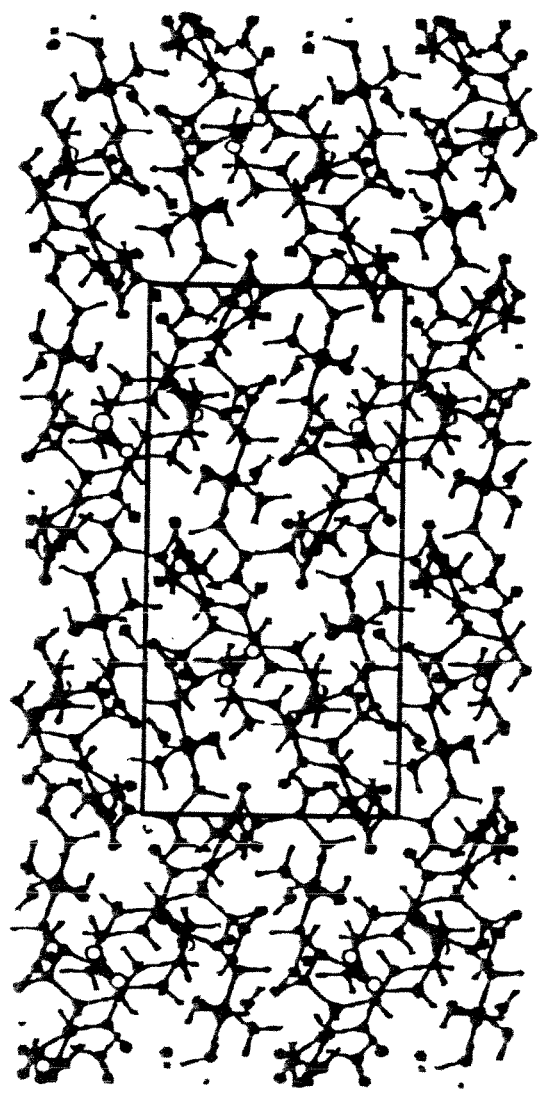
Figure 1N:
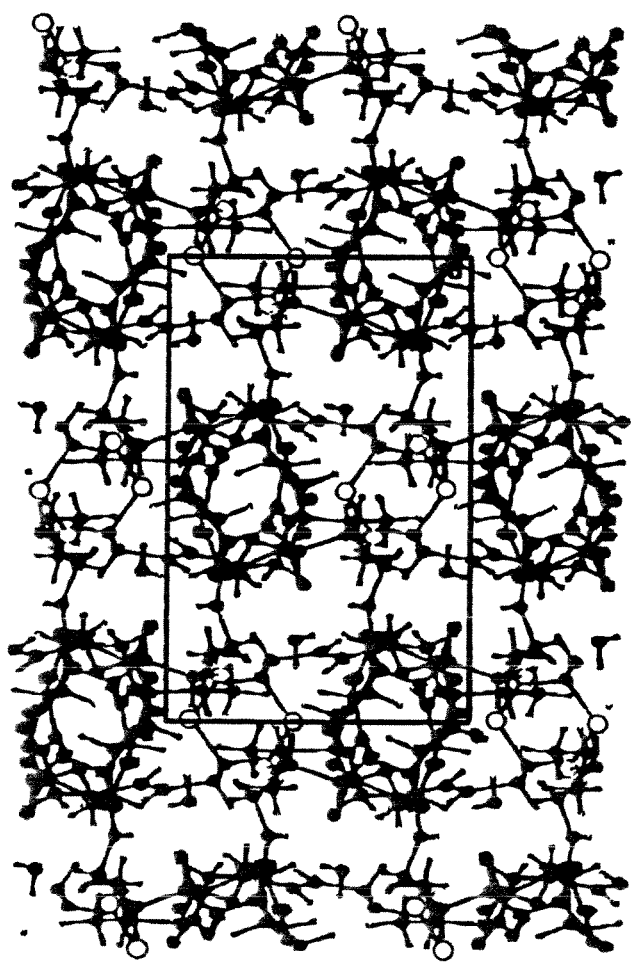

A comparison of the XRPD pattern final product for Compound I Form C (see FIGS. 1(c) and 1(d)); and the calculated pattern collected at subambient temperature (see FIGS. 1(i) and 1(j)) from the structure of Compound I, Form C, suggests that the XRPD patterns represent a single phase and that none of the observed reflections are attributed to Compound I Form A. The single crystal data were collected at cryogenic temperature, so minor, uneven shifting of 2θ peak positions due to temperature effects was observed.

The differential scanning calorimetry (DSC) thermogram for Compound I, Form C (see FIG. 1(e)) exhibits broad endothermic events at approximately 97° C. and 140° C. (min), ascribed to loss of solvent, based on the 5.3% weight loss observed in the thermogravimetric analysis (TGA) thermogram (see FIG. 1(f)). This weight loss corresponds to approximately 1.7 moles of water, which is similar to the result obtained from the single crystal data. However, the loss may include acetone, since the sample was crystallized from an acetone/water mixture. The DSC thermogram also exhibits an endotherm at approximately 257° C. (min) (see FIG. 1(e)). This endotherm is believed to correspond to the melt of Compound I Form A and apparent desolvation of solids. A minor exothermic event was observed at approximately 177° C. (see FIG. 1(e)). Based on the apparent melting temperature, this appears to represent recrystallization to Compound I Form A. The final weight loss from TGA suggests that decomposition is concurrent with the apparent melt observed by DSC, as it was for Compound I Form A. Solids were air-dried in a laboratory fume hood at ambient temperature for approximately 2.5 hours to remove residual solvent before the analyses, in order to obtain representative thermal data for Compound I, Form C.

One skilled in the art will be able to readily ascertain from the data presented that Form C may be isostructural with the methanol solvate reported in Shigematsu et al., The Journal of Antibiotics, Vol. 47, No. 3, "FR901228, A Novel Antitumor Bicyclic Depsipeptide Produced by *Chromobacterium violaceum* No. 968, pp. 311-314 (March 1994).

Example 3

Preparation and Characterization of Form D and/or Compositions Containing Compound I Form D Compound I Form A (1.20 g, 2.2 mmol) and acetone (38 mL) were charged to a glass Erlenmeyer flask, shaken, swirled, and bath sonicated for a few minutes, dissolving most of the solids. Undissolved solids were removed via filtration through a 0.2 µm nylon filter disc to a clean glass Erlenmeyer flask, resulting in a clear solution. Hexanes (152 mL) was added, which precipitated solids immediately, without agitation. The flask was left in a freezer overnight, allowing the solids to settle to the bottom of the flask. The clear supernatant was decanted off and aliquots of solid were removed for immediate X-ray powder diffraction analysis. The analysis showed that the solids consisted of Compound I Form D. Solids were recovered from the analysis sample for thermal and spectroscopic analyses. Unused material was stored in the freezer.

Exemplary data for Compound I Form D in the form of an XRPD, a DSC, a TGA and an FT-IR are depicted in FIGS. 2(a) through 2(f), supra. A summary of exemplary data presented in FIGS. 2(a) through 2(f) is as follows. As described in Example 8, one skilled in the art will be able to readily ascertain from the data presented herein that Compound I Form D may be isostructural with MEK solvate (Compound I Form J).

Form D is an unstable crystalline acetone solvate of Compound I that converts to Form A under ambient conditions. A crystal prepared from cold acetone solution was indexed. The indexing solution was determined to be an orthorhombic unit cell with the following cell parameters and calculated volume: a=9.093, b=15.581, c=23.141 Å, V=3278.57(9) Å$^3$. The formula weight was determined to be 598.81 g/mol. The cell parameters are similar to the cell obtained from the Compound I Form J crystal structure. The similarity between the two unit cells and XRPD patterns of Compound I Form D and Compound I Form J suggest the two samples are related crystal forms. Since Compound I Form J was determined to be a mono methyl ethyl ketone solvate of Compound I, it is likely that Form D is also a mono solvate of Compound I. Characterization of Compound I Form D is summarized in Table 4.

TABLE 4

Characterization of Compound I Form D

| Analysis | Result | Figure References |
|---|---|---|
| XRPD | Form D | 2(a), 2(b) |
| DSC | 91.4° C. (exo, max) 260.6° C. (endo, max) followed by decomp | 2(c) |
| TGA | 10.9 wt % loss to 63° C. | 2(d) |
| FT-IR | reference spectrum | 2(e), 2(f) |

An experimental Compound I Form D pattern is provided in FIG. 2(a) with an accompanying line list in FIG. 2(b). The pattern is consistent with a pattern for Compound I Form D and similar to a pattern for Compound I Form J as observed in the XRPD overlay presented in FIG. 6(a). This high resolution pattern of FIG. 2(a) was collected after storage of the material in a freezer and displayed presence of Compound I Form D and Compound I Form A, suggesting a mixture of phases, so the pattern generated from the material after storage in the freezer was used to generate a corresponding peak list for Compound I Form D (see FIG. 2(b)).

An FT-IR spectrum of Compound I Form D and accompanying peak list is provided as FIG. 2(e) and FIG. 2(f). To avoid the potential for form conversion from solvent loss, the solids for the FT-IR data were collected immediately upon removal from the freezer.

The TGA thermogram for Compound I Form D (see FIG. 2(d)) exhibits a weight loss of approximately 10.9% and the DSC thermogram (see FIG. 2(c)) exhibits a small exothermic event at approximately 91° C. These events appear to be mainly related to desolvation and recrystallization to Compound I Form A, respectively, based on the instability of Compound I Form D and tendency for conversion to Compound I Form A. The weight loss observed by TGA corresponds to slightly more than a mole of acetone. To avoid the potential for Form conversion from solvent loss, the solids were analyzed immediately upon removal from the freezer. Since no weight loss was observed prior to the start of the analysis, the weight loss observed is attributed to solvent loss from the crystal lattice, also suggesting Compound I Form D is an acetone solvate. The DSC thermogram also exhibits an endotherm at approximately 261° C. (min). The endotherm is believed to correspond to a melt of Compound I Form A and apparent desolvation of the solids. Final weight loss from TGA suggests that decomposition is concurrent with apparent melt observed by DSC, as it was for Compound I Form A.

Example 4

Preparation and Characterization of Form E and/or Compositions Containing Form E Compound I Form A (2.75 g, 5.1 mmol) and solution containing a mixture of t-butanol and water [60:40 (v/v)] (31 mL) were charged to a 50 mL Erlenmeyer flask. Solids remained. The sample was stirred overnight at ambient temperature and the resulting solids were collected by vacuum filtration. The recovered solids were transferred to weigh paper and dried under ambient conditions for approximately 2 hours. The dried solids were transferred to a glass vial and stored under ambient conditions. X-ray powder diffraction analysis showed the solids to consist of Compound I Form E. Solid recovery was 2.79 g (89%).

Exemplary data for Compound I Form E in the form of an XRPD, a DSC, a TGA an FT-IR, a Raman spectrum and single crystal structure data (e.g., ORTEP drawings, packing diagrams, positional parameters, bond distances and bond angles) are depicted in FIGS. 3(a) through 3(p), supra. A summary of exemplary data presented in FIGS. 3(a) through 3(p) is as follows. One skilled in the art will be able to readily ascertain from the data presented herein that Compound I, Form E may be isostructural with Compound I, Form H (see Example 6).

Compound I Form E is a crystalline mono-tert-butanol solvate of Compound I, as determined from single crystal data (see FIGS. 3(h) through 3(p)). The characterization of Compound I Form E is summarized in Table 5.

TABLE 5

Characterization of Compound I Form E

| Analysis | Result | Figure References |
|---|---|---|
| XRPD | Form E | 3(a), 3(b), 3(h), 3(i) |
| DSC | 158.1° C. (broad endo, peak) 255.3° C. (endo, max) followed by apparent decomp. | 3(c) |
| TGA | 10.9 wt % loss to 200° C. | 3(d) |
| Single Crystal X-ray (non-GMP) | Form E (mono tert-butanol solvate) | 3(h)-3(p) |
| FT-IR | reference spectrum | 3(e), 3(f) |
| Raman | reference spectrum | 3(g) |

Figure 3C:
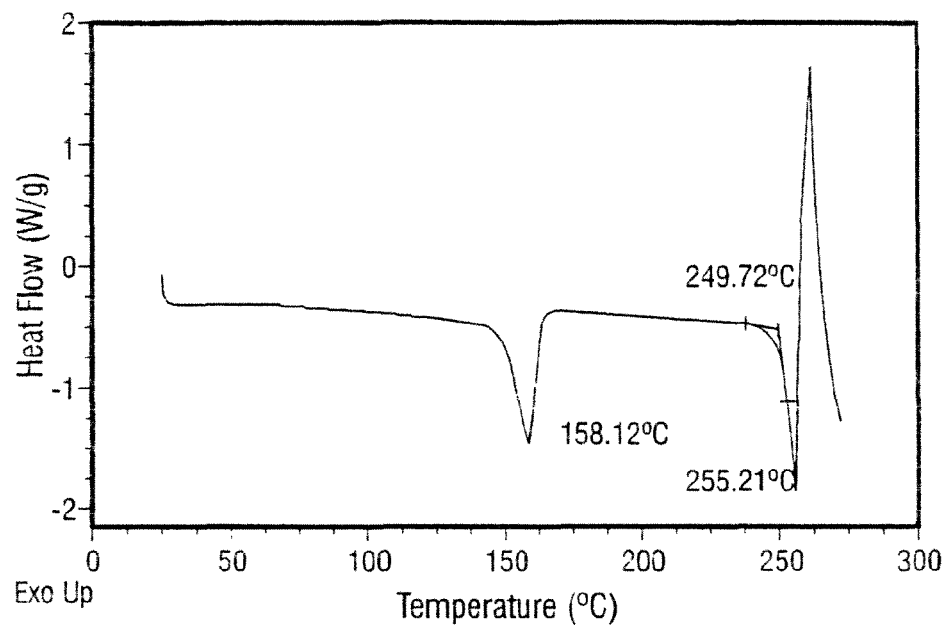
FIG. 3(c) depicts a DSC thermogram obtained for Compound I Form E.
Figure 3D:
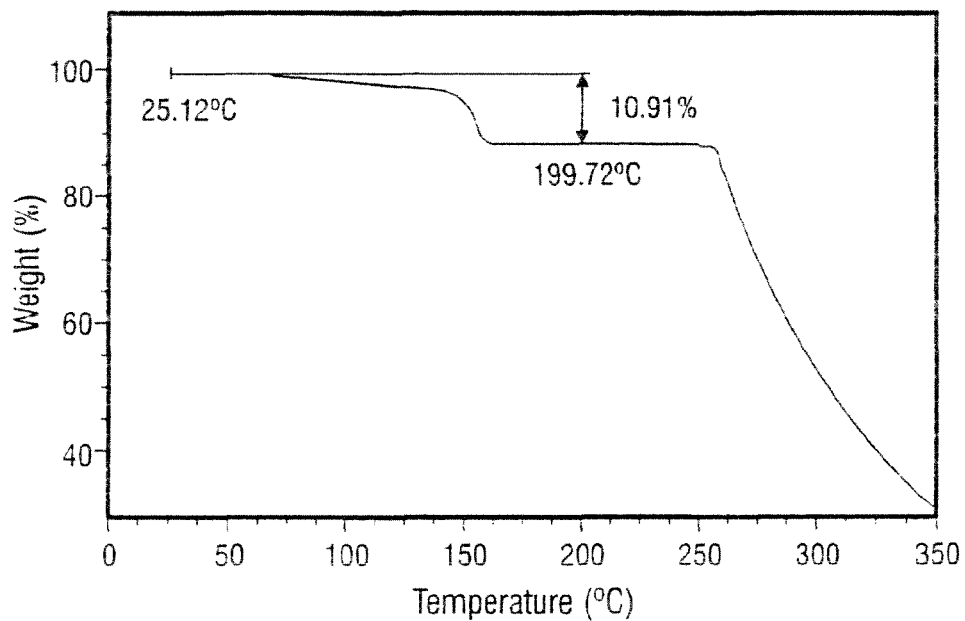
FIG. 3(d) depicts a TGA thermogram obtained for Compound I Form E.
Figures 3E, 3F:
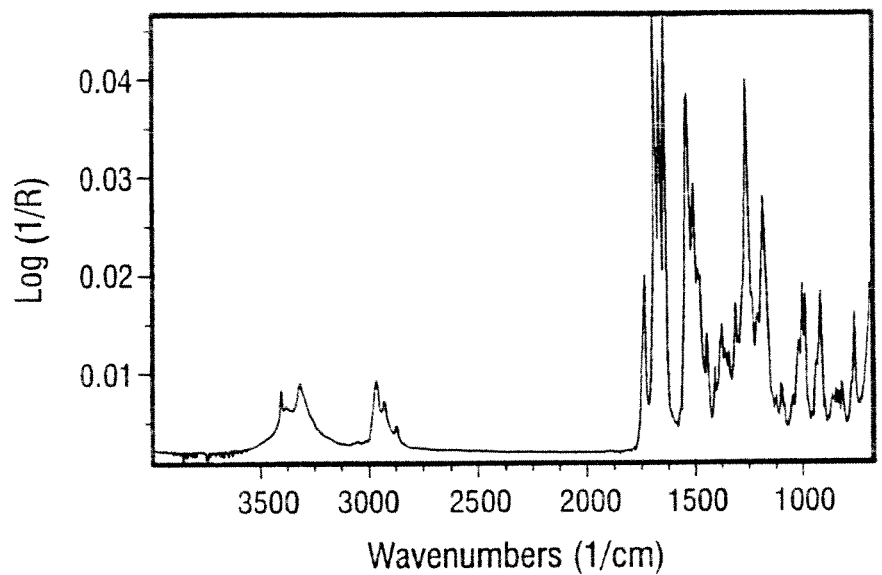
FIG. 3(e) depicts an FT-IR spectrum obtained for Compound I Form E.
FIG. 3(f) tabulates peak positions of bands present in the FT-IR spectrum of FIG. 3(e).
Figure 3G:
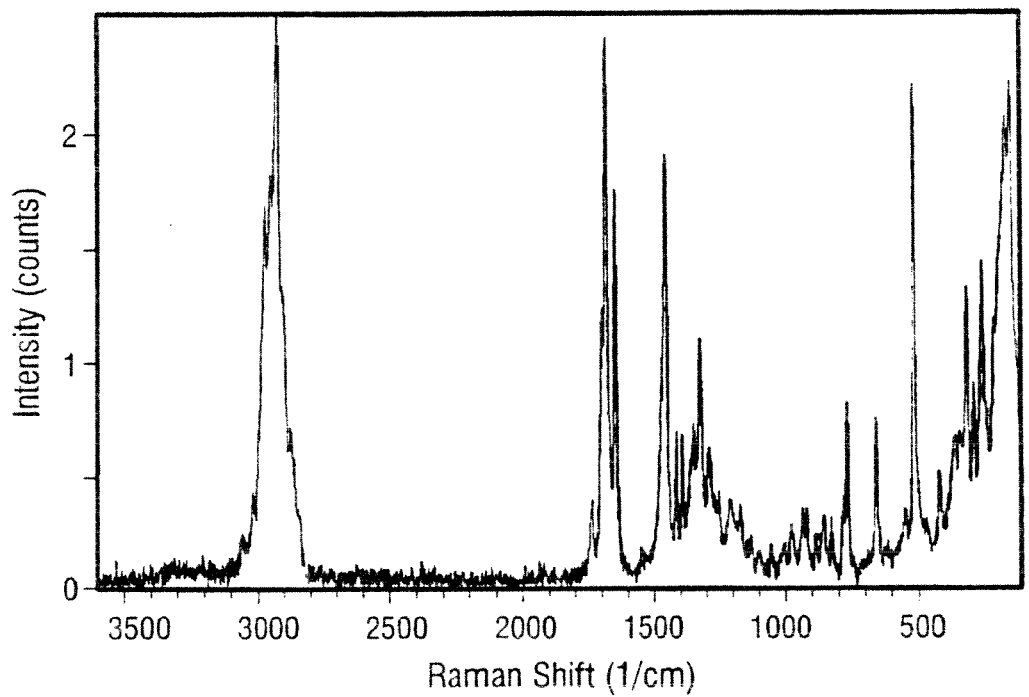
FIG. 3(g) depicts an FT-Raman spectrum for Compound I Form E.
Figure 3H:
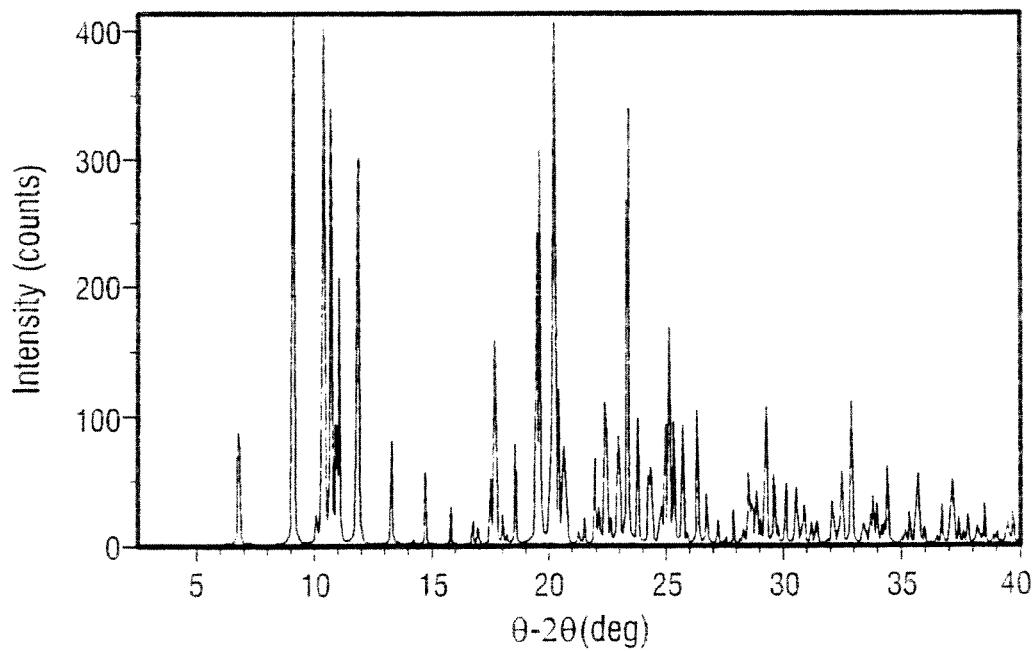
FIG. 3(h) depicts a calculated XRPD for Compound I Form E collected at subambient temperature.
Figure 3J:
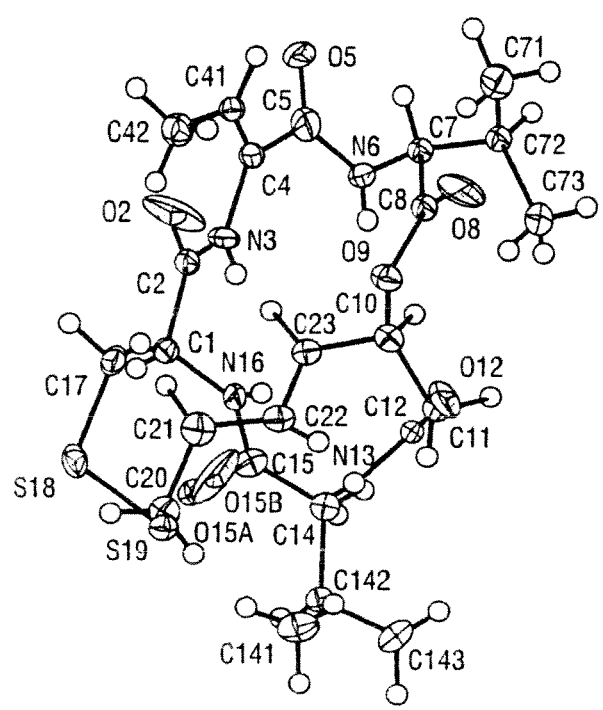
FIG. 3(j) depicts an ORTEP drawing of Compound I, Form E.
Figure 3K:
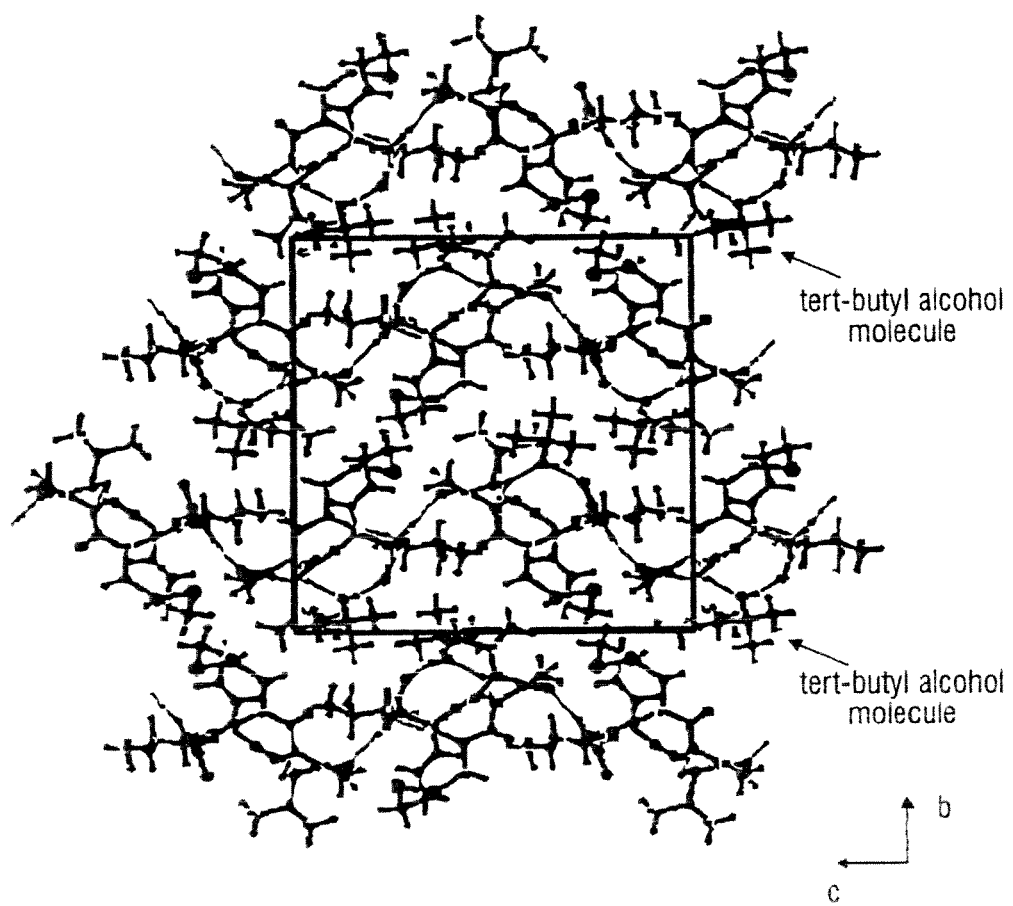
FIG. 3(k) depicts a packing diagram of Compound I, Form E viewed down the crystallographic a axis.
Figure 3L:
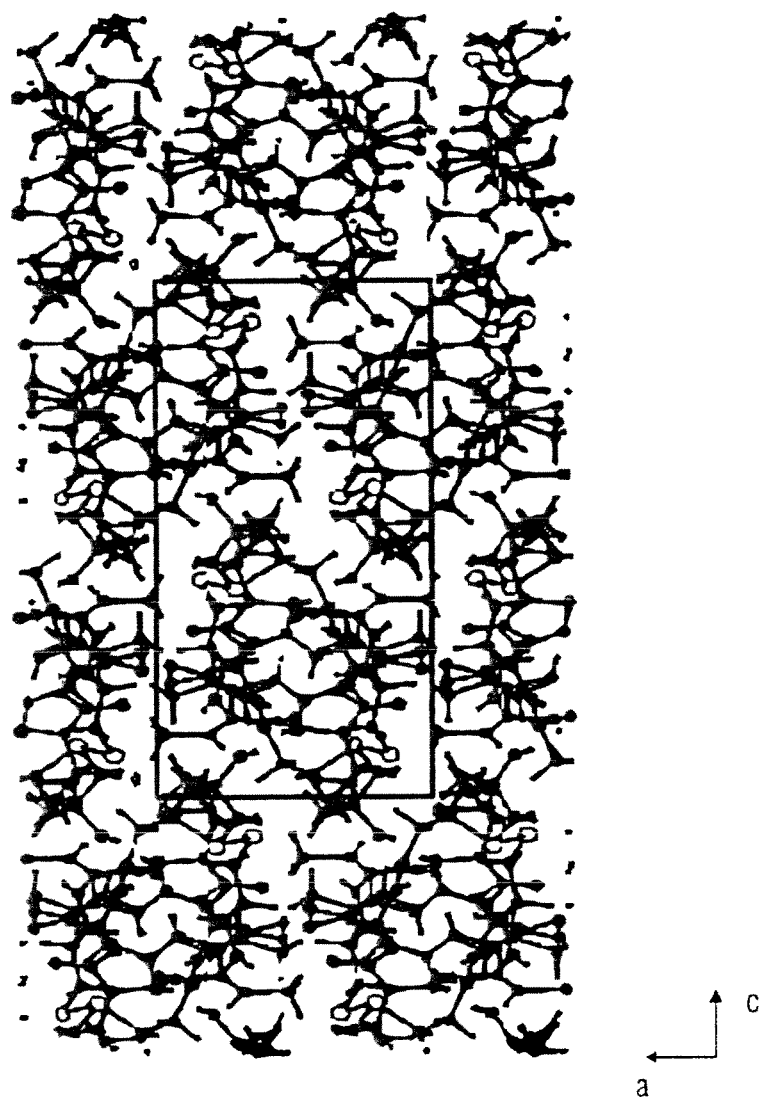
FIG. 3(l) depicts a packing diagram of Compound I, Form E viewed down the crystallographic b axis.
Figure 3M:
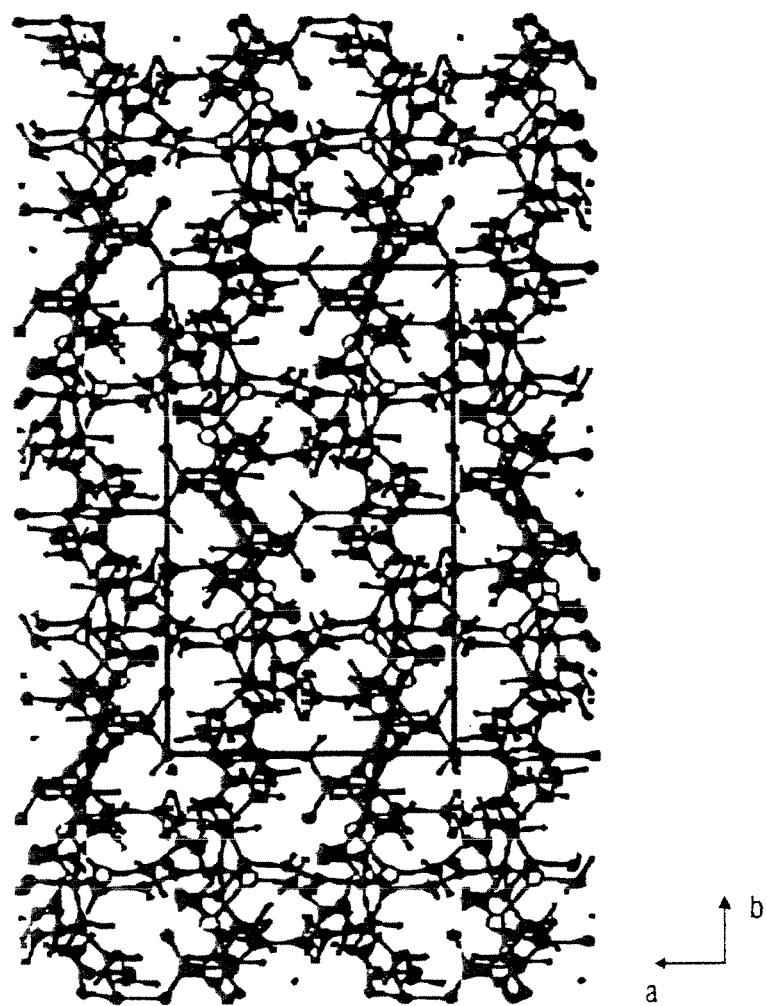
FIG. 3(m) depicts a packing diagram of Compound I, Form E viewed down the crystallographic c axis.

A comparison of the experimental (see FIGS. 3(a) and 3(b)) and calculated (see FIGS. 3(h) and 3(i)) XRPD patterns and accompanying peak lists of Compound I Form E are provided. The single crystal data were collected at cryogenic temperature, so minor uneven shifting of 2θ peak positions due to temperature effects was observed. FT-IR with an accompanying peak list (see FIGS. 3(e) and 3(f)) and FT-Raman spectra (see FIG. 3(g)) of Compound I Form E are provided.

The DSC thermogram for Compound I Form E (see FIG. 3(c)) exhibits an endothermic event at approximately 158° C. (min), ascribed to desolvation, based on the TGA thermogram (see FIG. 3(d)), and indicated by hot stage microscopy as partial loss of birefringence at approximately 157° C. Hot stage microscopy showed the specimen to melt at approximately 243° C., as indicated by an endotherm in the DSC at approximately 255° C. (min). Based on the melting temperature, it is believed that the sample desolvated to Compound I Form A prior to melt. The final weight loss from TGA suggests that decomposition is concurrent with the melt observed by hot stage microscopy, as it was for Compound I Form A.

Example 5

Preparation and Characterization of Form F and/or Compositions Containing Form F In one embodiment, compound I Form A (105.9 mg, 0.2 mmol) and chloroform (4 mL) were charged to a glass vial and bath conicated for approximately 1 minute, generating a clear solution, with a few undissolved particles. Additional Compound I Form A (281.7 mg, 0.5 mmol) was added. The resulting slurry was agitated on a rotating wheel under ambient conditions for ~12 hours. The sample was removed from the wheel and the remaining solids floated to the top of the solution. The solution was drawn off with a pipet and a portion was filtered through a 0.2 μm nylon filter disc to a clean glass vial. The vial was left open to evaporate in an ambient laboratory fume hood. The recovered solids were analyzed by X-ray powder diffraction (XRPD) and consist of Compound I Form F.

In another embodiment, Compound I Form A (740 mg, 1.4 mmol) and chloroform (30 mL) were charged to a glass vial and bath sonicated for a few minutes, producing a clear solution. Compound I Form A (750 mg, 1.4 mmol) was added to ensure excess solids for slurry. The resulting sample was agitated for approximately 4 days on a rotating wheel. Remaining solids floated to the top upon standing, generating a clear solution at the bottom of the vial. Approximately ¼ of the solution was drawn off to a clean glass vial and solids were precipitated via slow evaporation of the solvent (vial covered with perforated aluminum foil) in a laboratory fume hood. After approximately 2 days, no solvent was apparent. The solids consisting of Compound I Form F were left in a sealed vial at ambient temperature for approximately 1 day, and then stored in a freezer.

Exemplary data for Compound I Form F in the form of an XRPD and an FT-IR are depicted in FIGS. 9(a) through 9(l), supra.

Compound I Form F is a crystalline chloroform solvate of Compound I. The characterization of Compound I Form F is summarized in Table 6.

TABLE 6

Characterization of Compound I Form F

| Analysis | Result | Figure References |
|---|---|---|
| XRPD | Form F | 9(a)-9(f), 9(h), 9(i) |
| DSC | 83.6° C. (minor endo) | 9(j) |
|  | 97.3° C. (endo) |  |
|  | 256.4° C. (endo) |  |
| FT-IR | reference spectrum | 9(g), 9(h) |
| TGA | Form F | 9(k) |

Example 6

Preparation and Characterization of Form H and/or Compositions Containing Form H Compound I Form A (500 mg, 0.9 mmol) and chloroform (5 mL) were charged to a glass vial and bath sonicated for approximately 20 minutes, and generated a clear solution. Gentle shaking produced solid precipitate. The resulting mixture was agitated on a rotating wheel overnight at ambient temperature. Solids were floating on top of the liquid, so the liquid was drawn off with a pipette. Approximately ⅓ of the solids were dried via rotary evaporation over approximately 15 minutes, utilizing a water bath. The temperature range of the bath during evaporation was 57 to 64° C., as measured by a NIST-traceable thermometer. The recovered solids were stored under ambient conditions until analyzed by XRPD. The analysis showed the solids to consist of Compound I Form H. After XRPD analysis, the sample was stored in a freezer with desiccant. Solid recovery was 178 mg.

Exemplary data for Compound I Form H in the form of an XRPD, a DSC, a TGA, and an FT-IR are depicted in FIGS. 4(a) through 4(f), supra. A summary of exemplary data presented in FIGS. 4(a) through 4(f) is as follows. One skilled in the art will be able to readily ascertain from the data presented herein that Compound I, Form H may be isostructural with Compound I, Form E (see Example 4).

Compound I Form H is a crystalline chloroform solvate of Compound I. Characterization of Compound I Form H is summarized in Table 7.

TABLE 7

Characterization of Compound I Form H

| Analysis | Result | Figure References |
|---|---|---|
| XRPD | Form H | 4(a), 4(b) |
| DSC | 96.3° C. (broad endo, peak) | 4(c) |
|  | 256.7° C. (endo, max) |  |
|  | followed by apparent |  |
|  | decomp |  |
| TGA | 10.1 wt % loss to 150° C. | 4(d) |
| FT-IR | reference spectrum | 4(e), 4(f) |

Figure 4A:
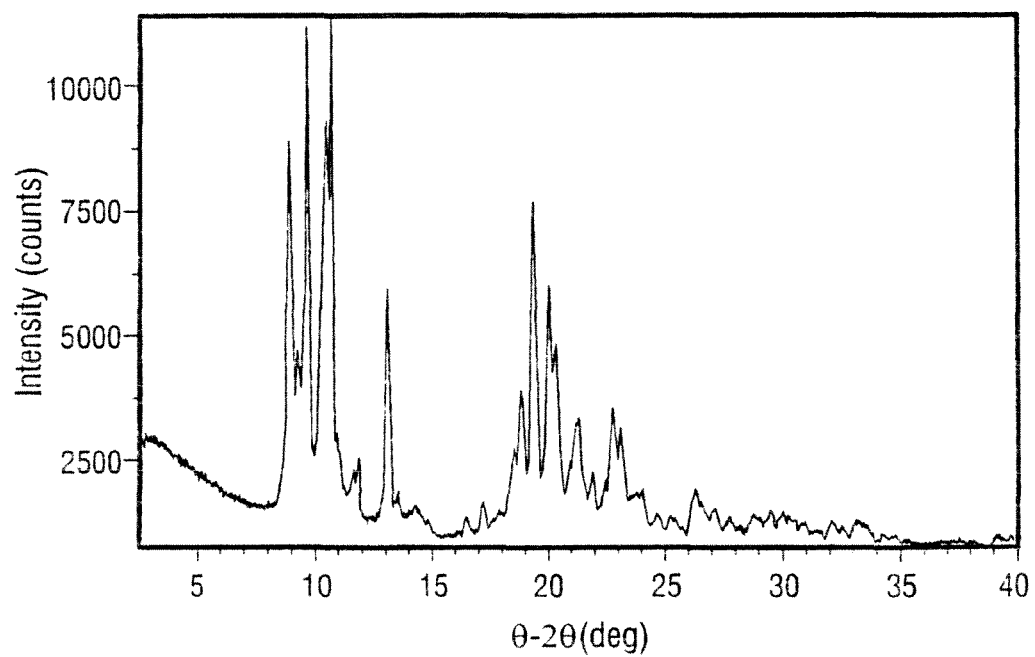
FIG. 4(a) depicts an XRPD for Compound I Form H collected at room temperature.

A high resolution XRPD pattern of Compound I Form H and an accompanying line list is provided in FIGS. 4(a) and 4(b). An FT-IR spectrum of Compound I Form H and an accompanying line list is provided in FIGS. 4(e) and 4(f).

Examination of Compound I Form H XRPD pattern displays reflections from both Compound I Form H and Compound I Form A patterns, suggesting the specimen examined was a mixture. The XRPD pattern generated using Compound I Form H appears to be consistent with the Form H portion of the pattern.

Figure 4C:
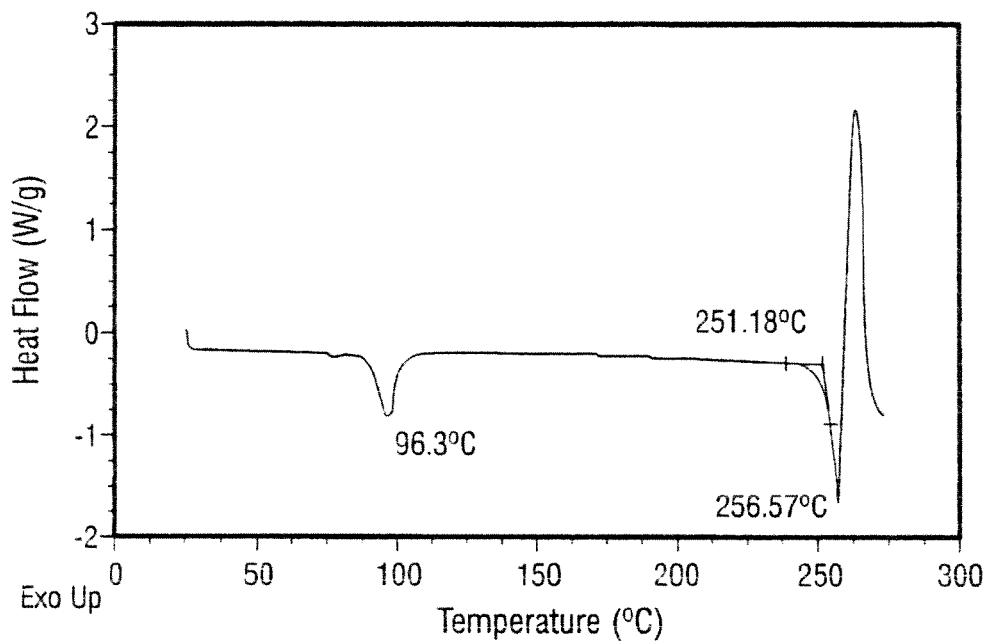
FIG. 4(c) depicts a DSC thermogram obtained for Compound I Form H.
Figure 4D:
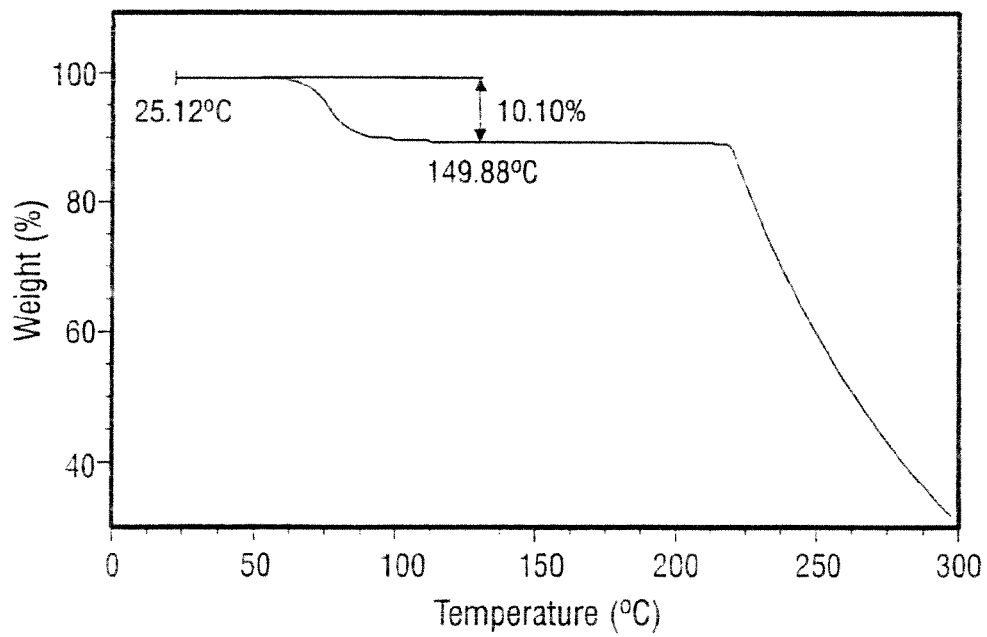
FIG. 4(d) depicts a TGA thermogram obtained for Compound I Form H.
Figures 4E, 4F:
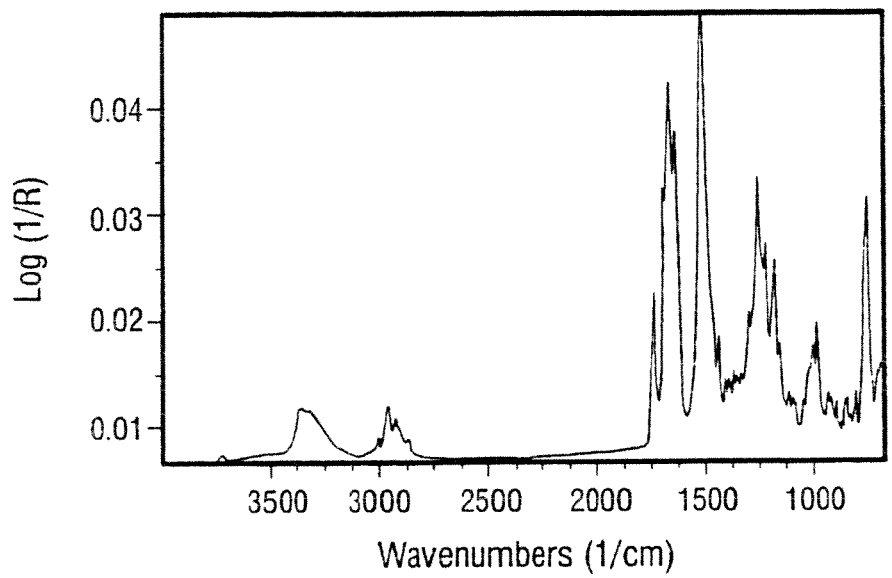
FIG. 4(e) depicts an FT-IR spectrum obtained for Compound I Form H.
FIG. 4(f) tabulates peak positions of bands present in the FT-IR spectrum of FIG. 4(e).

The DSC thermogram for Compound I Form H (see FIG. 4(c)) exhibits an endothermic event at approximately 96° C. (min). This event appears to be mainly related to desolvation, based on the weight loss of approximately 10.1% observed in the TGA thermogram for Compound I Form H (see FIG. 4(d)). This corresponds to more than 0.5 moles of chloroform. To avoid the potential for Form conversion from solvent loss, the solids were analyzed immediately upon removal from the freezer. Since no weight loss was observed prior to the start of the analysis, the weight loss observed is attributed to solvent loss from the crystal lattice, suggesting Compound I Form H is a solvate. The DSC thermogram (see FIG. 4(c)) also exhibits an endotherm at approximately 256° C. (min). The endotherm is believed to correspond to the melt of Compound I Form A and apparent desolvation of solids. Final weight loss from TGA (see FIG. 4(d)) suggests that decomposition is concurrent with the apparent melt observed by DSC, as it was for Compound I Form A.

Example 7

Preparation and Characterization of Form I and/or Compositions Containing Form I In one embodiment, compound I Form A (500 mg, 0.9 mmol) and chloroform (5 mL) were charged to a glass vial and bath sonicated for approximately 20 minutes, and generated a clear solution. Gentle shaking produced solid precipitate. The resulting mixture was agitated on a rotating wheel at ambient temperature for less than an hour and a portion of the solids was recovered for X-ray powder diffraction (XRPD) via filtration with a 0.22 μm nylon filter in a Swinnex Millipore filter body. The filter cake was not washed and the solids appeared dry upon recovery. The solids were gently crushed prior to XRPD analysis. The analysis showed presence of Compound I Form I and Compound I Form H, suggesting the recovered solids were a mixture of phases.

The remaining sample was returned to the wheel to slurry overnight. The solids were floating on top of the liquid, so the liquid was drawn off with a pipette. The remaining solids were stored in a sealed vial over desiccant in a freezer. An attempt to collect a high resolution XRPD data indicated the solids converted to Compound I Form H prior to analysis.

In another embodiment, compound I Form A, (517 mg, 1.0 mmol) and chloroform (5 mL) were charged to a glass vial and bath sonicated for approximately 20 minutes, generating a clear solution, with a trace of solid. The resulting mixture was agitated on a rotating wheel for approximately 1 month at ambient temperature. The solids were stored in the mother liquor in a refrigerator. A portion of the solids ("portion 1") was recovered for X-ray powder diffraction (XRPD) via filtration with a 0.22 μm nylon filter in a Swinnex Millipore filter body. The filter cake was not washed and the solids appeared dry upon recovery. The solids were gently crushed prior to XRPD analysis. The analysis showed that the solids consisted of Compound I Form I. Another portion ("portion 2") of the solids was recovered for solution proton nuclear magnetic resonance spectroscopy ($^1$H-NMR) by pipetting to a clean glass vial and decanting off the liquid. The XRPD and $^1$H-NMR samples were stored at ambient temperature in sealed vials prior to analysis.

In yet, another embodiment, compound I Form A (~180 mg, 0.3 mmol) was charged to a glass vial. The vial was left uncapped in a glass jar containing chloroform (~10 mL), for vapor stress of the solids. The solids were stressed for approximately 7 days before transfer to a freezer, where they remained under chloroform vapor.

Figure 5A:
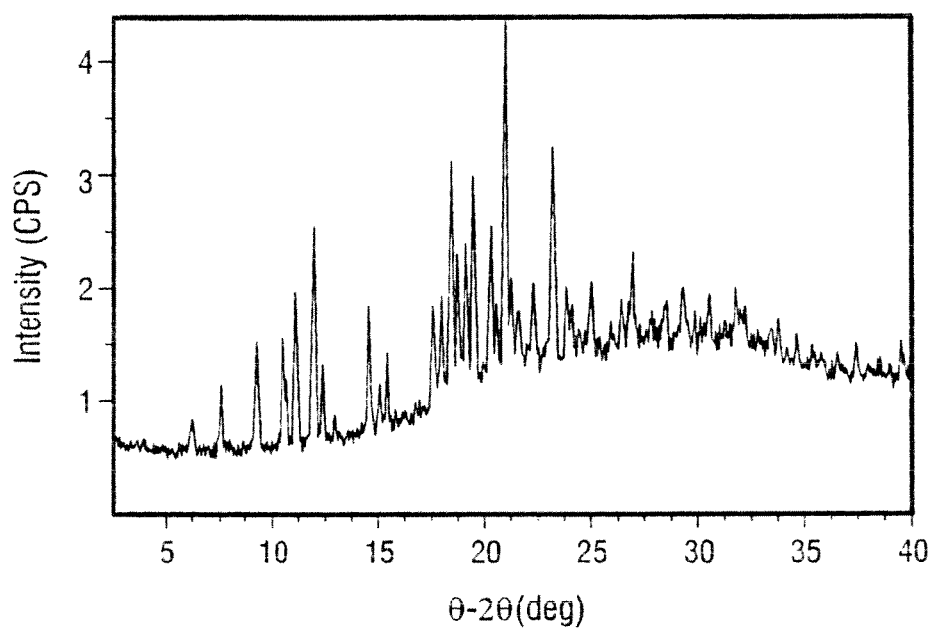
FIG. 5(a) depicts an XRPD for Compound I Form I collected at room temperature.
Figure 5C:
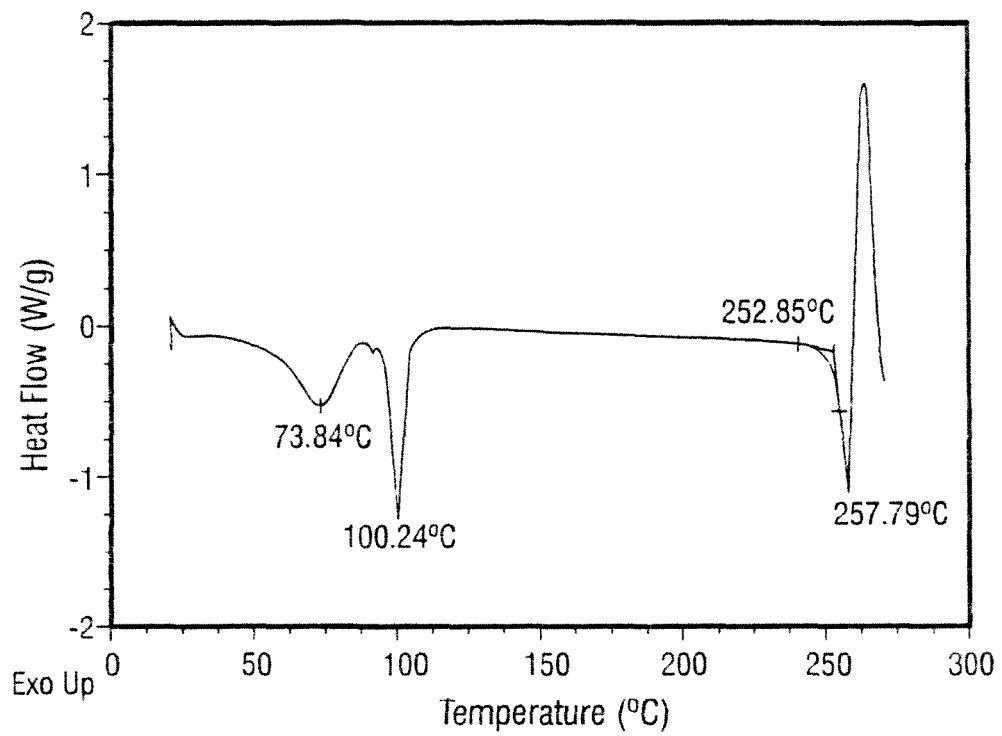
FIG. 5(c) depicts a DSC thermogram obtained for Compound I Form I.
Figure 5D:
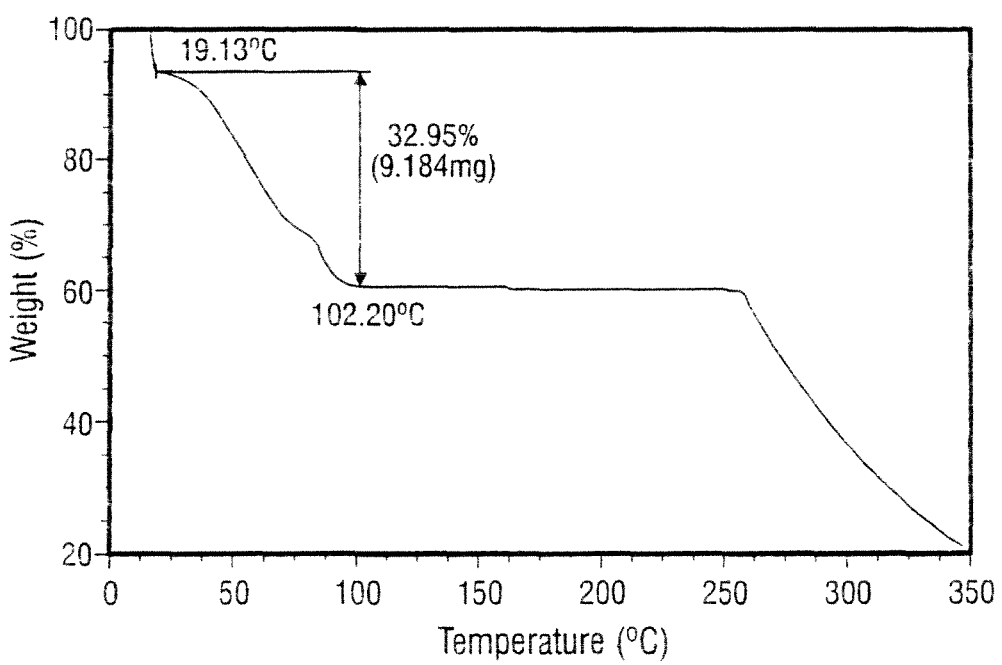
FIG. 5(d) depicts a TGA thermogram obtained for Compound I Form I.
Figures 5E, 5F:
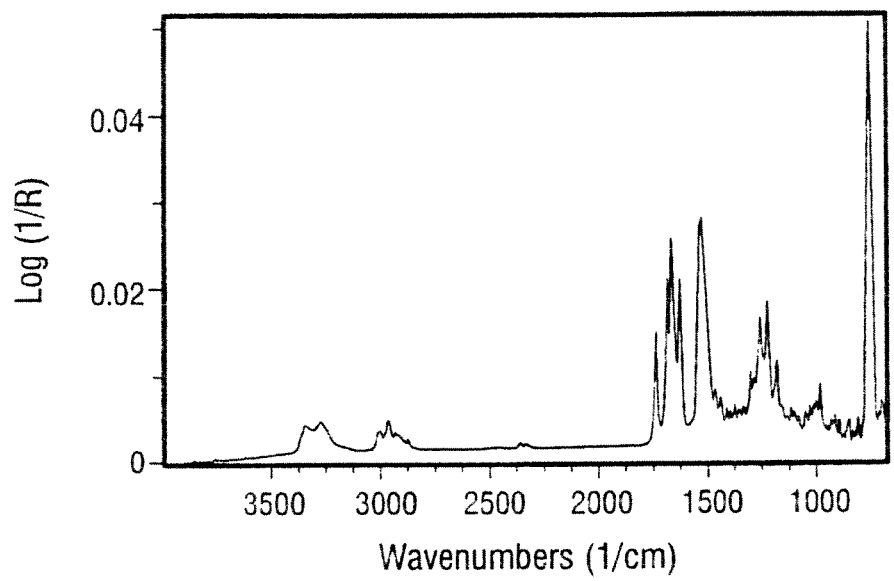
FIG. 5(e) depicts an FT-IR spectrum obtained for Compound I Form I.
FIG. 5(f) tabulates peak positions of bands present in the FT-IR spectrum of FIG. 5(e).
Figure 5G:
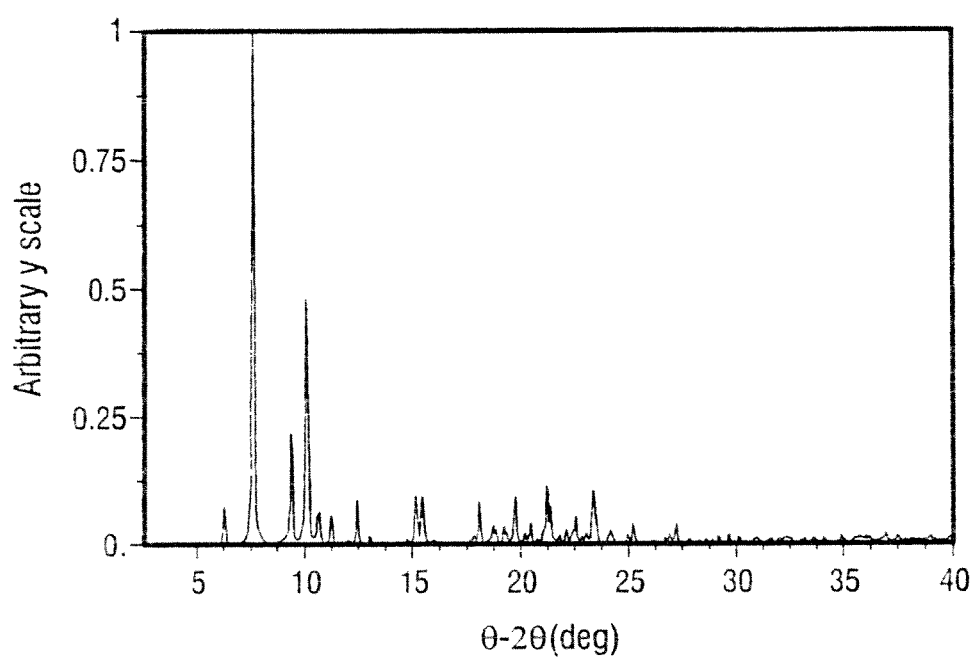
FIG. 5(g) depicts a calculated XRPD for Compound I Form I collected at subambient temperature.
Figure 5I:
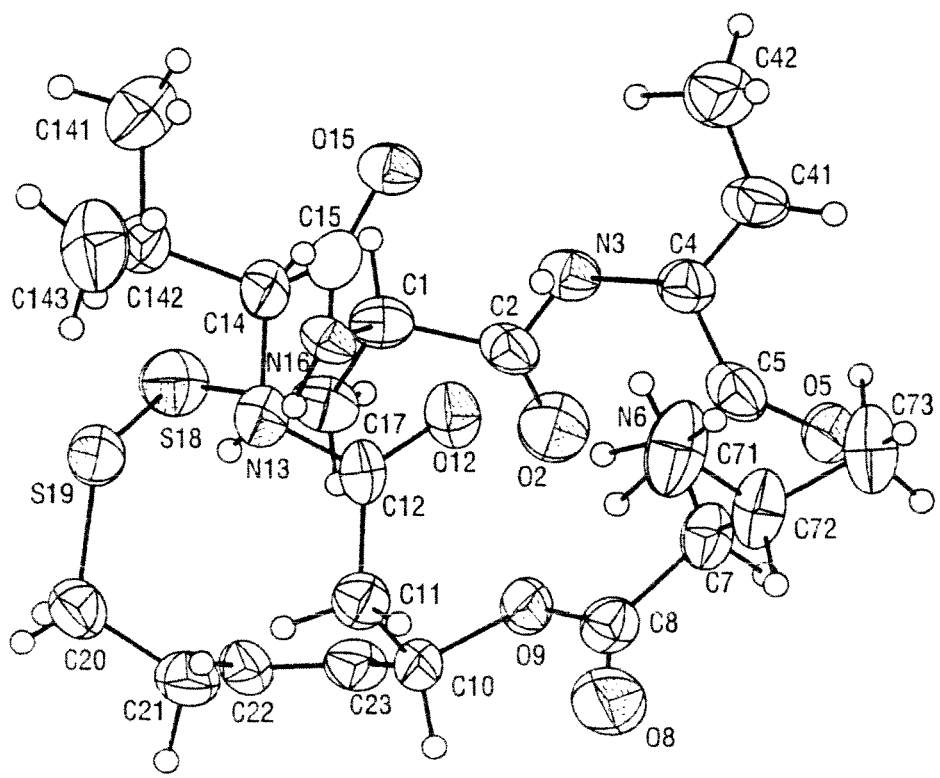
FIG. 5(i) depicts an ORTEP drawing of Compound I, Form I, chloroform not shown.
Figure 5J:
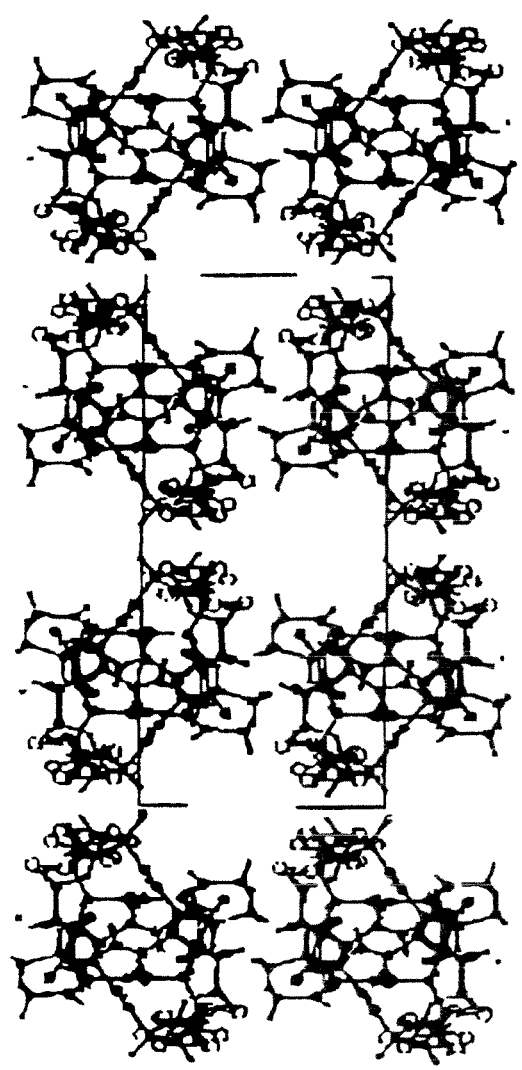
FIG. 5(j) depicts a packing diagram of Compound I, Form I viewed down the crystallographic a axis.
Figure 5K:
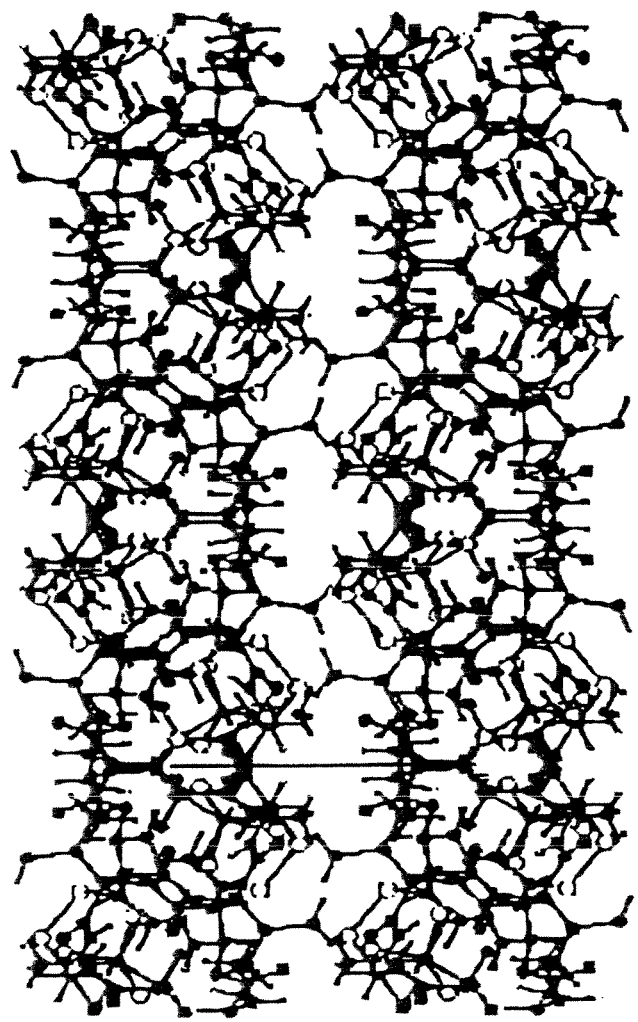
FIG. 5(k) depicts a packing diagram of Compound I, Form I viewed down the crystallographic b axis.
Figure 5L:
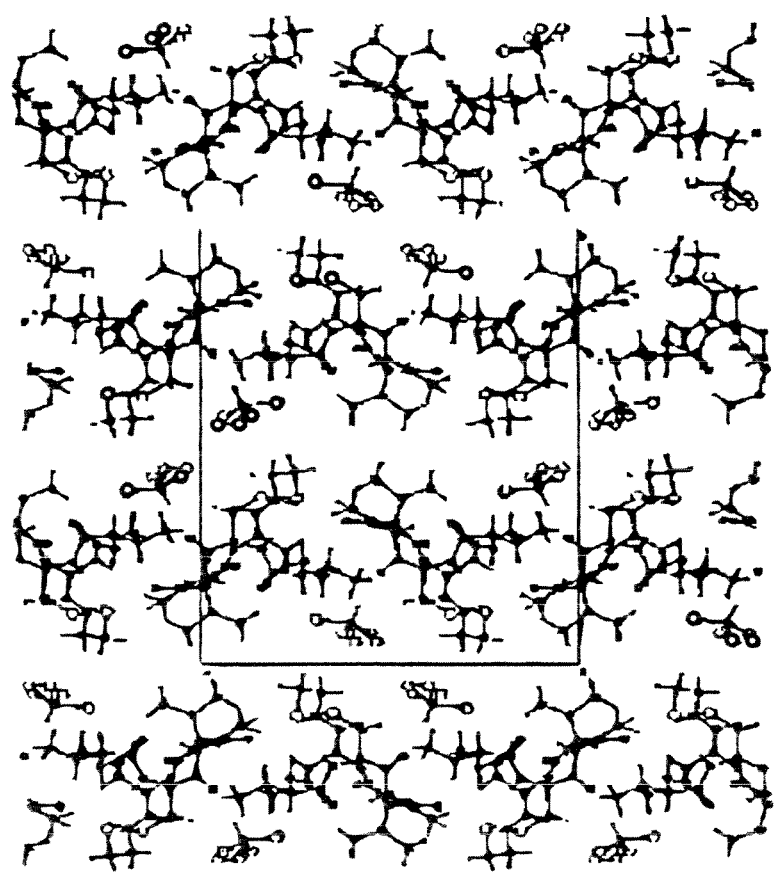
FIG. 5(l) depicts a packing diagram of Compound I, Form I viewed down the crystallographic c axis.
Figure 5P:
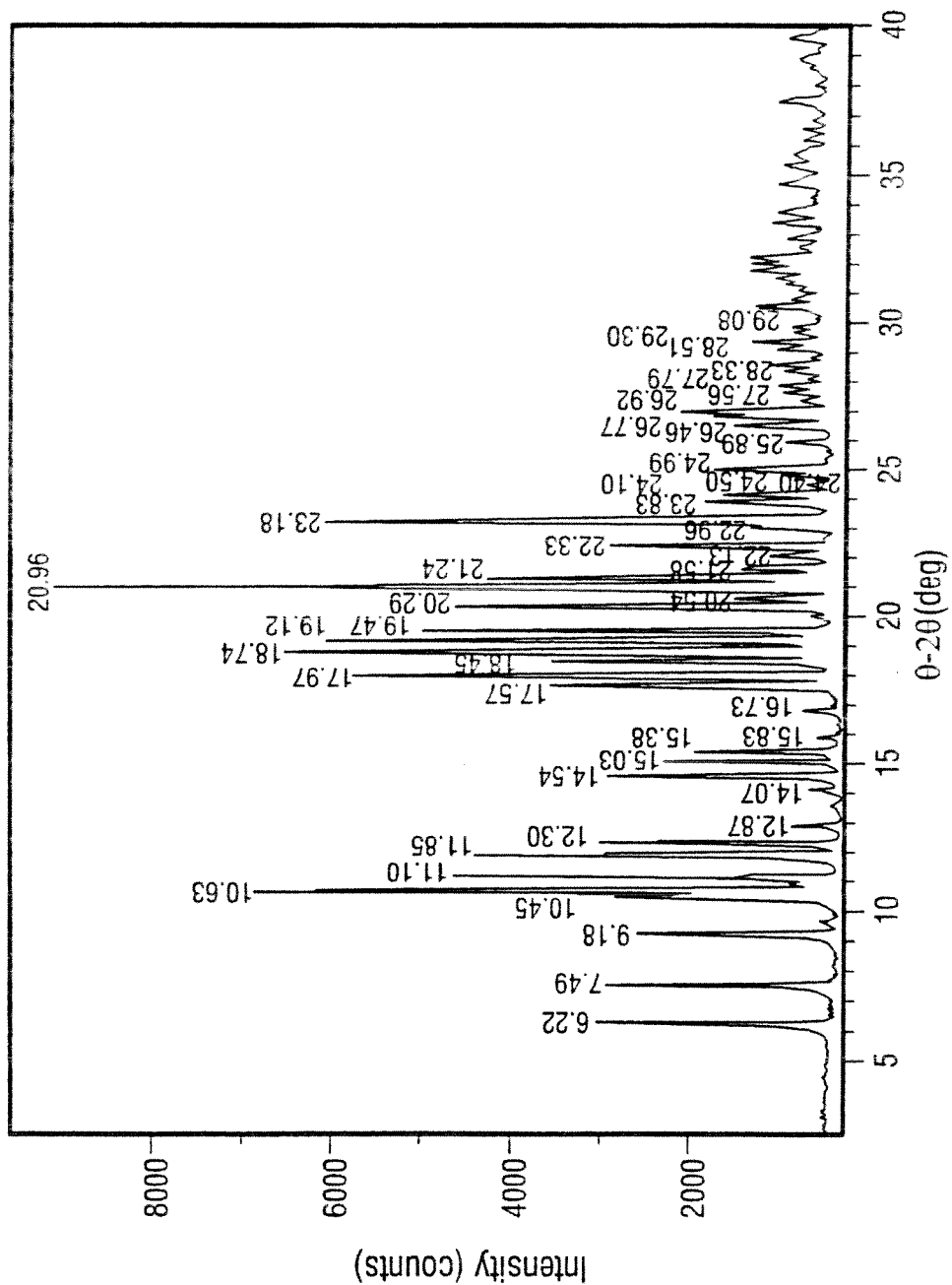
FIG. 5(p) depicts an XRPD for Compound I Form I.
Figure 5S:
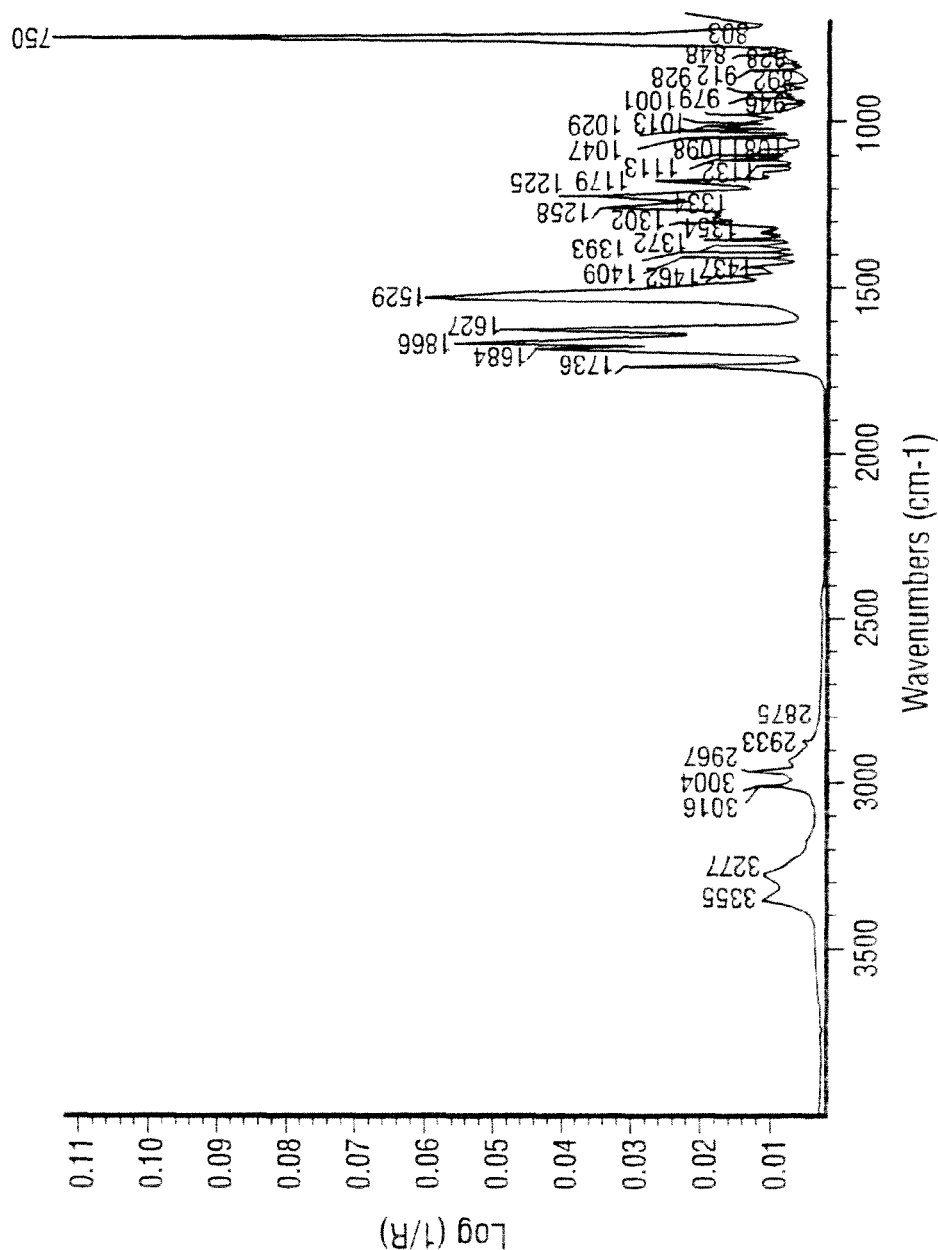
FIG. 5(s) depicts an FT-IR spectrum obtained for Compound I Form I.
Figures 5T, 5U:
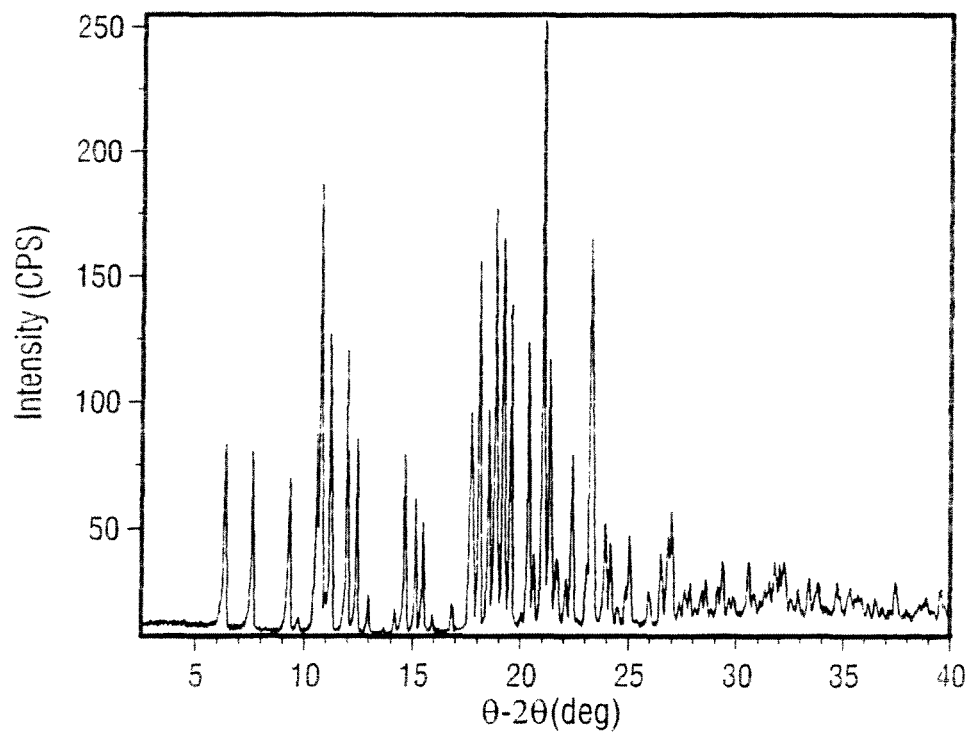
FIG. 5(t) tabulates peak positions of bands present in the FT-IR spectrum of FIG. 5(s).
FIG. 5(u) depicts Panalytical X-Pert Pro MPD PW3040 data for Compound I Form I.
Figure 5V:
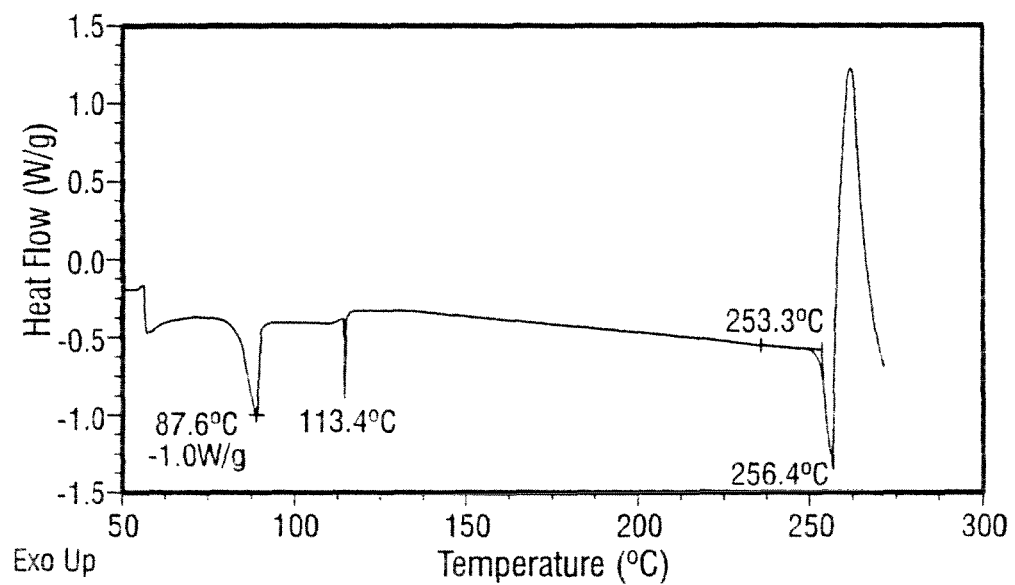
FIG. 5(v) depicts a DSC thermogram obtained for Compound I Form I.
Figure 5W:
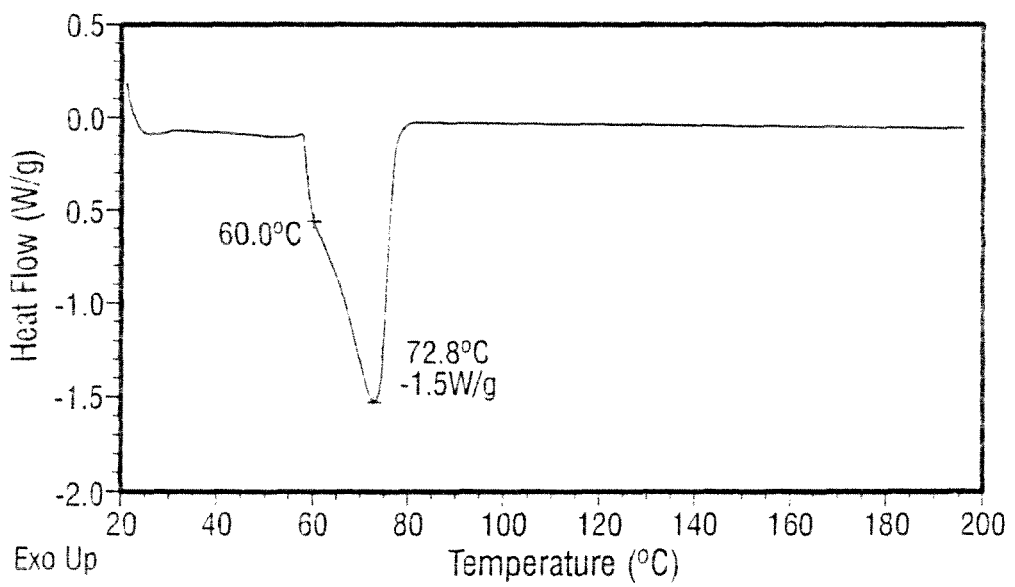
FIG. 5(w) depicts a DSC thermogram obtained for Compound I Form I.
Figure 5X:
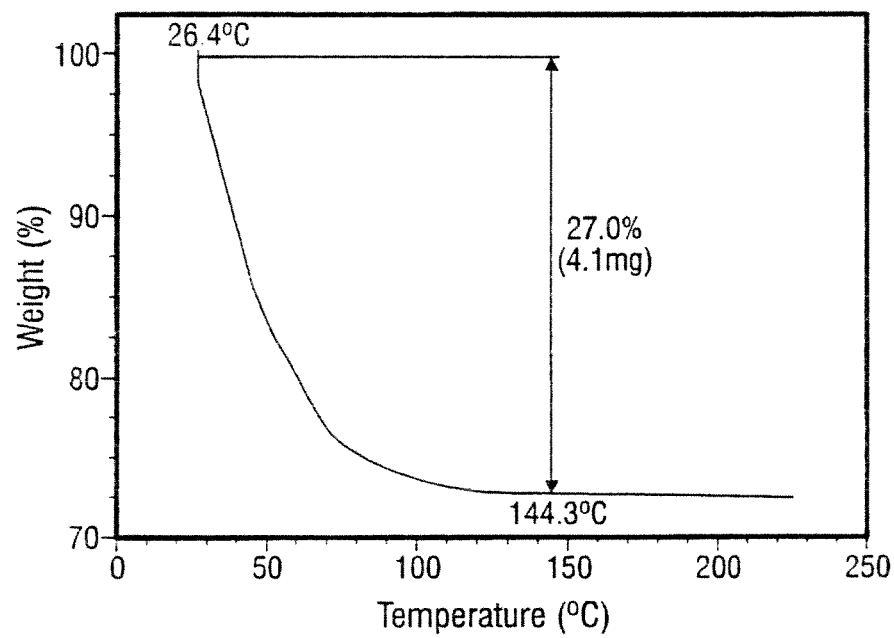
FIG. 5(x) depicts a TGA thermogram obtained for Compound I Form I.
Figure 5Y:
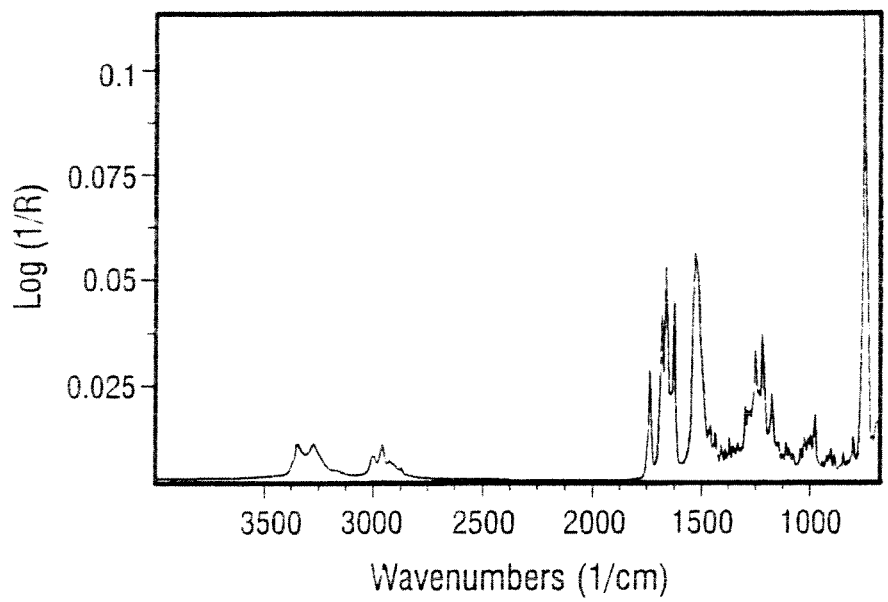
FIG. 5(y) depicts an FT-IR spectrum obtained for Compound I Form I.

Exemplary data for Compound I Form I in the form of XRPDs, a DSC, a TGA, an FT-IR, and single crystal structure data (e.g., ORTEP drawings, packing diagrams, positional parameters, bond distances and bond angles) are depicted in FIGS. 5(a) through 5(y), supra. A summary of exemplary data presented in FIGS. 5(a) through 5(y) is as follows.

Compound I Form I is a crystalline chloroform solvate of Compound I that converts to Form H under ambient conditions. The structure was solved for a crystal prepared from chloroform slurry. Based on Compound I Form I XRPD pattern from a sub sample of the bulk solids, it is believed the crystal was of Compound I Form I. The single crystal data (see FIGS. 5(g) through 5(o)) indicate chloroform solvate, the structure consisting of layers of Compound I molecules separated by residual electron density believed to be free chloroform and pockets containing refined chloroform molecules.

The experimental data for Compound I Form I is provided in FIGS. 5(a) to 5(y). Characterization of Compound I Form I is summarized in Table 8.

TABLE 8

Characterization of Compound I Form I

| Analysis | Result | Figure References |
| --- | --- | --- |
| XRPD | Form I | 5(a), 5(b), 5(p)-5(r) |
| DSC | 73.8° C. (broad endo, max) 100.2° C.(endo, min) 257.8° C. (endo, min) followed by decomp | 5(c) |
| TGA | 33.0 wt % loss 19 to 102° C. | 5(d), 5(x) |
| FT-IR | reference spectrum | 5(e), 5(f), 5(s), 5(t) |
| Single Crystal X-ray (non-GMP) | Form I (chloroform solvate) | 5(g)-5(o) |

The initial precipitate and the isolated solids from slurry in chloroform both exhibited an XRPD pattern consistent with Compound I Form I. The high resolution XRPD pattern collected on a sample of bulk solids appears to be Compound I Form H. Because Compound I Form H was prepared by drying solids exhibiting XRPD pattern for Compound I Form I, it is possible that the sample converted to Compound I Form I during data collection. In contrast, the initial XRPD data for Compound I Form I solids were collected on solids in a glass capillary, thus retarding the drying of the solids.

The DSC thermogram for Compound I Form I (see FIG. 5(c)) exhibits a broad endothermic event at approximately 74° C. and an endothermic event at approximately 100° C. (min). These events appear to be mainly related to desolvation, based on the weight loss of approximately 33% from 19 to 102° C. observed in the TGA thermogram (see FIG. 5(d)). This corresponds to more than 2 moles of chloroform. The TGA thermogram also exhibits weight loss prior to 19° C., which is likely due to residual chloroform; however, there appears to be a clear transition into the main weight loss. The DSC thermogram (see FIG. 5(c)) also exhibits an endotherm at approximately 258° C. (min). The endotherm is believed to correspond to the melt of Compound I Form A and the apparent desolvation of the solids. The final weight loss from TGA suggests that decomposition is concurrent with the apparent melt observed by DSC, as it was for Compound I Form A. In an attempt to avoid the potential for form conversion from solvent loss, the solids were analyzed immediately upon removal from the freezer.

An FT-IR spectrum of Compound I Form I (see FIGS. 5(e) and 5(s)) is provided. To avoid potential for Form conversion from solvent loss, solids were analyzed immediately upon removal from the freezer.

Example 8

Preparation and Characterization of Form J and/or Compositions Containing Form J In one embodiment, Compound I (56.4 mg) Form J was dissolved in methyl ethyl ketone (4.5 mL). The solution was filtered through a 0.2-μm nylon filter. The sample was placed in a vial capped with perforated aluminum foil (single pinhole) in a laboratory fume hood and allowed to evaporate to dryness under ambient conditions. The sample was stored under ambient conditions until indexed by single crystal X-ray. Crystallization may be performed using methods known to one of skill in the art.

In another embodiment, Compound I Form A (Sandoz lot 49800203, 1.03 g, 1.9 mmol) and methyl ethyl ketone (80 mL) were charged to an Erlenmeyer flask, briefly swirled and bath sonicated for a few minutes, producing a clear solution. Approximately half of the solution was filtered through a 0.2 μm nylon filter to a clean glass vial. The vial was capped and placed into a freezer, in order to precipitate solids from the solution. After approximately 5 days, the sample was removed from the freezer and the precipitated solids were isolated by decanting off the clear supernatant. The solids were stored wet with solvent in a freezer.

Exemplary data for Compound I Form J in the form of single crystal structure data (e.g., ORTEP drawings, packing diagrams, positional parameters, bond distances and bond angles) are depicted in FIGS. 6(a) through 6(j), supra. A summary of exemplary data presented in FIGS. 6(a) through 6(j) is as follows.

The single crystal structure of Compound I Form J confirmed the molecular structure and the contents of the unit cell. The sample crystallized in the chiral orthorhombic space group $P2_12_12_1$ and was determined to be a methyl ethyl ketone (MEK) solvate of Compound I. The structure of Compound I Form J (MEK solvate) consists of layers of Compound I molecules hydrogen bonded to neighboring Compound I molecule running perpendicular to the crystallographic c axis. The reflections in the experimental pattern of the acetone solvate (Compound I Form D) are represented in the calculated XRPD pattern of the MEK solvate (Compound I Form J), suggesting that the two forms may be isostructural (see Example 3).

Figure 6S:
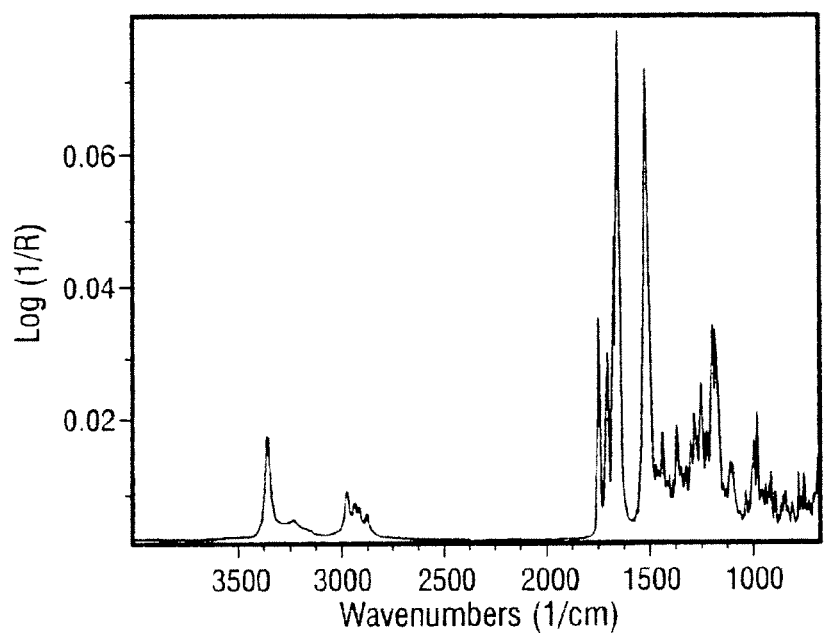
FIG. 6(s) depicts an FT-IR spectrum obtained for Compound I Form J.

Compound I Form J is a crystalline methyl ethyl ketone solvate of Compound I. The experimental data for Compound I Form J is provided in FIGS. 6(a) to 6(s). The characterization of Compound I Form J is summarized in Table 9.

TABLE 9

Characterization of Compound I Form J

| Analysis | Result | Figure References |
|---|---|---|
| XRPD | Form J | 6(a) 6(m) |
| DSC | 130.3° C. (endo) | 6(q) |
|  | 260.0° C. (endo) |  |
| FT-IR | reference spectrum | 6(n), 6(o) |
| TGA | Form J | 6(r) |

Example 9

Preparation and Characterization of Amorphous Compound I and/or Compositions Containing Amorphous Compound I Preparation from 9:1 Dioxane/Water Compound I (1.0652 g) was dissolved in 9:1 dioxane/water (10 mL). The solution was filtered through a 0.2-μm nylon filter, and frozen in a 300 mL round-bottom flask immersed in a bath of dry ice and isopropanol. The flask containing the frozen sample was attached to a lyophilizer and dried for approximately 4 days. After drying, the solids were isolated and stored in the freezer over desiccant until used.

Preparation by a Rotary Evaporator

Compound I (133.4 mg) was dissolved in dichloromethane (1.5 mL). The solution was filtered through a 0.2-μm nylon filter. The sample vial was placed on the rotary evaporator and immersed in a water bath at ambient temperature. The solvent was rapidly evaporated to dryness under vacuum. The solids were then stored in the freezer over desiccant until used.

Preparation by Fast Evaporation

Compound I (24.7 mg) was dissolved in a binary solvent mixture of water (1.5 mL) and dichloromethane (0.5 mL). The solution was filtered through a 0.2-μm nylon filter. The sample was placed uncapped in a laboratory fume hood and allowed to evaporate to dryness under ambient conditions. The solids were stored under ambient conditions until used.

Exemplary data for amorphous Compound I in the form of XRPD's, modulated DSC thermogram, TGA, FT-IR, FT-Raman spectroscopy and $^1$H NMR are depicted in FIGS. 7(a) through 7(f), supra. A summary of exemplary data (e.g., a summary of XRPD results in Table 10) are presented for amorphous Compound I below.

Figure 7A:
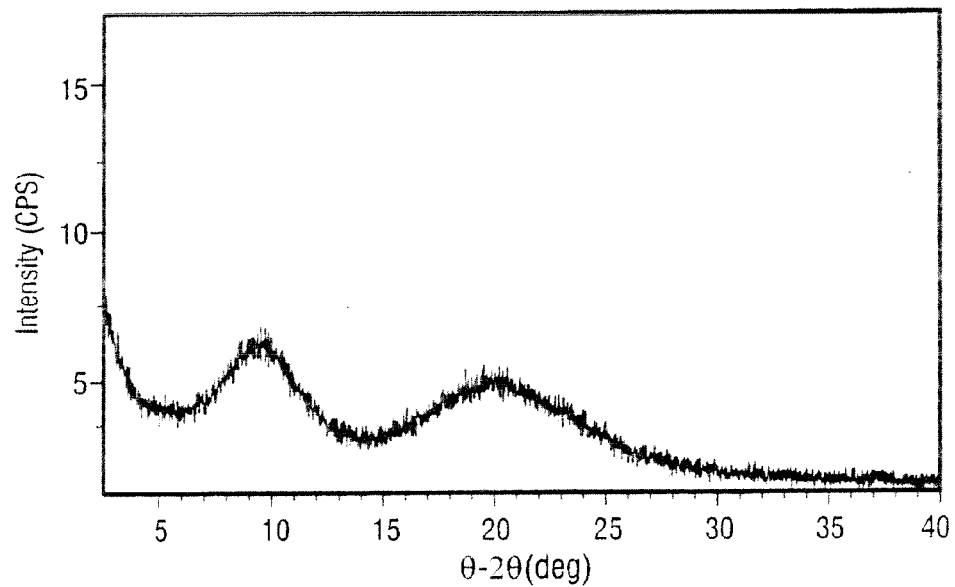
FIG. 7(a) depicts an XRPD for amorphous Compound I collected at room temperature.
Figure 7B:
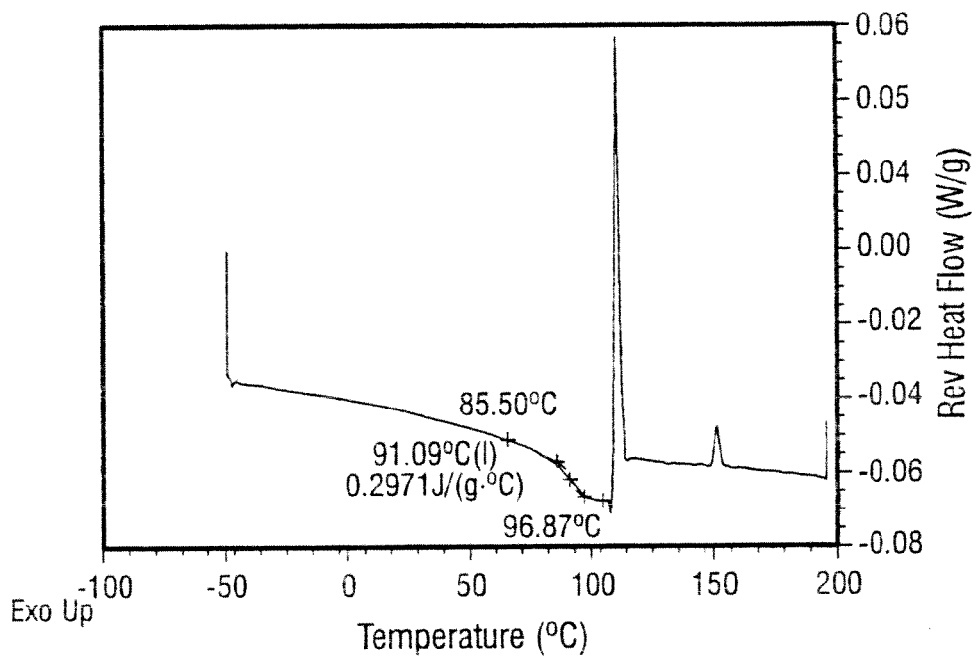
FIG. 7(b) depicts a modulated DSC thermogram obtained for amorphous Compound I.
Figure 7C:
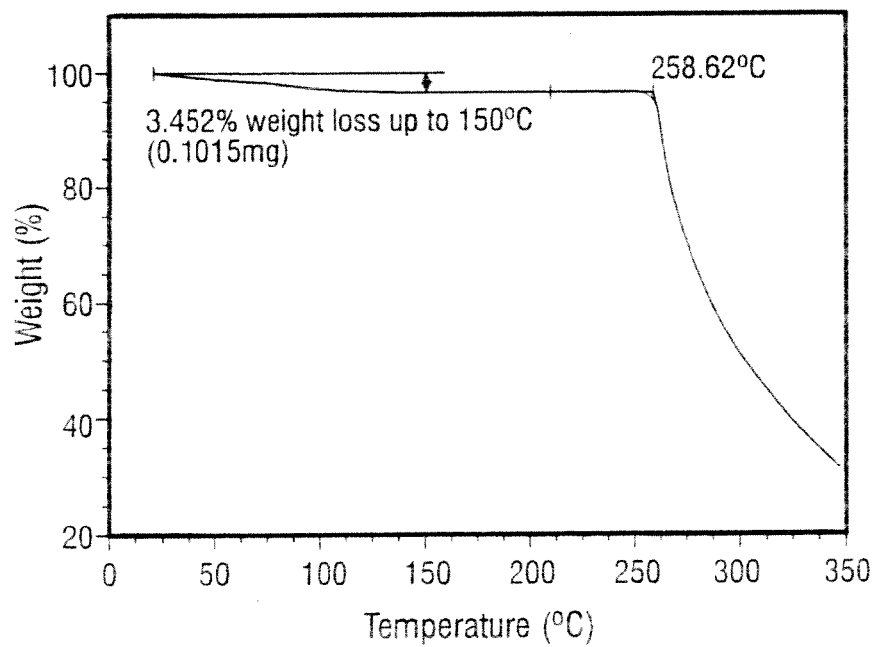
FIG. 7(c) depicts a TGA thermogram obtained for amorphous Compound I.
Figures 7D, 7E:
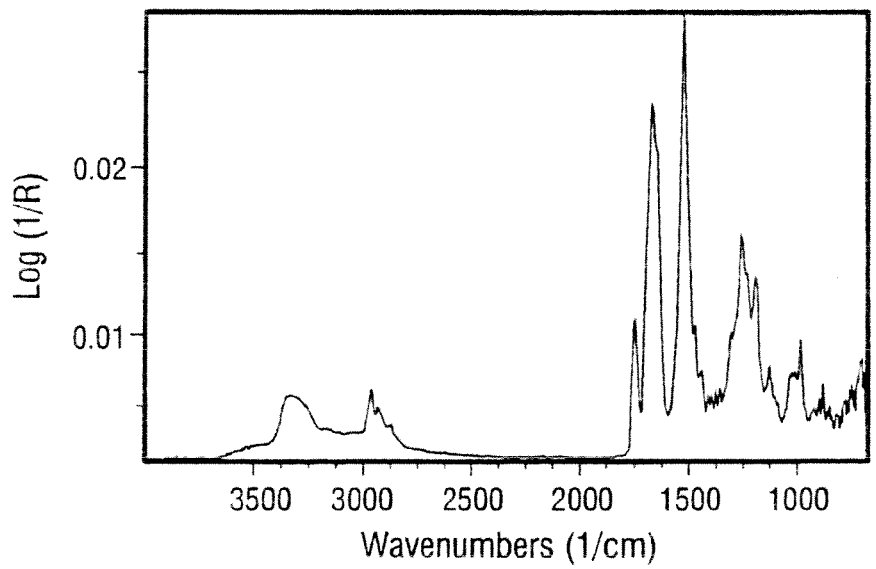
FIG. 7(d) depicts an FT-IR spectrum obtained for amorphous Compound I.
FIG. 7(e) tabulates peak positions of bands present in the FT-IR spectrum of FIG. 7(d).
Figure 7F:
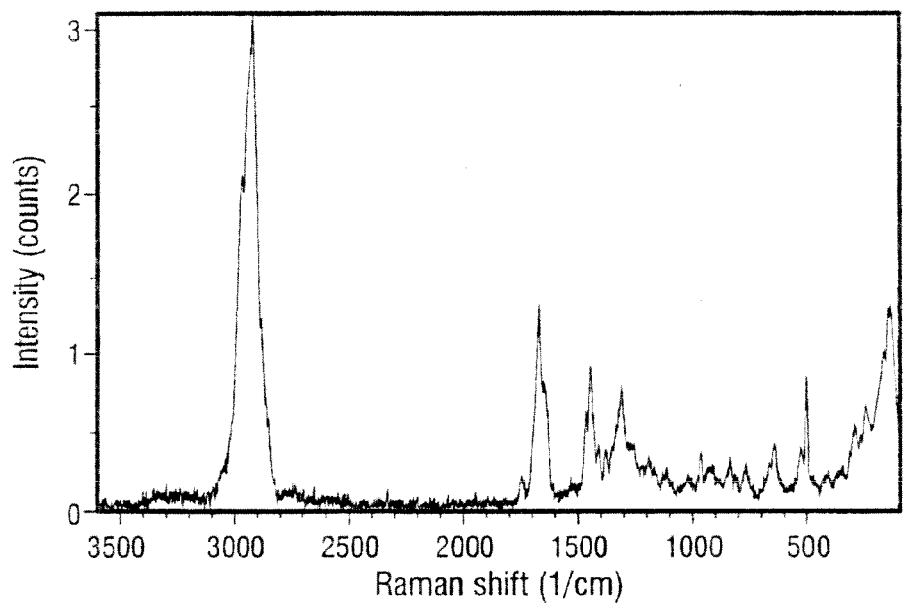
FIG. 7(f) depicts an FT-Raman spectrum for amorphous Compound I.

A high resolution XRPD pattern of amorphous Compound I is provided in FIG. 7(a). The modulated DSC thermogram for amorphous Compound I (see FIG. 7(b)) exhibits a glass transition temperature at approximately 91° C. Weight loss of approximately 3.5% was observed in the TGA thermogram (see FIG. 7(c)). An FT-IR spectrum of amorphous Compound I (see FIGS. 7(d) and 7(e)) and an FT-Raman spectrum (see FIG. 7(f)) are also provided.

TABLE 10

Preparation of X-ray Amorphous Compound I and/or Compositions Containing Amorphous Compound I

| Conditions | Description [a] | XRPD Result |
|---|---|---|
| rotary evaporation in dichloromethane (concentration: 268 mg/mL) | white solids, chunk, no B | x-ray amorphous + Form A |
| rotary evaporation in dichloromethane (concentration: 89 mg/mL) | white solids, chunk, no B | x-ray amorphous |
| fast evaporation (FE) in dichloromethane (concentration: 102 mg/mL) | white solids, irregular, B/E | not analyzed |

TABLE 10-continued

Preparation of X-ray Amorphous Compound I and/or
Compositions Containing Amorphous Compound I

| Conditions | Description [a] | XRPD Result |
|---|---|---|
| freeze drying in dioxane/water (9:1), 2 days | white solids, chunk, no B | x-ray amorphous |
| freeze drying in dioxane/water (9:1), 2 days, ~2 g scale-up | white solids, chunk, partial B | x-ray amorphous + Form A + Pattern K + peaks |
| freeze drying in dioxane/water (9:1), 2 days, ~2 g scale-up | white solids, chunk, no B | x-ray amorphous + Form K + peaks |
| freeze drying in dioxane/water (9:1), 4 days, ~1 g scale-up | white solids, chunk, no B | x-ray amorphous |
| freeze drying in dioxane/water (9:1), 4 days, ~1 g scale-up | white solids, chunk, no B | x-ray amorphous |

[a] B = birefringence, E = extinction.

Example 10

Preparation and Characterization of Compound I, Form K

In one embodiment, Compound I Form A (410 mg, 0.8 mmol) and nitromethane (20 mL) were charged to a glass vial and bath sonicated for several minutes, producing a clear solution. The solution was filtered through a 0.2 μm nylon filter to a clean glass vial and allowed to evaporate slowly (vial covered with perforated aluminum foil) in a laboratory fume hood. After approximately 12 days, the sample was split into approximately four equal portions to speed up the evaporation. The sample was continued as a slow evaporation for an additional 7 days. Two of the four vials were uncapped (fast evaporation) and allowed to evaporate overnight. The next day, a small amount of solvent was visible in only one of the samples. After the majority of the solvent was removed by decantation, the precipitated solids from the other three samples were pooled into the original sample. The recombined solids were stored in a sealed vial in a freezer.

Slow Evaporation (SE)

In another embodiment, solutions were prepared in various solvents at ambient temperature and passed through a 0.2-μm nylon filter into a glass vial. The filtered solution was allowed to evaporate at ambient in a vial covered with aluminum foil perforated with one or more pinholes. Any solids formed were isolated and analyzed. From nitromethane by slow evaporation, solids obtained display an XRPD pattern for Compound I, Form K (FIG. 8(a)).

Vapor Diffusion

In yet another embodiment, solutions were prepared with various solvents at ambient temperature and passed through a 0.2-μm nylon filter into a glass vial. This filled vial was placed in a glass vial containing an antisolvent and capped. In general, the anti-solvent is miscible with and, typically, more volatile than the solvent. The experiment was left undisturbed at ambient temperature. Any solids formed were isolated and analyzed.

Two scale-up lyophilization attempts (approx. 2-g scale using dioxane/water 9:1 v/v) were performed. The first attempt generated a disordered crystalline material with evidence of peaks also found in Form A and Form K as determined by visual comparison of XRPD. The second attempt generated a disordered crystalline material with evidence of peaks also found in Form K by visual comparison.

Compound I Form K is a crystalline nitromethane solvate of Compound I. The experimental data for Compound I Form K is provided in FIGS. 8(a) to 8(l). The characterization of Compound I Form K is summarized in Table 11.

TABLE 11

| Characterization of Compound I Form K | | |
|---|---|---|
| Analysis | Result | Figure References |
| XRPD | Form K | 8(a)-8(e), |
| DSC | 168.2° C. (endo) 259.2° C. (endo) | 8(i) |
| FT-IR | reference spectrum | 8(f), 8(g) |
| TGA | Form K | 8(k) |

Example 11

Preparation and Characterization of Compound I, Form L

Compound I, Form A (910 mg, 1.7 mmol) and acetone (48 mL) were charged to a glass beaker and stirred for several minutes, producing a clear solution. The solution was filtered through a 0.2 μm nylon filter to a clean glass beaker and the beaker was left uncovered in a glass jar containing methanol (~50 mL), in order to precipitate solids from the solution via vapor diffusion. After approximately 12 days, the precipitated solids were isolated by decanting off the clear supernatant. The solids were transferred to a clean glass vial and stored under methanol vapor in a freezer.

Compound I Form L is a crystalline methanole solvate of Compound I. The experimental data for Compound I Form L is provided in FIGS. 10(a) to 10(i). The characterization of Compound I Form L is summarized in Table 12.

TABLE 12

| Characterization of Compound I Form L | | |
|---|---|---|
| Analysis | Result | Figure References |
| XRPD | Form L | 10(a)-10(c) |
| DSC | 168.2° C. (endo) 259.2° C. (endo) | 10(g) |
| FT-IR | reference spectrum | 10(d), 10(e) |
| TGA | Form L | 10(h) |

Example 12

Preparation and Characterization of Compound I, Form N

In one embodiment, Compound I, Form N was vacuum dried at ambient temperature for approximately 5 hours, at approximately 50 mTorr, losing approximately 12.4% of the initial weight. The resulting solids were characterized by proton NMR spectroscopy. The spectrum showed that the solids contained approximately 1/3 mole nitromethane. Subsequently, the dried sample was characterized by DSC. The observed results are subject to the conditions used at the time of analysis. The DSC data collected in a crimped pan, exhibits a minor endothermic event at approximately 150° C., which may be related to volatiles loss on heating, and an intense endotherm at approximately 256° C. (onset). The remaining solids (43 mg) were dried for approximately 22 hours in a vacuum oven at approximately 42° C., at approximately 20 mTorr. The weight loss was not determined but the dried solids were characterized by XRPD. The resulting pattern contains XRPD peaks of Form N but exhibits additional unknown peaks, suggesting conversion had occurred. Therefore, subsequent solvent removal experiments were carried out at ambient temperature.

Form A (1.6 g, estimated) was slurried in nitromethane (9 mL) for approximately 5 days. Solids were recovered via vacuum filtration and washed with nitromethane (2×1 mL). The solids were left on the filter under vacuum for several minutes. Approximately 1.3 g of solid were recovered. The solids exhibited a mixture of rectangular plates and prisms by polarized light microscopy. The resulting high-resolution XRPD pattern was consistent with Form N.

Two ambient-temperature vacuum drying experiments were carried out in an attempt to remove the nitromethane from Form N. In one embodiment, 94.0 mg of solid were dried for approximately 16.5 hours, at approximately 20 mTorr, losing approximately 0.7% of the initial weight. In another embodiment, 308.3 mg of solid were dried for approximately 5 days, at approximately 5 mTorr, gaining approximately 0.7% of the initial weight (approximately 0.1% gain from 3 to 5 days). There appeared to be no change in the solids by polarized light microscopy and both samples exhibited Form N by high-resolution XRPD analysis. In one embodiment, the patterns exhibit a weak unknown peak at approximately 9.1 °2θ, which is more pronounced for the 5-day sample than the 16.5-hour sample. Both samples contained approximately 1/3 mole of nitromethane by proton NMR spectroscopy.

In one embodiment, the sample was characterized by DSC and TGA in an open pan configuration to ensure that solvent could freely leave during analysis. The observed results are subject to the conditions used at the time of analysis. The resulting DSC thermogram exhibits a broad endothermic event at approximately 161° C., with a shoulder at approximately 148° C. This event appears to be concurrent with the weight loss of approximately 4.9% from 130-160° C. observed in the TGA thermogram, which correlates to approximately 1/2 mole of nitromethane, assuming the weight loss is attributed only to solvent loss. The thermogram exhibits an endotherm at approximately 256-259° C. (onset). The final weight loss from TGA suggests that decomposition is concurrent with this endotherm.

In one embodiment, in order to remove the nitromethane from Form N sample, 152.4 mg of solid were slurried in acetonitrile (1 mL) for approximately 1 hour. Solids were recovered via vacuum filtration, washing with acetonitrile (4×1 mL). The solids were left on the filter under vacuum for several minutes to dry the solids. 97.7 mg of solid were recovered. In another embodiment, 309.5 mg of solid were slurried in water (4 mL) for approximately 24.5 hours. Solids were recovered via vacuum filtration, washing with water (2×1 mL). The solids were left on the filter under vacuum for approximately 1.5 hours to dry the solids. 270.4 mg of solid were recovered. There was no change in the solids by polarized light microscopy; however, by XRPD analysis, pattern T resulted from acetonitrile and a mixture of Forms C and A resulted from water. The high-resolution XRPD pattern for the solids from water slurry exhibited additional peaks present in the Form N XRPD pattern, suggesting incomplete conversion.

In addition, the proton NMR data for Form N suggests the material contains approximately 1/3 mole of nitromethane. The space group of the Form N solution ($P2_12_12$) can only exhibit less than one molecule of solvent in the asymmetric unit if the solvent position is partially occupied, i.e. some of the asymmetric units contain solvent molecules and others do not.

The experimental data for Compound I Form N is provided in FIGS. 11(a) to 11(c). The characterization of Compound I Form N is summarized in Table 13.

TABLE 13

Characterization of Compound I Form N

| Analysis | Result | Figure References |
|---|---|---|
| XRPD | Form N | 11(a) |
| DSC | 150.0° C. (event) | 11(b) |
|  | 259.2° C. (endo) |  |
| TGA | Form N | 11 (c) |

Characterization of solids from Compound I Form N preparation is summarized in Table 14.

TABLE 14

Characterization of Solids from Romidepsin Form N Preparation/Solvent Removal Attempts

| Starting Material (XRPD Result) | Conditions | Analysis | Result |
|---|---|---|---|
| (Form N + peaks) [a] | 10.3 mg, heated to 180° C. by DSC | DSC (crimped) XRPD | (sample preparation analysis) Form A + 2 weak peaks of Form N |
| (Form N) | 71.5 mg, RT vac dry 5 hours at 50 mTorr [b] | Weight Change DSC (crimped) | 12.4% wt loss on drying 150° C. (broad endo, min) 256° C. (endo, onset) with concurrent decomp |
| (Form N) | 43 mg 42° C. vac dry 22 hours at 20 mTorr [b] | XRPD | unknown + Form N |
| (Form A) | 1.5 g, 9 mL nitromethane, slurry 4 days, vac filter with acetone wash, RT vac dry 6 hours at 50 mTorr [b] | Initial Recovery Weight Change PLM HR XRPD | 0.9 g 0.4% wt loss on drying platy/bladed particles (B/E) Form B + peaks [c] |
|  | 1.6 g (estimated) 9 mL nitromethane, slurry 5 days, vac filter with nitromethane wash | Initial Recovery PLM HR XRPD | 1.3 g rectangular plates/prisms (B/E) Form N |

TABLE 14-continued

Characterization of Solids from Romidepsin Form N Preparation/Solvent Removal Attempts

| Starting Material (XRPD Result) | Conditions | Analysis | Result |
|---|---|---|---|
| (Form N) | 94.0 mg, RT vac dry 16.5 hours at 20 mTorr [b] | Weight Change | 0.7% wt loss on drying |
|  |  | PLM | rectangular plates/prisms (B/E) |
|  |  | HR XRPD | Form N + weak peak at 9.1 °2θ |
|  |  | ¹H-NMR | consistent with structure ⅓ mole nitromethane |
| (Form N) | 308.3 mg, RT vac dry 5 days at 5 mTorr [d] | Weight Change | 0.7% wt gain on drying [e] |
|  |  | PLM | rectangular plates/prisms (B/E) |
|  |  | HR XRPD | Form N + weak peak at 9.1 °2θ |
|  |  | DSC (open) | 161° C. (broad endo, min) with shoulder at 148° C. 259° C. (endo, onset) with concurrent decomp |
|  |  | TGA | 4.9% wt loss 130-160° C. (equates to ~0.5 mole nitromethane) |
|  |  | ¹H-NMR | consistent with structure ⅓ mole nitromethane |
|  | 152.4 mg, 1 mL acetonitrile, brief vortex, slurry 1 hour, vac filter with acetonitrile wash/dry several minutes | Initial Recovery | 97.7 mg |
|  |  | PLM | rectangular plates/prisms (B/E) [f] |
|  |  | XRPD | pattern T |
|  |  | Initial Recovery | 270.4 mg |
|  |  | PLM | rectangular plates/prisms (B/E) [f] |
|  | 309.5 mg, 4 mL water, brief vortex, slurry 24.5 hours, vac filter with water wash/ dry 1.5 hours | HR XRPD | Forms C + A + peaks [g] |

[a] Form N; additional weak peaks are present in the XRPD pattern at approximately 8.37, 11.37, 13.10, 16.23, and 21.86 °2θ.
[b] Vacuum pressure from in-line gauge for vacuum system.
[c] Additional peaks in the XRPD pattern present in XRPD pattern of Form A.
[d] Sample stored in covered container at RT for 1 day prior to drying. Sample dried in stand-alone oven; vacuum pressure for oven measured by McLeod gauge.
[e] 0.1% wt gain since check at 3 days.
[f] Particles appeared unchanged by solvent.
[g] Additional peaks in the XRPD pattern present in XRPD pattern of Form N.

Example 13

Solubility Studies

The ambient temperature solubility data for the Compound I Form A are summarized in Table 15. The solids exhibited apparent solubilities of well over 100 mg/ml for dimethylformamide (DMF), dichloromethane (DCM) and 2,2,2-trifluoroethanol (TFE). The material exhibited moderate solubility (e.g., >10 mg/ml) in the majority of solvent and solvent combinations tested. The only exception was isopropanol (IPA) at 4.6 mg/mL. Some solubility data was obtained on multiple samples as presented in Table 15 below.

TABLE 15

Solubility data for Compound I, Form A

| Solvents[a] | Results [mg/ml] | Solvents[b] | Results [mg/ml] |
|---|---|---|---|
| Acetone | 22.4, 28.2 | (1:0.2) Ethanol:TFE | 16.3 |
| (0.5:0.1) Acetone:DCM | 38 | (1.5:0.8) Ethyl Acetate:Acetone | 8.9 |
| (1:0.2) Acetonitrile (ACN):TFE | 17.9 | (1.5:1) Heptane:DCM | 8.0[d] |
| 2-Butanone (MEK) | 12.5 | Isopropanol (IPA) | 4.6 |
| (1:0.1)2-Butanone:TFE | 20.6 | (1:1)2-Propanol:Acetone | 11.5[d] |
| Chloroform | 26.5 | (4.5:3) Isopropyl Ether:Ethanol | 6.8 |
| Dichloromethane (DCM) | 135.3, 280 | (1.5:1) Methanol:TFE | 8.7[d] |
| Dimethylformamide (DMF) | 248.5 | Nitromethane | 23.6 |
| (1:0.5) Dioxane:Acetone | 13.3 | 2,2,2-trifluoroethanol (TFE) | 158.9 |
| Ethanol (EtOH) | 23.5 | (0.1:0.1) TFE:DCM | 97 |
| (1:1) Ethanol/IPA | 28[c] | (1:0.1) Toluene:TFE | 21.4 |
| (1:3) Ethanol/IPA | 10[c] | (1.5:0.5) Water:DCM | 12.4 |

[a] Ratio of solvents based on volume, in milliliters.
[b] Solubility assessment performed at ambient temperature, unless otherwise noted. Reported values are less than or equal to the actual solubility of Compound I in each test solution based on visual observation and therefore are approximate.
[c] Experiment performed on hot plate set to 70° C.
[d] Experiment performed on hot plate set to 60° C.

Example 14

Polymorph Screen

A series of solvent-based experiments were set up utilizing slurry, evaporation, crash precipitation, and vapor diffusion techniques. The samples were prepared with Compound I Form A and the experimental results are summarized in Tables 16 and 17.

In one embodiment, experiments using solvents from the crystallization processes for Forms A and B resulted in characterization of selected solids recovered from these experiments that displayed unique XRPD patterns designated as Forms A to E, H, and J, and are described below. Several unique XRPD patterns were also obtained from other experimental conditions, including an x-ray amorphous solid. No further characterization of these solids was performed. A summary of exemplary XRPD results for crystallization experiments are presented in Table 16.

TABLE 16

Summary of XRPD Results for Crystallization Experiments

| Solvent | Conditions | Habit/Description | XRPD Result |
|---|---|---|---|
| Dichloromethane (DCM) | fast evaporation | clear film | Form A (w/disorder) |
| Acetone | fast evaporation | white flakes | Form B + peaks (Form A) |

TABLE 16-continued

Summary of XRPD Results for Crystallization Experiments

| Solvent | Conditions | Habit/Description | XRPD Result |
|---|---|---|---|
| (1.5:1) MeOH:TFE | fast evaporation | opaque film | x-ray amorph |
| (1:0.2) EtOH:TFE | fast evaporation | film on vial walls | x-ray amorph |
| (1:1) IPA:Acetone | fast evaporation | opaque film | Form A (w/disorder) |
| (1.5:0.8) EtOAc:Acetone | fast evaporation | blades/needles on vial walls | Form A (w/disorder) |
| (1.5:1) Heptane:DCM | fast evaporation | sm needles on vial wall | Form A (w/disorder) |
| (1.5:0.5) Water:DCM | fast evaporation | white solids, agglomerates | x-ray amorphous |
| (1:0.1) MEK:TFE | fast evaporation | flakes | B + A |
| (1:0.2) ACN:TFE | fast evaporation | — | — |
| (1:0.1) Toluene:TFE | fast evaporation | Agglomerate solids | Form A |
| 2,2,2-Trifluoroethanol (TFE) | fast evaporation | clear film | similar to Form E |
| (1:0.5) Dioxane:Acetone | fast evaporation | long needles, asperites | Form A |
| (0.5:0.1) Acetone:DCM | fast evaporation | Agglomerate plates | Form B + peaks (Form A) |
| (0.1:0.1) TFE:DCM | fast evaporation | clear film | x-ray amorph |
| Methyl ethyl ketone (MEK) | slow evaporation | — | Form J similar to Form D |
| Dimethylformamide (DMF) | slow evaporation | no solids | — |
| (4.5:3) Isopropyl ether:EtOH | slow evaporation | thin film with B/E | similar to Form A + peaks |
| Chloroform | Slurry, vac dried, 60° C. | Dried solids | Form H |
| (1:3) Acetone/water | −5° C., 1 day seeded with Form C + peaks (Form A) | Dried solids | Form C + peaks (Form A) |
| (1:3) Acetone/water | −5° C., 41 days seeded with Form C + peaks (Form A) | Dried solids | Form C |

A summary of exemplary XRPD results for vapor diffusion experiments are presented in Table 17.

TABLE 17

Summary of XRPD Results for Vapor Diffusion Experiments

| Solvent[a] | Conditions | Habit/Description[b] | XRPD Result |
|---|---|---|---|
| Dichloromethane | Heptane | Agglomerate flakes | Form A |
|  | Water | white solids precipitate, undefined habit | — |
|  | Methanol | no solids | — |
|  | Heptane | Agglomerate blades with B/E | Form B (w/disorder) |
| Acetone | Water | white solids, undefined habit with B/E | Form A |
| (3.5:1) Isopropyl alcohol:Trifluoroethanol | Heptane | no solids | — |
|  | Water | white solids precipitate, undefined habit | — |
|  | Methanol | Agglomerated needles/blades with B/E | x-ray amorphous + peaks |
| Ethanol | Heptane | white solids precipitate, undefined habit | — |
|  | Water |  | — |
|  | Methanol |  | — |
| Trifluoroethanol | Heptane | no solids | — |
|  | Water | white solids precipitate, undefined habit | — |
|  | Methanol |  | — |

[a]Solvent ratios in parenthesis on volume basis, unless otherwise noted
[b]B: birefringence, E: extinction (E) under cross polars Example 15

Composition/Formulation

This example illustrates various components present in a representative formulation containing Compound I according to the present disclosure, which was formulated as a bulk solution batch using the following steps: (a) preparing a Compound I solid form; (b) preparing a compounding solution comprising tert-butyl alcohol and water; (c) combining Compound I solid form and the compounding solution to form a mixture; (d) adding povidone to the mixture; (e) adjusting the pH of the mixture by adding hydrochloric acid solution, resulting in a formulated solution; (f) performing sterile filtration of the formulated solution; and (g) lyophilizing the formulated solution under aseptic conditions, to yield a final composition comprising Compound I. The steps are detailed in Table 18 below.

TABLE 18

Various components of the bulk solution

| Component | Function | Quantity per 51 L Batch | Ref to Quality Standard |
|---|---|---|---|
| Compound I | Active pharmaceutical ingredient | 204 g | Internal |
| Povidone | Excipient | 408 g | USP |
| 0.1N hydrochloric acid | pH adjustment | 510 mL | NF/EP |

TABLE 18-continued

Various components of the bulk solution

| Component | Function | Quantity per 51 L Batch | Ref to Quality Standard |
|---|---|---|---|
| Nitrogen | Processing agent and inert atmosphere for vial Headspace | N/A | NF/EP |
| Water for Injection* | Processing agent | 22.3 kg | USP/EP |
| Tert-butyl alcohol* | Processing agent | 26.1 kg | ACS |

*Removed during lyophilization

Example 16

Preparation of Lyophilate

Preparation of Compounding Solution

Following preparation and sterilization of components (stoppers and vials) of equipment needed, all processing equipment was inspected to assure it was free from residual rinse water. Vessel 1, a 20 gallon, jacketed, stainless steel vessel, was purged with nitrogen NF/EP. The required amount of tert-butyl alcohol was added to Vessel 1. The temperature of the tert-butyl alcohol and compounding vessel were adjusted to 28 to 32° C. in advance to maintain this raw material as a free-flowing liquid. Following the addition of tert-butyl alcohol and initiation of mixing, the required amount of water for injection (WFI) was added and the solution was mixed to completeness for 10±2 minutes, to result in a final compounding solution of 56 L. A portion (25%) of the compounding solution was transferred to a second, smaller, jacketed, stainless steel vessel (Vessel 2) for use in subsequent compounding steps. Both vessels were temperature controlled at 28 to 32° C., and Vessel 1 was maintained with a nitrogen NF/EP overlay.

Preparation of Formulated Bulk Solution

Compound I solid form drug substance was weighed in an isolator and then transferred directly to the compounding solution tank (Vessel 1) by way of a single-use, disposable isolator transfer bag, to form a drug substance solution. The transfer bag was rinsed 3 times with a portion of the compounding solution from Vessel 2 and each rinse was added to the compounding solution tank.

The drug substance solution was mixed for 30±5 minutes at 28 to 32° C. Following dissolution of amorphous Compound I, the specified amount of povidone, USP, was added to the compounding vessel. The weighing container was rinsed once with a portion of the compounding solution and the rinse was transferred to the compounding tank that was mixed for 20±5 minutes at 28 to 32° C. to dissolve the povidone.

The pH of the bulk solution was adjusted with a predetermined amount of 0.1 N HCl solution and was mixed for 10±2 minutes at 28 to 32° C. to form a formulated bulk solution. The formulated bulk solution was sampled and the apparent pH was verified to be between 3.6 and 4.0. The QS volume of compounding solution required to achieve the calculated target weight was transferred from Vessel 2 to Vessel 1. The formulated bulk solution was mixed for 10±2 minutes at 28 to 32° C. and then sampled for quality control (QC) testing, including appearance, assay, density, pH, and bioburden. The compounding tank was sealed, and the temperature was maintained at 28 to 32° C. until sterile filtration.

Sterile Filtration of Formulated Bulk Solution

The compounding tank containing the formulated bulk solution was moved from the Class 100,000 compounding suite to an anteroom adjacent to the Class 10,000 filling suite. The formulated bulk solution was transferred via a 3/8" stainless-steel braided Teflon® hose passed through a port in the wall of the sterile filling suite to the filling suite by over pressurization with sterile nitrogen, NF/EP. The formulated bulk solution was first clarified through a Millipore Opticap® filter (0.22 µm Durapore® membrane) and then was sterilized by filtration through a filter assembly located within the aseptic core containing 2 Millipore Millipak® 0.22 µm Durapore® filters in series, into a sterile receiving vessel. The integrity of the product sterilizing filters was tested for pressure and flow pre- and post-filtration using Isopropyl Water (IPA)/Water (60%/40%) as the wetting solution. The minimum pressure hold value was 10 psi prior to filtration, and the maximum flow is 1.3 mL/min at 12 psi after filtration. The sterile-filtered formulated bulk solution was sampled for QC testing, including appearance, assay, density, and pH.

Aseptic Filling of Vials for Drug Product

Aseptic filling and stoppering of the sterile vials occurred under Class 100 conditions using an automated TL filling line. Process controls included defined weight checks of vials to verify accurate fill volume throughout the filling operation.

Immediately following filling of each vial, a sterile lyophilization stopper was partially seated in the vial and each tray of filled vials was moved to the loading area for the lyophilizer within the Class 100 aseptic area. Trays were immediately loaded onto precooled shelves in the lyophilizer.

Lyophilization

Vials containing compositions were lyophilized under aseptic conditions using a preprogrammed lyophilization cycle. A summary of the lyophilization cycle process and controls is provided in Table 19.

TABLE 19

Lyophilization Process and Controls

| Lyophilizer Program Segments | Process Set Points | Controls Limits |
|---|---|---|
| 1-4: Chamber loading and freezing | Load vials into chamber Ramp shelf temperature down to −45 ± 3° C. | Shelf temperature: 0 ± 3° C. Shelf temperature: −40° C. Product thermocouples: ≤−40° C. |
| 5: Hold | Hold at temperature for 2 ± 0.5 hours | Product thermocouples: ≤−40° C. |
| 6: Evacuate chamber | Evacuate chamber vacuum to 100-200 µm | Chamber pressure: 100-200 µm |
| 7-8: Ramp temperature and hold | Ramp shelf temperature up to −20 ± 3° C. over 3 hours (~8° C./hour) Hold for 2 ± 0.5 hours | Shelf temperature: ≥−23° C. Product thermocouples: ≥−23° C. |

TABLE 19-continued

Lyophilization Process and Controls

| Lyophilizer Program Segments | Process Set Points | Controls Limits |
| --- | --- | --- |
| 9: Ramp temperature; nitrogen sweep | Ramp shelf temperature up to 0 ± 3° C. over 2 ± 0.5 hours (~10° C./hour) Nitrogen sweep at 135 μm | Shelf temperature: 0 ± 3° C. Product thermocouples: ≥−3° C. Chamber pressure: 100-200 μm |
| 10: Ramp temperature and hold | Ramp shelf temperature up to 33 ± 3° C. over 6 hours (~6° C./hour) Hold at temperature for 2 hours | Shelf temperature: 33 ± 3° C. Product thermocouples: ≥27° C. Chamber pressure: 100-200 μm |
| 11: Terminal drying[1] | Pull chamber pressure to ≤100 μm Hold for 16 ± 1 hours | Shelf temperature: 33 ± 3° C. Product thermocouples: ≥27° C. Chamber pressure: <100 μm |
| 12: End cycle; stopper; hold for unloading[2] | Increase chamber pressure to 14 to 15 psia with Nitrogen NF/EP Ramp shelf temperature down to 5 ± 3° C. Seat stoppers | Shelf temperature: 5 ± 3° C. Product thermocouples: 5° C. Chamber pressure: 15 psia |
| 13: Product unloading | Ramp shelf temperature up to 20 ± 3° C. Open chamber and unload | Product thermocouples: ≥15° C. Chamber pressure: 14 psia |

[1]Total terminal drying time, including initial 2 hour hold, is 18 ± 1 hours
[2]The shelf is cooled to 5 ± 3° C. only if it is necessary to hold the product for an extended time prior to unloading.

In one embodiment, an additional step after the secondary drying following step 11 (Table 19) includes drying the vials at the temperature of 50° C. up to 24 hours at the pressure of 50 μm Hg. In another embodiment, an additional step includes drying the vials at the temperature of 50° C. up to 48 hours at the pressure of 50 μm Hg.

In another embodiment, an additional step after the secondary drying following step 11 (Table 19) includes drying the vials at the temperature of 60° C. up to 3 hours at the pressure of 100 μm Hg. In yet another embodiment, an additional step includes drying the vials at the temperature of 60° C. up to 6 hours at the pressure of 100 μm Hg. In another embodiment, an additional step includes drying the vials at the temperature of 60° C. up to 12 hours at the pressure of 100 μm Hg. In another embodiment, an additional step includes drying the vials at the temperature of 60° C. up to 24 hours at the pressure of 100 μm Hg. In another embodiment, an additional step includes drying the vials at the temperature of 60° C. up to 48 hours at the pressure of 100 μm Hg.

In another embodiment, an additional step after the secondary drying following step 11 (Table 19) includes drying the vials at the temperature of 70° C. up to 24 hours at the pressure of 25 mm Hg. In another embodiment, an additional step includes drying the vials at the temperature of 70° C. up to 48 hours at the pressure of 25 mm Hg.

Following completion of the cycle (Segment 12), the vials were backfilled with sterile nitrogen, NF/EP, at atmospheric pressure and the stoppers were completely seated prior to opening the lyophilizer chamber. The trays were unloaded and transferred to the sealing area.

Vials containing compositions were sealed immediately following unloading from the lyophilization chamber. Each seal was imprinted with the Composition lot number using a video jet printer incorporated into the automated sealing line. Seal inspection is performed every 15 minutes during the sealing operation.

Following sealing operations, Compound I composition vials were inspected, labeled and packaged and appropriate process validation and/or Evaluation was subsequently performed.

Equivalents

Those skilled in the art will recognize, or be able to ascertain using no more than routine experimentation, many equivalents to the specific embodiments of the disclosure, described herein. The scope of the present disclosure is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process. Furthermore, it is to be understood that the disclosure encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim.

Where elements are presented as lists, e.g., in Markush group format, it is to be understood that each subgroup of the elements is also disclosed, and any element(s) can be removed from the group. It should it be understood that, in general, where the disclosure, or aspects of the disclosure, is/are referred to as comprising particular elements, features, etc., certain embodiments of the disclosure or aspects of the disclosure consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of skill in the art, they may be excluded even if the exclusion is not set forth explicitly herein. Any particular embodiment of the compositions of the disclosure (e.g., any targeting moiety, any disease, disorder, and/or condition, any linking agent, any method of administration, any therapeutic application, etc.) can be excluded from any one or more claims, for any reason, whether or not related to the existence of prior art.

Publications discussed above and throughout the text are provided solely for their disclosure prior to the filing date of the present application. Nothing herein is to be construed as an admission that the inventors are not entitled to antedate such disclosure by virtue of prior disclosure.

The invention claimed is:

1. A crystalline form C of romidepsin comprising XRPD characteristic peaks at about 8.28 2θ, 11.45 2θ, 12.19 2θ, and 21.13 2θ.

2. A pharmaceutical composition comprising the crystalline form C of romidepsin of claim 1 and a pharmaceutically acceptable excipient.

* * * * *